US005827693A

United States Patent [19]
De Angelo et al.

[11] Patent Number: 5,827,693
[45] Date of Patent: Oct. 27, 1998

[54] EXPRESSION OF RECOMBINANT HEMOGLOBIN AND HEMOGLOBIN VARIANTS IN YEAST

[75] Inventors: Joseph De Angelo, Hamtramck; Nalini M. Motwani, Troy; Wajeeh Bajwa, Canton, all of Mich.; Joseph Bonaventura, Beaufort, N.C.

[73] Assignee: Apex Bioscience, Inc., Durham, N.C.

[21] Appl. No.: 484,686

[22] Filed: Jun. 7, 1995

Related U.S. Application Data

[63] Continuation of Ser. No. 368,407, Dec. 29, 1994, abandoned, which is a continuation of Ser. No. 876,290, Apr. 29, 1992, abandoned, which is a continuation-in-part of Ser. No. 684,611, Apr. 12, 1991, abandoned, which is a continuation-in-part of Ser. No. 614,359, Nov. 14, 1990, abandoned, which is a continuation-in-part of Ser. No. 509,918, Apr. 16, 1990, abandoned.

[51] Int. Cl.[6] ............................ C12P 21/06; C12N 15/00; C12N 1/14; C07K 14/805
[52] U.S. Cl. .................. 435/69.6; 435/320.1; 435/254.2; 536/235; 536/24.1; 530/385
[58] Field of Search ................................. 435/69.1, 69.6, 435/172.1, 172.3, 240.2, 252.3, 254.2, 320.1, 254.1; 530/385; 536/22.1, 23.5

[56] References Cited

U.S. PATENT DOCUMENTS

| 5,049,493 | 9/1991 | Khosia et al. | 435/69.1 |
| 5,523,215 | 6/1996 | Cousens et al. | 435/69.1 |

FOREIGN PATENT DOCUMENTS

WO 91/13158   9/1991   WIPO.

OTHER PUBLICATIONS

Motwani et al., 1996, "Production, purification, and characterization of recombinant human hemoglobin rainier expressed in Saccharomyces cerevisiae", *Protein Expression and Purification* 8:447–455.

J.R. Shaeffer, 1988, "ATP–dependent proteolysis of hemoglobin α chains in β–thalassemic hemolysates is ubiquitin–dependent", *J. of Biol. Chem.* 263:13663–13669.

L. Stryer, 1975, "Oxygen–transporting proteins: Myoglobin and hemoglobin", *Biochemistry* W.H. Freeman & Co. New York Chap.7 pp. 143–174.

Vierstra & Sullivan, 1988, "Hemin inhibits ubiquitin–dependent proteolysis in both a higher plant and yeast", *Biochem.* 27:3290–3295.

Braverman & Lester, 1981, "Evidence for increased proteolysis in intact β thalassemia erythroid cells", *Hemoglobin* 5:549–564.

Clements et al., 1989, "Expression and activity of a gene encoding rat cytochrome c in the yeast Saccharomyces cerevisae", *Gene* 83:1–14.

Datar et al., 1993, "Process economics of animal cell and bacterial fermentations: A case study analysis of tissue plasminogen activator", *BioTechnology* 11:349–357.

Edman et al., 1981, "Synthesis of hepatitis B surface and core antigens in E. coli", *Nature* 291:503–506.

Errede et al., 1981, "Studies on transposable elements in yeast I. ROAM mutations causing increased expression of yeast genes: Their activation by signals directed toward conjugation functions and their formation by insertion of Tyl repetitive elements", *Cold Spring Harbor Symposia on Quantitative Biology* 45:593–607.

Errede et al., 1984, "Identification of regulatory regions within the Tyl transposable element that regulate Iso–2–Cytochrome c production in the CYC7–H2 yeast mutant", *Molecular and Cellular Biology* 4:1393–1401.

Hallewell et al., 1987, "Amino terminal acetylation of authentic human Cu,Zn superoxide dismutase produced in yeast", *BioTechnology* 5:363.

Kingsman et al., 1990, "High–efficiency yeast expression vectors based on the promoter of the phosphoglycerate kinase gene", *Methods in Enzymology* 185:329–341.

Kohno et al., 1990, "Refolding of recombinant proteins", *Methods in Enzymology* 185:187–195.

Rosenberg et al., 1990, "Glyceraldehyde–3–phosphate dehydrogenase–derived expression cassettes for constitutive synthesis of heterologous proteins", *Methods in Enzymology* 185:341–351.

Shinar & Rachilewitz, 1990, "Oxidative denaturation of red blood cells in thalassemia", *Semin. Hamatol.* 27:70–82.

Valenzuela et al., 1982, "Synthesis and assembly of hepatitis B virus surface antigen particles in yeast", *Nature* 298:347–350.

Wickramasinghe & Hughes, 1984, "Globin chain precipitation, deranged iron metabolism and dyserythropoiesis in some thalassemia syndromes", *Haematologia* 17:35–56.

(List continued on next page.)

*Primary Examiner*—Karen Carlson
*Attorney, Agent, or Firm*—Pennie & Edmonds LLP

[57] ABSTRACT

The invention is directed to a substantially pure mammalian globin chain or heme-binding fragment thereof. The invention is further directed to recombinant DNA vectors capable of expressing at least one globin chain or substantially homologous variant thereof in yeast. The invention also relates to methods for expressing at least one globin chain or substantially homologous variant thereof in yeast. Expressed alpha-like globin and beta-like globin chains or variants thereof may be combined with a source of heme to produce hemoglobin or a substantially homologous variant thereof. Additionally, expressed gamma-globin chains may be combined with a source of heme to produce hemoglobin or a substantially homologous variant thereof. The invention also relates to methods for expressing hemoglobin or variants thereof in yeast where the heme is produced by the yeast and ligated to globins to form hemoglobin in vivo. The hemoglobin produced by the methods of the present invention may be used in applications requiring a physiological oxygen carrier such as in blood substitute solutions and as in plasma expanders or in applications requiring a physiological oxygen carrier.

185 Claims, 69 Drawing Sheets

OTHER PUBLICATIONS

Wickramasinghe et al., 1984, "The fate of excess β–globin chains within erythropoietic cells in α–thalassemia 2 trait, x–thalassemia 1 trait, haemoglobin H disease and haemoglobin Q–H disease: An electron microscope study", *Br. J. Haematol.* 56:473–482.

Wickramasinghe et al., 1986, "Studies of erythropoietic cells in heterozygotes and homozygotes for haemoglobin Constant Spring and in heterozygotes for both haemoglobin Constant Spring and α–thalassemia 1 trait: Extent of globin chain precipitation and cell cycle sitribution", *Clin. Lab. Haematol.* 8:187–198.

J.A. Titus, 1983, Plasmid DNA in colorless filamentous gliding bacteria, Arch. Microbiol. 134:38–44.

Looker et al., 1992, A human recombinant haemoglobin designed for use as a blood substitute, Nature 356: 258–260.

Hoffman et al., 1990, Expression of fully functional tetrameric human hemoglobin in *Escherichia coli,* Proc. Natl. Acad. Sci. USA 87: 8521–8525.

Jhiang et al., 1989, The structures of the gene encoding chain c of the hemoglobin of the earthworm, *Lumbricus terrestris,* J. Biol Chem. 264(32): 19003–19008.

Adams et al., 1987, Hb Mississippi [$\beta_{44}$ (CD$_3$) Ser → Arg]: a new variant with analogous properties, Hemoglobin 11(5): 435–452; Adams et al., (1988) Chem. Abs. 108: 545, abst. 129475.

Nagai et al., 1988, Refolding and crystallographic studies of eukaryotic proteins produced in *Escherichia coli,* Biochem. Soc. Trans. 16: 108–110.

Scarpulla et al., 1986, Functional expression of Rat cytochrome C in *Saccharomyces cerevisiae,* Proc. Natl. Acad. Sci. USA 83: 6352–6356.

Nagai et al., 1985, Oxygen binding properties of human mutant hemoglobins synthesized in *Escherichia coli,* Proc. Natl. Acad. Sci. USA 82: 7252–7255.

Dickerson et al., 1983, Hemoglobin: structure, function, evolution, and pathology; Benjamin/Cummings, Menlo Park, CA, pp. 146–158.

Erhart et al., 1983, The presence of a defective LEU2 gene on $2\mu$ DNA recombinant plasmids of *Saccharomyces cerevisiae* is responsible for curing and high copy number, J. Bact. 156 (2): 625–635.

Gibb, E.A., 1981, Increased subunit association of a new super stable variant hemoglobin motown, Clin. Res. 29(4):795A.

Lauer et al., 1980, The chromosomal arrangement of human α–like globin genes: sequence homology and α globin gene deletions, Cell 20: 119–130.

Altay et al., 1976, Hemoglobin Hacettepe of $\alpha_2\beta_2$ 127(H5)Gln→Glu, Biochem. Biophys. Acta. 434: 1–3.

Oshino et al., 1973, Studies on yeast hemoglobin. The properties of yeast hemoglobin and its physiological function in the cell, Eur. J. Biochem. 35: 23–33.

Oshino et al., 1973, Purification and molecular properties of yeast hemoglobin, Eur. J. Biochem. 39: 581–590.

Oshino et al., 1972, Yeast hemoglobin–reductase complex, Biochem. Biophys. Res. Comm. 46(3): 1055–1060.

U.S. Patent No. 5,028,588, issued Jul. 2, 1991, by Hoffman and Nagai.

Wagenbach et al., 1991, Synthesis of wild type and mutant human hemoglobins in *Saccharomyces cerevisiae,* Biotechnology 9:57–61.

European Patent Publication No. 0 402 300 A2, dated Dec. 12, 1990.

PCT International Publication No. WO 88/09179, dated Dec. 1, 1988.

PCT International Publication No. WO 90/13645, dated Nov. 15, 1990.

PCT International Publication No. WO 89/03883, dated May 5, 1989.

Greaves et al., 1990, A transgenic mouse model of sickle cell disorder, Nature 343:183–185.

Hanscombe et al., 1989, High–level, erythroid–specific expression of the human α–globin gene in transgenic mice and the production of human hemoglobin in murine erythrocytes, Genes & Dev. 3:1572–1581.

Dobson et al., 1989, Identification of the latency–associated transcript promoter by expression of rabbit beta–globin mRNA in mouse sensory nerve ganglia latently infected with a recombinant herpes simplex virus, J. Virol. 63:3844–3851.

Springer and Sligar, 1987, High–level expression of sperm whale myoglobin in *Escherichia coli,* Proc. Natl. Acad. Sci. USA 84:8961–8965.

Miller et al., 1988, Design of retrovirus vectors for transfer and expression of the human β–Globin Gene, J. Virol. 62:4337–4345.

Walder, 1988, The use of recombinant hemoglobin as a blood substitute, Biotechnology 88:357–362.

Brinigar et al., Expression of human β–globin c–DNA in *E. coli.* streptomyces & yeast, Symposium on oxygen binding heme proteins, structure, dynamics, function and genetics, Asilomar Conf. Grounds, Pacific Grove, Calif. Oct. 9–13, 1988.

Karlsson et al., 1986, Stable gene transfer and tissue–specific expression of a human globin gene using adenoviral vectors, Eur. Mol. Biol. Organ. 5(9):2377–2385.

Nagai et al., 1985, Oxygen binding properties of human mutant hemoglobins synthesized in *Escherichia coli,* Proc. Natl. Acad. Sci. USA 82:7252–7255.

Lau et al., 1984, Amplification and expression of human α–globin genes in Chinese hamster ovary cells, Molecular and Cellular Biology 4:1469–1475.

Goossens et al., 1980, Triplicated α–globin loci in humans, Proc. Natl. Acad. Sci. USA 77:518–521.

Wilson et al., 1978, Insertion of synthetic copies of human globin genes into bacterial plasmids, Nucleic Acids Res. 5:563–581.

U.S. Patent No. 4,880,734, issued Nov. 14, 1989, by Burke et al.

U.S. Patent No. 4,876,197, issued Oct. 24, 1989, by Burke et al.

U.S. Patent No. 4,870,013, issued Sep. 26, 1989, by Gelfand et al.

U.S. Patent No. 4,615,974, issued Oct. 7, 1986, by Kingsman and Kingsman.

U.S. Patent No. 4,766,068, issued Aug. 23, 1988, by Oeda et al.

Langford et al., 1983, Yeast is unable to excise foreign intervening sequences from hybrid gene transcripts, Proc. Natl. Acad. Sci. USA, 80:1496–1500.

Halfter et al., 1989, Isolation and DNA–binding characteristics of a protein involved in transcription activation of two divergently transcribed, essential yeast genes, EMBO Journal, 8:3029–3037.

U.S. Patent No. 4,826,763, issued May 2, 1989, by Norris et al.

U.S. Patent No. 4,801,542, issued Jan. 31, 1989, by Murray et al.

U.S. Patent No. 4,775,622, issued Oct. 4, 1988, by Hitzeman et al.
European Patent Publication No. 0 132 309 A3, dated Jan. 30, 1985.
Hitzeman et al., 1981, Expression of a human gene for interferon in yeast, Nature 293:717–722.
Beggs et al., 1980, Abnormal expression of chromosomal rabbit β–globin gene in *Saccharomyces cerevisiae,* Nature 283:835–840.
Hinnen et al., 1978, Transformation of yeast, Proc. Natl. Acad. Sci. USA 75:1929–1933.
U.S. Patent No. 4,853,370, issued Aug. 1, 1989, by Ecanow et al.
U.S. Patent No. 4,738,952, issued Apr. 19,1988, by Ecanow and Ecanow.
U.S. Patent No. 4,710,488, issued Dec. 1, 1987, by Wong.
U.S. Patent No. 4,670,417, issued Jun. 2, 1987, by Iwasaki et al.
U.S. Patent No. 4,650,786, issued Mar. 17, 1987, by Wong.
U.S. Patent No. 4,584,130, issued Apr, 22, 1986, by Bucci and Bucci.
U.S. Patent No. 4,600,531, issued Jul. 15, 1986, by Walder.
Bove, 1986, Transfusion–transmitted diseases: current problems and challenges, Progress in Hematology 14:123–147.
U.S. Patent No. 4,473,563, issued Sep. 25, 1984, by Nicolau et al.
U.S. Patent No. 4,412,989, issued Nov. 1, 1983, by Iwashita et al.
U.S. Patent No. 4,377,512, issued Mar. 22, 1983, by Ajisaka and Iwashita.
U.S. Patent No. 4,321,259, issued Mar. 23, 1982, by Nicolau and Gershone.
U.S. Patent No. 4,301,144, issued Nov. 17, 1981, by Iwashita and Katsumi.
Sehgal et al, 1984, Polymerized pyridoxylated hemoglobin: evolution of a new blood substitute, Surgery 95:433–438.
U.S. Patent No. 4,192,869, issued Mar. 11, 1980, by Nicolau and Gersonde.
U.S. Patent No. 4,061,736, issued Dec. 6, 1977, by Morris and Bonsen.
Goldman and Morton, 1981, Computerized doppler tomography: ultrasonic imaging and analysis of blood flow, Clinical Research 29:795A.
Yanagi et al, 1989, Expression of human erythropoietin cDNA in human lymphoblastoid Namalwa cells: the inconsistency of a stable expression level with transient expression efficiency, Gene 76:19–26.
U.S. Patent No. 4,840,896, issued Jun. 20, 1989, by Reddy et al.
Broach et al., 1983, Vectors for high–level, inducible expression of cloned genes, in Experimental manipulation of gene expression, Inouye (Ed.), Academic Press, New York, pp. 84–115.
U.S. Patent No. 4,758,571, issued Jul. 19, 1988, by Curtius et al.
U.S. Patent No. 4,701,455, issued Oct. 20, 1987, by Nichol et al.
U.S. Patent No. 4,550,109, issued Oct. 29, 1985, by Folkers and Laesecke.
U.S. Patent No. 4,665,182, issued May 12, 1987, by Nichol et al.
McCormick and Atassi, 1990, Hemoglobin binding with haptoglobin: delineation of the haptoglobin binding site on the α–chain of human hemoglobin, J. Protein Chemistry, 9:735–742.

Adams et al., 1987, HB Mississippi [β44(CD3)SER→ARG]: A new variant anomalous properties, Hemoglobin 11:435–452.
Shih et al., 1987, Hemoglobin chico [β66(E10)Lys→Thr]: a new variant with decreased oxygen affinity, Hemoglobin 11:453–464.
Tondo, 1982, Increased erythrocyte glutathion reductase activity in a hemoglobin porto alegre (β9 Ser → Cys) Carrier, Biochemical and Biophysical Research Communications 105:1381–1388.
Bonaventura and Bonaventura, 1980, Anionic control of function in vertebrate hemoglobins, Amer. Zool. 20:131–138.
Bonaventura and Bonaventura, 1980, Competition in oxygen–linked anion binding to normal and variant human hemoglobins, Hemoglobin 4:275–289.
Bonaventura and Bonaventura, 1978, Anionic control of hemoglobin function, in Biochemical and Clinical Aspects of Hemoglobin Abnormalities, Caughey (Ed.), Academic Press, New York, pp. 647–663.
Moo–Penn et al., 1977, Hemoglobin raleigh (β1 valine→acetylalanine). Structural and functional characterization, Biochemistry 16:4872–4879.
Winslow et al., 1976, A human "nonsense" mutation leading to a shortened βchain, J. Clinical Investigation 57:772–781.
Nagel et al., 1976, A mutant causing clinically apparent cyanosis, New England Journal Medicine, 295:125–130.
Schneider et al., 1975, Haemoglobin Titusville α94 Asp→Asn: A new haemoglobin with a lowered affinity for oxygen, Biochim. Biophys. Acta 400:365–373.
Tondo et al., 1974, Functional properties of hemoglobin porto alegre ($\alpha_2^A\beta^9$ Ser→Cys) and the reactivity of its extra cysteinyl residue, Biochim. Biophys. Acta 342:15–20.
Riggs and Gibson, 1973, Oxygen equilibrium and kinetics of isolated subunits from hemoglobin Kansas (hemoglobin A/β chains), Proc. Nat. Acad. Sci. USA 70:1718–1720.
Greer and Prutz, 1971, Three dimensional structure of haemoglobin Rainier, Nature New Biology 230:260–264.
Perutz, 1974, Mechanism of denaturation of haemoglobin by alkali, Nature 247:341–344.
Labossiere et al., 1972, Hemoglobin deer lodge: $\alpha_2\beta_2^2$ His→Arg, Clin. Biochem. 5:46–50.
Tentori et al., 1972, Hemoglobin Abruzzo: beta 143 (H21) His→Arg, Clin. Chim. Acta 38:258–262.
Blackwell et al., 1971, Hemoglobin ta–li: $\beta 8_3$ Gly→Cys, Biochim. Biophys. Acta 243:467–474.
Bonaventura and Riggs, 1967, Hemoglobin Kansas, a human hemoglobin with a neutral amino acid substitution and an abnormal oxygen equilibrium, J. Biol. Chem. 243:980–991.
Stamatoyannopoulas et al., 1968, Hemoglobin Rainier ($\beta^{145}$ tyrosine→histidine): alkali–resistant hemoglobin with increased oxygen affinity, Science 159:741–743.
Schroeder et al, 1968, Evidence for multiple structural genes for the γ chain of human fetal hemoglobin, Proc. Natl. Acad. Sci. USA 60:537–544.
Tondo et al., 1963, Hemoglobin porto alegre, a possible polymer of normal hemoglobin a Caucasian Brazilian family, Amer. J. Human Genetics 15:265–279.
Honig and Adams, 1986, Normal human hemoglobins and their globin subunits, Human Hemoglobin Genetics, Springer–Verlag, New York, pp. 29–33, 354, 361, 365, 377, 386, 390, 413, 418–419.
Kutlar et al., 1989, The types of hemoglobins and globin chains in hydrops fetalis, Hemoglobin 13:671–683.

Cohen–Solal et al., 1982, Cloning and nucleotide sequence analysis of human embryonic ζ–globin cDNA, DNA 1:355–363.

Spritz et al., 1980, Complete nucloetide sequence of the human Δ–globin gene, Cell 21:639–646.

Baralle et al., 1980, The primary structure of the human ε–globin gene, Cell 21:621–626.

Slightom et al., 1980, Human Fetal $^G\gamma$–and $^A\gamma$–globin genes: complete nucleotide sequences suggest that DNA can be exchanged between these duplicated genes, Cell 21:627–638.

Lawn et al., 1980, The nucleotide sequence of the human β–globin gene, Cell 21:647–651.

Efstratiadis et al, 1980, The structure and evolution of the human β–globin gene family, Cell 21:653–668.

Marotta et al., 1977, Human β–globin messenger RNA, J. Biol. Chem., 252:5040–5053.

U.S. Patent No. 4,711,845, issued Dec. 8, 1987, by Gelfand et al.

Wakabayashi et al., 1986, Primary sequence of a dimeric bacterial hemoglobin from vitreoscilla, Nature 322:481–483.

PCT International Publication No. WO 85/05035, dated Nov. 21, 1985.

PCT International Publication No. WO 83/01783, dated May 26, 1983.

P.J. Kretschmer, 1980, Hemoglobin switching in sheep, J. Biol. Chem. 255:3204–3211.

Ogden, J.E., *Trends Biotechnol.,* 10:91–96 (1992).

Ogden et al., *Biomater. Artif. Cells. Immob. Biotech.,* 19:457 (1991).

Wagenbach et al., *Bio/Technology,* 9:57–61 (1991).

Schimerti et al. "Rumivant globin . . . " Nuc. Acids Res. 12:3 1984.

Fritsch et al. "Molecular Cloning . . . " Cell 19: pp. 959–972 1980.

```
  1  TCT CTG ACC AAG ACT GAG AGG ACC ATC ATT GTG TCC ATG TGG GCC AAG ATC   51
  1  Ser Leu Thr Lys Thr Glu Arg Thr Ile Ile Val Ser Met Trp Ala Lys Ile   17

52  TCC ACG CAG GCC GAC ACC ATC GGC ACC GAG ACT CTG GAG AGG CTC TTC CTC  102
 18  Ser Thr Gln Ala Asp Thr Ile Gly Thr Glu Thr Leu Glu Arg Leu Phe Leu   34

103  AGC CAC CCG CAG ACC AAG ACC TAC TTC CCG CAC TTC GAC CTG CAC CCG GGG  153
 35  Ser His Pro Gln Thr Lys Thr Tyr Phe Pro His Phe Asp Leu His Pro Gly   51

154  TCC GCG CAG TTG CGC GCC CAC GGC TCC AAG GTG GTG GCC GCC GTG GGC GAC  204
 52  Ser Ala Gln Leu Arg Ala His Gly Ser Lys Val Val Ala Ala Val Gly Asp   68

205  GCG GTG AAG AGC ATC GAC GAT ATC GGC GCC GCC CTG TCC AAG CTG AGC GAG  255
 69  Ala Val Lys Ser Ile Asp Asp Ile Gly Ala Ala Leu Ser Lys Leu Ser Glu   85

256  CTG CAC GCC TAC ATC CTG CGC GTG GAC CCG GTC AAC TTC AAG CTC CTG TCC  306
 86  Leu His Ala Tyr Ile Leu Arg Val Asp Pro Val Asn Phe Lys Leu Leu Ser  102

307  CAC TGC CTG CTG GTC ACC CTG GCC GCG CGC TTC CCC GCC GAC TTC ACG GCC  357
103  His Cys Leu Leu Val Thr Leu Ala Ala Arg Phe Pro Ala Asp Phe Thr Ala  119

358  GAG GCC CAC GCC GCC TGG GAC AAG TTC CTA TCG GTC GTA TCC TCT GTC CTG  408
120  Glu Ala His Ala Ala Trp Asp Lys Phe Leu Ser Val Val Ser Ser Val Leu  136

409  ACC GAG AAG TAC CGC                                                  423
137  Thr Glu Lys Tyr Arg                                                  141
```

FIG. 1A

| Pos | | | | | | | | | | Pos |
|---|---|---|---|---|---|---|---|---|---|---|
| 1 | GTG | CAT | TTT | ACT | GCT | GAG | GAG | AAG | GCT | 51 |
| 1 | Val | His | Phe | Thr | Ala | Glu | Glu | Lys | Ala | 17 |
| | GCC | GTC | ACT | AGC | CTG | TGG | AGC | AAG | | |
| | Ala | Val | Thr | Ser | Leu | Trp | Ser | Lys | | |
| 52 | ATG | AAT | GTG | GAA | GAG | GCT | GGA | GCC | GGT | 102 |
| 18 | Met | Asn | Val | Glu | Glu | Ala | Gly | Ala | Gly | 34 |
| | GGA | GAA | GCC | TTG | GGC | AGG | CTC | CTC | GTT | GTT |
| | Gly | Glu | Ala | Leu | Gly | Arg | Leu | Leu | Val | Val |
| 103 | TAC | CCC | TGG | ACC | CAG | AGA | TTT | TTT | GAC | 153 |
| 35 | Tyr | Pro | Trp | Thr | Gln | Arg | Phe | Phe | Asp | 51 |
| | AGC | TTT | GGA | AAC | CTG | TCG | TCT | CCC | | |
| | Ser | Phe | Gly | Asn | Leu | Ser | Ser | Pro | | |
| 154 | TCT | GCC | ATC | CTG | GGC | AAC | CCC | AAG | GTC | 204 |
| 52 | Ser | Ala | Ile | Leu | Gly | Asn | Pro | Lys | Val | 68 |
| | AAG | GCC | CAT | GGC | AAG | AAG | GTG | CTG | | |
| | Lys | Ala | His | Gly | Lys | Lys | Val | Leu | | |
| 205 | ACT | TCC | TTT | GGA | GAT | GCT | ATT | AAA | AAC | 255 |
| 69 | Thr | Ser | Phe | Gly | Asp | Ala | Ile | Lys | Asn | 85 |
| | ATG | GAC | AAC | CTC | AAG | CCC | GCC | TTT | | |
| | Met | Asp | Asn | Leu | Lys | Pro | Ala | Phe | | |
| 256 | GCT | AAG | CTG | AGT | GAG | CTG | CAC | TGT | GAC | 306 |
| 86 | Ala | Lys | Leu | Ser | Glu | Leu | His | Cys | Asp | 102 |
| | AAG | CTG | CAT | GTG | GAT | CCT | GAG | AAC | | |
| | Lys | Leu | His | Val | Asp | Pro | Glu | Asn | | |
| 307 | TTC | AAG | CTC | CTG | GGT | AAC | GTG | ATT | ATT | 357 |
| 103 | Phe | Lys | Leu | Leu | Gly | Asn | Val | Ile | Ile | 119 |
| | CTG | GCT | ACT | CAC | TTT | GGC | | | | |
| | Leu | Ala | Thr | His | Phe | Gly | | | | |
| 358 | AAG | GAG | TTC | ACC | CCT | GAA | GTG | CAG | GCT | 408 |
| 120 | Lys | Glu | Phe | Thr | Pro | Glu | Val | Gln | Ala | 136 |
| | GCC | TGG | CAG | AAG | CTG | GTG | TCT | GCT | | |
| | Ala | Trp | Gln | Lys | Leu | Val | Ser | Ala | | |
| 409 | GTC | GCC | ATT | GCC | CTG | GGC | CAT | AAG | TAC | 438 |
| 137 | Val | Ala | Ile | Ala | Leu | Gly | His | Lys | Tyr | 146 |
| | CAC | | | | | | | | | |
| | His | | | | | | | | | |

FIG. 1B

| | | | | | | | | | |
|---|---|---|---|---|---|---|---|---|---|
| 1<br>1 | GGT<br>Gly | CAT<br>His | TTC<br>Phe | ACA<br>Thr | GAG<br>Glu | GAC<br>Asp | AAG<br>Lys | GCT<br>Ala | ACT<br>Thr | ATC<br>Ile | ACA<br>Thr | AGC<br>Ser | CTG<br>Leu | TGG<br>Trp | GGC<br>Gly | AAG<br>Lys | 51<br>17 |
| 52<br>18 | GTG<br>Val | AAT<br>Asn | GTG<br>Val | GAA<br>Glu | GAT<br>Asp | GCT<br>Ala | GGA<br>Gly | GGA<br>Gly | GAA<br>Glu | ACC<br>Thr | CTG<br>Leu | GGA<br>Gly | AGG<br>Arg | CTC<br>Leu | CTG<br>Leu | GTT<br>Val | GTC<br>Val | 102<br>34 |
| 103<br>35 | TAC<br>Tyr | CCA<br>Pro | TGG<br>Trp | ACC<br>Thr | CAG<br>Gln | AGG<br>Arg | TTC<br>Phe | TTT<br>Phe | GAC<br>Asp | AGC<br>Ser | TTT<br>Phe | GGC<br>Gly | AAC<br>Asn | CTG<br>Leu | TCC<br>Ser | TCT<br>Ser | GCC<br>Ala | 153<br>51 |
| 154<br>52 | TCT<br>Ser | GCC<br>Ala | ATC<br>Ile | ATG<br>Met | GGC<br>Gly | AAC<br>Asn | CCC<br>Pro | AAA<br>Lys | GTC<br>Val | AAG<br>Lys | GCA<br>Ala | CAT<br>His | GGC<br>Gly | AAG<br>Lys | AAG<br>Lys | GTG<br>Val | CTG<br>Leu | 204<br>68 |
| 205<br>69 | ACT<br>Thr | TCC<br>Ser | TTG<br>Leu | GGA<br>Gly | GAT<br>Asp | GCC<br>Ala | ATA<br>Ile | AAG<br>Lys | CAC<br>His | CTG<br>Leu | GAT<br>Asp | GAT<br>Asp | CTC<br>Leu | AAG<br>Lys | GGC<br>Gly | ACC<br>Thr | TTT<br>Phe | 255<br>85 |
| 256<br>86 | GCC<br>Ala | CAG<br>Gln | CTG<br>Leu | AGT<br>Ser | GAA<br>Glu | CTG<br>Leu | CAC<br>His | TGT<br>Cys | GAC<br>Asp | AAG<br>Lys | CTG<br>Leu | CAT<br>His | GTG<br>Val | GAT<br>Asp | CCT<br>Pro | GAG<br>Glu | AAC<br>Asn | 306<br>102 |
| 307<br>103 | TTC<br>Phe | AAG<br>Lys | CTC<br>Leu | CTG<br>Leu | GGA<br>Gly | AAT<br>Asn | GTG<br>Val | CTG<br>Leu | GTG<br>Val | ACC<br>Thr | GTT<br>Val | TTG<br>Leu | GCA<br>Ala | ATC<br>Ile | CAT<br>His | TTC<br>Phe | GGC<br>Gly | 357<br>119 |
| 358<br>120 | AAA<br>Lys | GAA<br>Glu | TTC<br>Phe | ACC<br>Thr | CCT<br>Pro | GAG<br>Glu | GTG<br>Val | CAG<br>Gln | GCT<br>Ala | TCC<br>Ser | TGG<br>Trp | CAG<br>Gln | AAG<br>Lys | ATG<br>Met | GTG<br>Val | ACT<br>Thr | GCA<br>Ala | 408<br>136 |
| 409<br>137 | GTG<br>Val | GCC<br>Ala | AGT<br>Ser | GCC<br>Ala | CTG<br>Leu | TCC<br>Ser | TCC<br>Ser | AGA<br>Arg | TAC<br>Tyr | CAC<br>His | | | | | | | | 438<br>146 |

FIG. 1C

```
  1 GTG CAT CTG ACT CCT GAG GAG AAG ACT GCT GTC AAT GCC CTG TGG GGC AAA    51
  1 Val His Leu Thr Pro Glu Glu Lys Thr Ala Val Asn Ala Leu Trp Gly Lys    17

52 GTG AAC GTG GAT GCA GTG GGT GGT GAG GCC CTG GGC AGG TTA CTG GTG GTC   102
 18 Val Asn Val Asp Ala Val Gly Gly Glu Ala Leu Gly Arg Leu Leu Val Val    34

103 TAC CCT TGG ACC CAG AGG TTC TTT GAG TCC TTT GGG GAT CTG TCC TCT CCT   153
 35 Tyr Pro Trp Thr Gln Arg Phe Phe Glu Ser Phe Gly Asp Leu Ser Ser Pro    51

154 GAT GCT GTT ATG GGC AAC CCT AAG GTG AAG GCT CAT GGC AAG AAG GTG CTA   204
 52 Asp Ala Val Met Gly Asn Pro Lys Val Lys Ala His Gly Lys Lys Val Leu    68

205 GGT GCC TTT AGT GAT GGC CTG GCT CAC CTG GAC AAC CTC AAG GGC ACT TTT   255
 69 Gly Ala Phe Ser Asp Gly Leu Ala His Leu Asp Asn Leu Lys Gly Thr Phe    85

256 TCT CAG CTG AGT GAG CTG CAC TGT GAC AAG CTG CAC GTG GAT CCT GAG AAC   306
 86 Ser Gln Leu Ser Glu Leu His Cys Asp Lys Leu His Val Asp Pro Glu Asn   102

307 TTC AGG CTC TTG GGC AAT GTG CTG GTG TGT GTG CTG GCC CGC AAC TTT GGC   357
103 Phe Arg Leu Leu Gly Asn Val Leu Val Cys Val Leu Ala Arg Asn Phe Gly   119

358 AAG GAA TTC ACC CCA CAA ATG CAG GCT GCC TAT CAG AAG GTG GTG GCT GGT   408
120 Lys Glu Phe Thr Pro Gln Met Gln Ala Ala Tyr Gln Lys Val Val Ala Gly   136

409 GTC GCT AAT GCC TTG GCT CAC AAG TAC CAT                               438
137 Val Ala Asn Ala Leu Ala His Lys Tyr His                               146
```

FIG. 1D

| | | | | | | | | |
|---|---|---|---|---|---|---|---|---|
| 1<br>1 | GTG<br>Val | CTG<br>Leu | TCT<br>Ser | CCT<br>Pro | GCC<br>Ala | GAC<br>Asp | AAG<br>Lys | ACC<br>Thr | AAC<br>Asn | GTC<br>Val | AAG<br>Lys | GCC<br>Ala | TGG<br>Trp | GGC<br>Gly | AAG<br>Lys | GTT<br>Val | 51<br>17 |
| 52<br>18 | GGC<br>Gly | GCG<br>Ala | CAC<br>His | GCT<br>Ala | GGC<br>Gly | GAG<br>Glu | TAT<br>Tyr | GGT<br>Gly | GCG<br>Ala | GAG<br>Glu | GCC<br>Ala | CTG<br>Leu | GAG<br>Glu | AGG<br>Arg | ATG<br>Met | TTC<br>Phe | CTG<br>Leu | 102<br>34 |
| 103<br>35 | TCC<br>Ser | TTC<br>Phe | CCC<br>Pro | ACC<br>Thr | AAG<br>Lys | ACC<br>Thr | TAC<br>Tyr | TTC<br>Phe | CCG<br>Pro | CAC<br>His | TTC<br>Phe | GAC<br>Asp | CTG<br>Leu | AGC<br>Ser | CAC<br>His | GGC<br>Gly | 153<br>51 |
| 154<br>52 | TCT<br>Ser | GCC<br>Ala | CAG<br>Gln | GTT<br>Val | AAG<br>Lys | GGC<br>Gly | CAC<br>His | GGC<br>Gly | AAG<br>Lys | AAG<br>Lys | GTG<br>Val | GCC<br>Ala | GAC<br>Asp | GCG<br>Ala | CTG<br>Leu | ACC<br>Thr | AAC<br>Asn | 204<br>68 |
| 205<br>69 | GCG<br>Ala | GTG<br>Val | CAC<br>His | GTG<br>Val | GAC<br>Asp | GAC<br>Asp | ATG<br>Met | CCC<br>Pro | AAC<br>Asn | GCG<br>Ala | CTG<br>Leu | TCC<br>Ser | GCC<br>Ala | CTG<br>Leu | AGC<br>Ser | GAC<br>Asp | 255<br>85 |
| 256<br>86 | CTG<br>Leu | CAC<br>His | GCG<br>Ala | CAC<br>His | AAG<br>Lys | CTT<br>Leu | CGG<br>Arg | GTG<br>Val | GAC<br>Asp | CCG<br>Pro | GTC<br>Val | AAC<br>Asn | TTC<br>Phe | AAG<br>Lys | CTC<br>Leu | CTA<br>Leu | AGC<br>Ser | 306<br>102 |
| 307<br>103 | CAC<br>His | TGC<br>Cys | CTG<br>Leu | CTG<br>Leu | GTG<br>Val | ACC<br>Thr | CTG<br>Leu | GCC<br>Ala | GCC<br>Ala | CAC<br>His | CTC<br>Leu | CCC<br>Pro | GCC<br>Ala | GAG<br>Glu | TTC<br>Phe | ACC<br>Thr | CCT<br>Pro | 357<br>119 |
| 358<br>120 | GCG<br>Ala | GTG<br>Val | CAC<br>His | GCC<br>Ala | TCC<br>Ser | CTG<br>Leu | GAC<br>Asp | AAG<br>Lys | TTC<br>Phe | CTG<br>Leu | GCT<br>Ala | TCT<br>Ser | GTG<br>Val | AGC<br>Ser | ACC<br>Thr | GTG<br>Val | CTG<br>Leu | 408<br>136 |
| 409<br>137 | ACC<br>Thr | TCC<br>Ser | AAA<br>Lys | TAC<br>Tyr | CGT<br>Arg | | | | | | | | | | | | | 423<br>141 |

FIG. 1E

| Pos | | | | | | | | | | | | | | | | | Pos |
|---|---|---|---|---|---|---|---|---|---|---|---|---|---|---|---|---|---|
| 1 | GTG | CAC | CTG | ACT | CCT | GAG | GAG | AAG | TCT | GCC | GTT | ACT | GCC | CTG | TGG | GGC | AAG | 51 |
| 1 | Val | His | Leu | Thr | Pro | Glu | Glu | Lys | Ser | Ala | Val | Thr | Ala | Leu | Trp | Gly | Lys | 17 |
| 52 | GTG | AAC | GTG | GAT | GAA | GTT | GGT | GGT | GAG | GCC | CTG | GGC | AGG | CTG | CTG | GTG | GTC | 102 |
| 18 | Val | Asn | Val | Asp | Glu | Val | Gly | Gly | Glu | Ala | Leu | Gly | Arg | Leu | Leu | Val | Val | 34 |
| 103 | TAC | CCT | TGG | ACC | CAG | AGG | TTC | TTT | GAG | TCC | TTT | GGG | GAT | CTG | TCC | ACT | CCT | 153 |
| 35 | Tyr | Pro | Trp | Thr | Gln | Arg | Phe | Phe | Glu | Ser | Phe | Gly | Asp | Leu | Ser | Thr | Pro | 51 |
| 154 | GAT | GCT | GTT | ATG | GGC | AAC | CCT | AAG | GTG | AAG | GCT | CAT | GGC | AAG | AAA | GTG | CTC | 204 |
| 52 | Asp | Ala | Val | Met | Gly | Asn | Pro | Lys | Val | Lys | Ala | His | Gly | Lys | Lys | Val | Leu | 68 |
| 205 | GGT | GCC | TTT | AGT | GAT | GGC | CTG | GCT | CAC | CTG | GAC | AAC | CTC | AAG | GGC | ACC | TTT | 255 |
| 69 | Gly | Ala | Phe | Ser | Asp | Gly | Leu | Ala | His | Leu | Asp | Asn | Leu | Lys | Gly | Thr | Phe | 85 |
| 256 | GCC | ACA | CTG | AGT | GAG | CTG | CAC | TGT | GAC | AAG | CTG | CAC | GTG | GAT | CCT | GAG | AAC | 306 |
| 86 | Ala | Thr | Leu | Ser | Glu | Leu | His | Cys | Asp | Lys | Leu | His | Val | Asp | Pro | Glu | Asn | 102 |
| 307 | TTC | AGG | CTC | CTG | GGC | AAC | GTG | CTG | GTC | TGT | GTG | CTG | GCC | CAT | CAC | TTT | GGC | 357 |
| 103 | Phe | Arg | Leu | Leu | Gly | Asn | Val | Leu | Val | Cys | Val | Leu | Ala | His | His | Phe | Gly | 119 |
| 358 | AAA | GAA | TTC | ACC | CCA | CCA | GTG | CAG | GCT | GCC | TAT | CAG | AAA | GTG | GTG | GCT | GGT | 408 |
| 120 | Lys | Glu | Phe | Thr | Pro | Pro | Val | Gln | Ala | Ala | Tyr | Gln | Lys | Val | Val | Ala | Gly | 136 |
| 409 | GTG | GCT | AAT | GCC | CTG | GCC | CAC | AAG | TAT | CAC | | | | | | | | 438 |
| 137 | Val | Ala | Asn | Ala | Leu | Ala | His | Lys | Tyr | His | | | | | | | | 146 |

FIG. 1F

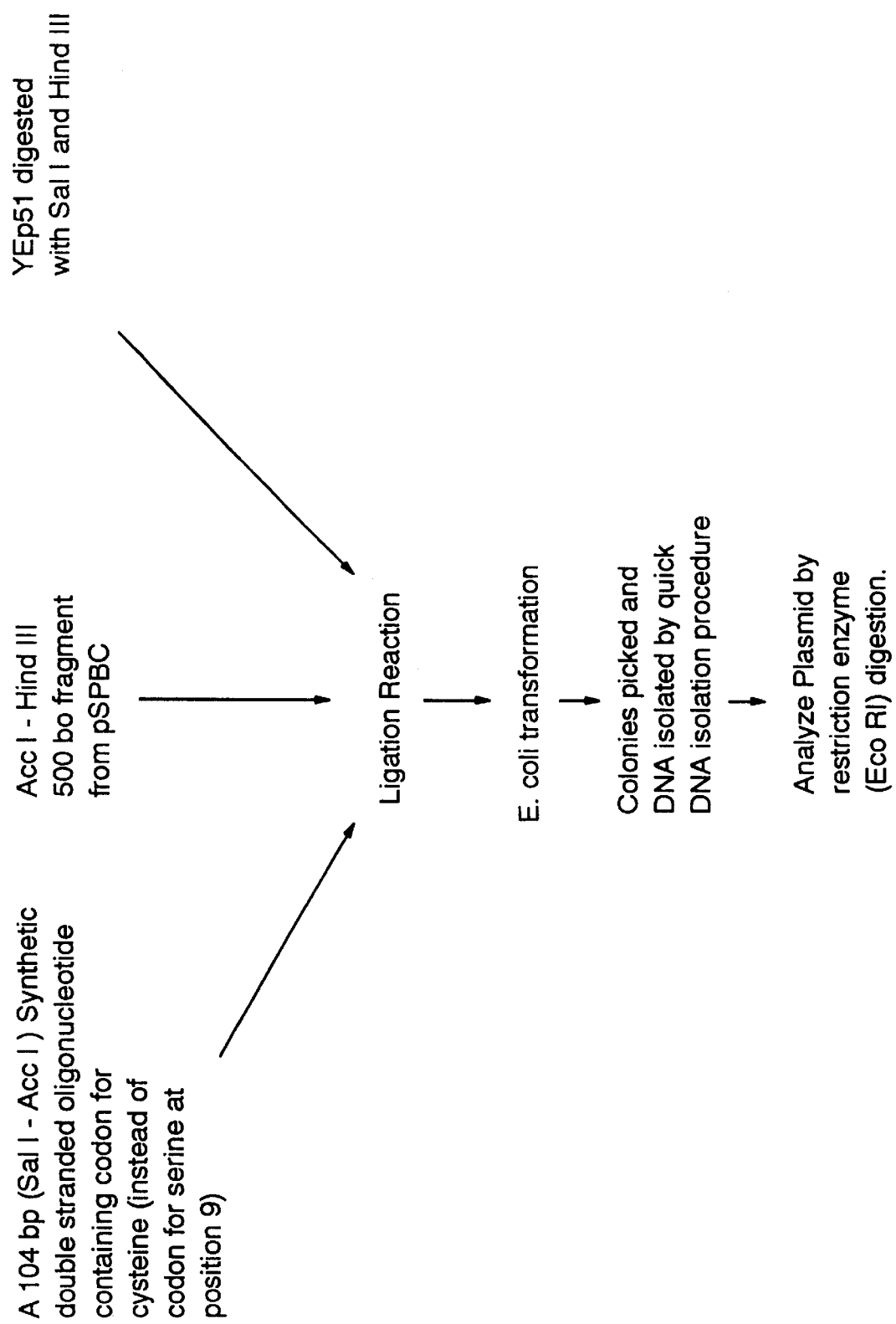

I. 519-A-1:

SalI
5'AAGGGTCGACAATATAAAATGGTGTGTCTCCTGCCGACAAGACCAACGTCAAGGC3'

II. 519-A-3:

BamHI
5' GGGAATTCCCGGGGATCCTTAACGGTATTTGGAGGTCAGCACGGTGCTCACAGAAG

CCAGGAACTTGTCCAGGGAGGCGTGCACCGCAGGGG 3'

FIG. 10

GAM-5-S (5'-end primer)

SalI    Met
5'CAAGTTGGGTCGACAAAAAAATATGGGTCATTTCACAGAGAGGAGGACAAGGCTACTATCAAGCCT
GTGG 3'

GAM-3-H (3'-end primer)

Hind III
5' GCCCGATGCTAAGCTTGGTCAGTGGTATCTGGAGGACAGGGCACTGGCCACTGC 3'

FIG. 14

```
          Nco I   10           20           30           40           50
5'       CCATGGGTCA   TTTCACAGAG   GAGGACAAGG   CTACTATCAC   AAGCCTGTGG
3'       GGTACCCAGT   AAAGTGTCTC   CTCCTGTTCC   GATGATAGTG   TTCGGACACC 60           70           80           90          100
         GGCAAGGTGA   ATGTGGAAGA   TGCTGGAGGA   GAAACCCTGG   GAAGGCTCCT
         CCGTTCCACT   TACACCTTCT   ACGACCTCCT   CTTTGGGACC   CTTCCGAGGA

110   Nco I  120          130          140          150
         GGTTGTCTAC   CCATGGACCC   AGAGGTTCTT   TGACAGCTTT   GGCAACCTGT
         CCAACAGATG   GGTACCTGGG   TCTCCAAGAA   ACTGTCGAAA   CCGTTGGACA 160          170          180          190          200
         CCTCTGCCTC   TGCCATCATG   GGCAACCCCA   AAGTCAAGGC   ACATGGCAAG
         GGAGACGGAG   ACGGTAGTAC   CCGTTGGGGT   TTCAGTTCCG   TGTACCGTTC 210          220          230          240          250
         AAGGTGCTGA   CTTCCTTGGG   AGATGCCATA   AAGCACCTGG   ATGATCTCAA
         TTCCACGACT   GAAGGAACCC   TCTACGGTAT   TTCGTGGACC   TACTAGAGTT
                            Pvu II
                260          270          280          290          300
         GGGCACCTTT   GCCCAGCTGA   GTGAACTGCA   CTGTGACAAG   CTGCATGTGG
         CCCGTGGAAA   CGGGTCGACT   CACTTGACGT   GACACTGTTC   GACGTACACC

Bam HI 310          320          330          340          350
         ATCCTGAGAA   CTTCAAGCTC   CTGGGAAATG   TGCTGGTGAC   CGTTTTGGCA
         TAGGACTCTT   GAAGTTCGAG   GACCCTTTAC   ACGACCACTG   GCAAAACCGT
                            Eco RI
                360          370          380          390          400
         ATCCATTTCG   GCAAAGAATT   CACCCCTGAG   GTGCAGGCTT   CCTGGCAGAA
         TAGGTAAAGC   CGTTTCTTAA   GTGGGGACTC   CACGTCCGAA   GGACCGTCTT
                                       Bal I
                410   Pst I  420          430          440          450
         GATGGTGACT   GCAGTGGCCA   GTGCCCTGTC   CTCCAGATAC   CACTGAGCCT
         CTACCACTGA   CGTCACCGGT   CACGGGACAG   GAGGTCTATG   GTGACTCGGA 460          470          480          490          500
         CTTGCCCATG   ATTCAGAGCT   TTCAAGGATA   GGCTTTATTC   TGCAAGCAAT
         GAACGGGTAC   TAAGTCTCGA   AAGTTCCTAT   CCGAAATAAG   ACGTTCGTTA 510          520          530
         ACAAATAATA   AATCTATTCT   GCTGAGAGAG   TCAC 3'
         TGTTTATTAT   TTAGATAAGA   CGACTCTCTC   AGTG 5'
```

FIG. 13

PRIMER 5EPSL-13
5'-CTG AT gtc A TCA TGG TGC ATT TTA CTG CTG AGG-3'
         SalI

PRIMER INPE-1-14
5' CTG GAG GTG AAG CCT TGG GCA GGC TCC TCG TTG TTT AC-3'

PRIMER INPE-2-15
5'-GTA AAC AAC GAG GAG CCT GCC CAA GGC TTC ACC TCC AG-3'

PRIMER INPE-3-16
5'-GCA TGT GGA TCC TGA GAA CTT CAA GCT CCT GGG TAA CGT GAT G-3'

PRIMER INPE-4-17
5'-CAT CAC GTT ACC CAG GAG CTT GAA GTT CTC AGG ATC CAC ATG C-3'

PRIMER 3EPH-18
5'-TGA TAG aag ctt TCA GTG GTA CTT ATG GCC CAG GGC-3'
              HindIII

FIG.17

PRIMER 5ZETASAC
5': CAG TC gag ctc A TGT CTC TGA CCA AGA CT-3'
              SacI PRIMER ZETA3HSLS
5': TAT TA gca tgc gtc gac aag ctt T TAG CGG TAC TTC TCG GT-3'
           SphI     SalI    HindIII

FIG.19

I. G-5-9CY        SalI
   5'    CAAGTTGGGTCGACAAAAAAATATGCCTCATTTCAGAGGAGGACACAAGTGTACTAT 3'

II. GAM-3-H           HindIII
    5'    GCCCGATGCTAAGCTTGGTGAGTGGTATCTGGAGGACAGGGCACTGGCCACTGC 3'

FIG.23

I. 51-A3-SL        SalI
   5'    AAGGTCGACAATATAAAATGGTGCTGTCTCCTGCCCGACAAGACCA
         ACGTCAAGGCCCTGGGCCAAGG 3'

II. A-HIN3-3        HindIII
    5'    CGGGTCCACCCGAAGCTTGTGCCGCGTGCAG 3'

FIG.26

Mu-145Cy 5' GCC CTG GCC CAC AAG TGT CAC TAA GCT CGC 3'
(Tyr->Cys)

Mu-66Th 5' G AAG GCT CAT GGC AAG ACT GTG CTC GGT GCC TTT AG 3' (Lys->Thr)

Mu-9Cy 5' CT CCT GAG GAG AAG TGT GCC GTT ACT
(Ser->Thr)

FIG. 21 a: B-G127-5 (5'-end primer):

EcoRI
5' CATCACTTTGGCAAAGAATTCACCCCACCAGTGGAGGCTGCCTATCAGAAAGTG 3'
                                    * b: Beta-3-H (3'-end primer):

HindIII
5' ATCGCGAAGCTTTTAGTGATACTTGTGGGCCA 3'

FIG. 24 a: A-Tit-5 (5'-end primer):

```
            HindIII      *
5' GACCTGCACGCGCACAAGCTTCGGGTGAACCCGGTCA 3'
``` b: G10T3H (3'-end primer):

```
         HindIII
5' AGCTAGCTAAGCTTGCTATATTCTTGTGCTACCGTCCATATCTT 3'
```

FIG. 25 a: B44C-5 (5'-end primer):

```
                  Acc I                              **
5' AGGCTGCTGGTGTCTACCCTTGGACCCAGAGGTTCTTTGAGTGTTTGGGGATCTGTC 3'
``` b: Beta-3-H (3'-end primer):

```
            Hind III
5' ATCCGGAAGCTTTTAGTGATACTTGTGGGCCA 3'
```

FIG. 27

FIG.28 a: A104Ser (5'-END PRIMER):
                        HindIII
5' CTGCACGGCCACAAGCTTCGGGTGGACCCGGTCAACTTCAAGCTCCTAAGCCACTCC
   CTGCTGGTG 3' b: G10T3H (3'-END PRIMER):
                        HindIII
5' AGCTAGCTAAGCTTGCTATATTCTTGTGCTACCGTCCATATCTT 3'

FIG.30

I. Z-BST-5        BstEII
   5' CACTGCCTGCTGGTCACCCTGGCCCTGCCCCTTCCCCGCCCGAC 3'

II. Z2-3-H                HindIII
    5' TTTACCAGACGATAACGTTATCGCTTAGCGGTACTTCTCCGTCAGGACAGAGGATAC 3'

FIG.31

A: Z-5-SAL(5'-END PRIMER):
            SalI
5' CAAGTTGGGTCGACAAAAAAATATGTCTCTGACCAAGACTGAGAGGACCATCATTGTG 3'

B: Z-A95-3 (3'-END PRIMER):
                                                           BstEII
5' GCCCGCCGGCCAGGGTGACCAGGCAGTGGGACAGCAGGAGCTTGAAGTTGACCCGGTTCACGCGCA 3' a: Z-5-SAL (5'-end primer):

SalI
5' CAAGTTGGGTCGACAAAAAAATATGTCTCTGACCAAGACTGAGAGGACCATCATTGTG 3' b: Z-104S-B (3'-end primer):

*
5' GCGGCGGCGGGCCAGGGTGACCAGCAGGCAGTGGGACAGGAGCTTGAAGTTGACCGGGTTCACGCGCA 3'

FIG.29

I. G2-MOT-5          Eco RI
5'    CATTTCGGCAAAGAATTCACCCCTGAGGTGGAGGCTTCC 3'

II. GAM-3-H          Hind III
5'    GCCCGATGCTAAGCTTGGTCAGTGGTATCTGGAGGACAGGGCACTGGCCACTGC 3'

FIG.32

I. B-BOY2-5          Sal I
5'    CAAGTTGGGTCGACAAAAAAAT ATG TTG ACT GCT GAGGAGAAGTCT
                               Met Leu Thr Ala
      GCCGTTACTGCCCTGTGG 3'

II. Beta-3-H          Hind III
5'    ATCGCGAAGCTTTTAGTGATACTTGTGGGCCA 3'

FIG.33

I. B-2ARG-5          Sal I
5'    TTTAAAAAAGTCGACATGGTGCGCATGACTCCT 3'

II. Beta-3-H          Hind III
5'    ATCGCGAAGCTTTTAGTGATACTTGTGGGCCA 3'

FIG.34

I. BN-5-SAL
                     Sal I
5'    CAAGTTGGGTCGACAAAAAAATATGGTGCACCTGACTCCTGAGGAGAAGTCTGCC 3'

II. B-143A-3
                     Hind III
5'    ATCGCGAAGCTTTTAGTGATACTTGCCGGCCAG 3'

FIG.35

I. BN-5-SAL        SalI

5' CAAGTTGGGTCGACAAAAAATATGGTGCACCTGACTCCTGAGGAGAAGTCTGCC 3'

II. B-145T-3       Hind III

5' AAAATCGCGAAGCTTTA------CTTGTGGGCCAG 3'
                      DELETION OF
                       GTGATA

FIG.36 a: GAM-5-S (5'-end primer):

SalI
5' CAAGTTGGGTCGACAAAAAATATGGGTCATTTCACAGAGGAGGACAAG
   GCTACTATCAAGCCTGTGG 3' b: G66T-3 (3'-end primer):

XcmI                            *
5' CCCTTGAGATCATCCAGGTGCTTTATGGCATCTCCCAAGGAAGTCAGCACCGTCTTGCC 3'

FIG.37 a: BN-5-Sal (5'-end primer):

SalI
5' CAAGTTGGGTCGACAAAAAATATGGTGCACCTGACTCCTGAGGAGAAGTCTGCC 3' b: B-B3-Tal (3'-end primer):

BamHI
5' GAAGTTCTCAGGATCCACGTGTCAGCTTGTCACAGTGCAGCTCACTCAGTGTGGCAA
           *
   AGGTGCACTTGAG 3'

FIG. 38

```
TDH3-5'   5' PRIMER,   5'-----ATcccgggAAGGTTGAAACCAGTTCCCTG---3'
                                  -141      SmaI              -121
                                       +28        +48
TDH3-3'   3' PRIMER,   3'-----GTGTGTATTATTGTTTTACcacgtgCGC--5'
                                                    ApaI
```

FIG. 41

```
                                          +33          +46
PRIMER GAL1-10-5':   5'-TTgagctcCCCAGAAATAAGGC-3'
                              SacI
                       +347          +361
PRIMER GAL1-10-3':   3'-TCTTCCAAAAAAATCgggcccGT-5'
                                       SmaI
```

FIG. 44

```
5' GATCAAAAAT CATCGCTTCG CTGATTAATT ACCCAGAAA TAAGGTAAA AAACTAATCG
        10         20         30      Gal1-10-5 40      50         60
    CATTATCATC CTATGGTTGT TAATTTGATT CGTTCATTTG AAGGTTTGTG GGGCCAGGTT
        70         80         90        100        110        120
    ACTGCCAATT TTTCCTCTTC ATAACCATAA AAGCTAGTAT TGTAGAATCT TTATTGTTCG
       130        140        150        160        170        180
    GAGCAGTGCG GCGCGAGGCA CATCTGCGTT TCAGGAACGC GACCGGTGAA GACGAGGACG
       190        200        210        220        230        240
    CACGGAGGAG AGTCTTCCTT CGGAGGGCTG TCACCCGCTC GGCGGCTTCT AATCCGTACT
       250        260        270        280        290        300
    TCAATATAGC AATGAGCAGT TAAGCGTATT CCAAAGAGAA GGTTTTTTA
       310        320        330        340    350 Gal1-10-3 360
    GCTAAGATA ATGGGGCTCT TTACATTCC ACAACATATA AGTAAGATTA GATATGGATA
       370        380        390        400        410        420
    TGTATATGGA TATGTAATGC GTGGTAATGC CATGTAATAT GATTATTAAA CTTCTTTGCG
       430        440        450        460        470        480
    TCCATCCAAA AAAAAAGTAA GAATTTTTGA AAATTCAATA TAAATGACAG CTCAGTTACA
       490        500        510        520        530        540
    AAGTGAAAGT ACTTCTAAAA TTGTTTTGGT TACAGGTGGT GCTGGATACA TTGGTTCACA
       550        560        570        580        590        600
    CACTGTGGTA GAGCTAATTG AGAATGGATA TGACTGTGTT GTTGCTGATA ACCTGTCGAA
       610        620        630        640        650        660
TTC 3'
```

FIG. 43

1. Primer 51-A-1:

SalI          Met
   5' AAGGGTCGACAATATAAAATGGTGCTGTCTCCTGCCGACAAGACCAACGTCAAGGC 3'

2. Primer 519-A-3:

BamHI
   5' GGGAATTCCCGGGATCCTTAACGGTATTTGGAGGTCAGCACGGTGCTCCACAGAAG
   CCAGGAACTTGTCCAGCAGGGAGGCG 3'

FIG. 48

1. Primer G10T-5B:

BamHI
5' AGCTAGCTGGATCCGGTAGATACATTGATGCTATCAATCAAGAGAACTGG 3'

2. Primer G10T3ESS:

EcoRI  SalI  SphI
5' AGCTAGCTGAATTCGTCGACGCATGCGTAACGAAATAAATCCCGGGCTCGTGC 3'

FIG. 49

5' primer:

5'---GCTAgtcgacCCCCAGAAATAAGGC---3'
         SalI

3' primer:

---------TDH3-3' sequences---------
3'-TTGTGGTTCTTGAATCAAAGCTTATTTGTGTATTTATTTGTTTT
-------alpha-globin-------sequences--------
ACCACGAGAGGACGGCTGTGTTCTGGTTGCAGTtccggaCCCCG--5'
                                       StuI

FIG. 50

5' primer:

5'---ATCGCgtcgacATGGTGCTGTCTCCTGCCGACAAGACCAACGTCAAGGCCTG---3'
         SalI

3' primer:

3'---GTGAGCACCGTGCTGACCTCCAAATACCGTTAAcctaggttcgaaGCGT---5'
                                                BamHI HindIII

FIG. 51

5' Primer-5TDH3-3X:

Xbal Bglll SalI

5'GACGAGAtctagaagatctgtcgacATGGTGCTGTCTCCCTGCCGACAAGACCAACG 3'

3' primer-G10T3ESS:

EcoRI SalI SphI

5'-AGCTAGCTgaattcgtcgacgcatgcGTAACGAAATAAATCCGGGCTCGTGC-3'

FIG. 54

5' primer for ADH2-UAS:

5'-CGATCGgagctcCATTAACGGCTTTCGCTCATAA-3'
         SacI

3' primer for ADH2-UAS:

3'-GTGTCCTCTCGTATCTTTACCCCAAagatctGCGCGA-5'
                                 XbaI

FIG. 60

5' Primer

XbaI

5'-AGC GCC tct aga AAG GTT GAA ACC AGT TCC CTC-3'

3' Primer-ADH-t-SBS:

SacI    BamHI    SphI

5'-AAT TT gag ctc gga tcc gca tgc GCA TGC CGG TAG AGG TGT GGT CAA
TAA GAG CGA CCT CAT GC-3'

FIG. 62

5' primer: 5TG-ApaL
         ApaLI
5'-TGA TCG ATG gtg cac TTC ACA GAG GAG GAC AAG GCT ACT ATC ACA-3'

3' primer: ADHSBS-3''-C GTA CTC CAG CGA GAA TAA GTG GTG TGG AGA
          TGG CCG TAC G
          SphI  BamHI
          cgt acg cct agg ctc gag TT TAA-5'
                      SacI

FIG. 63

EXPRESSION OF RECOMBINANT HEMOGLOBIN AND HEMOGLOBIN VARIANTS IN YEAST

This application is a continuation of application Ser. No. 08/368,407, filed Dec. 29, 1994, now abandoned, which is a continuation-in-part of application Ser. No. 07/684,611 filed Apr. 12, 1991, now abandoned, which is a continuation-in-part of application Ser. No. 07/614,539, filed Nov. 14, 1990, now abandoned which is a continuation-in-part of application Ser. No. 07/509,918, filed Apr. 16, 1990 and now abandoned, the entire contents of each are incorporated herein by reference.

TABLE OF CONTENTS
1. FIELD OF THE INVENTION
2. BACKGROUND OF THE INVENTION
   - 2.1. USE OF HEMOGLOBIN AS A BLOOD SUBSTITUTE
     - 2.1.1. EXPRESSION OF RECOMBINANT HEMOGLOBIN
     - 2.1.2. CHEMICAL MODIFICATION OF HEMOGLOBIN
     - 2.1.3. HEMOGLOBIN VARIANTS
   - 2.2. EXPRESSION OF HETEROLOGOUS DNA IN YEAST
3. SUMMARY OF THE INVENTION
4. BRIEF DESCRIPTION OF THE FIGURES
5. DETAILED DESCRIPTION OF THE INVENTION
   - 5.1. ISOLATION AND CLONING OF GLOBIN
   - 5.2. GLOBIN VARIANTS
   - 5.3. EXPRESSION OF HEMOGLOBIN
   - 5.3.1. EXPRESSION OF HEMOGLOBIN IN YEAST
   - 5.4. USES FOR EXPRESSED RECOMBINANT HEMOGLOBINS
6. EXAMPLE 1: EXPRESSION OF NATURAL BETA-GLOBIN IN A YEAST EXPRESSION VECTOR CONTAINING GAL10 PROMOTER AND ADH1 TERMINATOR
   - 6.1. MATERIALS
   - 6.2. CLONING OF THE BETA-GLOBIN GENE INTO THE YEAST EXPRESSION VECTOR YEp51
   - 6.3. CLONING OF THE ADH1-TERMINATOR SEQUENCES INTO YEpWB51/NAT
   - 6.4. TRANSFORMATION OF YEAST STRAIN Sc340 WITH YEp51T/NAT
   - 6.5. QUANTITATION OF RNA FROM SC340 CELLS TRANSFORMED WITH PLASMIDS YEp51, YEp51T/NAT
   - 6.6. WESTERN BLOT ANALYSIS OF EXPRESSED BETA-GLOBIN
7. EXAMPLE 2: CLONING OF ALPHA-GLOBIN INTO A YEAST EXPRESSION VECTOR
   - 7.1. MATERIALS
   - 7.2. ISOLATION OF THE ALPHA-GLOBIN GENE
   - 7.3. PREPARATION OF THE YEAST EXPRESSION VECTOR
   - 7.4. LIGATION AND TRANSFORMATION
   - 7.5. DNA SEQUENCING
8. EXAMPLE 3: EXPRESSION OF NATURAL GAMMA-GLOBIN IN A YEAST EXPRESSION VECTOR CONTAINING GAL10 PROMOTER AND ADH1 TERMINATOR
   - 8.1. MATERIALS
   - 8.2. CLONING OF THE GAMMA-GLOBIN GENE INTO THE YEAST EXPRESSION VECTOR YEp51T/NAT
   - 8.3. TRANSFORMATION AND GROWTH OF YEAST STRAIN Sc340 CELLS WITH PLASMID YEp51T/G
   - 8.4. WESTERN BLOT ANALYSIS OF EXPRESSED GAMMA-GLOBIN
9. EXAMPLE 4: CLONING OF EPSILON-GLOBIN cDNA IN A YEAST EXPRESSION VECTOR AND EXPRESSION OF EPSILON-GLOBIN IN YEAST
   - 9.1. MATERIALS
   - 9.2. SYNTHESIS OF EPSILON-GLOBIN cDN
   - 9.3. CLONING OF EPSILON-GLOBIN cDNA WITH YEAST EXPRESSION VECTOR YEp51NT1
   - 9.4. TRANSFORMATION OF YEAST STRAIN Sc1041 WITH YEp51T/ε3
   - 9.5. WESTERN BLOT ANALYSIS OF EXPRESSED GLOBIN
10. EXAMPLE 5: CLONING OF ZETA-GLOBIN cDNA INTO A YEAST EXPRESSION VECTOR AND EXPRESSION OF ZETA-GLOBIN IN YEAST
    - 10.1. MATERIALS
    - 10.2. CLONING OF ZETA-GLOBIN cDNA IN YEAST EXPRESSION VECTOR pYES2
    - 10.3. TRANSFORMATION OF YEAST STRAIN Sc1041 WITH YES2-ζ2
    - 10.4. WESTERN BLOT ANALYSIS OF EXPRESSED-GLOBIN
11. EXAMPLE 6: EXPRESSION OF VARIANT GLOBINS
    - 11.1. MATERIALS AND METHODS
      - 11.1.1. DNA FRAGMENT ISOLATION
      - 11.1.2. DNA LIGATION AND E. COLI TRANSFORMATION
      - 11.1.3. PLASMID DNA ANALYSIS
      - 11.1.4. YEAST TRANSFORMATION
    - 11.2. SYNTHESIS OF OLIGONUCLEOTIDES
    - 11.3. IN VITRO MUTAGENESIS
      - 11.3.1. STRAINS
      - 11.3.2. TRANSFECTION OF CJ236
      - 11.3.3. ISOLATION OF URACIL CONTAINING DNA
      - 11.3.4. KINASING OF OLIGONUCLEOTIDES
      - 11.3.5. SYNTHESIS OF THE MUTAGENIC STRAND
      - 11.3.6. TRANSFECTION OF MV1190 CELLS
      - 11.3.7. ANALYSIS OF TRANSFORMANTS BY SEQUENCING
    - 11.4. CONSTRUCTION OF PLASMID YEp51NT1
    - 11.5. CLONING OF VARIANT GLOBINS
      - 11.5.1. CLONING OF PORTO ALEGRE (9 Ala→Cys) γ-GLOBIN GENE
      - 11.5.2. CLONING OF THE MOTOWN (127 Gln→Glu) β-GLOBIN GENE
      - 11.5.3. CLONING OF THE TITUSVILLE (94 Asp-Asn)α-GLOBIN GENE
      - 11.5.4. CLONING OF THE β-MISSISSIPPI (44 Ser→Cys) β-GLOBIN GENE
      - 11.5.5. CLONING OF 104-Ser (104 Cys→Ser) ALPHA-GLOBIN GENE
      - 11.5.6. CLONING OF 104-Ser (104 Cys→Ser) ZETA-GLOBIN GENE
      - 11.5.7. CLONING OF TITUSVILLE (94 Asp-Asn) ζ-GLOBIN GENE
      - 11.5.8. CLONING OF ALPHA-GLOBIN GENE CONTAINING ALPHA TITUSVILLE AND ALPHA-104 Ser MUTATIONS: 94 Asp-Asn; 104 Cys-→Ser)

11.5.9. CLONING OF THE MOTOWN GAMMA-GLOBIN GENE: (127 Gln-→Glu)
11.5.10. CLONING OF THE BOVI2 β-GLOBIN GENE (Met Leu Thr Ala Glu Glu . . . )
11.5.11. CLONING OF β-2 Arg GLOBIN GENE: (2 His-Arg)
11.5.12. CLONING OF THE 143 Arg BETA-GLOBIN GENE: (143 His-Arg)
11.5.13. CLONING OF THE 145 Term BETA-GLOBIN GENE: (145 Tyr-→TAA)
11.5.14. CLONING OF THE CHICO (66 Lys-→Thr) γ-GLOBIN GENE
11.5.15. CLONING OF THE CHICO (66 Lys-→Thr) β-GLOBIN GENE
11.5.16. CLONING OF THE RAINIER (145 Tyr-→Cys) β-GLOBIN GENE
11.5.17. CLONING OF THE TALI (83 GLY-→CYS) β-GLOBIN GENE
11.6. EXPRESSION OF VARIANT GLOBINS
  11.6.1. EXPRESSION OF GAMMA-GLOBIN MOTOWN IN A YEAST
    11.6.1.1. TRANSFORMATION OF YEAST STRAIN Sc1114 WITH pNT1/γ-Mot2
    11.6.1.2. WESTERN BLOT ANALYSIS OF EXPRESSED GLOBIN
  11.6.2. EXPRESSION OF BETA-GLOBIN Bov2 IN YEAST
    11.6.2.1. WESTERN BLOT ANALYSIS OF EXPRESSED GLOBIN
  11.6.3. EXPRESSION OF ZETA-GLOBIN 104 SER IN YEAST
    11.6.3.1. TRANSFORMATION OF YEAST STRAIN Sc340 WITH pNT1/ Z104S
    11.6.3.2. WESTERN BLOT ANALYSIS OF EXPRESSED GLOBIN
  11.6.4. EXPRESSION OF BETA-GLOBIN TaLi IN YEAST
  11.6.5. EXPRESSION OF GAMMA-GLOBIN PORTO ALEGRE IN YEAST
  11.6.6. EXPRESSION OF GAMMA-GLOBIN CHICO IN YEAST
  11.6.7. EXPRESSION OF BETA-GLOBIN MISSISSIPPI IN YEAST
  11.6.8. EXPRESSION OF BETA-GLOBIN RAINIER IN YEAST
  11.6.9. EXPRESSION OF BETA-GLOBIN MOTOWN IN YEAST
12. EXAMPLE 7: COEXPRESSION OF ALPHA-GLOBIN AND BETA-GLOBIN BOV2 IN YEAST
  12.1. TRANSFORMATION OF YEAST STRAINS Sc389 WITH pUT/2A AND pNT1/β-Bov2
  12.2. WESTERN BLOT ANALYSIS OF EXPRESSED GLOBIN
  12.3. DETECTION OF HEMOGLOBIN IN YEAST BY CARBON MONOXIDE DIFFERENCE SPECTRUM
13. EXAMPLE 8: COEXPRESSION OF ALPHA-GLOBIN AND BETA-GLOBIN 143 ARG IN YEAST
  13.1. TRANSFORMATION OF YEAST STRAIN Sc340 WITH pUT/2A AND pNT1/β143Arg
  13.2. WESTERN BLOT ANALYSIS OF EXPRESSED GLOBIN
  13.3. DETECTION OF HEMOGLOBIN IN YEAST BY CARBON MONOXIDE DIFFERENCE SPECTRUM
14. EXAMPLE 9: COEXPRESSION OF ALPHA-GLOBIN AND BETA-GLOBIN 145 TERM IN YEAST
  14.1. TRANSFORMATION OF YEAST STRAIN Sc340 WITH pUT/2A AND pNT1/β145T
  14.2. WESTERN BLOT ANALYSIS OF EXPRESSED GLOBIN
  14.3. DETECTION OF HEMOGLOBIN IN YEAST BY CARBON MONOXIDE DIFFERENCE SPECTRUM
  14.4. WESTERN BLOT ANALYSIS OF EXPRESSED ALPHA AND BETA GLOBINS
15. EXAMPLE 10: COEXPRESSION OF ALPHA-GLOBIN AND GAMMA-GLOBIN MOTOWN IN YEAST
  15.1. TRANSFORMATION OF YEAST STRAIN Sc1114 WITH pUT/2A AND pNT1/γ-Mot2
  15.2. WESTERN BLOT ANALYSIS OF EXPRESSED GLOBIN
  15.3. DETECTION OF HEMOGLOBIN IN YEAST BY CARBON MONOXIDE DIFFERENCE SPECTRUM
16. EXAMPLE 11: COEXPRESSION OF ZETA-GLOBIN 104 SERINE AND BETA-GLOBIN IN YEAST
  16.1. TRANSFORMATION OF YEAST STRAIN Sc1114 WITH pNT1/Z104S AND YEp51T/NAT
  16.2. WESTERN BLOT ANALYSIS OF EXPRESSED GLOBIN
  16.3. DETECTION OF HEMOGLOBIN IN YEAST BY CARBON MONOXIDE DIFFERENCE SPECTRUM
17. EXAMPLE 12: COEXPRESSION OF ALPHA-GLOBIN AND BETA-GLOBIN 2 ARG IN YEAST
  17.1. TRANSFORMATION OF YEAST STRAIN Sc1090 WITH pUT/2A AND pNT1/β2Arg
  17.2. WESTERN BLOT ANALYSIS OF EXPRESSED GLOBIN
  17.3. DETECTION OF HEMOGLOBIN IN YEAST BY CARBON MONOXIDE DIFFERENCE SPECTRUM
18. EXAMPLE 13: EXPRESSION OF HEMOGLOBIN PORTLAND I IN YEAST
  18.1. TRANSFORMATION OF YEAST STRAIN Sc1012 WITH pYES2-ζ2 AND YEp51T/G
  18.2. WESTERN BLOT ANALYSIS OF EXPRESSED GLOBIN
  18.3. DETECTION OF HEMOGLOBIN IN YEAST BY CARBON MONOXIDE DIFFERENCE SPECTRUM
19. EXAMPLE 14: EXPRESSION OF BETA-GLOBIN IN A YEAST EXPRESSION VECTOR CONTAINING A HYBRID PROMOTER AND ADH1 TRANSCRIPTION TERMINATION SEQUENCE
  19.1. MATERIALS
  19.2. CONSTRUCTION OF PLASMID L19βt CONTAINING BETA-GLOBIN GENE AND THE ADH1 TERMINATOR
  19.3. CONSTRUCTION OF PLASMID pUC19-HβAt
  19.4. CLONING OF GAL1-10 UAS INTO pUC19-HβAt
  19.5. CLONING OF THE HYBRID PROMOTER-BETA-GLOBIN GENE CASSETTE IN SHUTTLE VECTOR, YEp13
  19.6. TRANSFORMATION OF YEAST STRAIN Sc340 CELLS WITH pNML-V-G-1
  19.7. WESTERN BLOT ANALYSIS OF EXPRESSED BETA-GLOBIN
20. EXAMPLE 15: EXPRESSION OF HEMOGLOBIN PORTLAND II IN YEAST
  20.1. TRANSFORMATION OF YEAST STRAIN Sc1041 WITH pYES2-ζ2 AND pNM-V-G-1
  20.2. WESTERN BLOT ANALYSIS OF EXPRESSED GLOBIN
  20.3. DETECTION OF HEMOGLOBIN IN YEAST BY CARBON MONOXIDE DIFFERENCE SPECTRUM 21. EXAMPLE 16: COEXPRESSION OF ALPHA-GLOBIN AND BETA-GLOBIN MISSISSIPPI IN YEAST
   21.1. TRANSFORMATION OF YEAST STRAIN Sc389 WITH pUT/2A AND pNT1/βMiss
   21.2. WESTERN BLOT ANALYSIS OF EXPRESSED GLOBIN
   21.3. DETECTION OF HEMOGLOBIN IN YEAST BY CARBON MONOXIDE DIFFERENCE SPECTRUM
22. EXAMPLE 16: COEXPRESSION OF ALPHA-GLOBIN TITUSVILLE AND BETA-GLOBIN IN YEAST
   22.1. TRANSFORMATION OF YEAST STRAIN Sc1114 WITH pNT1/2ATit and YEp51T/NAT
   22.2. WESTERN BLOT ANALYSIS OF EXPRESSED GLOBIN
   22.3. DETECTION OF HEMOGLOBIN IN YEAST BY CARBON MONOXIDE DIFFERENCE SPECTRUM
23. EXAMPLE 18: COEXPRESSION OF ALPHA-GLOBIN TITUSVILLE/104 SERINE AND BETA-GLOBIN IN YEAST
   23.1. TRANSFORMATION OF YEAST STRAIN Sc1114 WITH pNT1/2ATiS and YEp51T/NAT
   23.2. WESTERN BLOT ANALYSIS OF EXPRESSED GLOBIN
   23.3. DETECTION OF HEMOGLOBIN IN YEAST BY CARBON MONOXIDE DIFFERENCE SPECTRUM
24. EXAMPLE 19: COEXPRESSION OF ALPHA-GLOBIN AND BETA-GLOBIN MOTOWN IN YEAST
   24.1. TRANSFORMATION OF YEAST STRAIN Sc389 WITH pUT/2A AND pNT1β-Mot
   24.2. WESTERN BLOT ANALYSIS OF EXPRESSED GLOBIN
   24.3. DETECTION OF HEMOGLOBIN IN YEAST BY CARBON MONOXIDE DIFFERENCE SPECTRUM
   24.4. WESTERN BLOT ANALYSIS OF EXPRESSED ALPHA AND BETA-GLOBINS
25. EXAMPLE 20: EXPRESSION OF THE PORTO ALEGRE BETA-GLOBIN IN A YEAST EXPRESSION VECTOR CONTAINING THE GAL10 PROMOTER
   25.1. MATERIALS
   25.2. CLONING OF THE PORTO ALEGRE BETA-GLOBIN GENE INTO THE YEAST EXPRESSION VECTOR YEp51
   25.3. TRANSFORMATION OF Sc340 CELLS WITH YEpWB51/PORT
   25.4. QUANTITATION OF RNA FROM SC340 CELLS TRANSFORMED WITH PLASMIDS YEp51AND YEp51WB/PORT
   25.5. WESTERN BLOT ANALYSIS OF EXPRESSED PORTO ALEGRE BETA-GLOBIN
26. EXAMPLE 21: COEXPRESSION OF ZETA-GLOBIN TITUSVILLE AND GAMMA-GLOBIN IN YEAST
   26.1. TRANSFORMATION OF YEAST STRAIN Sc1115 WITH pNT1/z95An AND YEp51T/G
   26.2. WESTERN BLOT ANALYSIS OF EXPRESSED GLOBIN
   26.3. DETECTION OF HEMOGLOBIN IN YEAST BY CARBON MONOXIDE DIFFERENCE SPECTRUM
27. EXAMPLE 22: COEXPRESSION OF ALPHA-GLOBIN AND GAMMA-GLOBIN CHICO IN YEAST
   27.1. TRANSFORMATION OF YEAST STRAIN Sc340 WITH pUT/2A AND pNT1/γ-Chi
   27.2. WESTERN BLOT ANALYSIS OF EXPRESSED GLOBIN
   27.3. DETECTION OF HEMOGLOBIN IN YEAST BY CARBON MONOXIDE DIFFERENCE SPECTRUM
28. EXAMPLE 23: COEXPRESSION OF ALPHA-GLOBIN AND GAMMA-GLOBIN PORTO ALEGRE IN YEAST
   28.1. TRANSFORMATION OF YEAST STRAIN Sc1115 WITH pUT/2A AND pNT1/γ-PORT
   28.2. WESTERN BLOT ANALYSIS OF EXPRESSED GLOBIN
   28.3. DETECTION OF HEMOGLOBIN IN YEAST BY CARBON MONOXIDE DIFFERENCE SPECTRUM
29. EXAMPLE 19: COEXPRESSION OF ALPHA-GLOBIN AND BETA-GLOBIN PORTO ALEGRE IN YEAST
   29.1. TRANSFORMATION OF YEAST STRAIN Sc1090 WITH pUT/2A AND YEpWB51T/PORT
   29.2. WESTERN BLOT ANALYSIS OF EXPRESSED GLOBIN
   29.3. DETECTION OF HEMOGLOBIN IN YEAST BY CARBON MONOXIDE DIFFERENCE SPECTRUM
30. DEPOSIT OF MICROORGANISMS

1. FIELD OF THE INVENTION

The invention is directed to a substantially pure globin chain or heme-binding fragment thereof. The globin chain may be an alpha-like globin chain or a beta-like globin chain or variant thereof. The invention is further directed to an expression vector which specifically comprises DNA sequences encoding at least one globin chain or heme-binding fragment thereof operably linked to a yeast promoter. The invention is also directed to methods for producing a globin chain or heme binding fragment thereof in yeast and methods for producing hemoglobin in yeast. Hemoglobin produced by methods of the present invention may be used in applications requiring physiological oxygen carriers such as in blood substitute solutions, or as in a plasma expander.

2. BACKGROUND OF THE INVENTION

2.1. USE OF HEMOGLOBIN AS A BLOOD SUBSTITUTE

Transfusion of a patient with donated blood has a number of disadvantages. Firstly, there may be a shortage of a patient's blood type. Secondly, there is a danger that the donated blood may be contaminated with infectious agents such as hepatitis viruses, cytomegalovirus, Epstein-Barr virus, serum parvoviruses, syphilis, malaria, filariasis, trypanosomiasis, babsiosis, pathogenic bacteria, and HIV (Bove, 1986, Progr. Hematol. 14: 123–145). Thirdly, donated blood has a limited shelf life.

An alternative to transfusion involves the use of a blood substitute. A blood substitute is an oxygen carrying solution that also provides the oncotic pressure necessary to maintain blood volume. Two types of substitutes have recently been studied, fluorocarbon emulsions and hemoglobin solutions.

Hemoglobin as it exists within the red blood cell is composed of two alpha-like globin chains and two beta-like globin chains, each with a heme residue. One alpha-like globin chain and one beta-like globin chain combine to form a dimer which is very stable. Alpha-like and beta-like globin genes are each a family of related globin genes which are expressed at different stages of development and regulated by oxygen tension, pH, and the development from embryo to fetus to newborn. Two dimers then line up in antiparallel fashion to form tetramers. The binding of dimers to form the tetramers is not as strong as in the case of monomers binding to associate into dimers. The tetramers, therefore, have a tendency to fall apart to form dimers and there is always an equilibrium between tetramers, dimers, and monomers. At high concentrations of globin, the predominant form is the tetramer; with dilution, the dimer becomes the predominant form. This equilibrium is also affected by solvent, salts, pH and other factors as the forces binding the monomers together are primarily electrostatic.

The alpha-like globin genes are clustered together on chromosome 16 and include genes encoding the embryonic zeta globin chain and the adult alpha globin chain, present in both the fetus and newborn. The beta-like globin genes reside on chromosome 11 and include genes encoding the embryonic epsilon-globin chain, the fetal gamma-globin chain, and the adult delta-globin and adult beta-globin chains. Two types of gamma-globin chains have been identified, $^G$gamma and $^A$gamma, which differ by the presence of a single glycine or alanine residue, respectively, at amino acid 135 (Schroeder et al., 1968, Proc. Natl. Acad. Sci. U.S.A. 60: 537–544). The gamma-globin chain has been found to contain a polymorphic site at position 75, which also can be occupied either by isoleucine or threonine. A variety of hemoglobins may be formed (reviewed in Kutlar et al., 1989, Hemoglobin 13: 671–683 and Honig and Adams, Human Hemoglobin Genetics, Springer Verlag, New York pp. 29–33). Examples include HbA (alpha$_2$beta$_2$), HbA$_2$ (alpha$_2$delta$_2$), HbF (alpha$_2$gamma$_2$), HbBarts (gamma$_4$), HbH (beta$_4$), and Hb PortlandI (zeta$_2$gamma$_2$), Hb Portland II (zeta$_2$beta$_2$), Hb Portland III (zeta$_2$delta$_2$) Hb Gower I (zeta$_2$epsilon$_2$), and Hb Gower II (alpha$_2$epsilon$_2$).

There are obstacles however to using native hemoglobin as a blood substitute. Firstly, large dosages are required (Walder, 1988, Biotech '88, San Francisco, Nov. 14–16, 1988). A single unit (450 ml) of a 10% hemoglobin solution contains 45 g of protein. It is estimated that at least 12 million units of blood are used in the U.S. per year. Therefore the production of 450,000 kg of hemoglobin per year would be required. Secondly, it is important to obtain hemoglobin that is free from infectious agents and toxic substances. Thirdly, as mentioned, although hemoglobin is normally a tetramer of 64,000 molecular weight, it can dissociate to form alpha-beta dimers. The dimers are rapidly cleared by the kidneys and the residence time is much too short for cell-free hemoglobin to be useful as a blood substitute. Fourthly, cell-free hemoglobin has too high an oxygen affinity to effectively release oxygen to the tissues due to the absence of 2,3-diphosphoglycerate (2,3-DPG). Efforts to restore 2,3-DPG have been unsuccessful since 2,3-DPG is rapidly eliminated from the circulation.

Several approaches have been taken to circumvent these difficulties. These include the expression of hemoglobin via recombinant DNA systems, chemical modification of hemoglobin, and the production of hemoglobin variants.

2.1.1. EXPRESSION OF RECOMBINANT HEMOGLOBIN

Human embryonic zeta-globin (Cohen-Sohal, 1982, DNA 1:355–363), human embryonic epsilon-globin (Baralle et al., 1980, Cell 21: 621–630), human fetal gamma-globin (Slightom et al., 1980, Cell 21: 627–630), human adult delta-globin (Spritz et al., 1980, Cell 21: 639–645), human adult alpha-globin genomic DNA (Liebhaber et al., 1980, Proc. Natl. Acad. Sci. U.S.A. 77: 7054–7058) and human adult beta-globin cDNA (Marotta et al., 1977, J. Biol. Chem. 252: 5040–5053) have been cloned and sequenced.

Both human adult alpha- and beta-globins have been expressed in bacterial systems. Nagai et al. (1985, Proc. Natl. Acad. Sci. U.S.A. 82: 7252–7255 and 1984, Nature (London) 309: 810–812) expressed adult beta-globin in E. coli as a hybrid protein consisting of the 31 amino-terminal residues of the lambda cII protein, an Ile-Glu-Gly-Arg linker, and the complete human adult beta-globin chain. The hybrid was cleaved at the single arginine with blood coagulation factor Xa, resulting in the liberation of the beta-globin chain. PCT Application No. PCT/US88/01534 (Publication No. WO 88/091799, published Dec. 1, 1988) discloses the expression of a DNA sequence encoding the adult alpha-globin gene and the N-terminal 20 amino acid sequence of beta-globin in which the alpha- and beta-globin sequences are separated by spacer DNA encoding a Factor Xa cleavage site.

Efforts have also been made to secrete beta-globin into the periplasm of E. coli, in which the beta-globin gene was inserted behind an OmpA secretion signal sequence (Brinigar et al., 1988, Symposium on Oxygen Binding Heme Proteins-Structure, Dynamics, Function and Genetics). However, it was found that though the fusion was correctly processed, the beta-globin was not secreted.

Nagai et al. (1985, Proc. Natl. Acad. Sci. U.S.A. 82: 7252–7255) have also reported the reconstitution of adult beta-globin expressed in E. coli and adult alpha-globin obtained by conventional sources along with a heme source to obtain hemoglobin. However, it would not be possible in E. coli to produce recombinant hemoglobin that has the same functional properties as normal human hemoglobin because of E. coli's inability to remove the N-formyl-methionine by post-translational processing. The amino terminus is known to be critical in determining the oxygen binding properties of human hemoglobin as has been shown in the case of Hb Raleigh (Moo-Penn, et al., 1977, Biochemistry, 16: 4872–4879). Furthermore, the hemoglobin produced in bacteria can contain E. coli endotoxins.

Attempts have also been made to express hemoglobin in yeast. Reports from two groups indicate that yeast cells were unable to excise the intervening sequences in both alpha- and beta-globin precursor mRNA (Langford et al., 1983, Proc. Natl. Acad. Sci. U.S.A. 80:1496–1500 and Beggs et al., 1980, Nature (London) 283: 835–840). An attempt was also made to secrete beta-globin in Streptomyces by constructing a plasmid having a GalK-FX-beta-globin sequence behind a beta-galactosidase secretion signal sequence (Brinigar et al., 1988, Symposium on Oxygen Binding Heme Proteins Structure, Dynamics, Function and Genetics). GalK-FX-beta-globin however remained within the cells under conditions where galactokinase was secreted.

Recently, the construction of two yeast plasmids containing adult beta-globin was reported (Brinigar et al., 1988, Symposium on Oxygen Binding Heme Proteins Structure, Dynamics, Function and Genetics). One contained a constitutive promoter, glyceraldehyde-3-phosphate dehydrogenase and ubiquitin fused directly to adult beta-globin, and the other contained metallothionein, an inducible promoter, and ubiquitin fused directly to beta-globin. It was reported that in both instances, both intracellular soluble and intracellular insoluble adult beta-globin was obtained. No further details were disclosed regarding the construction of the plasmids or the quantity of adult beta-globin obtained.

The expression of globin in mammalian cells has also been reported. The construction of recombinant herpes simplex virus, adenovirus, SV-40, and retrovirus vectors containing a DNA sequence encoding the human adult beta-globin gene has been disclosed (Dobson et al., 1989, J. Virol. 63: 3844–3851; Yanagi et al., 1989, Gene 76: 19–26; Miller et al., 1988, J. Virol. 62: 4337–4345; and Karlsson et al., 1985, EMBO J 5: 2377–2386). The expression of human adult alpha-globin genes in Chinese hamster ovary cells which involved introducing a recombinant DNA molecule containing the normal human adult alpha-globin gene and a hybrid gene containing the 5' promoter-regulator region of the mouse metallothionein gene linked to a SV2-cDNA dihydrofolate reductase gene has also been disclosed (Lau et al., 1984, Mol. Cell Biol. 4: 1469–1475). However, the expression of the globin genes was found to be rather low due to low efficiency of gene transfer.

2.1.2. CHEMICAL MODIFICATION OF HEMOGLOBIN

One approach that has been taken to circumvent the problem of dissociation of the hemoglobin tetramer to a dimer has been to chemically modify the hemoglobin by either intramolecular or intermolecular crosslinking. Examples of such modification include crosslinking with polyalkylene glycol (Iwashita, U.S. Pat. No. 4,412,989 and 4,301,144), with polyalkylene oxide (Iwasake, U.S. Pat. No. 4,670,417); with a polysaccharide (Nicolau, U.S. Pat. Nos. 4,321,259 and 4,473,563); with inositol phosphate (Wong, U.S. Pat. Nos. 4,710,488 and 4,650,786); with a bifunctional crosslinking agent (Morris et al., U.S. Pat. No. 4,061, 736); with insulin (Ajisaka, U.S. Patent No. 4,377,512); and with a crosslinking agent so that the hemoglobin composition is intramolecularly crosslinked between lys 99 alpha$_1$ and lys 99 alpha$_2$ (Walder, U.S. Pat. No. 4,598,064).

Hemoglobin has also been chemically modified to decrease the oxygen affinity of isolated hemoglobin. One approach has involved polymerization with pyridoxal phosphate (Sehgal et al., 1984, Surgery, 95: 433–438). Another approach has involved the use of reagents that mimic 2,3-DPG (Bucci et al., U.S. Pat. No. 4,584,130). Although these compounds do lower the oxygen affinity of hemoglobin, the affinity is still relatively high.

2.1.3. HEMOGLOBIN VARIANTS

Categories of naturally occuring hemoglobin variants include: variants which autopolymerize, variants which prevent the dissociation of the tetramer, variants with lowered intrinsic oxygen affinity, and variants that are stable in alkali. Examples of autopolymerizing hemoglobin variants include Hb Porto Alegre, Hb Mississippi, and Hb TaLi.

Hb Porto Alegre is a beta chain variant first reported by Tondo et al. (1974, Biochem. Biophys. Acta 342: 15–20; 1963, Am. J. Human Genet. 15: 265–279). The beta-9 serine is replaced by cysteine which is able to form disulfide bonds with other cysteine residues. Through these crosslinks, Hb Porto Alegre forms poly-tetramers. These polymers however do not form in the blood of Hb Porto Alegre carriers. It has been shown that Hb Porto Alegre carriers have a two-fold elevated level of glutathione and three-fold elevated level of glutathione reductase which prevents the polymerization of the Hb Porto Alegre within the red blood cells (Tondo et al., 1982, Biochem. Biophys. Res. Commun. 105: 1381–1388). The exact structure of these polymers is not known.

Hb Mississippi is a recently isolated polymerizing variant of hemoglobin. The new variant was first reported by Adams et al. (1987, Hemoglobin 11: 435–452). The beta-44 serine is replaced by cysteine in this variant resulting in inter-tetramer disulfide bonds. This variant is believed to form polymers with as many as ten tetramers.

Hb TaLi is another known polymerizing beta variant. The beta-83 glycine is replaced by cysteine. This variant was first reported in 1971 (Blackwell et al., 1971, Biochem. Biophys. Acta 243:467–474). This variant also forms inter-tetramer crosslinks.

Another group of variants include those with nondissociating tetramers. One example is Hb Rainier, a well characterized variant of the beta chain (Greer and Perutz, 1971, Nature New Biology 230:261 and Statoyannopoulos et al., 1968, Science 159:741). The beta-145 tyrosine is replaced by cysteine. This cysteine is able to form disulfide crosslinks with beta-93 cysteine which is present in natural beta-globin. This disulfide bond is intra-tetramer, i.e. it is formed between the two beta subunits within a tetramer. This covalent disulfide bond stabilizes the tetramer form and prevents the dissociation of the tetramer into its constituent dimers. Hb Rainier has also been found to have a high affinity for oxygen, a reduced Hill coefficient, and only half the alkaline Bohr effect of normal hemoglobin.

Another group of variants includes those that are stable in alkali. Hb Motown/Hacettepe is a variant reported to be stable in alkali (Gibb and Rucknagel, 1981, Clinical Research 29:795A and Altay et al., 1976, Biochem. Biophys. Acta 434:1–3). The beta-127 glutamine is replaced by glutamic acid in this variant. This portion of the beta chain is involved in the alpha$_1$beta$_1$ interface between the monomers forming a dimer. The substituted glutamic acid forms an ionic bond with alpha-31 arginine. This is a stronger bond than that formed between the alpha-31 arginine and the normal beta-127 glutamine and is believed to be responsible for the increased stability of Hb Motown/Hacettepe. HbF (fetal hemoglobin) and bovine hemoglobin are also in this group of alkali stable variants (Perutz, 1974, Nature 247:341).

There are also over 30 naturally occurring hemoglobin variants which exhibit lowered oxygen affinity.

Several examples of such variants are disclosed in PCT Application No. PCT/US88/01534 (Publication No. WO 88/091799, published Dec. 1, 1988); Bonaventura and Bonaventura, 1980, In: Abnormal Human Hemoglobins and Red Cell Enzymes, Huisman, T., Ed., Marcel Dekker, NY, Hemoglobin 4 (3 & 4): 275–289 and Bonaventura and Bonaventura, 1978, in Biochemical and Clinical Aspects of Hemoglobin Abnormalities, Caughey, W. S., Ed., Academic Press, NY, pp. 647–663. There seems in a group of these low oxygen affinity mutants to be a generalizable relationship between the intrinsic oxygen affinity of an alpha$_2$beta$_2$ hemoglobin and the cluster of positively charged residues that are involved in the binding of 2,3-DPG and other anionic allosteric cofactors of hemoglobin function (Bonaventura and Bonaventura, 1980, Amer. Zool. 20: 131–138).

One example of a low oxygen affinity mutant is Hb Chico where the beta-66 lysine is replaced by threonine (Shih et al., 1987, Hemoglobin 11: 453–464). The P$_{50}$ of Hb Chico's red blood cells is 38 mm Hg compared with normal red blood cell controls with P$_{50}$ of 27 mm Hg. All other properties, i.e. Hill coefficient and alkaline Bohr effect are normal.

Another low oxygen affinity variant is Hb Raleigh, a beta chain variant in which beta-1 valine is replaced by alanine (Moo-Penn et al., 1977, Biochemistry 16:4873). A post-translational modification of the amino-terminal alanine results in the formation of acetylalanine. Because the positively charged amino group of valine is involved in 2,3-DPG binding, the acetylation results in a decreased charge cluster in the DPG binding site. This charge difference acts to decrease the oxygen affinity of Hb Raleigh and to lessen the effect of DPG which lowers the oxygen affinity of normal HbA. The Hill coefficient (cooperativity) and alkaline Bohr effect (pH dependent oxygen binding) are unaffected by this change.

Hb Titusville (alpha-94 aspartate to asparagine) is one of a group of low affinity hemoglobin variants with altered $alpha_1beta_2$ contacts (Schneider et al., 1975, Biochem. Biophys. Acta 400: 365). The $alpha_1beta_2$ interface is stabilized by two different sets of hydrogen bonds between the alpha and beta subunits. One set stabilizes the T-structure which is the low-affinity form and the other stabilizes the R-state which is the high affinity form. It is the shifting back and forth between these two sets of bonds and alternating between the T- and R-states which is responsible for the positive cooperativity. The deoxyhemoglobin is primarily in the T-state. For hemoglobin with one oxygen bound, the amount of R-state molecules increases and therefore binds oxygen with a higher affinity. In hemoglobin with two oxygens bound, there is an even higher proportion of R state molecules. In Hb Titusville, the R-state bonds are disrupted. The alpha-94 aspartate would normally form a non-covalent bond with beta-102 asparagine. Because this bond is disrupted, the equilibrium is pushed in the direction of the T-state and Hb Titusville's oxygen affinity is very low.

Hb Beth Israel is another variant affecting the $alpha_1beta_2$ interface which destabilizes the high oxygen affinity R-state (Nagel et al., 1976, New Eng. J. Med. 295: 125–130). The beta-102 asparagine is replaced by serine. The whole blood of an Hb Beth Israel patient has a $P_{50}$ of 88 mm Hg as compared with the normal value of 27. The Hill coefficient is biphasic with a value of 1.0 at the high end and 1.8 at the low end. The Bohr effect is normal. A hemolysate of Hb Beth Israel has a P50 of 17 mm Hg and a Hill coefficient of 1.65 at the bottom and 1.29 at the top of the curve as compared to a P50 of 5.6 and a Hill coefficient of 2.72 for normal hemoglobin.

Another example of a low affinity human hemoglobin mutant is Hb Kansas (PCT Application No. PCT/US88/01534, Publication No. WO 88/091799, published Dec. 1, 1988 and Bonaventura and Riggs, 1968, J. Biol. Chem. 243: 980–991). The beta-102 asparagine is replaced by threonine. It has been shown that isolated Hb Kansas' heme-containing beta-globin chains have lowered oxygen affinity (Riggs and Gibson, 1973, Proc. Natl. Acad. Sci. U.S.A. 70: 1718–1720).

2.2. EXPRESSION OF HETEROLOGOUS DNA IN YEAST

With the advent of recombinant DNA technology, efforts have been made to express heterologous DNA in a variety of prokaryotic and eukaryotic systems. One such system is yeast.

Yeast has a number of advantages over bacteria and other eukaryotes as a system for the production of polypeptides or proteins encoded by recombinant DNA. Yeast has been used in large scale fermentations for centuries, so the technology for fermenting yeast is well known and a number of yeast hosts are commercially available. Additionally, yeast can be grown to higher densities than bacteria and many other types of eukaryotic cells, and is readily adaptable to continuous fermentation processing. Since yeast is a eukaryotic organism, yeast may be capable of glycosylating expression products, may exhibit the same codon preferences as higher organisms, and may remove the amino terminal methionine during post-translational processing.

A number of heterologous proteins have been expressed in yeast. Examples include interferon (Hitzeman and Leung, U.S. Pat. No. 4,775,622, issued Oct. 4, 1988; Hitzeman et al., Canadian Patent No. 1,205,026, issued May 27, 1986; Hitzeman et al., 1981, Nature (London) 293: 717); platelet derived growth factor (Murray et al., U.S. Pat. No. 4,801, 542, issued Jan. 31, 1989); glucagon (Norris et al., U.S. Pat. No. 4,826,763, issued May 2, 1989).

Heterologous proteins expressed in yeast have been linked to a wide variety of promoters. Examples include operably linking heterologous proteins to SV40 and RSV promoters (Gelfand et al., U.S. Pat. No. 4,8710,013, issued Sep. 26, 1989). Additionally, DNA sequences encoding heterologous proteins have been linked to yeast promoters, which are inducible. European Patent Application Publication No. 132,309, published Jan. 30, 1985 discloses the construction of a plasmid containing the yeast galactose-induced promoters for galactokinase (GAL1) and UDP-galactose epimerase (GAL10), hereinafter referred to as the GAL-1-10 promoter, which is bidirectional. Another example of a bidirectional yeast promoter is the YPT1/TUB2 intergene sequence which contains overlapping binding sites for the transcription factor BAF1 (Halfter et al., 1989, EMBO J. 8: 3029–3037). Broach et al. (Manipulation of Gene Expression, ed. Inouye, 1983) disclose a plasmid containing a GAL10 upstream activator sequence which promotes transcription and an alcohol dehydrogenase transcription (ADH1) terminator sequence to prevent run through transcription derived from YEp51. Kingsman et al., U.S. Pat. No. 4,615,974, issued Oct. 7, 1986 disclose the use of the 5' regions of the yeast phosphoglycerate kinase genes as a promoter of the transcription of interferon. Hitzeman et al., Canadian Patent No. 1,205,026, issued May 27, 1986 disclose the use of the 5' flanking sequence of the ADH1 structural gene to promote the transcription of interferon. Burke et al., U.S. Pat. No. 4,876,197, issued Oct. 24, 1989 disclose a DNA construct comprising a first transcription regulatory region obtained from the yeast lcohol dehydrogenase II gene (ADH2), the regulatory region of acid phosphatase (PHO5) or the regions regulated by GAL4, which provides for inducible transcriptional regulation and a second transcriptional initiation region from the yeast glyceraldehyde-3-phosphate dehydrogenase gene (TDH3) and a terminator region.

3. SUMMARY OF THE INVENTION

The invention is directed to a substantially pure mammalian globin chain or heme-binding fragment thereof. "Substantially pure" as defined herein refers to a globin chain that is free of erythrocyte membrane components and E. coli endotoxins. The globin chain may be an alpha-like globin chain or variant thereof or beta-like globin chain or variant thereof. The alpha-like globin chain may be selected from the group including but not limited to an embryonic zeta-globin chain and an adult alpha-globin chain. The beta-like globin chain may be selected from the group including but not limited to an embryonic epsilon-globin chain, a fetal gamma-globin chain, an adult delta-globin chain, and an adult beta-globin chain. Hemoglobin consisting essentially of an alpha-like and beta-like globin chain may be obtained by mixing alpha-like globin and beta-like globin or variants thereof with a source of heme. Hemoglobin consisting essentially of gamma-globin chains or variants thereof may be obtained by mixing the gamma-globin chains or variants thereof with a source of heme. Hemoglobin consisting essentially of an alpha-like and beta-like globin chain and hemoglobin consisting essentially of a gamma-globin chain or variant thereof may be used in applications requiring physiological oxygen carriers such as in blood substitute solutions, or as in a plasma expander.

The globin chains or heme-binding fragments thereof of the present invention may be obtained by expressing a recombinant DNA vector comprising a DNA sequence encoding at least one globin chain or heme binding fragment thereof in yeast. The invention is therefore directed to a recombinant DNA vector capable of expressing a globin chain or heme-binding fragment thereof in a yeast cell comprising:

(a) a DNA sequence encoding a globin chain or heme-binding fragment thereof;

(b) a yeast transcriptional promoter which promotes the transcription of the DNA sequence encoding the globin chain or heme-binding fragment thereof;

(c) a DNA sequence encoding a yeast selectable marker or functionally active portion thereof; and (d) a yeast replication origin.

A yeast transcriptional promoter may be selected from the group including but not limited to a yeast inducible transcriptional promoter, a yeast constitutive transcriptional promoter, a yeast hybrid promoter, and a yeast bidirectional promoter. The recombinant vector may further comprise a transcription termination sequence.

The recombinant DNA vector may be capable of expressing an alpha-like globin chain or beta-like globin chain or variant thereof. In another embodiment, the vector may be capable of expressing two globin chains. In one embodiment, the vector may be capable of expressing an alpha-like globin chain and a beta-like globin chain or variants thereof. In specific embodiments, the vector may be capable of expressing a non-variant alpha-like globin chain and a variant beta-like globin chain; alternatively, the recombinant vector may be capable of expressing a variant alpha-like globin chain and a non-variant beta-like globin chain; or the recombinant vector may be capable of expressing a variant alpha-like globin chain and a variant beta-like globin chain.

The invention is further directed to a method for producing at least one globin chain or heme-binding fragment thereof in a yeast cell comprising:

(a) introducing into a yeast cell a recombinant DNA vector comprising: (i) a DNA sequence encoding a globin chain or heme-binding fragment thereof; (ii) a yeast transcriptional promoter which promotes the transcription of the DNA sequence encoding the globin chain or functionally active portion thereof; (iii) a DNA sequence encoding a yeast selectable marker or functionally active portion thereof; and (iv) a yeast replication origin or functionally active portion thereof; and (b) growing the yeast cell in an appropriate medium such that the globin chain or heme-binding fragment thereof is expressed.

The invention is also directed to a method for producing hemoglobin comprising an alpha-like globin chain or substantially homologous variant thereof and a beta-like globin chain or substantially homologous variant thereof comprising the steps of:

(a) introducing into a yeast cell a recombinant DNA vector comprising: (i) a first DNA sequence encoding an alpha-like globin chain or substantially homologous variant thereof, or heme-binding fragment of the alpha-like globin chain or substantially homologous variant thereof; (ii) a second DNA sequence encoding a beta-like globin chain or substantially homologous variant thereof or heme-binding fragment of the beta-like globin chain or substantially homologous variant thereof; (iii) a first yeast transcriptional promoter which promotes the transcription of the first DNA sequence; (iv) a second yeast transcriptional promoter which promotes the transcription of the second DNA sequence; (v) a DNA sequence encoding at least one yeast selectable marker or functionally active portion thereof; and (vi) a yeast replication origin or functionally active portion thereof;

(b) growing the yeast cell such that the alpha-like globin chain or substantially homologous variant thereof, or heme-binding fragment of the alpha-like globin chain or substantially homologous variant thereof, and a beta-like globin chain or substantially homologous variant thereof or heme-binding fragment of the beta-like globin chain or substantially homologous variant thereofare expressed;

(c) isolating the the alpha-like globin chain or substantially homologous variant thereof, or heme-binding fragment of the alpha-like globin chain or substantially homologous variant thereof, and a beta-like globin chain or substantially homologous variant thereof or heme-binding fragment of the beta-like globin chain or substantially homologous variant thereof from the yeast cell; and (d) combining the alpha-like globin chain or substantially homologous variant thereof, or heme-binding fragment of the alpha-like globin chain or substantially homologous variant thereof, and a beta-like globin chain or substantially homologous variant thereof or heme-binding fragment of the alpha-like globin chain or substantially homologous variant thereof, with a source of heme.

The invention is further directed to a method for producing hemoglobin comprising an alpha-like globin chain or substantially homologous variant thereof and a beta-like globin chain or substantially homologous variant thereof in a heme-producing yeast cell comprising:

(a) introducing into a yeast cell a recombinant DNA vector comprising: (i) a first DNA sequence encoding an alpha-like globin chain or substantially homologous variant thereof or heme-binding fragment of the alpha-like globin chain or substantially homologous variant thereof; (ii) a second DNA sequence encoding a beta-like globin chain or substantially homologous variant thereof or heme-binding fragment of the beta-like globin chain or substantially homologous variant thereof; (iii) a first yeast transcriptional promoter which promotes the transcription of the first DNA sequence; (iv) a second yeast transcriptional promoter which promotes the transcription of the the DNA sequence encoding the second DNA sequence; (v) a DNA sequence encoding at least one yeast selectable marker or functionally active portion thereof; and (vi) a yeast replication origin or functionally active portion thereof; and (b) growing the yeast cell in an appropriate medium such that the alpha-like globin chain or substantially homologous variant thereof or heme-binding fragment of the beta-like globin chain or substantially homologous variant thereof, and a alpha-like globin chain or substantially homologous variant thereof or heme-binding fragment of the beta-like globin chain or substantially homologous variant thereof are expressed and assembled together with heme in the yeast cell to form hemoglobin.

The invention is also directed to a method for producing hemoglobin comprising an alpha like-globin chain or variant thereof and a beta-like globin chain or variant thereof comprising the steps of:

(a) introducing into a yeast cell two recombinant DNA vectors in which the first recombinant DNA vector comprises: (i) a DNA sequence encoding an alpha like-globin chain or substantially homologous variant thereof or heme-binding fragment of the alpha like-globin chain or substantially homologous variant thereof; (ii) a yeast transcriptional promoter which promotes the transcription of the DNA sequence encoding the alpha like-globin chain or substantially homologous variant thereof or heme-binding fragment of the alpha-like globin chain or substantially homologous variant thereof; and (iii) a DNA sequence encoding at least one yeast selectable marker or functionally active portion thereof; and (iv) a yeast replication origin or functionally active portion thereof, and in which the second recombinant DNA vector comprises (i) a DNA sequence encoding a beta-like globin chain or substantially homologous variant thereof or heme-binding fragment of the beta-like globin chain or substantially homologous variant thereof; (ii) a yeast transcriptional promoter which promotes the transcription of the DNA sequence encoding the beta-like globin chain or substantially homologous variant thereof or heme-binding fragment of the beta-like globin chain or substantially homologous variant thereof; and (iii) a DNA sequence encoding at least one yeast selectable marker or functionally active portion thereof; and (iv) a yeast replication origin or functionally active portion thereof; and (b) growing the yeast cell such that the alpha-like globin chain or substantially homologous variant thereof, or heme-binding fragment of the alpha-like globin chain or substantially homologous variant thereof, and a beta-like globin chain or substantially homologous variant thereof or heme-binding fragment of the beta-like globin chain or substantially homologous variant thereof are expressed;

(c) isolating the the alpha-like globin chain or substantially homologous variant thereof, or heme-binding fragment of the alpha-like globin chain or substantially homologous variant thereof, and beta-like globin chain or substantially homologous variant thereof or heme-binding fragment of the beta-like globin chain or substantially homologous variant thereof from the yeast cell; and (d) combining the alpha-like globin chain or substantially homologous variant thereof, or heme-binding fragment of the alpha-like globin chain or substantially homologous variant thereof, and a beta-like globin chain or substantially homologous variant thereof or heme-binding fragment beta like-globin chain or substantially homologous variant thereof with a source of heme.

The invention is also directed to a method for producing hemoglobin comprising an alpha-like globin chain or substantially homologous variant thereof or heme-binding fragment of the alpha-like globin chain or substantially homologous variant thereof, and a beta-like globin chain or substantially homologous variant thereof or heme-binding fragment of the beta-like globin chain or substantially homologous variant thereof, comprising the steps of:

(a) introducing into a first yeast cell a recombinant DNA vector comprising: (i) a DNA sequence encoding an alpha-like globin chain or substantially homologous variant thereof or heme-binding fragment of the alpha-like globin chain or substantially homologous variant thereof; (ii) a yeast transcriptional promoter which promotes the transcription of the DNA sequence encoding the alpha-like globin chain or substantially homologous variant thereof or heme-binding fragment of the alpha-like globin chain or substantially homologous variant thereof; and (iii) a DNA sequence encoding at least one yeast selectable marker or functionally active portion thereof; and (iv) a yeast replication origin or functionally active portion thereof;

(b) introducing into a second yeast cell a recombinant DNA vector comprises (i) a DNA sequence encoding a beta-like globin chain or substantially homologous variant thereof or heme-binding fragment of the beta-like globin chain or substantially homologous variant thereof; (ii) a yeast transcriptional promoter which promotes the transcription of the DNA sequence encoding the beta-like globin chain or substantially homologous variant thereof or heme-binding fragment of the beta-like globin chain or substantially homologous variant thereof; and (iii) a DNA sequence encoding at least one yeast selectable marker or functionally active portion thereof; and (iv) a yeast replication origin or functionally active portion thereof;

(c) growing the first yeast cell such that the alpha-like globin or substantially homologous variant thereof or heme-binding fragment of the alpha-like globin chain or substantially homologous variant thereof is expressed;

(d) growing the second yeast cell such that the beta-like globin chain or substantially homologous variant thereof or heme-binding fragment of the beta-like globin chain or substantially homologous variant thereof is expressed;

(e) isolating the alpha-like globin chain or substantially homologous variant thereof or heme-binding fragment of the alpha-like globin chain or substantially homologous variant thereof from the first yeast cell;

(f) isolating the beta-like globin chain or substantially homologous variant thereof or heme-binding fragment of the beta-like globin chain or substantially homologous variant thereof from the second yeast cell; and (g) combining the isolated alpha-like globin chain or substantially homologous variant thereof or heme-binding fragment of the alpha-like globin chain or substantially homologous variant thereof or heme-binding fragment of the alpha-like globin chain or substantially homologous variant thereof, and the isolated beta-like globin chain or substantially homologous variant thereof, or heme-binding fragment of the beta-like globin chain or substantially homologous variant thereof, with a source of heme.

The invention is also directed to a method for producing hemoglobin comprising an alpha-like globin chain or substantially homologous variant thereof or heme-binding fragment of the alpha-like globin chain or substantially homologous variant thereof, and a beta-like globin chain or substantially homologous variant thereof or heme-binding fragment of the beta-like globin chain or substantially homologous variant thereof, comprising the steps of:

(a) introducing into a yeast cell two recombinant DNA vectors in which the first recombinant DNA vector comprises: (i) a DNA sequence encoding an alpha-like globin chain or substantially homologous variant thereof or heme-binding fragment of the alpha-like globin chain or substantially homologous variant thereof; (ii) a yeast transcriptional promoter which promotes the transcription of the DNA sequence encoding the alpha-like globin chain or substantially homologous variant thereof or heme-binding fragment of the alpha-like globin chain or substantially homologous variant thereof; and (iii) a DNA sequence encoding at least one yeast selectable marker or functionally active portion thereof; and (iv) a yeast replication origin or functionally active portion thereof; and in which the second recombinant DNA vector comprises (i) a DNA sequence encoding a beta-like globin chain or substantially homologous variant thereof or heme-binding fragment of the beta-like globin chain or substantially homologous variant thereof; (ii) a yeast transcriptional promoter which promotes the transcription of the DNA sequence encoding the beta-like globin chain or substantially homologous variant thereof or heme-binding fragment of the beta-like globin chain or substantially homologous variant thereof; and (iii) a DNA sequence encoding at least one yeast selectable marker or functionally active portion thereof; and (iv) a yeast replication origin; and (b) growing the yeast cell in an appropriate medium such that the alpha-like globin chain or substantially homologous variant thereof or heme-binding fragment of the alpha-like globin chain or substantially homologous variant thereof, and a beta-like globin chain or substantially homologous variant thereof or heme-binding fragment of the beta-like globin chain or substantially homologous variant thereof are expressed and assembled together with heme in the yeast cell to form hemoglobin.

The invention is also directed to recombinant vectors capable of expressing a globin chain or a heme-binding fragment thereof in yeast. The recombinant vector may be capable of expressing two globin chains or heme-binding fragments thereof. The globin chains may in a specific embodiment comprise an alpha-like globin and a beta-like globin chain or variants thereof. The invention also relates to methods for expressing at least one globin chain in yeast. Expressed alpha-globin and beta-globin chains or variants thereof may be combined with a source of heme to produce hemoglobin or a variant thereof. The invention also relates to methods for expressing hemoglobin in yeast where hem which is produced by the yeast or obtained from an exogenous source, is ligated to the globin to form functional hemoglobins in vivo.

4. BRIEF DESCRIPTION OF THE FIGURES

FIGS. 1A–F shows the nucleotide sequences of the embryonic zeta (SEQ ID NO:1) (1A), embryonic epsilon (SEQ ID NO:2) (1B), fetal gamma (SEQ ID NO:3) (1C), adult delta (SEQ ID NO:4) (1D), adult alpha (SEQ ID NO:5) (1E) and adult beta (SEQ ID NO:6) (1F) chains of human hemoglobin. The deduced amino acid sequences (SEQ ID NO:65–70, respectively) are shown underneath. The AUG start codon and the corresponding amino-terminal methionine which is removed by methionine aminopeptidase in a post-translational modification are not shown in the figures.

FIG. 2 shows a partial restriction map of the plasmid pSPβC. The complete insert of the beta-globin gene is shown by the double line and the plasmid sequences are shown by a single line. Restriction sites shown above the line are A=AccI; E=EcoRI; F=SfaNI; H=HindIII; N=NcoI; and B=BamHI. The line above the restriction sites represents the coding region of the beta-globin gene. Numbers below the lines represent length in base pairs from an EcoRI site present in the vector.

FIG. 3A shows the strategy used to clone the adult beta-globin gene into YEp51.

Figure 8:
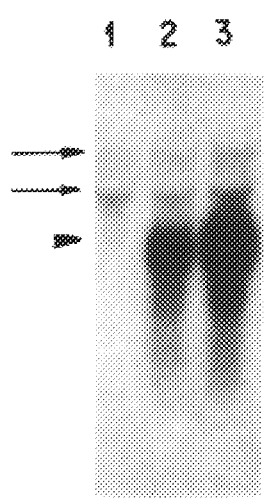

FIG. 8 shows an autoradiograph of total RNA extracted from yeast strain Sc340 transformed with YEp51(340g2C) YEp51T/NAT (340g2B) and YEp51T/PORT (340g2P). Total RNA was subjected to electrophoresis on a 1.1% agarose gel, transferred to the Hybond paper and probed with an ApaLI-HindIII fragment (600 bp) of the beta-globin gene from plasmid mp18βHS. The level of a control RNA (CYH2) was determined with the plasmid mp19CYH22 (9.0 kb) which carries the coding region of the CYH2 gene. 20 μg of the total RNA was loaded into each lane. Sample in each lane is as follows: Lane 1: 340g2C, Lane 2: 340g2B, and Lane 3: 340g2P. β marks the beta-globin mRNA. The CYH2 mRNA is marked with C1 (precursor form) and C2 (mature mRNA). Numbers on the side indicate the length in nucleotides.

Figure 9A:
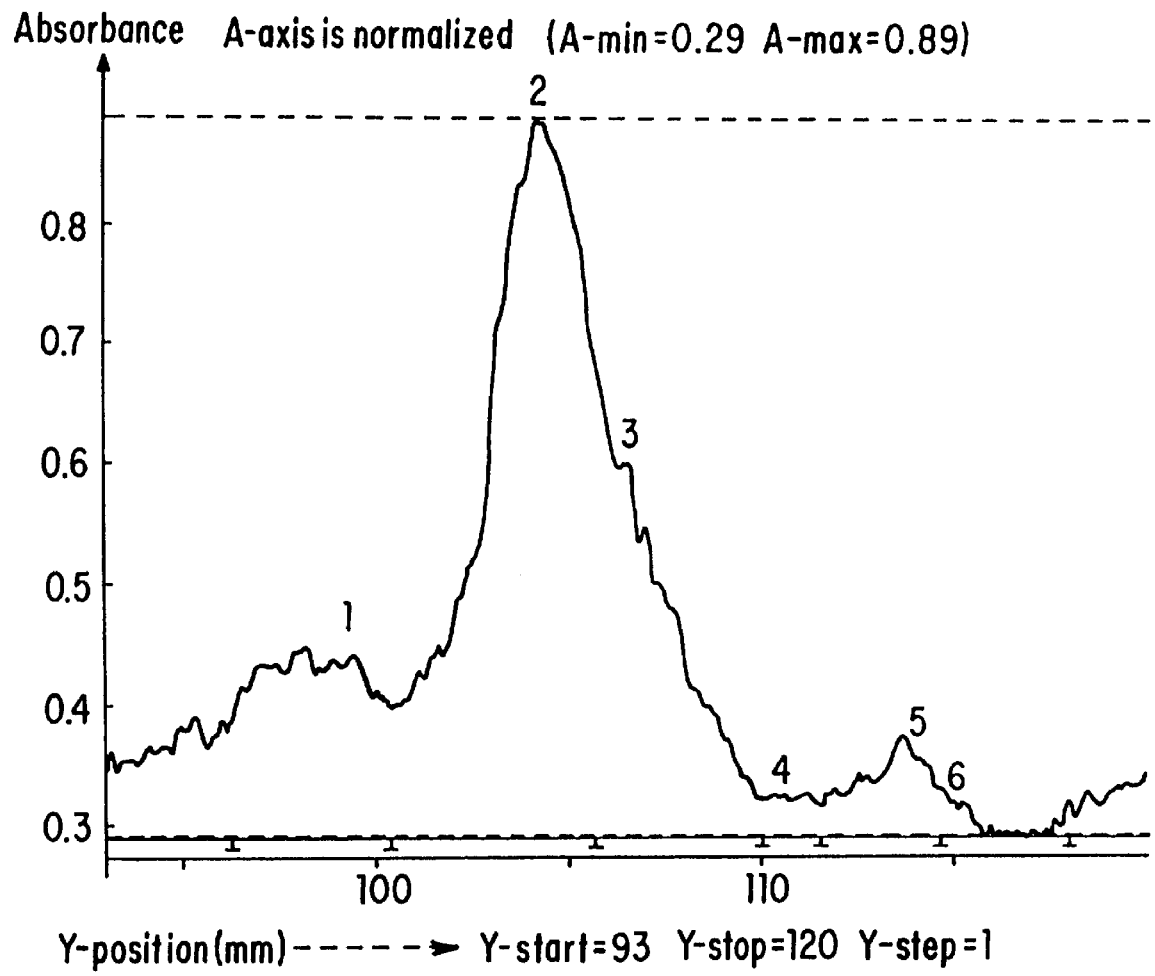
Figure 9B:
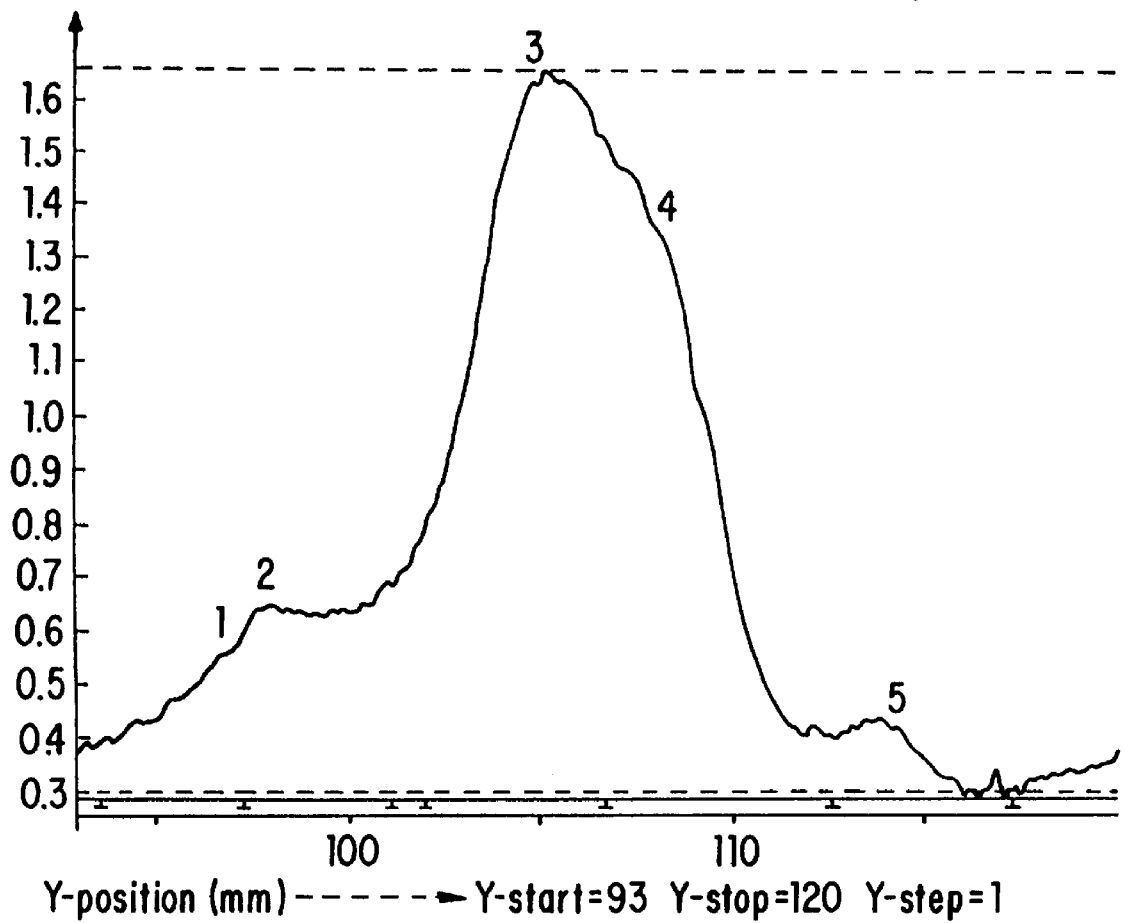

FIG. 9 shows the results of scanning an autoradiograph containing both beta-globin and CYH2 mRNA obtained from a Northern Blot using an LKB gel scanner. The large peak in A (340g2B) represents the beta-globin mRNA and two small peaks at either side of the large peak represent the CYH2 mRNA. FIG. 9B shows the results of scanning an autoradiograph containing both Porto Alegre beta-globin mRNA and CYH2 mRNA obtained from a Northern blot using an LKB scanner. The large peak in B (340g2P) represents the Porto Alegre beta-globin mRNA and the two small peaks at either side of the large peak represent the CYH2 mRNA.

FIG. 10 shows the sequences of and restriction sites present on 519-A-1 (5'-end primer) and 519-A-3 (3'-end primer). These primers were used to synthesize alpha-globin DNA.

Figure 11:
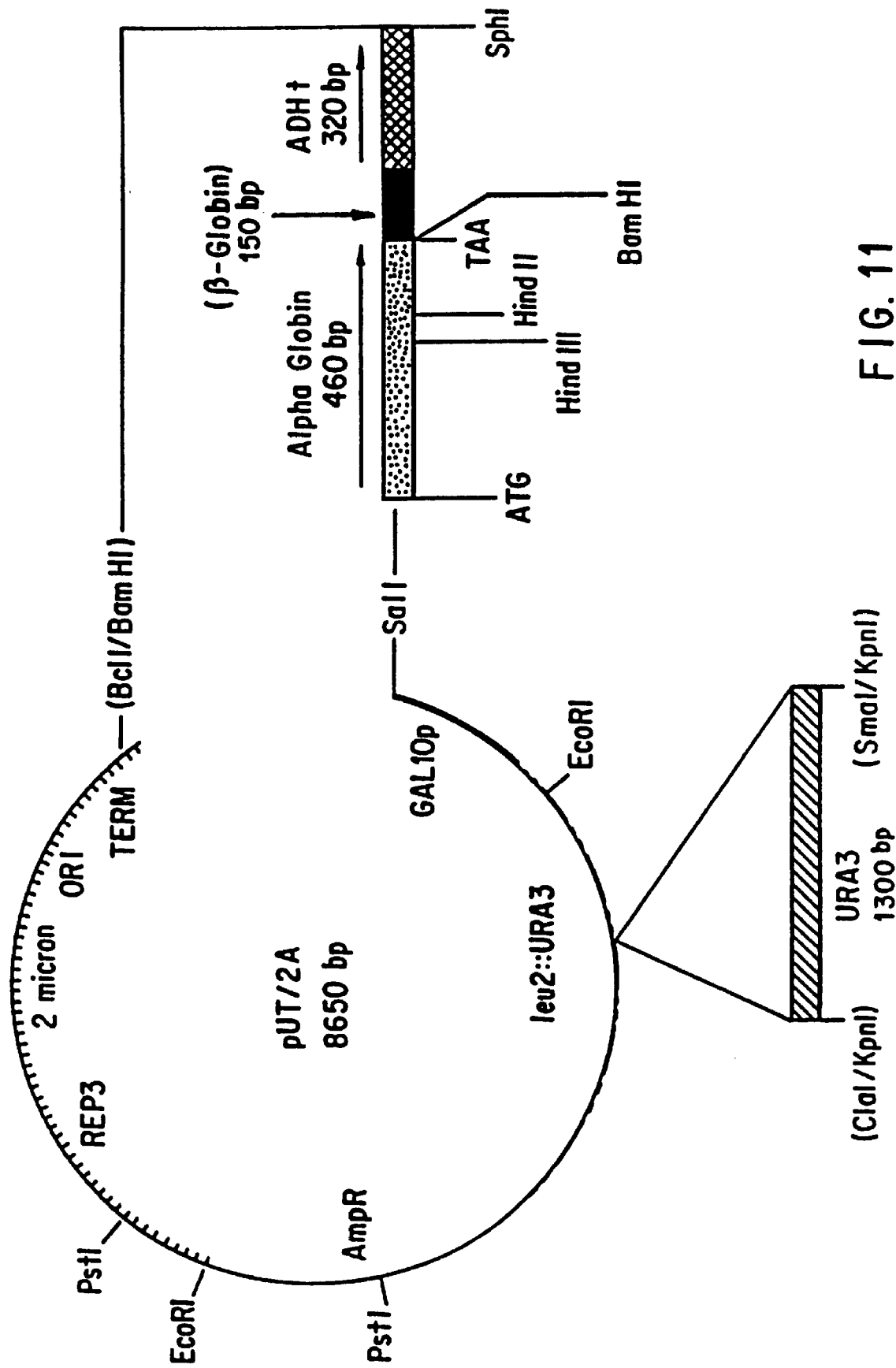

FIG. 11 shows the restriction map of pUT/2A.

Figure 12:
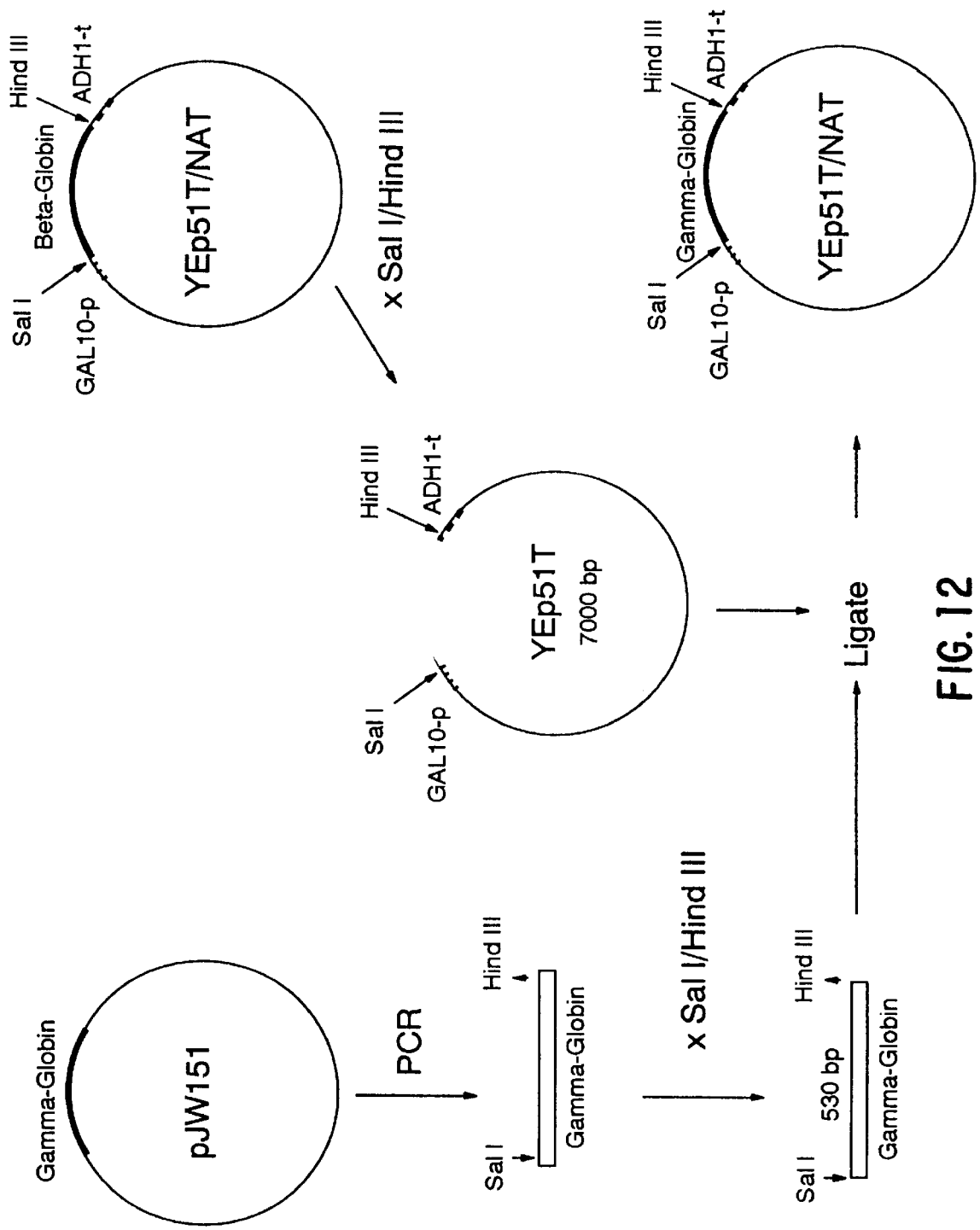

FIG. 12 shows the construction of YEp51T/G.

FIG. 13 shows the DNA sequence of the gamma globin gene.

FIG. 14 shows the sequences of and restriction sites present on GAM-5-S (5'-end primer) GAM-3-H (3'-end primer). These primers were used to synthesize gamma-globin DNA.

Figure 15:
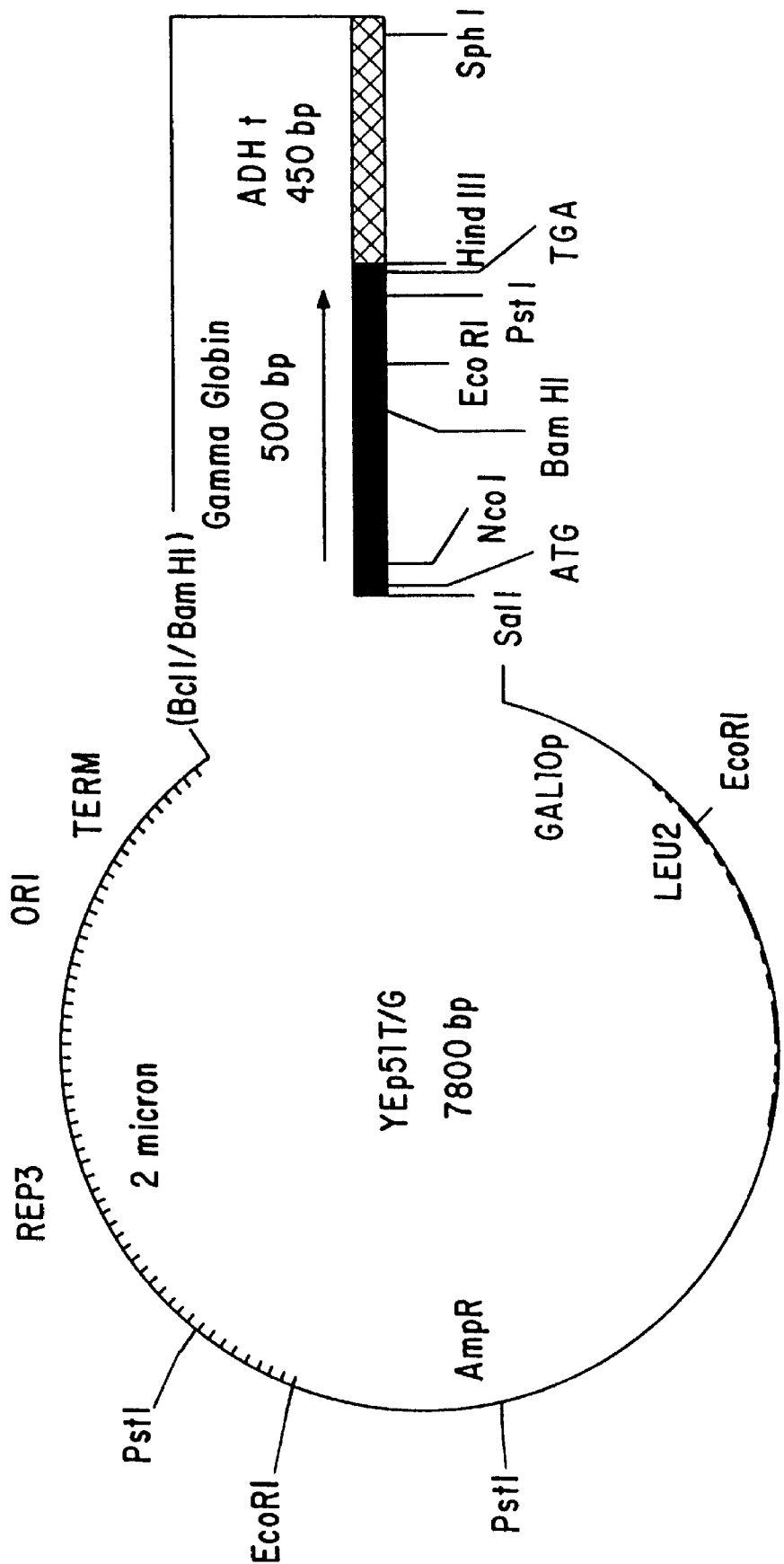

FIG. 15 shows the restriction map of plasmid YEp51T/G.

Figure 16:
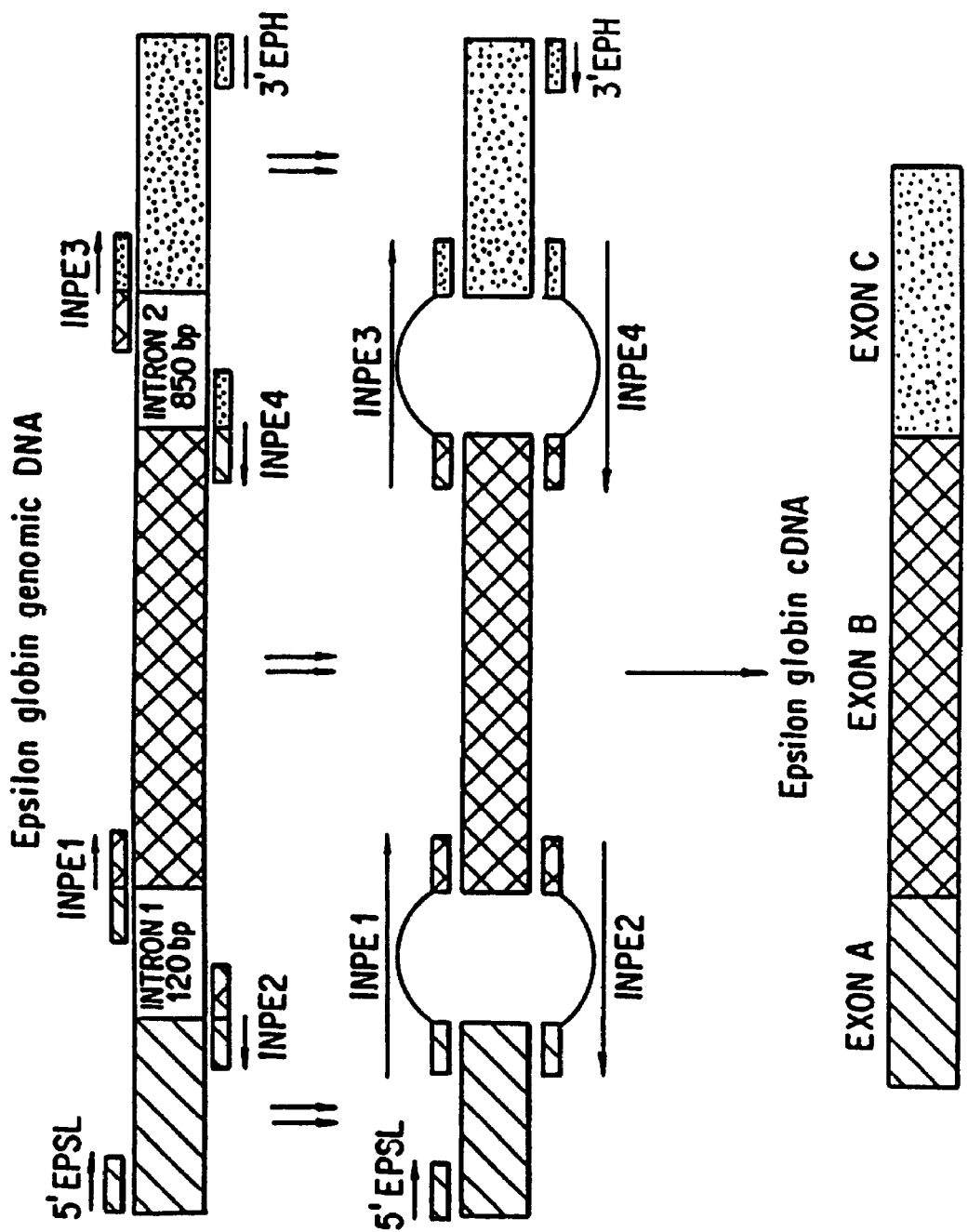

FIG. 16 shows the structure of the epsilon globin genome.

FIG. 17 shows the sequences of the primers used to construct the epsilon cDNA: 5EPSL-13, INPE-1-14, INPE-2-15, INPE-3-16, INPE-4-17, and 3EPH-18.

Figure 18:
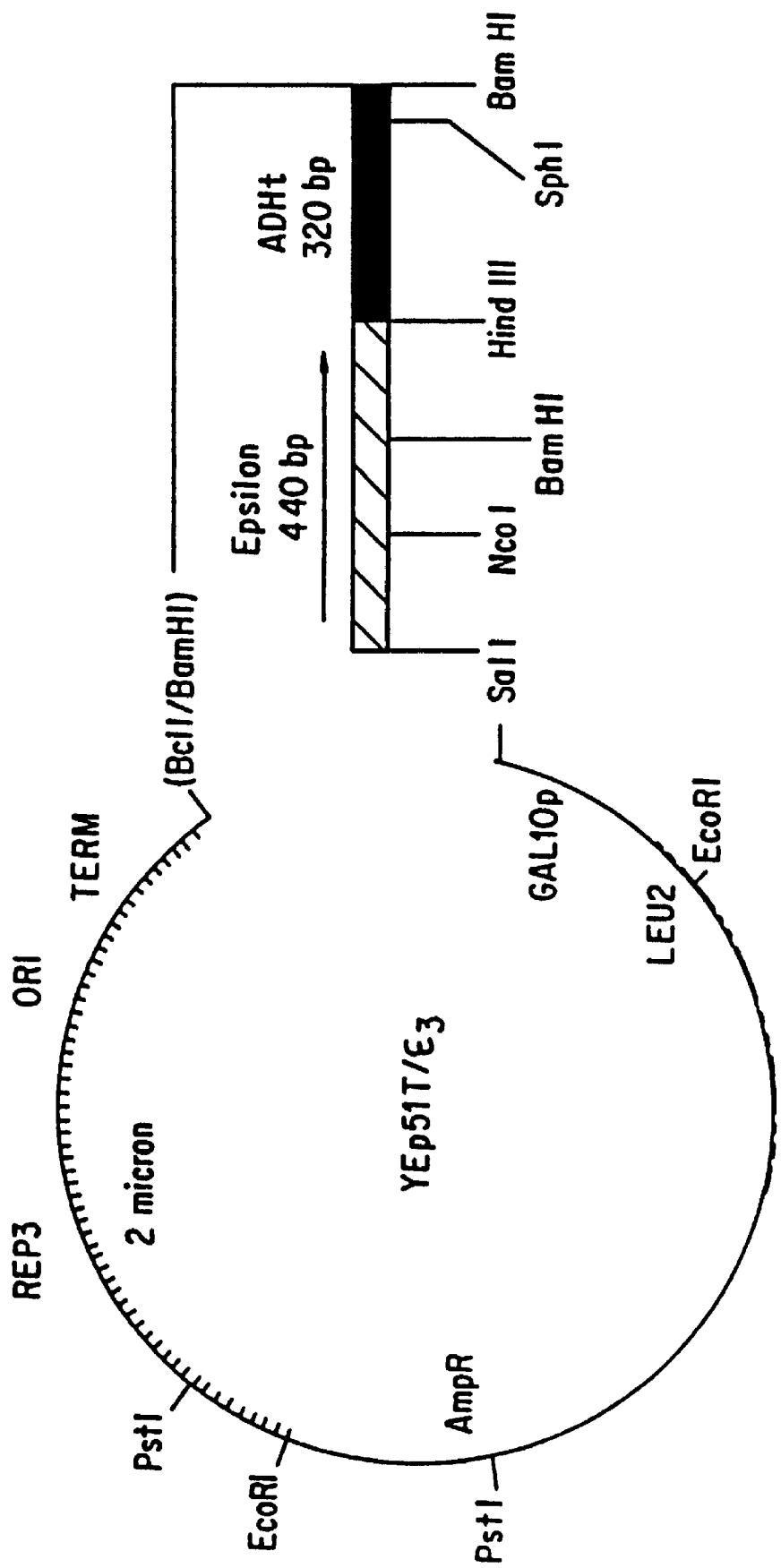

FIG. 18 shows the restriction map of plasmid YEp51T/ε3.

FIG. 19 show the sequence of and restriction sites present on 5ZETASAC (5'-end primer) and ZETA3HSLS (3'-end primer). These primers were used to synthesize zeta-globin cDNA.

Figure 20:
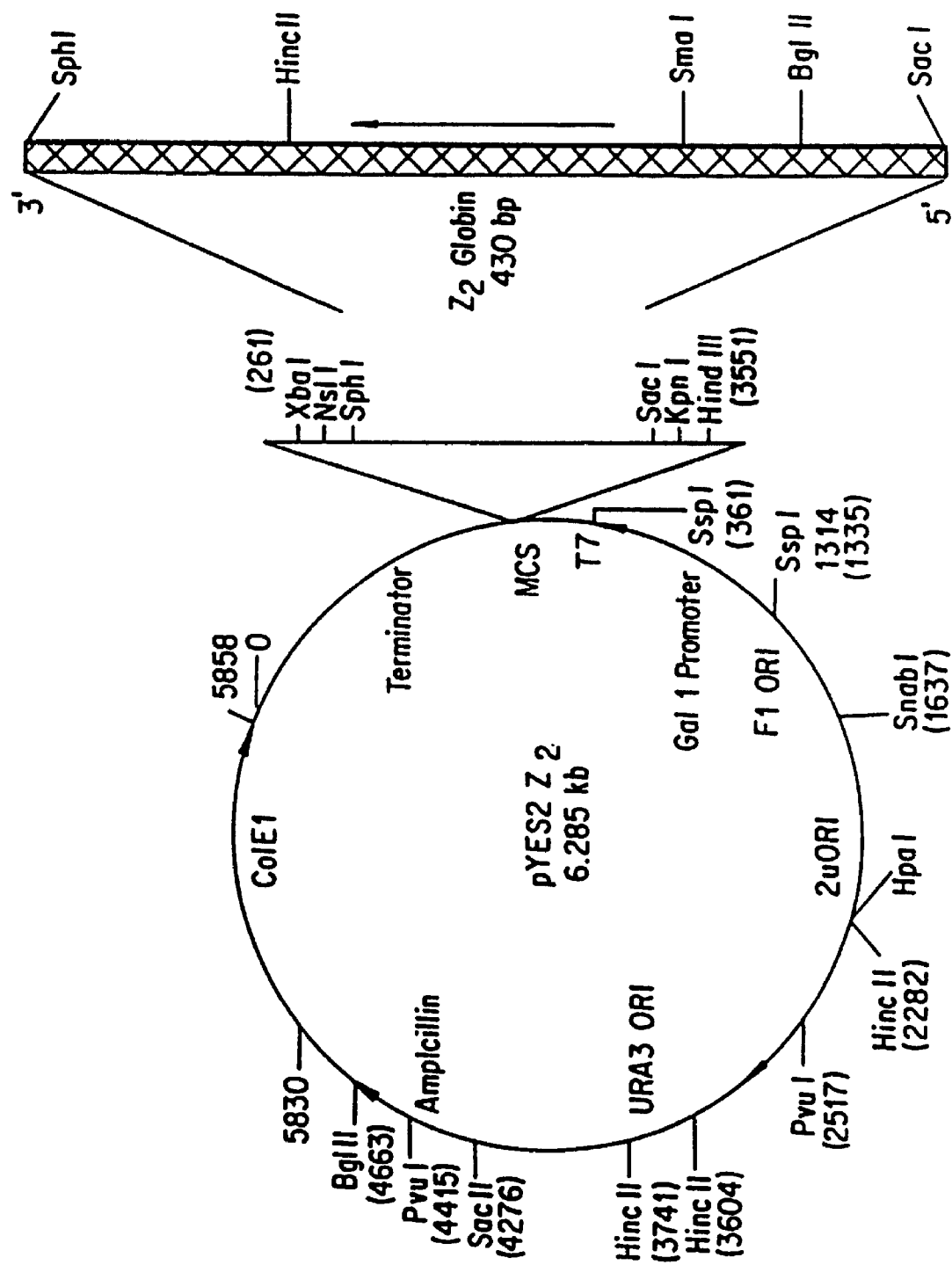

FIG. 20 shows the restriction map of plasmid YES2ζ2.

FIG. 21 shows the sequences of Mu-145Cy, Mu-66Th, and Mu-9Cy.

Figure 22:
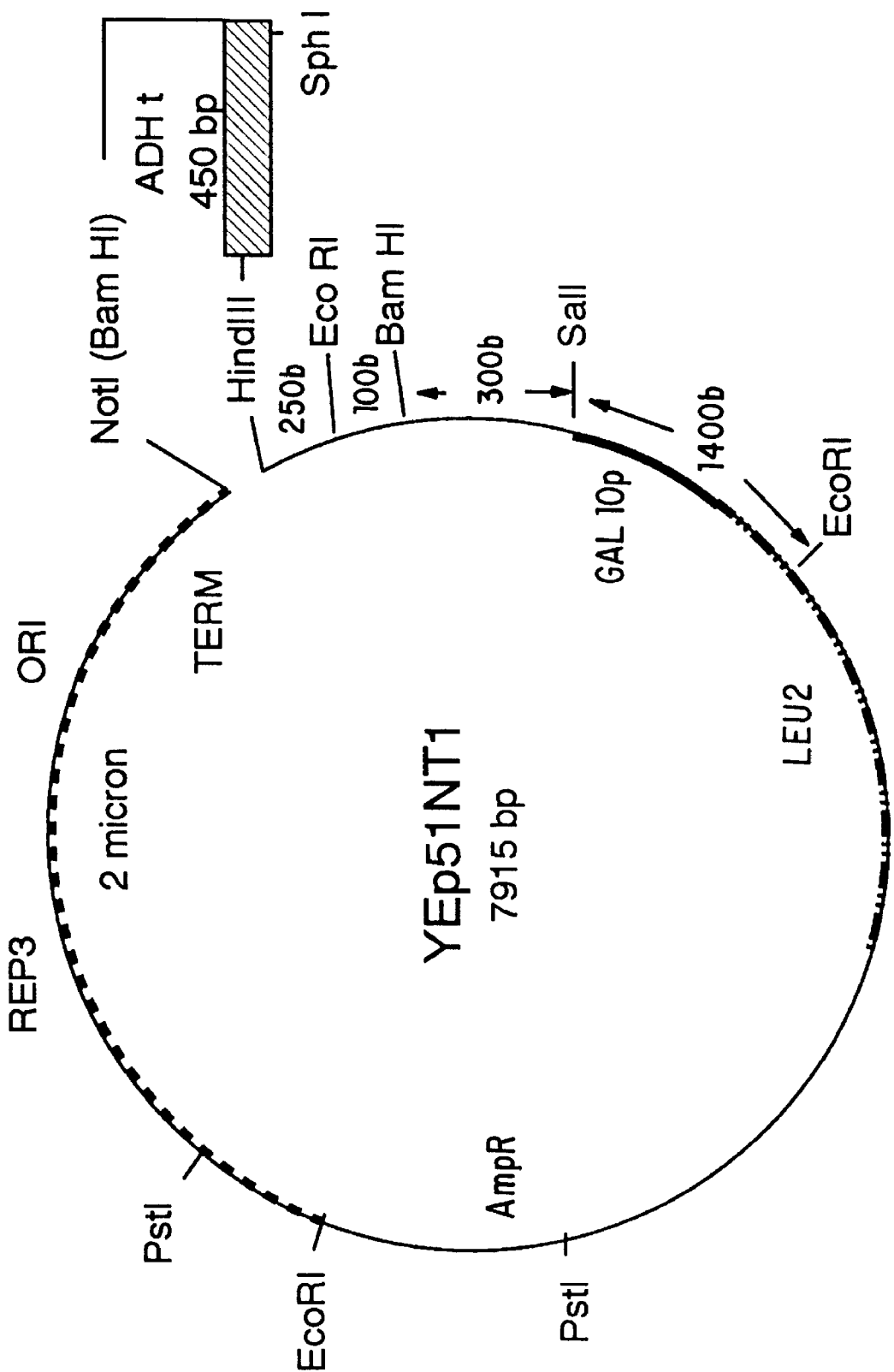

FIG. 22 shows a restriction map of YEp51NT1.

FIG. 23 shows the sequences of and the restriction sites on 5'-end primer, G-5-9CY and the 3'-end primer, GAM-3-H. Site specific mutations are shaded.

FIG. 24 shows the sequences of and the restriction sites on 5'-end primer, B-G127-5 and the 3'-end primer, Beta-3-H.

FIG. 25 shows the sequences of and the restriction sites on the 5'-end primer, A-Tit-5 and the 3'-end primer, G10T3H.

FIG. 26 shows the sequences of and the restriction sites on the 5'-end primer, 51-A3-SL and the 3'-end primer, A-Hin3-3.

FIG. 27 shows the sequences of and the restriction sites on the 5' and 3' primers used to synthesize by PCR the Mississippi β-globin gene. Site specific mutations are shaded.

FIG. 28 shows the sequences of and the restriction sites on 5'-end primer, A104S-5 and the 3'-end primer, G10T3H.

FIG. 29 shows the sequences of and the restriction sites on 5'-end primer, Z-5-SAL and the 3'-end primer, Z-104S-B.

FIG. 30 shows the sequences of and the restriction sites on 5'-end primer, Z-BST-5 and the 3'-end primer, Z2-3-H.

FIG. 31 shows the sequences of and the restriction sites on 5'-end primer, Z-5-SAL and the 3'-end primer, Z-A95-3.

FIG. 32 shows the sequences of and the restriction sites on 5'-end primer, G2-Mot-5 and the 3'-end primer, GAM-3-H.

FIG. 33 shows the sequences of and the restriction sites on 5'-end primer (the Met Leu Thr Ala peptide shown has the sequence identifier SEQ ID NO:71), B-Bov2-5 and the 3'-end primer, Beta-3-H.

FIG. 34 shows the sequences of and the restriction sites on 5'-end primer, B-2ARG-5 and the 3'-end primer, Beta-3-H.

FIG. 35 shows the sequences of and the restriction sites on 5'-end primer, BN-5-SAL and the 3'-end primer, B-143A-3.

FIG. 36 shows the sequences of and the restriction sites on 5'-end primer, BN-5-SAL and the 3'-end primer, B-145-T-3.

FIG. 37 shows the sequences of and the restriction sites on 5'-end primer, GAM-5-S and the 3'-end primer, G66T-3.

FIG. 38 shows the sequences of and the restriction sites on the 5'-end primer, BN-5-Sal and the 3'-end primer, B-B3-Tal.

Figure 39:
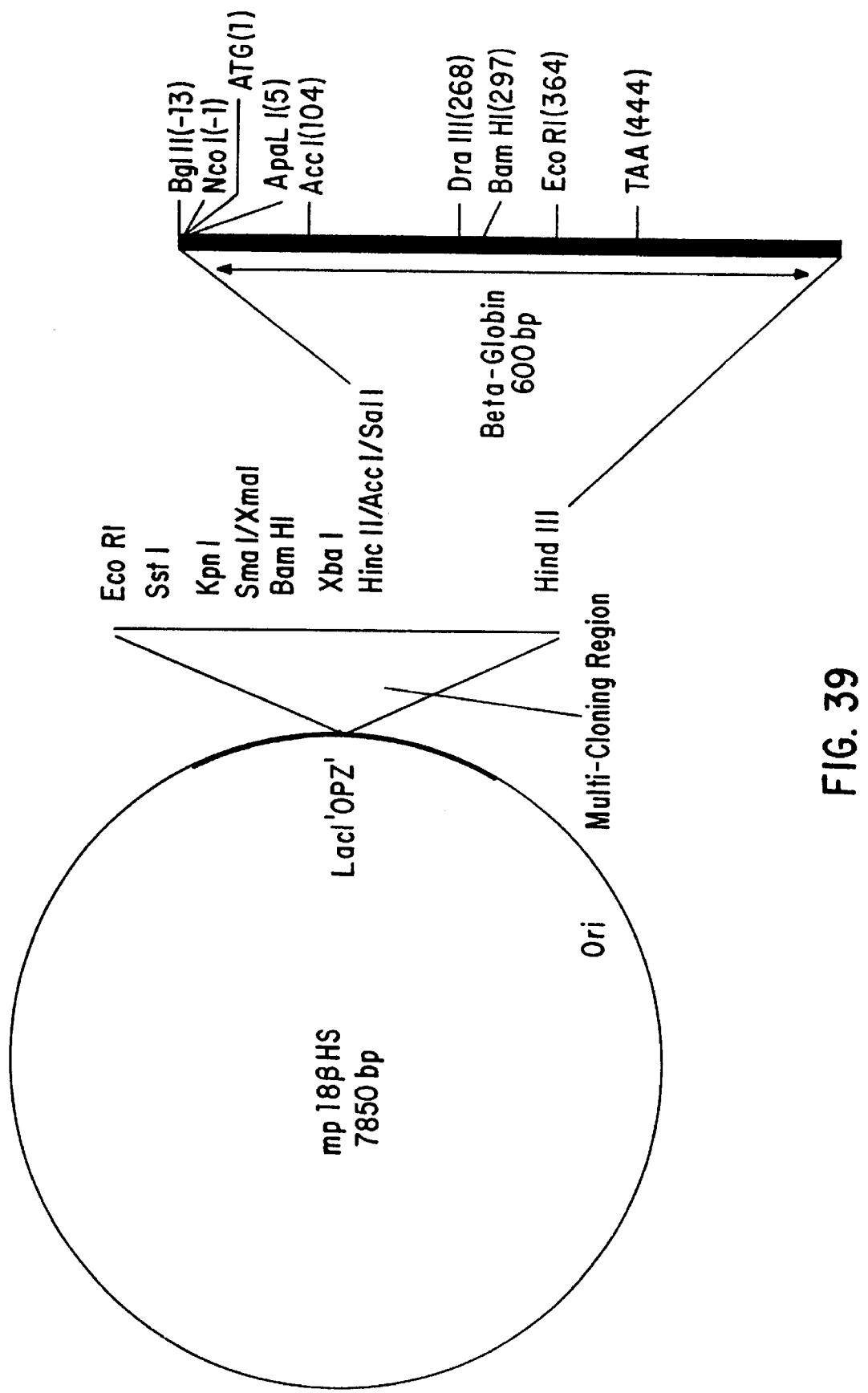

FIG. 39 shows a map of mp18βHS.

Figure 40:
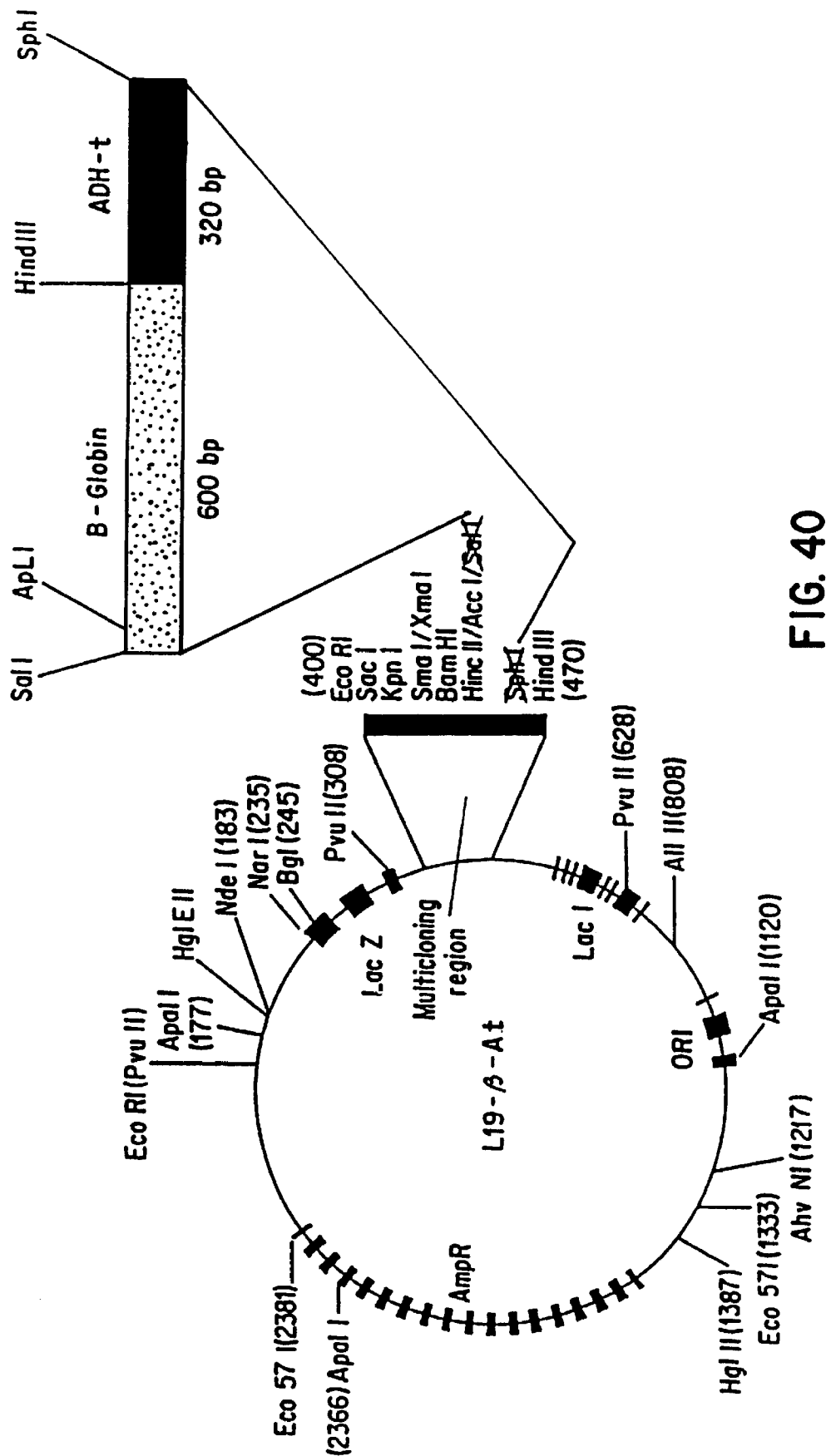

FIG. 40 shows a map of L19βAt.

FIG. 41 shows the sequence of TDH3-5' and TDH3-3'.

Figure 42:
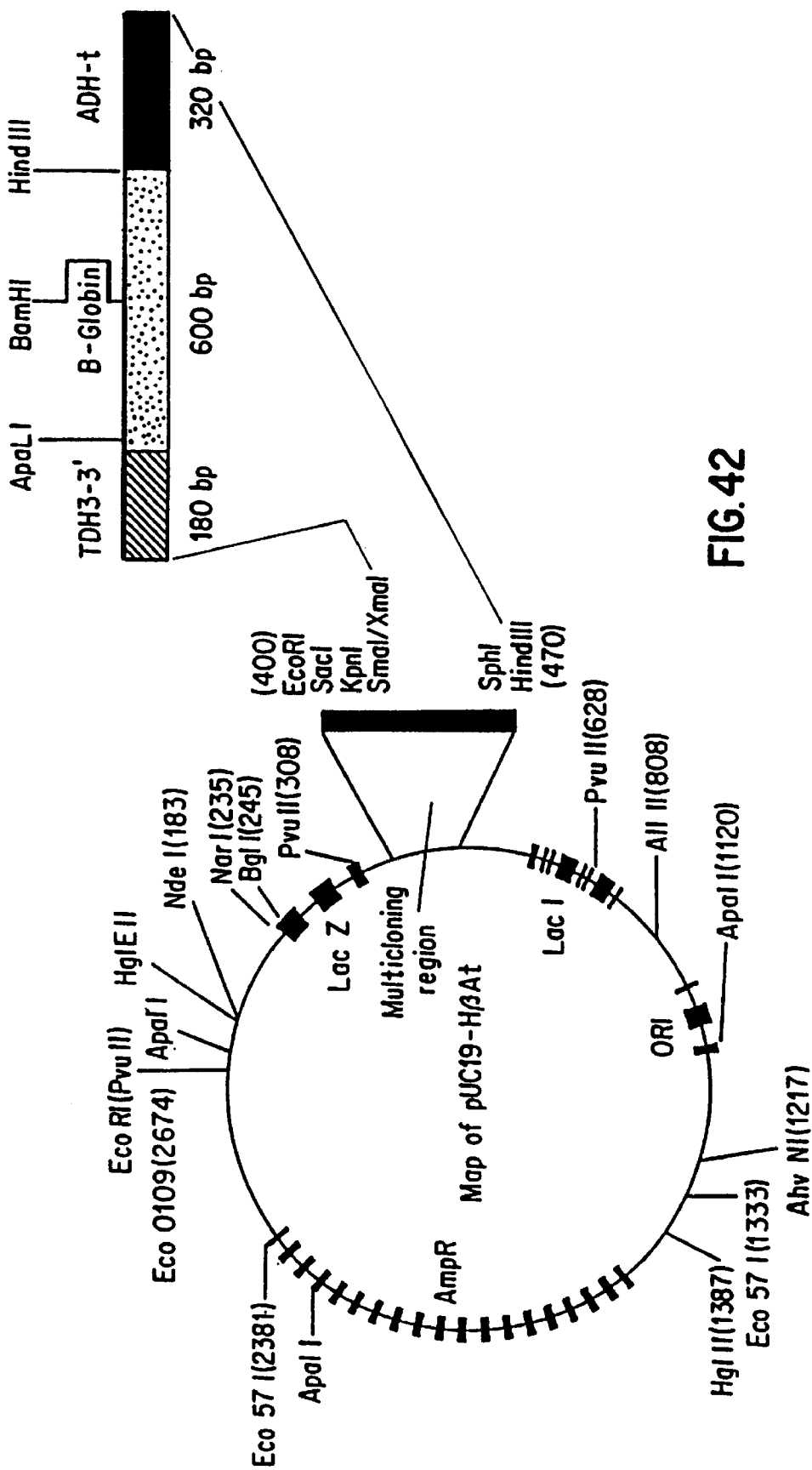

FIG. 42 shows the restriction map of plasmid pUC19-HβAt.

FIG. 43 shows part of the GAL1-10 promoter sequence.

FIG. 44 shows the sequences of the primers, GAL1-10-5' and GAL1-10-b 3'.

Figure 45:
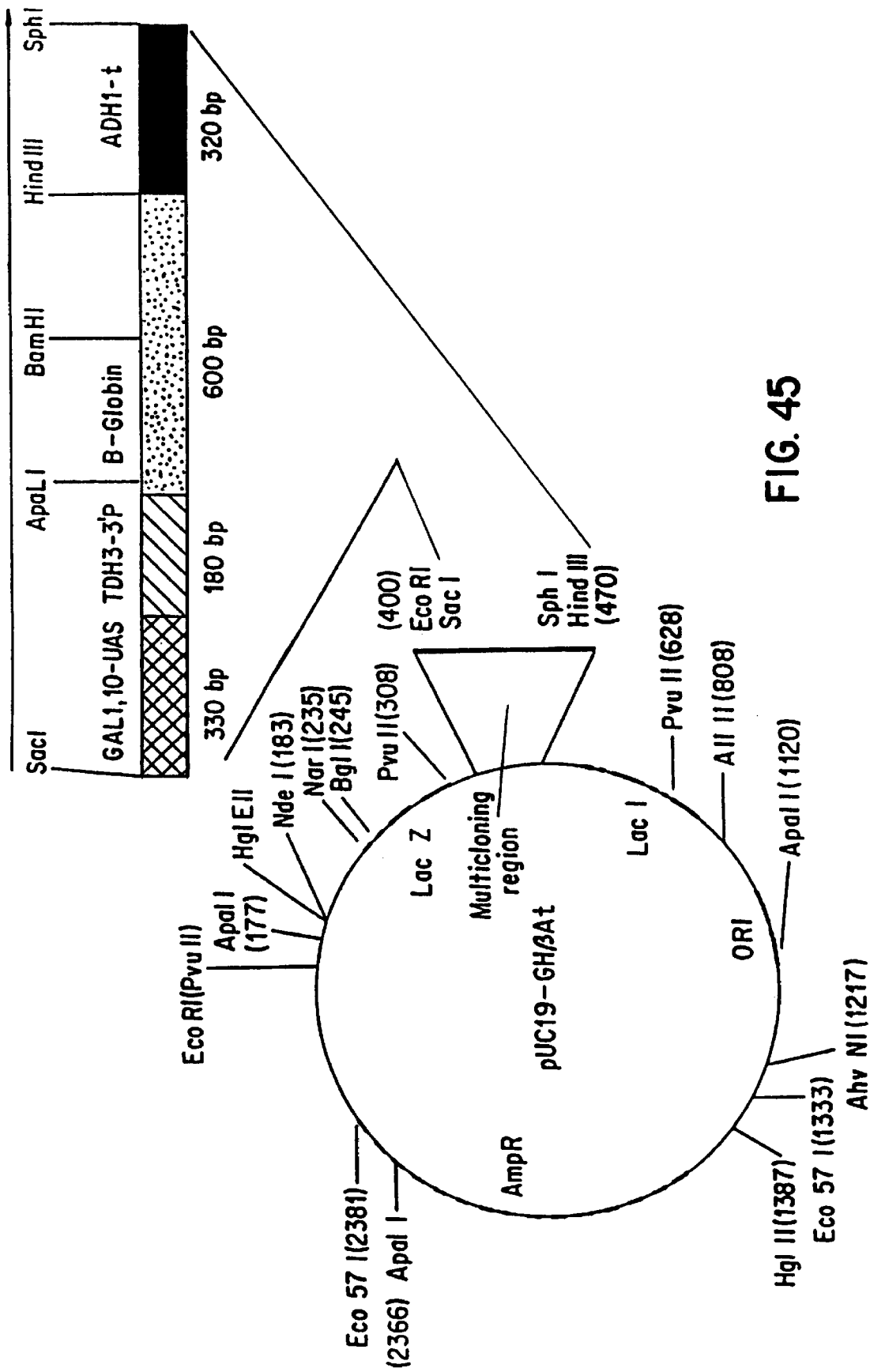

FIG. 45 shows the restriction map of plasmid pUC19-GHβAt.

Figure 46:
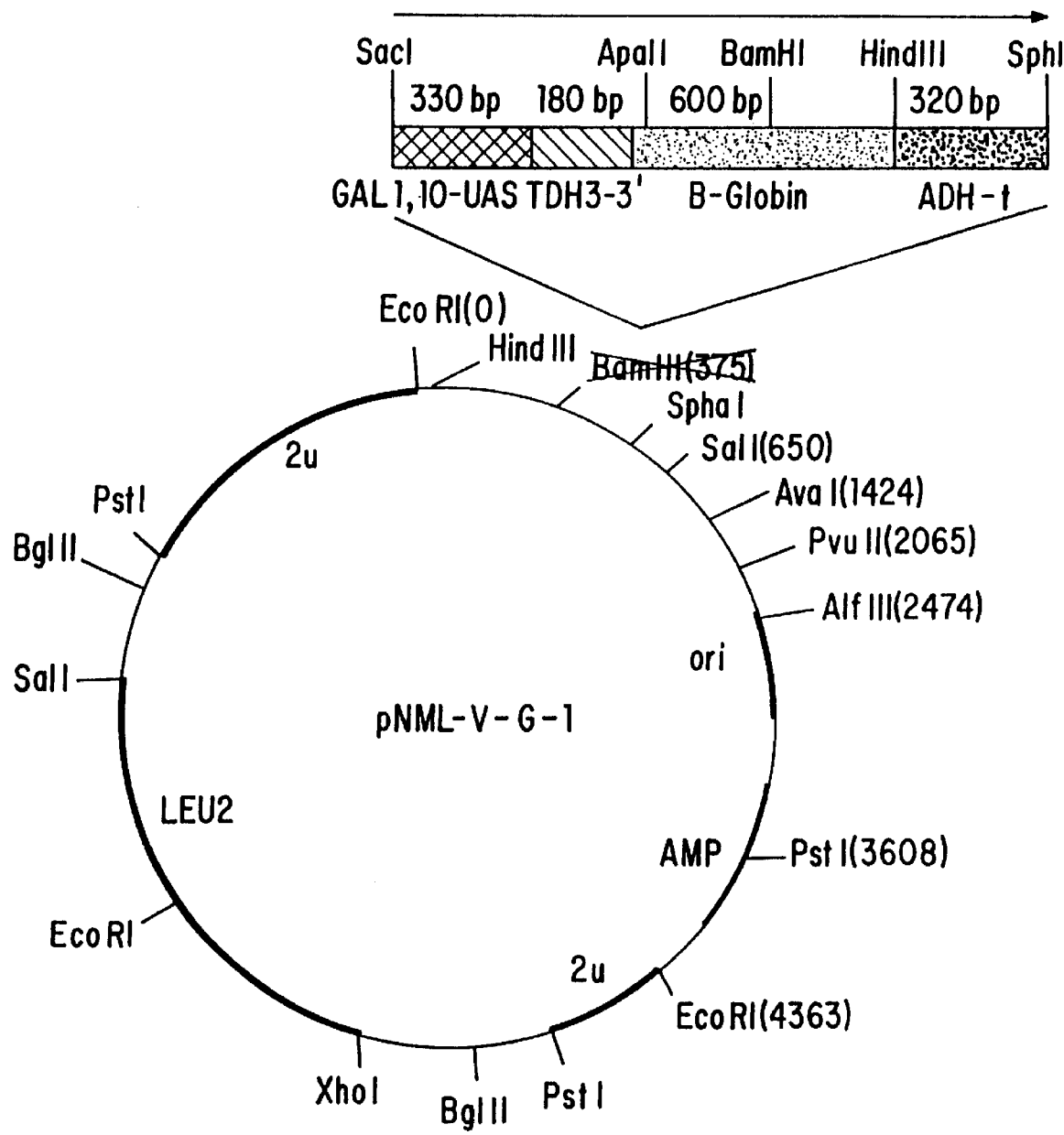

FIG. 46 shows the restriction map of plasmid pNML-V-G-1.

Figure 47:
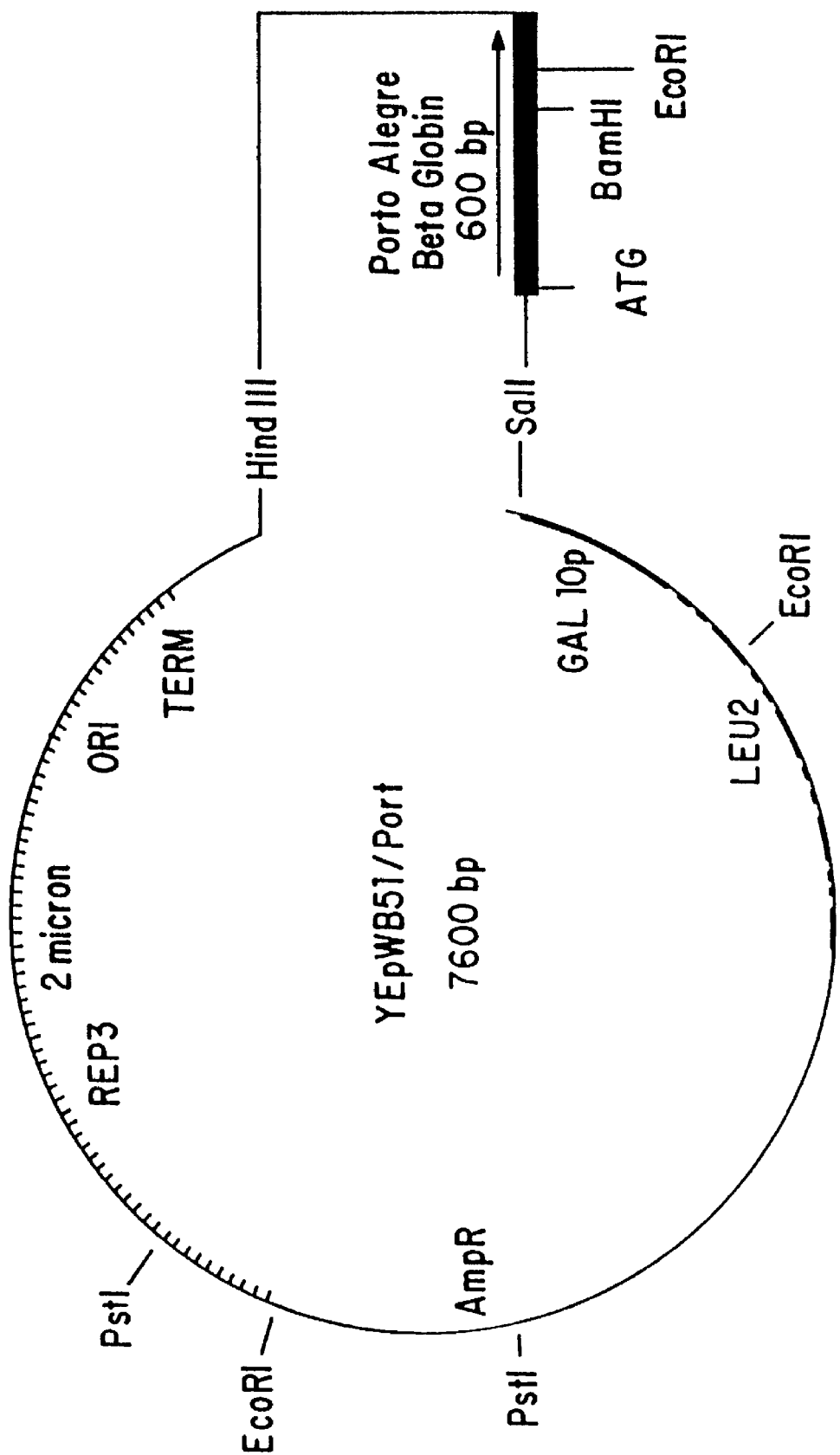

FIG. 47 shows the restriction map of plasmid YEpWB51/PORT.

FIG. 48 shows the sequences of and restriction sites present on primers 51-A-1 and 519-A-3.

FIG. 49 shows the sequences of an restriction sites present on primers G10T-5B and G10T3ESS.

FIG. 50 shows the sequences of and restriction sites present on the 5' and 3' primers used to synthesize the hybrid promoter-first 36 bases of alpha-globin.

FIG. 51 shows the sequences of and restriction sites present on the 5' and 3' primers used to synthesize the 3' alpha globin gene fragment.

Figure 52:
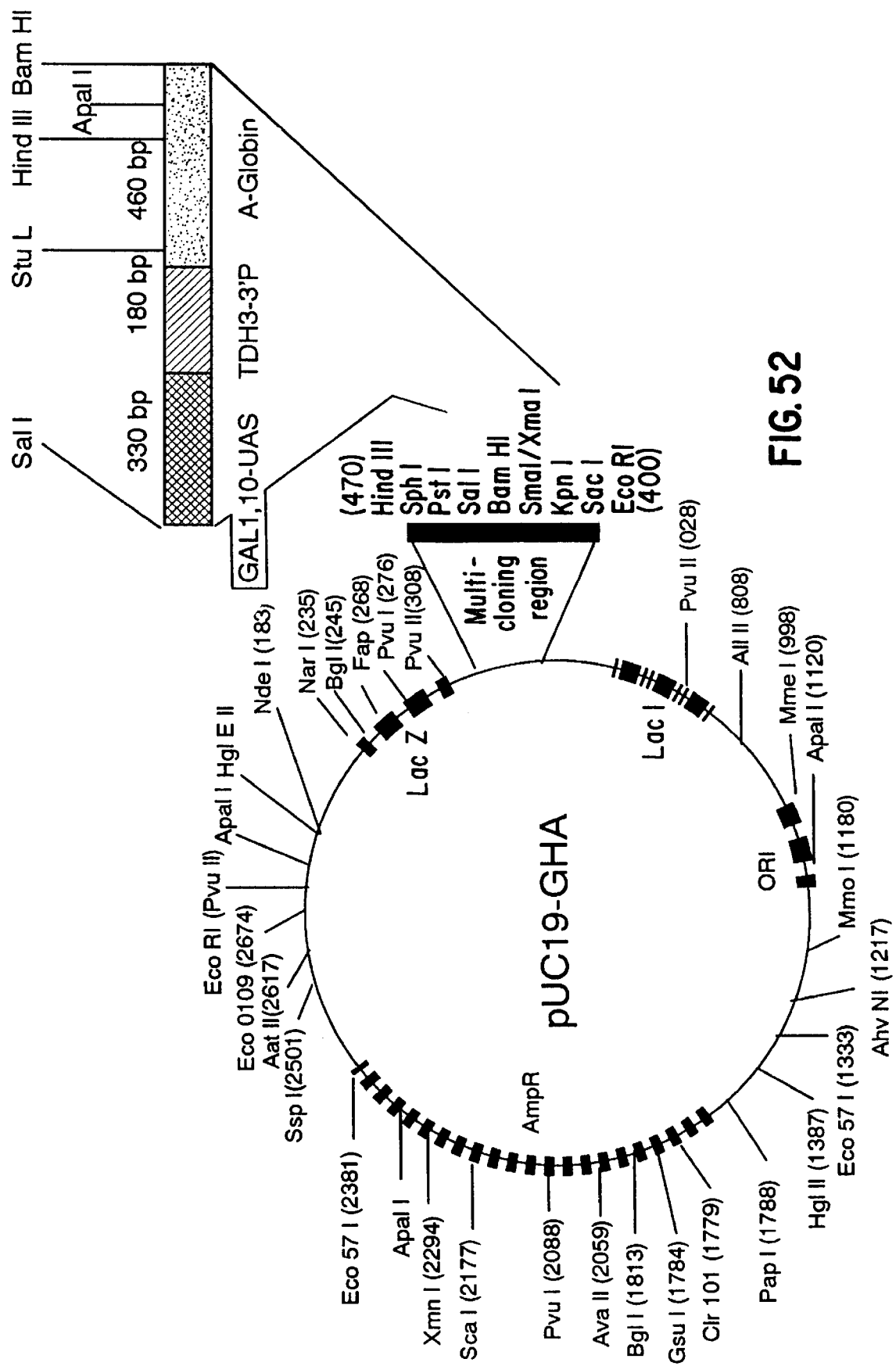

FIG. 52 shows the restriction map of plasmid pUC19-GHA.

Figure 53:
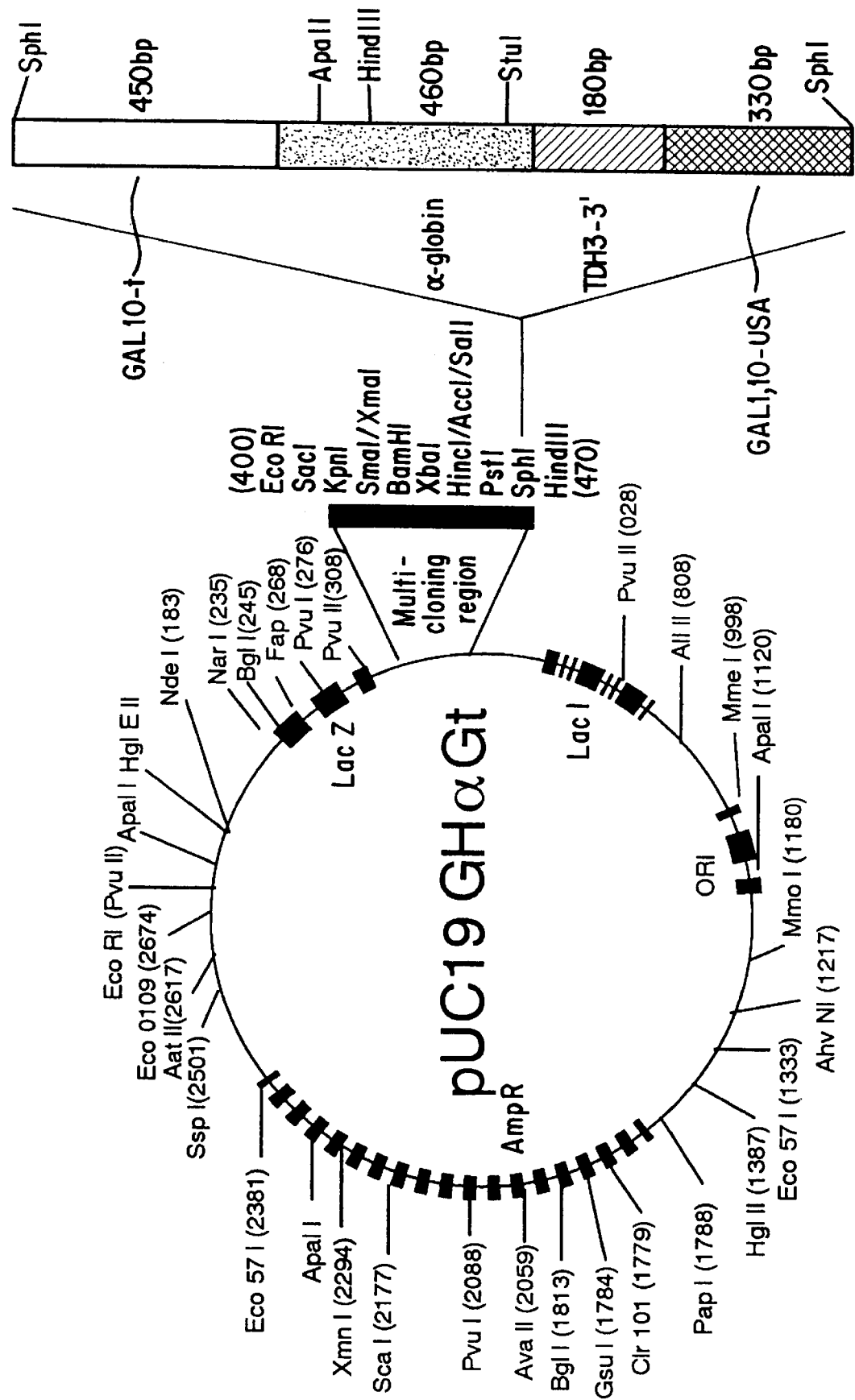

FIG. 53 shows the restriction map of plasmid pUC19-GHαGt.

FIG. 54 shows the sequences and restriction sites of primers used for synthesizing the HαGt DNA fragment.

Figure 55:
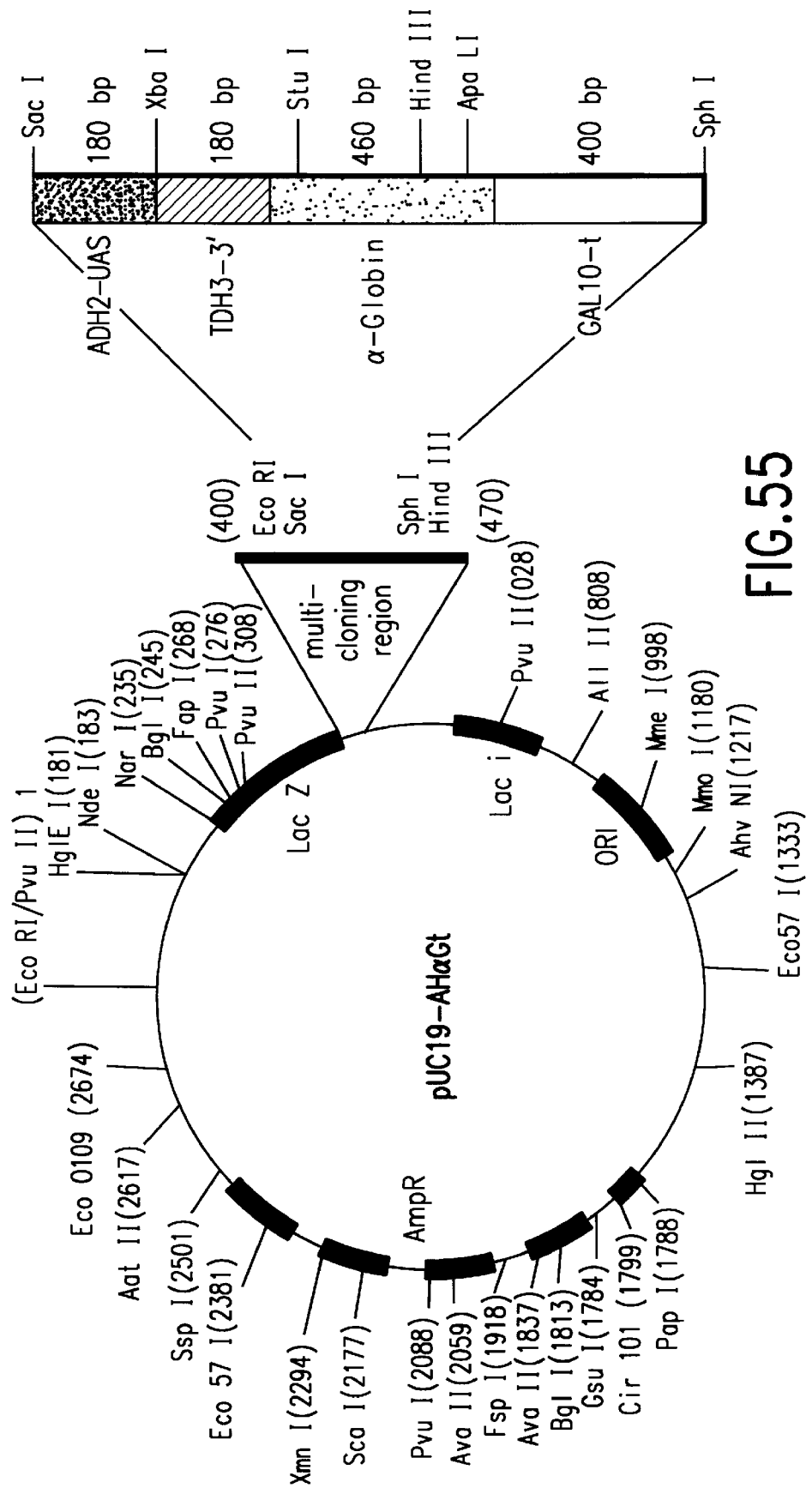

FIG. 55 shows the restriction map of pUC19-AHαGt.

Figure 56:
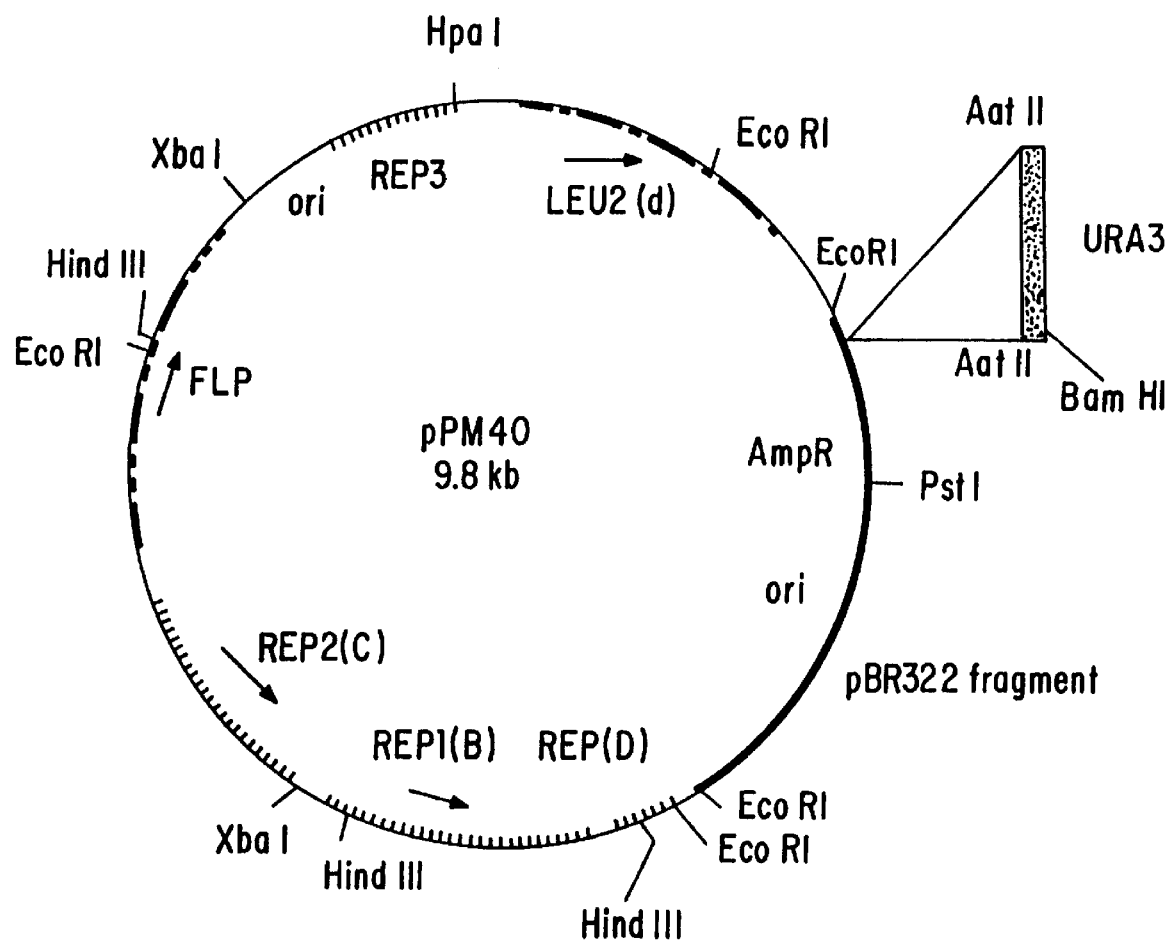

FIG. 56 shows the restriction map of pPM40.

Figure 57:
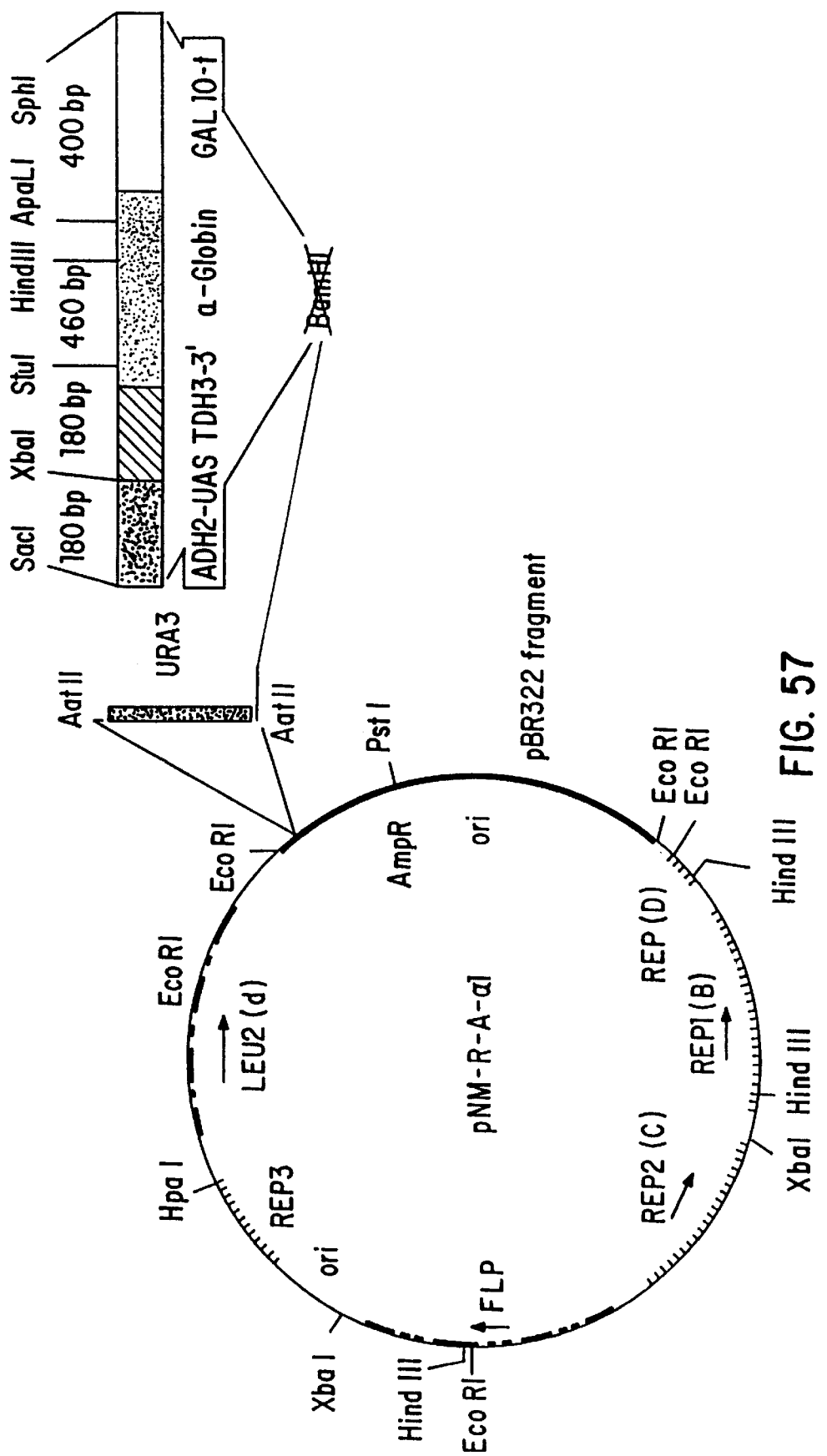
Figures 1, 58A:
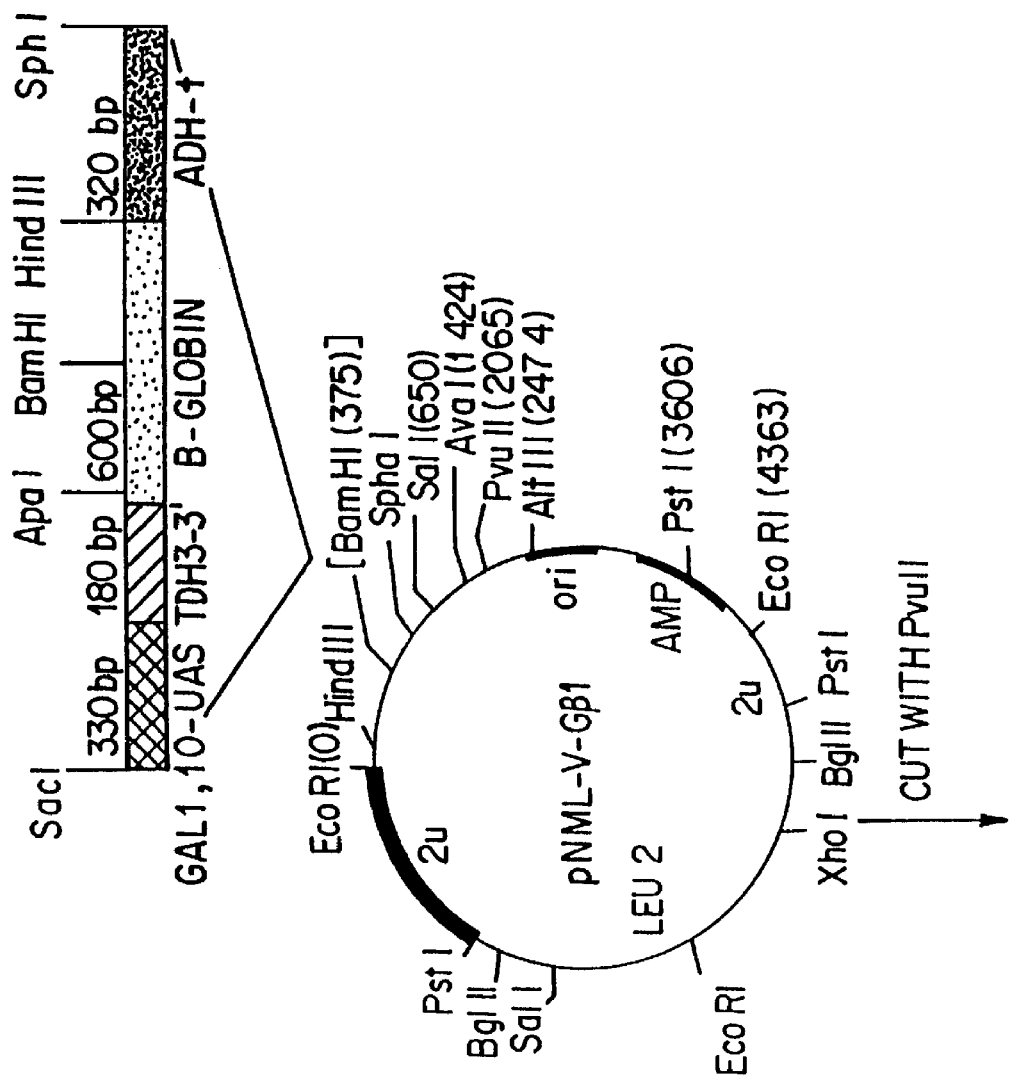
Figures 2, 58A:
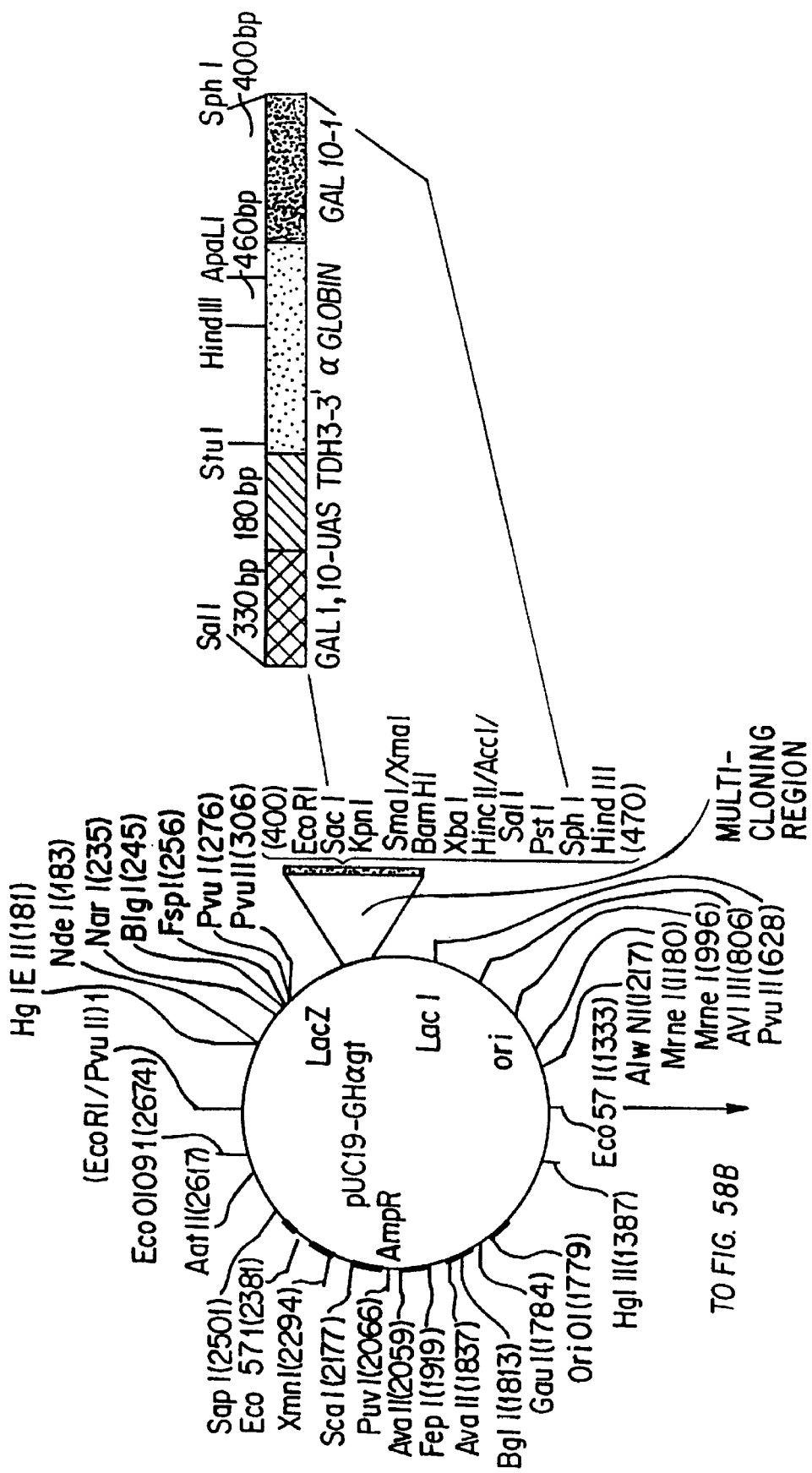
Figure 58B:
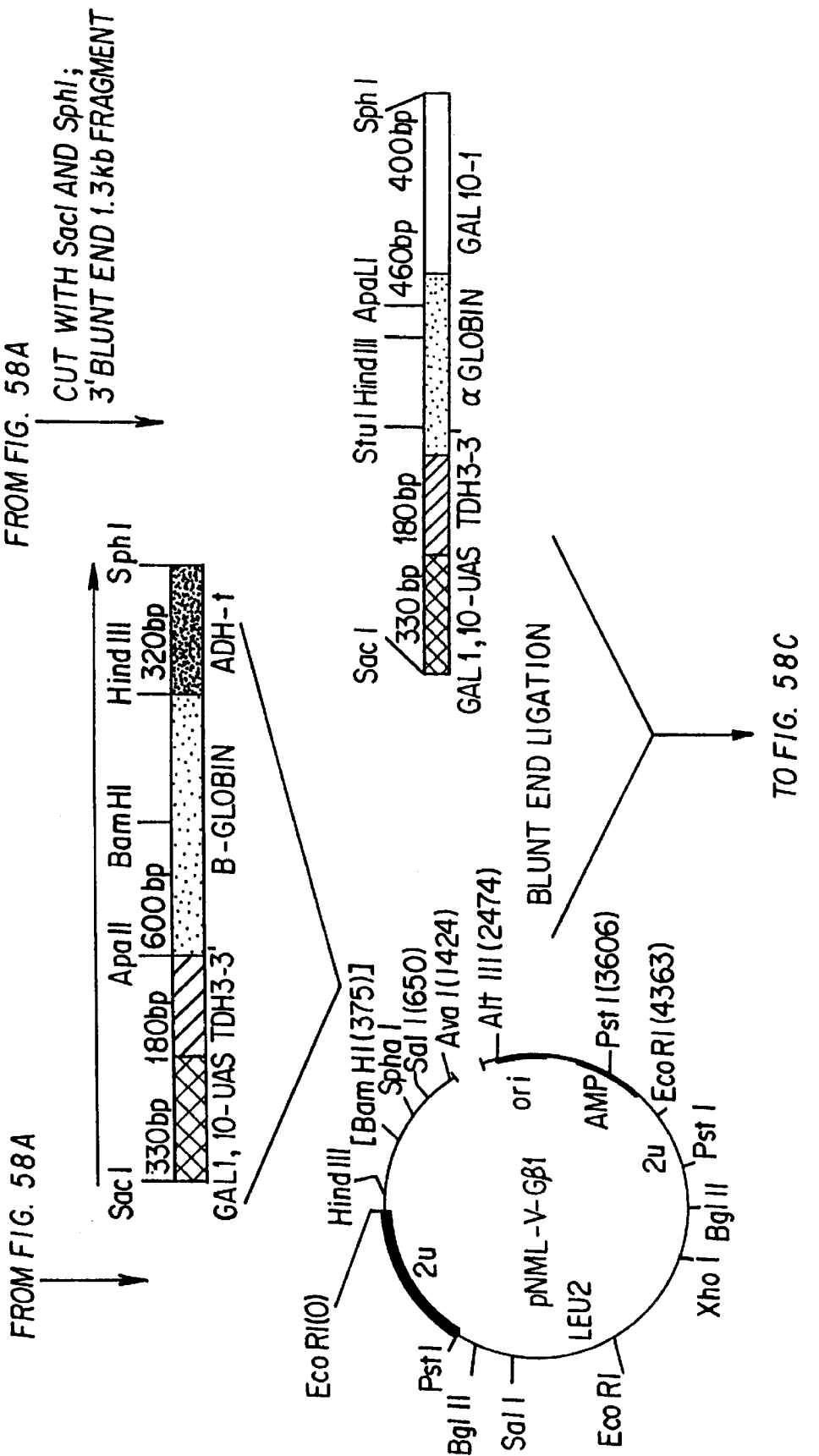
Figures 1, 58C:
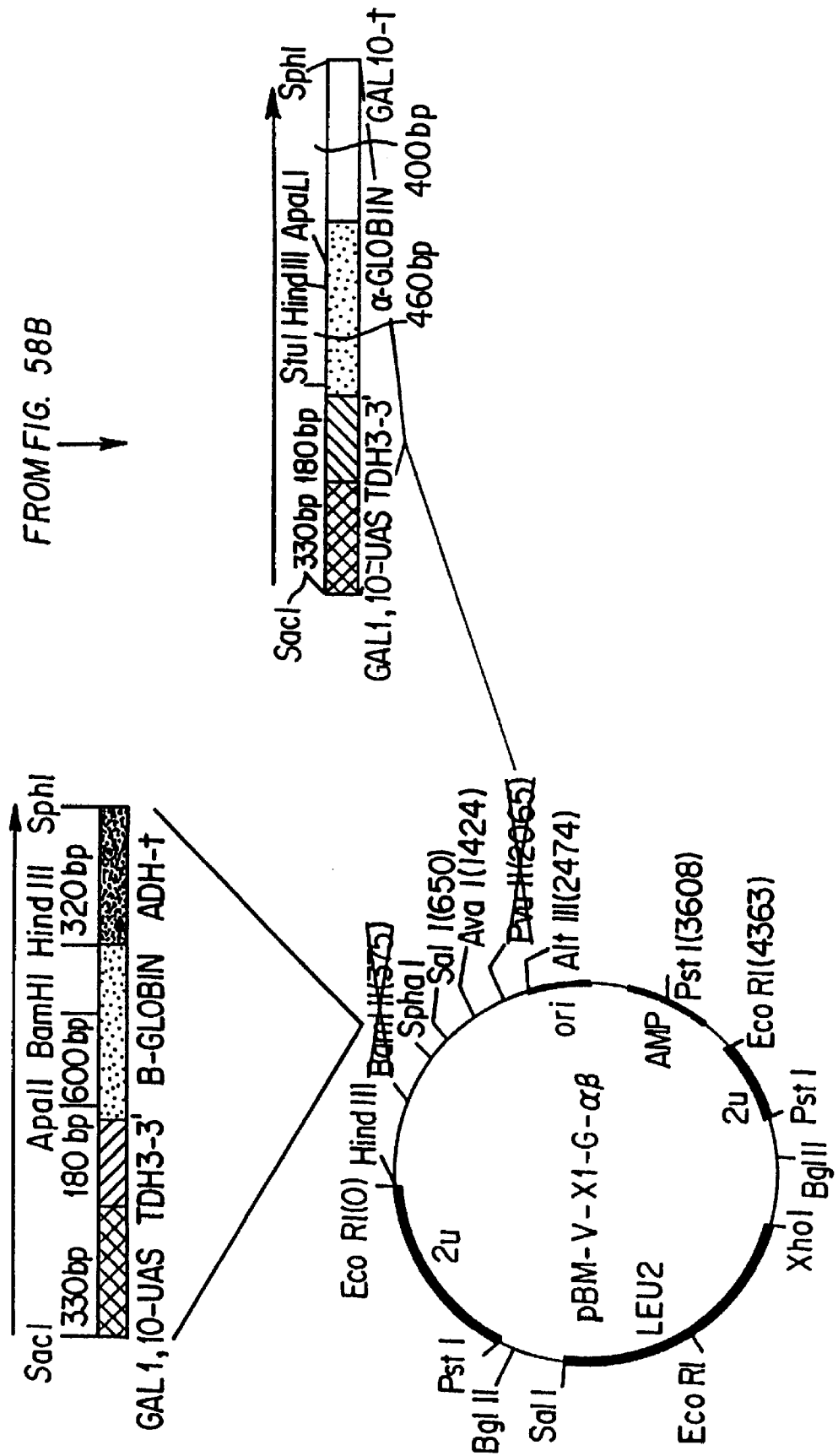
Figures 2, 58C:
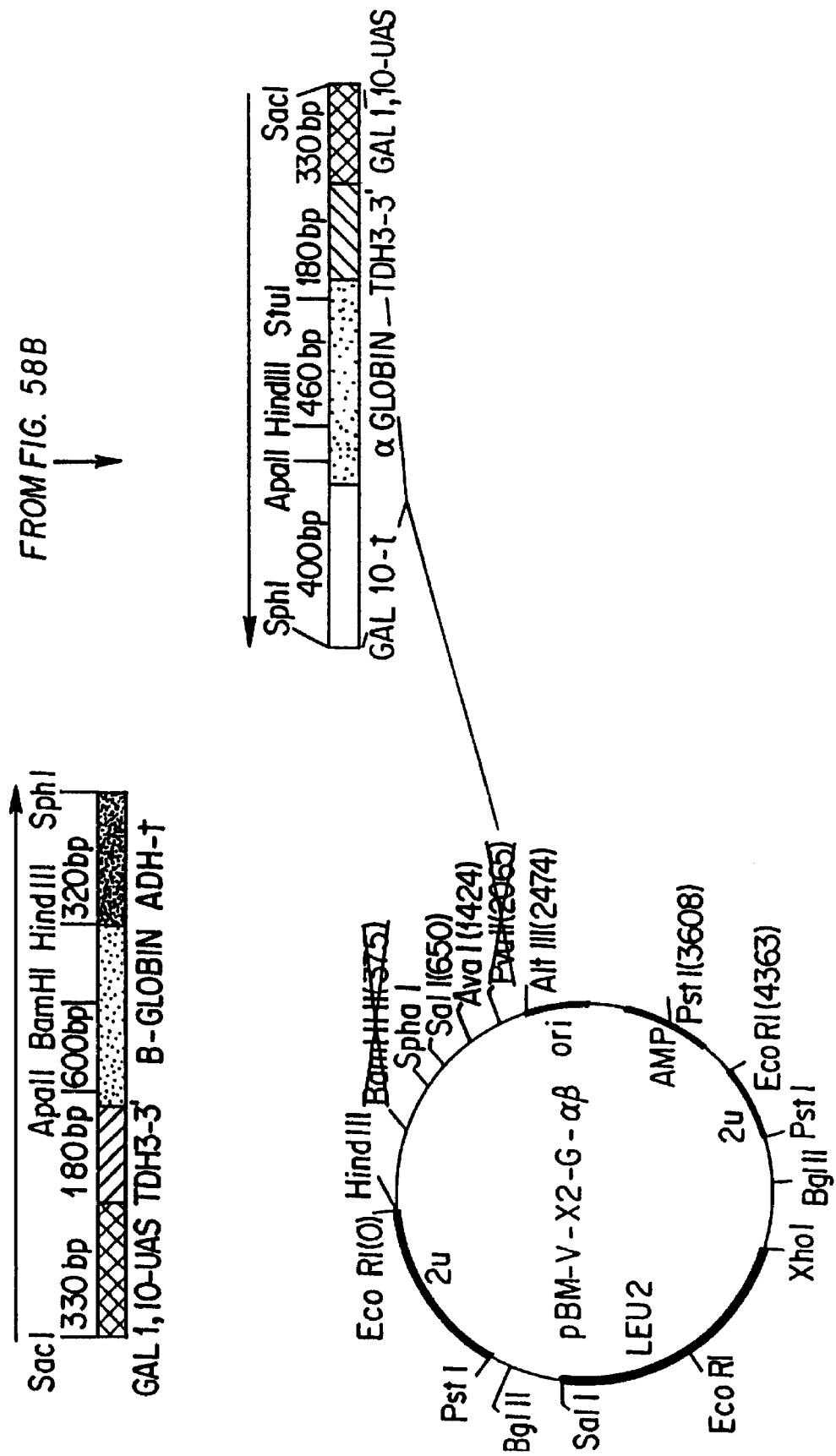
Figures 1, 59A:
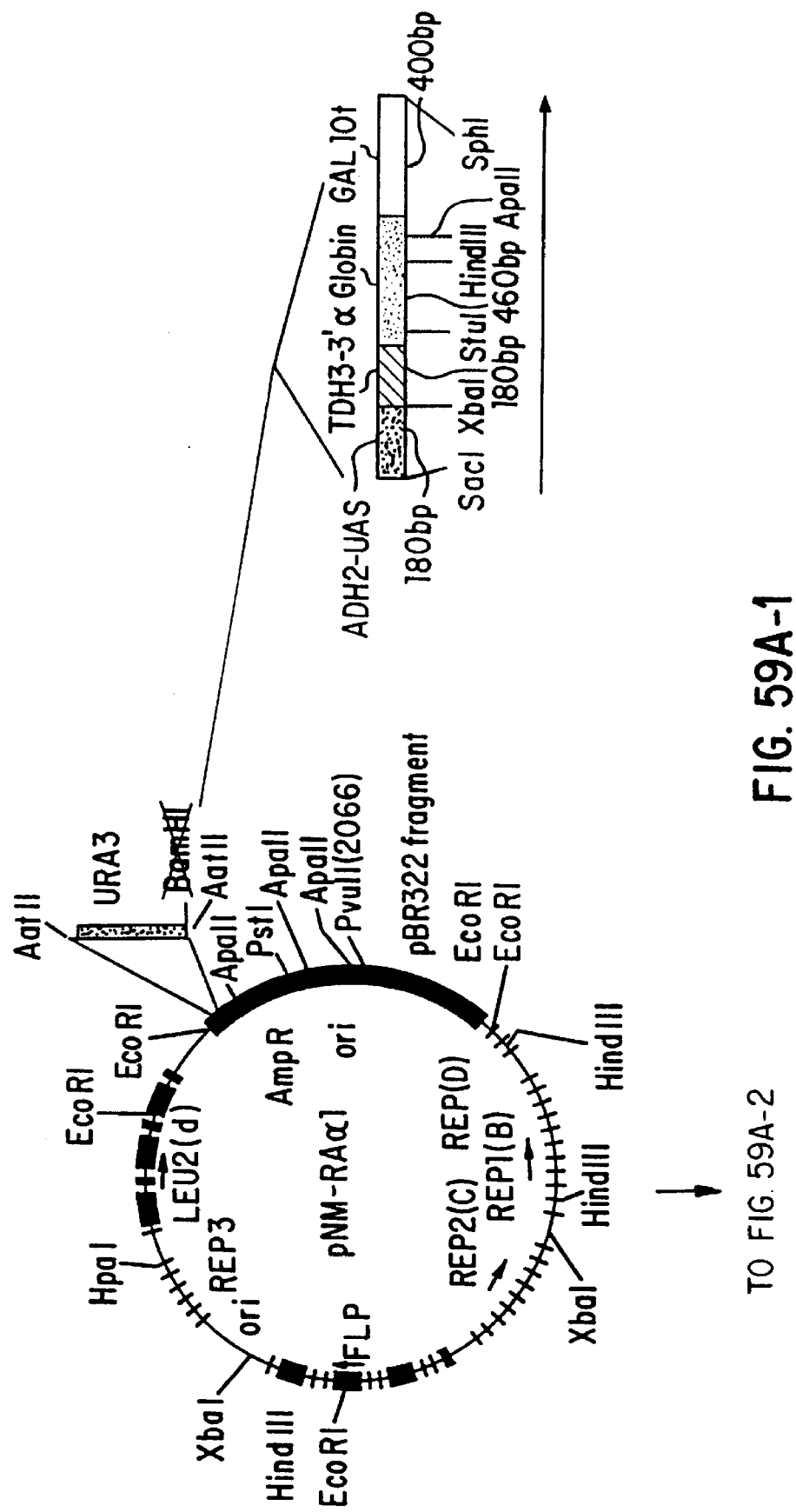
Figures 2, 59A:
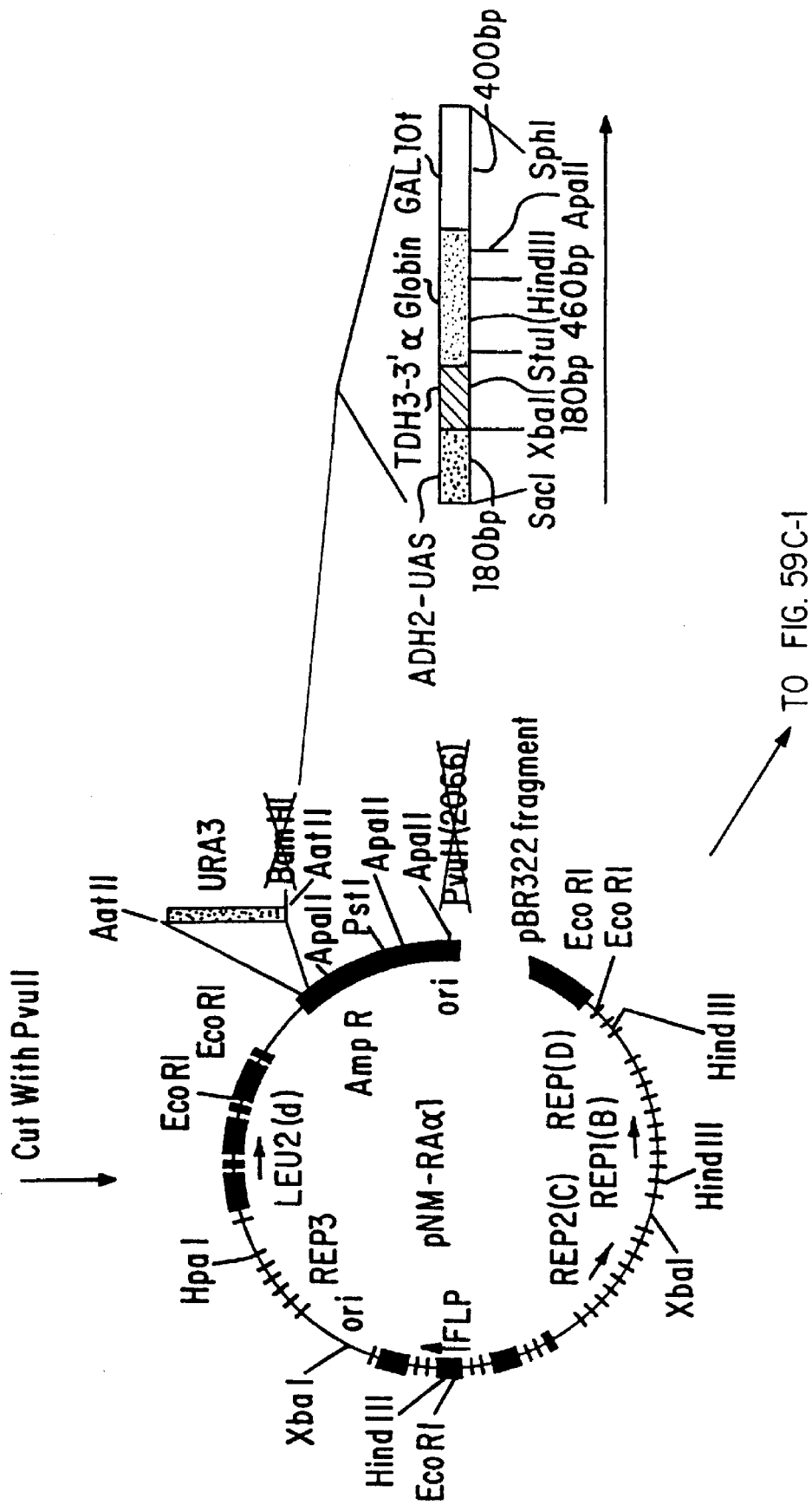
Figure 59B:
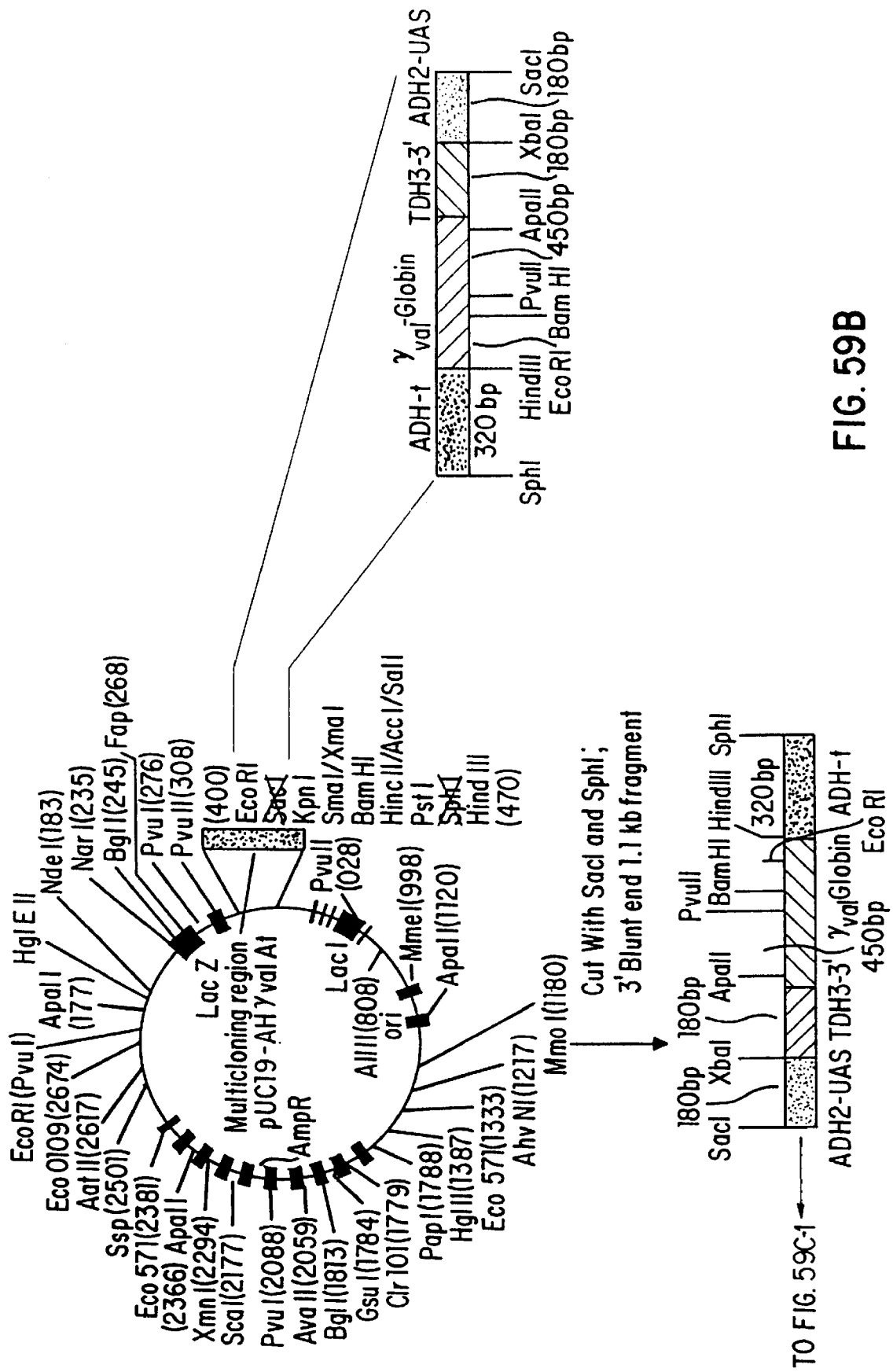
Figures 1, 59C:
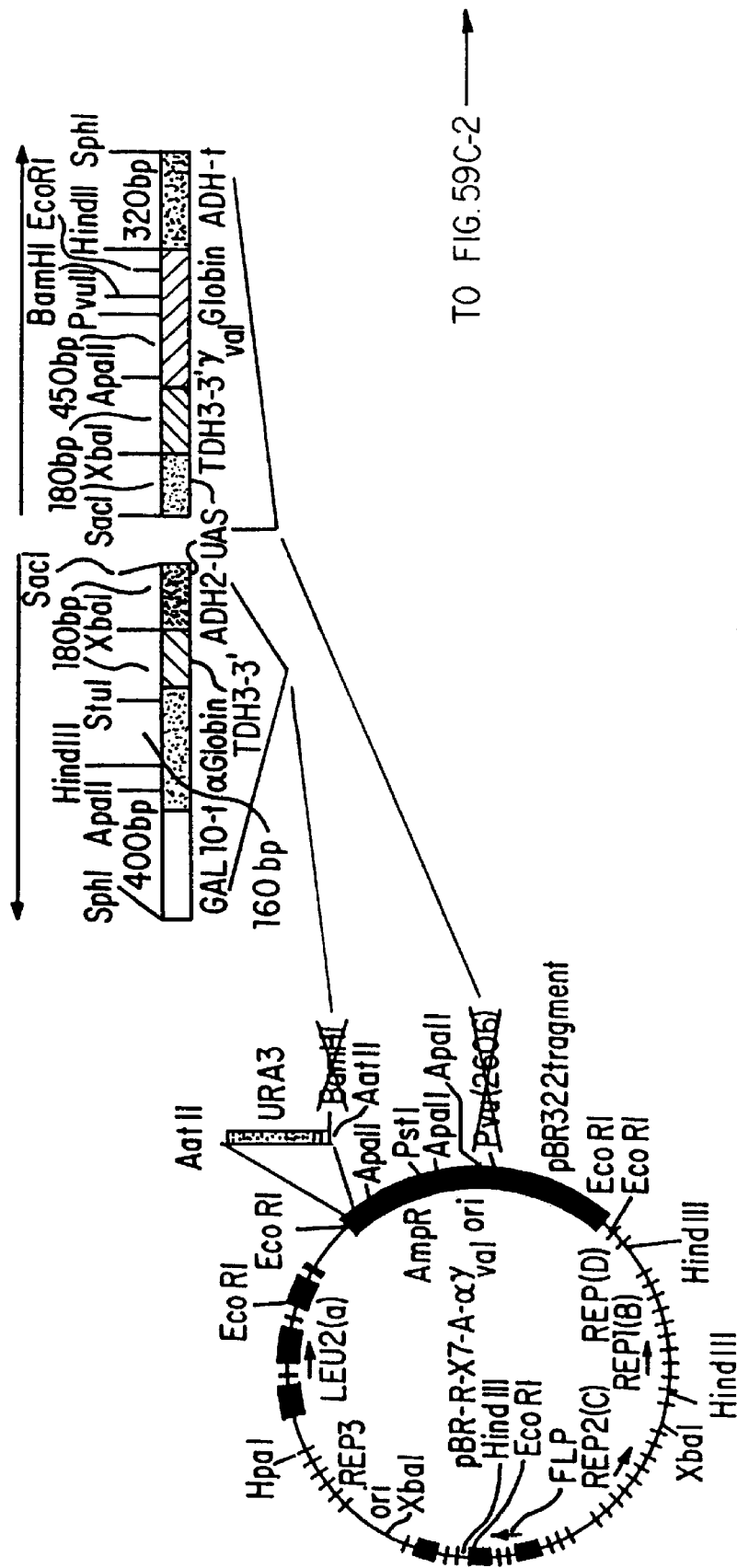
Figures 2, 59C:
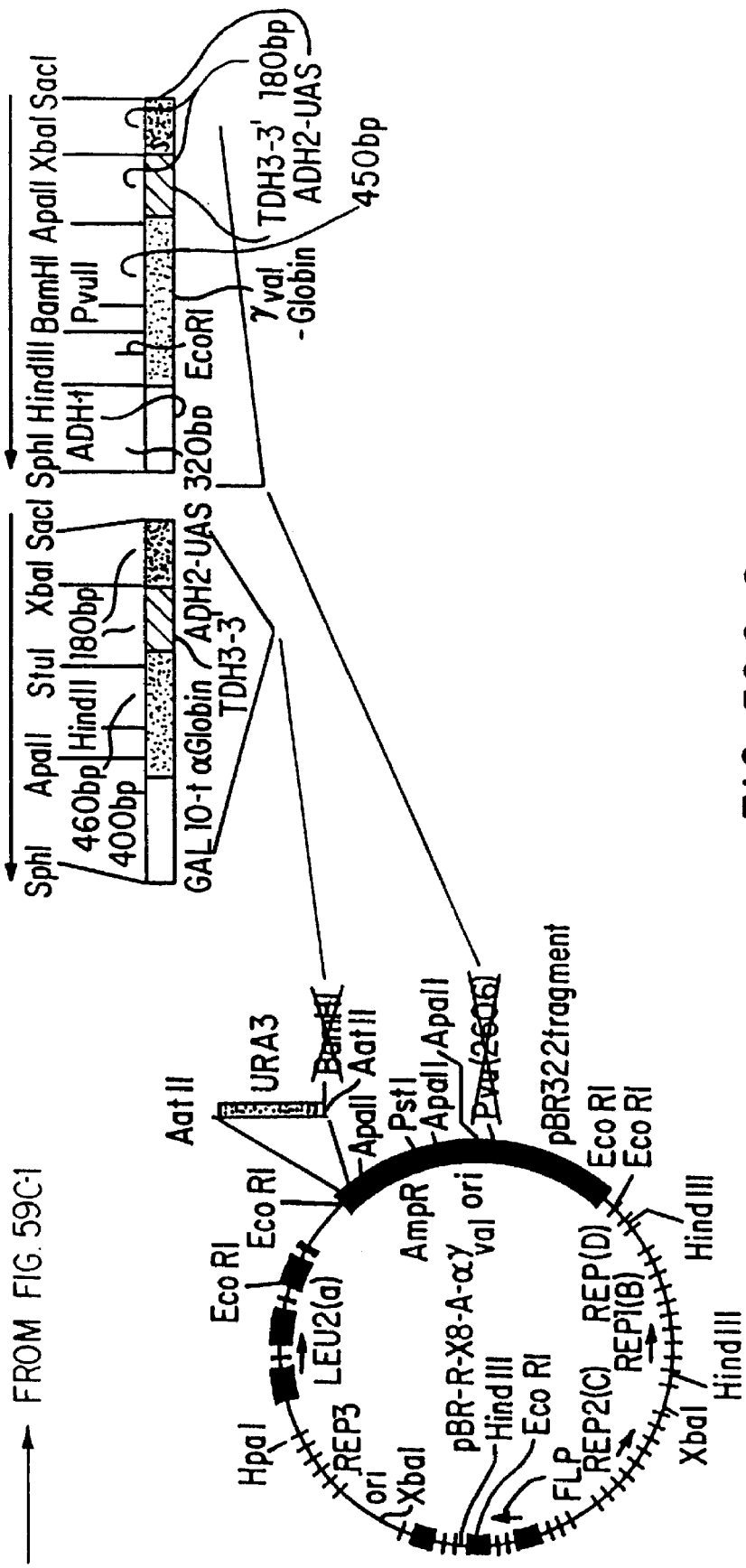

FIG. 57 shows the restriction map of PNM-R-A-α1.

FIG. 58 shows the strategy used for cloning the GHαGt cassette into the yeast vector carrying GHβAt expression cassette.

FIG. 59 shows the strategy used for cloning AHγ$_{val}$At into pNM-R-A-α1.

FIG. 60 shows the sequences of and restriction sites present on the 5' and 3' primers used for synthesizing the ADH2-UAS DNA fragment.

Figure 61:
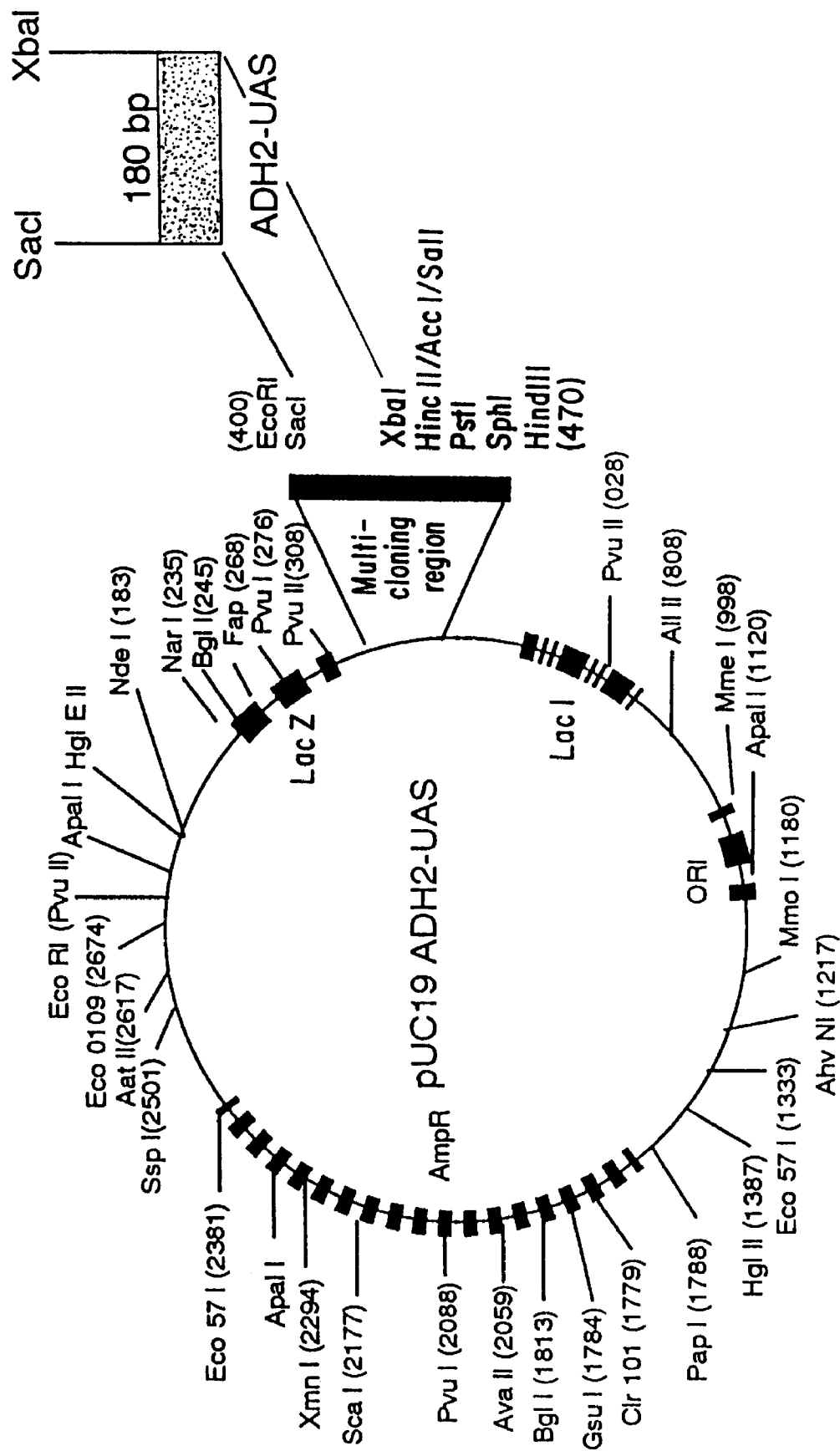

FIG. 61 shows the map of plasmid pUC19-ADH2-UAS.

FIG. 62 shows the sequences of and restriction sites present on the 5' primer, 5TDH3-3X and the 3' primer, ADH-t-SB.

FIG. 63 shows the sequences of and the restriction sites present on the 5' primer, 5TG-ApaL and the 3' primer, ADHSBS-3' used to synthesize gamma(val) globin DNA.

Figure 64:
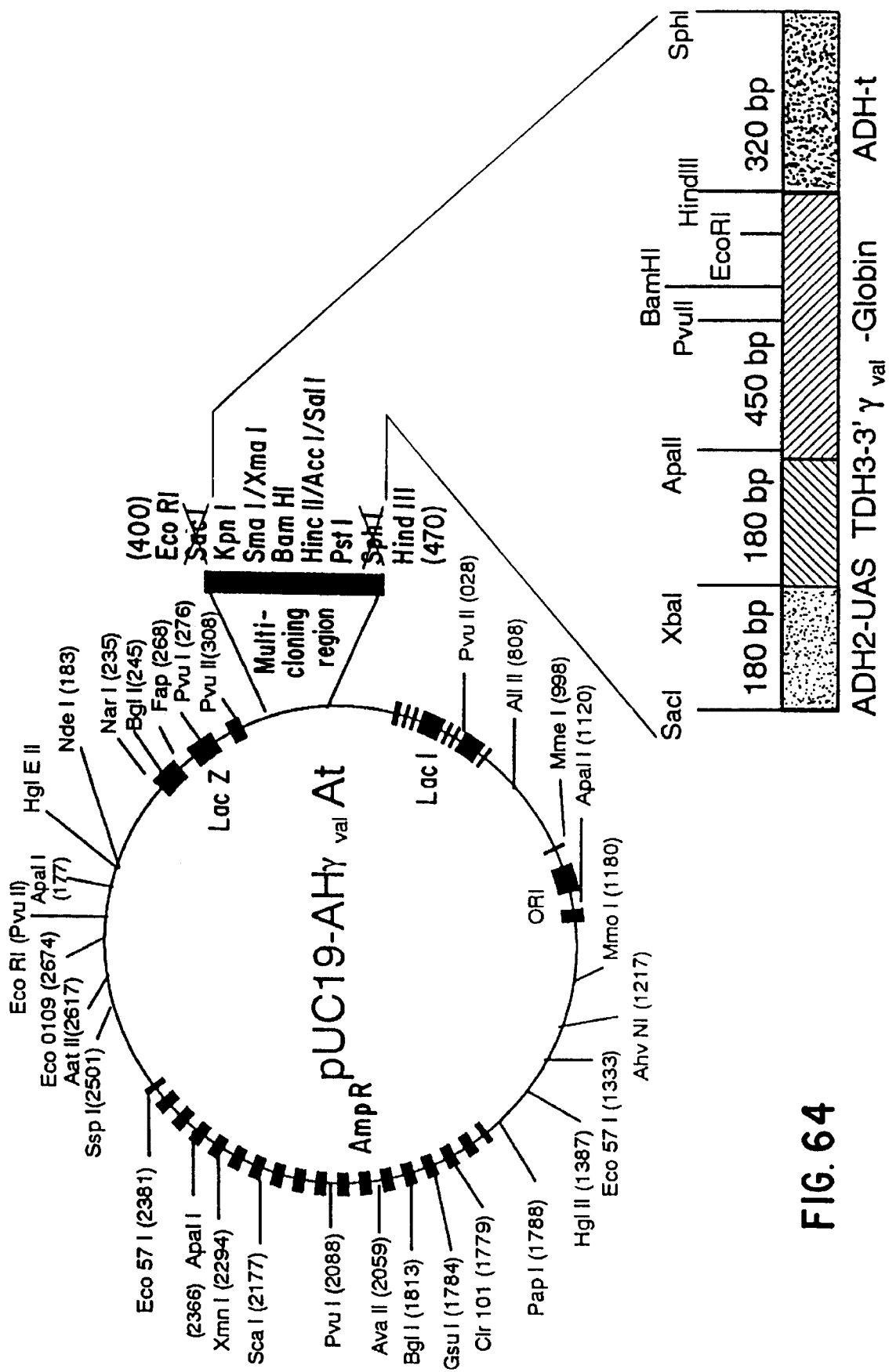

FIG. 64 shows the map of plasmid pPUC19-AHγ$_{val}$At.

5. DETAILED DESCRIPTION OF THE INVENTION

The invention is directed to a substantially pure mammalian globin chain or heme-binding fragment thereof. In a preferred aspect, the invention is directed to a substantially pure human globin chain or heme-binding fragment thereof. The globin chain may be an alpha-like globin chain or variant thereof or beta-like globin chain or variant thereof. The alpha-like globin chain may be selected from the group including but not limited to an embryonic zeta-globin chain and an adult alpha-globin chain. The beta-like globin chain may be selected from the group including but not limited to an embryonic epsilon-globin chain, a fetal gamma-globin chain, an adult delta-globin chain, and an adult beta-globin chain. In a specific embodiment, poly alpha-like globin or poly beta-like globin may result.

Alpha-like globin and beta-like globin may be mixed with a source of heme to obtain hemoglobin comprising alpha-like globin and beta-like globin. Gamma-globin may be mixed with a source of heme to obtain hemoglobin comprising gamma-globin. Hemoglobin produced by methods of the present invention may be used in applications requiring physiological oxygen carriers such as in blood substitute solutions, or in a plasma expander. In a specific embodiment, a poly-hemoglobin may result.

The invention is also directed to recombinant vectors capable of expressing a globin chain or heme binding fragment thereof in yeast. The recombinant vector may be capable of expressing two globin chains or heme-binding fragments thereof. The globin chains may in a specific embodiment comprise an alpha-like globin and a beta-like globin chain or variants thereof. The invention also relates to methods for expressing at least one globin chain in yeast. Expressed alpha-globin and beta-globin chains or variants thereof may be combined with a source of heme to produce hemoglobin or a variant thereof. The invention also relates to methods for expressing hemoglobin in yeast where heme which is produced by the yeast or obtained from an exogenous source, is ligated to the globin to form functional hemoglobins in vivo.

5.1. ISOLATION AND CLONING OF GLOBIN

The nucleotide sequence of the genes encoding the human embryonic zeta-globin (SEQ ID NO:1), the human embryonic epsilon-globin, (SEQ ID NO:2) the human fetal gamma-globin (SEQ ID NO:3), the human adult delta globin (SEQ ID NO:4), the human adult alpha-globin (SEQ ID NO:5) and the human adult beta-globin (SEQ ID NO:6) chains and their derived amino acid sequences (SEQ ID NO:65–70 respectively) are depicted in FIGS. 1A–F respectively. These include but are not limited to nucleotide sequences comprising all or portions of the nucleotide sequence depicted in FIGS. 1A–F which are altered by the substitution of different codons that encode the same or a functionally equivalent amino acid residue thus producing a silent change as well as amino acid sequences comprising all or portions of the amino sequence depicted in FIGS. 1A, 1B, 1C, 1D, 1E, or 1F (SEQ ID NO: 1–6) which are altered by the substitution of functionally equivalent amino acid residues within the sequence thus producing a silent change and derivatives thereof which are modified or processed.

The genes encoding alpha-like globin and beta-like globin chains may be isolated from hemoglobin containing cells using procedures known in the art. The DNA encoding alpha-like globin and/or beta-like globin may be obtained by standard procedures known in the art from cloned DNA (e.g. a DNA "library"), by chemical synthesis, by cDNA cloning or by the cloning of genomic DNA, or fragments thereof, purified from for example human reticulocytes (see for example, Maniatis et al., 1989, Molecular Cloning: A Laboratory Manual, Cold Spring Harbor Laboratory, Cold Spring Harbor, N.Y.). DNA encoding alpha-like or beta-like globin DNA may also be obtained using polymerase chain reaction (PCR) technology (see for example Mullis et al., U.S. Pat. No. 4,800,159, 1989). Clones derived from genomic DNA may contain regulatory and intron DNA regions, in addition to coding regions; clones derived from cDNA will contain only exon sequences. Whatever the source, a globin gene should be molecularly cloned into a suitable vector for propagation of the gene.

In the molecular cloning of the gene from genomic DNA, DNA fragments are generated, some of which will encode the desired globin gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the globin may be accomplished in a number of ways. For example, if an amount of a globin gene or its specific RNA, or a fragment thereof, is available and can be purified and labeled, the generated DNA fragments may be screened by nucleic acid hybridization to the labelled probe (Benton and Davis, 1977, Science 196:180 and Grunstein and Hogness, 1975, Proc. Natl. Acad. Sci. U.S.A. 72:3961). Those DNA fragments with substantial homology to the probe will hybridize. If a purified globin-specific probe is unavailable, nucleic acid fractions enriched in globin sequences may be used as a probe, as an initial selection procedure. It is also possible to identify the appropriate fragment by restriction enzyme digestion(s) and comparison of fragment sizes with those expected according to a known restriction map if such is available. Further selection on the basis of the properties of the gene, or the physical or chemical properties of its expressed product, as described infra, can be employed after the initial selection.

The globin gene can also be identified by mRNA selection by nucleic acid hybridization followed by in vitro translation. In this procedure, fragments are used to isolate complementary mRNAs by hybridization. In vitro translation products of the isolated mRNAs identifies the mRNA, and therefore the complementary DNA fragments that contain the globin sequences.

Alternatives to isolating the globin genomic DNA include, but are not limited to, chemically synthesizing the gene sequence itself from the known sequence or making cDNA to the mRNA which encodes the globin gene.

The identified and isolated gene or cDNA can then be inserted into an appropriate cloning vector. A large number of vector-host systems known in the art may be used. Possible vectors include, but are not limited to, cosmids, plasmids or modified viruses, but the vector system must be compatible with the host cell used. Such vectors include, but are not limited to, bacteriophages such as lambda derivatives, or plasmids such as pBR322, pUC, PGEM1®, or Bluescript® plasmid derivatives. Recombinant molecules can be introduced into host cells via transformation, transfection, infection, electroporation, etc.

In an alternative embodiment, the gene may be identified and isolated after insertion into a suitable cloning vector, in a "shot gun" approach. Enrichment for a globin gene, for example, by size fractionation or subfractionation of cDNA, can be done before insertion into the cloning vector.

The globin gene is inserted into a cloning vector which can be used to transform, or infect appropriate host cells so that many copies of the gene sequences are generated. This can be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and globin gene may be modified by homopolymeric tailing.

In specific embodiments, transformation of host cells with recombinant DNA molecules that incorporate an isolated globin gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

After the globin-containing clone has been identified, grown, and harvested, its DNA insert may be characterized using procedures known in the art. The cloned DNA or cDNA corresponding to the globin gene can be analyzed by methods including but not limited to Southern hybridization (Southern, 1975, J. Mol. Biol. 98:503–517), restriction endonuclease mapping (Maniatis et al., 1989, Molecular Cloning, A Laboratory Manual, Cold Spring Harbor Laboratory, Cold Spring Harbor, N.Y.), and DNA sequence analysis. DNA sequence analysis can be performed by any techniques known in the art, including but not limited to chemical methods (Maxam and Gilbert, 1980, Meth. Enzymol. 65:499–560), enzymatic methods (see e.g. Innes, 1988, Proc. Natl. Acad. Sci. U.S.A. 85:9436; Tabor and Richardson, 1987, Proc. Natl. Acad. Sci. U.S.A. 84:4767; and Sanger et al., 1977, Proc. Natl. Acad. Sci. U.S.A. 74:5463), or the use of an automated DNA sequenator (see for example Martin et al., 1985, Biotechnology 3:911–915).

5.2. GLOBIN VARIANTS

The production and use of globin variants are also envisioned and within the scope of the present invention. The term "globin variant" as defined herein refers to a globin whose nucleotide sequence has been altered in such a fashion so as to result in the alteration of the structure or function of the globin, but so that the globin still remains functionally active as defined by the ability to reversibly bind to oxygen. The variant may be naturally occurring or non-naturally occurring. Categories of hemoglobin variants include but are not limited to variants which autopolymerize; variants in which the tetramer does not dissociate under physiological conditions in vivo; variants with lowered intrinsic oxygen affinity, i.e. a hemoglobin having a $P_{50}$ of at least about 10 mm Hg under physiological conditions; variants that are stable in alkali; variants that are stable in acid; variants which do not autoxidize; variants which have a lowered binding affinity to haptoglobin; variants with an increased intrinsic oxygen affinity, i.e. a hemoglobin having a $P_{50}$ of at most about 1 mm Hg under physiological conditions.

As discussed in Section 2.1.3. supra, globin variants which autopolymerize include but are not limited to Hb Porto Alegre (beta-9 or gamma-9 serine is replaced with cysteine), Hb Mississippi (beta-44 serine is replaced with cysteine), or Hb Ta-Li (beta-83 glycine is replaced with cysteine).

As also disclosed in Section 2.1.3., supra, an example of a variant in which the tetramer does not dissociate includes but is not limited to Hb Rainier (beta-145 tyrosine is replaced by cysteine).

Alkali stable hemoglobin variants are those in which the dimers do not dissociate into monomers in the presence of alkali. An example is Motown/Hacettepe (beta-127 or gamma-127 glutamine is replaced with glutamic acid). HbF may also be considered an alkali stable variant. It has been shown that the alpha-104 cysteine causes the hemoglobin to be susceptible to alkali denaturation (Perutz, 1974, Nature 247:371). Examples of non-naturally occurring alkali stable variant include but are not limited to variants in which serine replaces either the alpha-104 or zeta-104 cysteine.

Examples of variants which have a lowered oxygen affinity include but are not limited to Hb Chico (beta-66 or gamma-66 lysine is replaced by threonine); Hb Raleigh (beta-1 valine is replaced by alanine); Hb Titusville (alpha-94 or zeta-94 aspartate to asparagine); Hb Beth Israel (beta-102 asparagine is replaced with serine); and Hb Kansas (beta-102 asparagine to threonine).

It has additionally been shown that bovine hemoglobin has a lower oxygen affinity than human HbA (Perutz, 1971, Nature 247:341). This is thought to be due the N-terminal amino acid sequence of beta-globin, Met Leu Thr Ala Glu Glu. Therefore, one hemoglobin variant may have an N-terminal beta-globin sequence of Met Leu Thr Ala Glu Glu. Therefore, one hemoglobin variant may comprise (a) a variant globin chain or heme-binding fragment thereof which (i) is substantially homologous to a mammalian adult beta-globin chain, and (ii) comprises an N-terminal beta-globin sequence of Met Leu Thr Ala Glu Glu; (b) a mammalian alpha-like globin chain or heme binding fragment thereof; and (c) heme, and which variant has the ability to bind to oxygen at a low oxygen affinity and is free of erythrocyte membrane components and *E. coli* endotoxins. The term "substantially homologous" as used herein refers to the ability of a DNA sequence encoding a first globin chain to hybridize to a DNA sequence encoding a second globin chain under stringent conditions, for example, at about 0.1× SSC at a temperature of about 65° C. For example, if a globin variant is substantially homologous to an adult beta-globin chain, a DNA sequence encoding the globin variant is capable of hybridizing to a DNA sequence encoding the adult beta-globin chain under stringent conditions.

In yet another embodiment, the hemoglobin variant may be a a variant having an increased oxygen affinity, a high oxygen affinity variant. Examples include but are not limited to HbA Deer Lodge (beta-2 histidine is replaced with arginine) (Labossiere et al., 1972, Clin. Biochem. 5: 46–50); HbA Abruzzo (beta-143 histidine is replaced with arginine) (Tentori et al., 1972, Clin. Chim. Acta 38: 258–262); and HbA McKees Rocks (beta-145 tyrosine is replaced with a termination sequence) (Winslow et al., 1976, J. Clin. Invest. 57: 772–781).

Acid stable hemoglobin variants may include those that replace the histidine at the alpha-103 position with an amino acid that is not ionized in acid (Perutz, 1974, Nature 247:341). Examples of such amino acids include serine, threonine, leucine, and alanine.

Haptoglobin nonbinding variants are those with variation in the alpha-121–127 sequence. This sequence has been shown to be involved in the binding of haptoglobin (McCormick and Atorssi, 1990, J. Prot. Chem. 9:735).

In another embodiment, variants may be contructed in which there are mutations at more than one position on a globin chain. For example, the globin chain may have the structure of an autopolymerizing variant and a low oxygen affinity variant. For example, a variant may be constructed which combines the mutations of HbF Titusville and replacement of the zeta-104 cysteine residue with serine. This may result in the formation of a tetramer with the desirable properties of lowered oxygen affinity and stability in alkali.

In yet another embodiment of the invention, variants may be constructed in which there are mutations in both the alpha and beta chains of the globin. One variant may be constructed which combines the mutations of Hb Porto Alegre, Hb Rainier and Hb Titusville and may result in the formation of an alpha$_2$beta$_2$ tetramer with desirable properties of autopolymerization, tetramer stabilization, and lowered oxygen affinity. The tetramer may be formed by a double mutant of the beta-globin and a single mutant of the alpha-globin. Another variant may be constructed which combines the mutations of Hb Porto Alegre, Hb Rainier, Hb Chico, and Hb Titusville. This variant may combine four mutations, three in the beta-globin and one in the alpha-globin. Such a combination may be used to optimize oxygen affinity, cooperativity, and alkaline Bohr effect to obtain a globin that is well suited as a physiological oxygen carrier in an oxygen delivery system.

The globin variants may be produced by various methods known in the art. The manipulations which result in their production can occur at the gene or protein level. The globin may be altered at the gene level by site-specific mutagenesis using procedures known in the art. One approach which may be taken involves the use of synthetic oligonucleotides to construct variant globins with base substitutions. In one embodiment, a short oligonucleotide containing the mutation is synthesized and annealed to the single-stranded form of the wild-type globin gene (Zoller and Smith, 1984, DNA 3:479–488). The resulting short heteroduplex can serve as primer for second strand synthesis by DNA polymerase. At the 5' end, a single-stranded nick is formed which is closed by DNA ligase. In another embodiment, two complementary oligonucleotides are synthesized, each containing the mutant sequence. The duplex that forms after annealing these complementary oligonucleotides, can be joined to a larger DNA molecule by DNA ligase provided that the ends of both molecules have complementary single-stranded "sticky" ends. Another approach which may be taken involves introducing a small single-stranded gap in the DNA molecule followed by mis-repair DNA synthesis i.e., the misincorporation of a non-complementary nucleotide in the gap (Botstein and Shortle, 1985, Science 229:1193). The incorporation of a thiol nucleotide into the gap may minimize the excision of the non-complementary nucleotide. Alternatively, a globin variant may be prepared by chemically synthesizing the DNA encoding the globin variant using procedures known in the art (see, for example, Froehler, 1986, Nucl. Acids Res. 14:5399–5407 and Caruthers et al., 1982, Genetic Engineering, J. K. Setlow and A. Hollaender eds., Plenum Press, New York, vol. 4, pp. 1–17). In a preferred embodiment, fragments of the variant globin are chemically synthesized and these fragments are subsequently ligated together. The resulting variant globin strands may be amplified using procedures known in the art, e.g. PCR technology and subsequently inserted into a cloning vector as described in Section 5.1., supra. In a specific embodiment, site-specific mutants may be created by introducing mismatches into the oligonucleotides used to prime the PCR amplification (Jones and Howard, 1990, Biotechniques 8:178–180).

Manipulations of the globin sequence may be carried out at the protein level. Any of numerous chemical modifications may be carried out by known techniques including but not limited to specific chemical cleavage by cyanogen bromide, trypsin, chymotrypsin, papain, V8 protease, $NaBH_4$, acetylation, formylation, oxidation, reduction, etc. Alternatively, the variant globin protein may be chemically synthesized using procedures known in the art, such as commercially available peptide synthesizers and the like. Such standard techniques of polypeptide synthesis can be found described in such publications as Merrifield, 1963, J. Chem. Soc. 85:2149–2154 and Hunkapillar et al., 1984, Nature (London) 310:105–111).

5.3. EXPRESSION OF HEMOGLOBIN

The nucleotide sequence coding for a globin chain is inserted into an appropriate expression vector, i.e. a vector which contains the necessary elements for the transcription and translation of the inserted protein-coding sequence. A variety of host-vector systems may be utilized to express the DNA sequence encoding the globin chain. These include but are not limited to mammalian cell systems infected with virus (e.g. vaccinia virus, adenovirus, etc.); insect cell systems infected with virus (e.g. baculovirus); yeast containing yeast vectors; and bacteria transformed with plasmid DNA, cosmid DNA, or bacteriophage DNA. In a preferred aspect, the host cell is a yeast cell.

5.3.1. EXPRESSION OF HEMOGLOBIN IN YEAST

Special considerations however have to be taken into account when expressing globin chains in yeast. Different signals regulating the expression of sequences encoding globin chains in yeast are required than when expressing such sequences in procaryotic systems or mammalian systems. For example, a yeast replication origin is required in a recombinant DNA vector capable of expressing a globin sequence in order for there to be replication of such a vector and thus significant expression. The nucleotide sequence coding for the alpha-like and/or beta-like chain of globin is inserted into a vector which may be expressed in yeast. In one embodiment, one DNA sequence encoding one globin chain or variant thereof is inserted into the recombinant DNA vector. In another embodiment, one DNA sequence encoding two globin chains or variants thereof may be inserted into the recombinant DNA vector. In yet another embodiment, two DNA sequences, each encoding one globin chain or variant thereof is inserted into the recombinant DNA vector. In a specific embodiment, one DNA sequence encodes an alpha-like globin chain or variant thereof and the second DNA sequence encodes a beta-like globin chain or variant thereof.

In a further embodiment, the yeast cell is a member of the species *Saccharomyces cerevisiae*. Such a vector comprises in addition to the DNA sequence encoding the globin: (a) a yeast transcriptional promoter which promotes the transcription of the DNA sequence encoding the globin chain; (b) a DNA sequence encoding a yeast selectable marker or functionally active portion thereof; and (c) a yeast replication origin or functionally active portion thereof.

The first component of the vector, a yeast transcriptional promoter comprises two components: (a) a transcriptional regulatory region which contains a structural gene distal region, or activator sequence which provides for regulated (inducible) or constitutive transcription and (b) the transcriptional initiation region which includes the transcription initiation site, the "TATA" sequence, capping sequence as appropriate, and an RNA polymerase binding sequence, which includes nucleotides upstream from the initiation site for directing the initiation of synthesis of the messenger RNA. In a preferred embodiment, the activator sequence is an upstream activator sequence. The transcriptional regulatory region will preferably be at least 100 base pairs (bp) and will not exceed 3000 base pairs. The regulatory region may begin at least about 200 bp from the initiation codon, usually at least about 300 bp and may begin at 400 bp or farther upstream from the initiation codon. The transcriptional initiation region will be at least about 150 bp, more usually at least about 200 bp, usually not more than about 600 bp, and preferably about 400 bp. The sequence may extend in the downstream direction of transcription from about bp −10 to about bp −25 (relative to transcription initiation at +1).

In one embodiment, the yeast transcriptional promoter is an inducible promoter. Inducible promoters may be unidirectional or bidirectional. Unidirectional inducible promoters in a preferred embodiment are located upstream from the DNA sequence encoding the globin chain. Unidirectional inducible promoters may include but are not limited to promoters which are regulated by galactose (e.g. UDP-galactose epimerase (GAL10), galactokinase (GAL1)), glucose (e.g. alcohol dehydrogenase II (ADH2)), and phosphate (e.g. acid phosphatase (PHO5)). In another embodiment, the inducible promoter may be a bidirectional promoter. A bidirectional promoter may be located upstream (5' of the ATG startcodon) from the DNA sequence encoding a globin chain on the plus strand at one of its ends and upstream from the DNA sequence encoding a globin chain on the minus strand at its other end; and thereby, control the transcription of both. In a specific embodiment, such a bidirectional promoter is GAL1-10.

The promoter may also be a constitutive promoter. In a specific embodiment, the constitutive promoter is a promoter of glyceraldehyde-3-phosphate dehydrogenase III (TDH3) transcription and is herein after referred to as the TDH3 promoter. Other constitutive promoters include but are not limited to glyceraldehyde-3-phosphate dehydrogenase II (TDH2), glyceraldehyde-3-phosphate dehydrogenase I (TDH1), alcohol dehydrogenase I (ADH1), phosphoglycerate kinase (PGK), pyruvate kinase (PYK), enolase (ENO), and triose phosphate isomerase (TPI). Such promoter sequences will be at least about 200 bp and will not exceed about 5000 base pairs.

In another embodiment, the promoter can be a hybrid promoter, in which the sequence containing the transcriptional regulatory region is obtained from one source and the sequence containing the transcription initiation region is obtained from a second source. In one embodiment, the sequence containing the transcriptional regulatory region is an upstream activating sequence of a yeast inducible promoter. The inducible promoter can be a unidirectional or a bidirectional promoter. The sequence containing the transcriptional initiation region may be obtained from the transcriptional initiation region of a constitutive promoter. In a specific embodiment, the hybrid promoter comprises a transcriptional regulatory region which is the upstream activation sequence of the GAL10 promoter and a transcription initiation region which contains the transcription initiation region of the TDH3 promoter. In another specific embodiment, the hybrid promoter can regulate the expression of two separate DNA sequences in opposite orientations if the hybrid promoter comprises an upstream activating sequence with transcription initiation sites located on both sides, thereby forming a bidirectional promoter. In a very specific embodiment, a GAL1-10 upstream activating sequence may be flanked on either side by the initiation region of the TDH3 promoter. DNA encoding a globin chain is located downstream from each TDH3 sequence. In another embodiment, the ADH2 UAS may be used in place of the GAL1-10 UAS. In still other embodiments, the transcriptional initiation region of the TDH3 promoter can be substituted by TDH1, TDH2, PGK, ENO, TPI, CYC1, or PYK.

Another component of the recombinant DNA vector is a sequence encoding a yeast selectable marker. The recombinant DNA vector in one embodiment may contain more than one such sequence. A yeast selectable marker provides for selective pressure for survival of yeast cells expressing the marker. In a preferred aspect, the selectable marker complements a genetic defect in the host strain. For example, URA3 can be used as a selectable marker in a yeast strain which is deficient in the URA3 gene product. Such sequences may include but are not limited to the LEU2 gene, the URA3 gene, the HIS3 gene, the LYS2 gene, the HIS4 gene, the ADE8 gene, the CUP1 gene, and the TRP1 gene. Another example of such a sequence includes the leu2d gene which is a promoter defective LEU2 gene. In a preferred embodiment, the leu2d gene is inserted into a multicopy recombinant DNA vector. A yeast cell transformed by a vector comprising the LEU2 or leu2d gene may grow in leucine free media; a yeast cell transformed by a vector comprising the URA3 gene may grow in uracil free media; a yeast cell transformed by a vector comprising the LYS3 gene may grow in lysine free media, a yeast cell transformed by a vector comprising the HIS3 gene may grow in histidine free media, a yeast cell transformed by a vector comprising the ADE8 gene may grow in adenine free media, a yeast cell transformed by a vector comprising the HIS4 gene may grow in histidine free media, a yeast cell transformed by a vector comprising the CUP1 gene may grow in media containing levels of copper inhibitory to the host strain without plasmid; and a yeast cell transformed by a vector comprising the TRP1 gene may grow in tryptophan free media. The recombinant DNA vector may also comprise a DNA sequence encoding a functionally active portion of a yeast selectable marker. The term "functionally active portion" as defined herein is a portion of the sequence that encodes a portion of the marker which provides an effective amount of selective pressure for the survival of yeast cells expressing the portion of the marker.

The recombinant vector also comprises a yeast replication origin or functionally active portion of the replication origin which effects replication of the vector. Any replication origin useful in yeast may be employed which provides for efficient replication and maintenance (reviewed for example in Kingsman and Kingsman, U.S. Pat. No. 4,615,974, issued Oct. 7, 1986). Examples of such replication origins include but are not limited to the $2\mu$ plasmid replication system, or a functionally active portion thereof and autonomous replicating sequences (ARS). Examples of ARS include but are not limited to ARS1 or ARS3. The replication origins may be of high or low copy number, depending on the effect of the construct on the viability of the host. The vector may further comprise centromeric sequences (CEN) which may provide meiotic and mitotic stability. Examples of CEN sequences include but are not limited to CEN3, CEN4, and CEN11.

The expression vector may further comprise but does not always require a transcription termination sequence. A transcription termination sequence may include the necessary transcription signals for termination and polyadenylation and may be derived from any yeast sequence. In a specific embodiment, the transcription termination sequence is the alcohol dehydrogenase I (ADH1) termination sequence. Other termination sequences suitable for use include but are not limited to those of iso-1-cytochrome c (CYC1), UDP-glucose-4-epimerase (GAL10), phosphoglycerate kinase (PGK), acid phosphatase (PHO5), enolase (ENO), and triose phosphate isomerase (TPI). The transcription termination sequence is at least about 100 bp and should not exceed about 1500 bp. In a preferred embodiment, the transcription termination sequence ranges from about 150 bp to about 1200 bp.

The expression vectors of the present invention may be constructed using recombinant DNA procedures known in the art. Such procedures were disclosed in detail in Section 5.1., supra. Specific examples of yeast expression vectors and their construction, comprising sequences encoding adult beta-globin under the control of the hybrid promoter containing the GAL1-10 promoter, and the TDH3 promoter, are disclosed in Section 19. A specific example of a yeast expression vector and its construction, comprising sequences encoding the adult alpha-globin chain under the control of a hybrid promoter are disclosed in Section 7. A specific example of a yeast expression vector and its construction, comprising sequences encoding the gamma-globin chain under the control of the GAL10 inducible promoter is disclosed in Section 8. Specific examples of globin variants are disclosed in Section 11. A specific example of a yeast expression vector and its construction, comprising sequences encoding the zeta-globin chain under the control of a the GAL10 promoter is disclosed in Section 10. Specific examples of the expression of hemoglobin by coexpression of plasmids comprising sequences encoding alpha-like and beta-like globin are disclosed in Sections 12–18, 20–24, and 26–28. Specific examples of the construction and expression of globin variants are disclosed in Sections 11 and 25.

The expression vectors of the present invention may be propagated in yeast using procedures known in the art. The expression vectors may be propagated in yeast which may or may not be capable of producing heme. The yeast can be transformed with one or more of the expression vectors using procedures known in the art (e.g. the spheroplast method, (Hinnen et al., 1978, Proc. Natl. Acad. Sci. U.S.A. 75:1929–1933) or the lithium acetate method (Ito et al., 1983, J. Bact. 153:163–168)). Transformants may be selected by the presence of the marker (selectable) gene function in the transformant. For example, a leu2-yeast cell transformed with an expression vector comprising a LEU2 marker gene is selected by virtue of its ability to grow in leucine free media. The transformed yeast cells may be grown in media comprising a nitrogen and carbon source as well as essential vitamins, minerals, and trace elements (Hinnen et al., 1978, Proc. Natl. Acad. Sci. U.S.A. 75:1929–1933). If the vector comprises an inducible promoter, the media should also comprise the inducer.

If the expression vector comprises DNA sequences encoding both an alpha-like globin chain and beta-like globin chain or a beta-like globin chain (e.g., gamma-globin chain), hemoglobin may be expressed in the yeast cell transformed with the vector. In one embodiment, the heme is produced by the yeast and ligated to the globin to form functional hemoglobins in vivo. In another embodiment, the yeast cell may be deficient in components required for heme production, for example 5-aminolevulinic acid. Hemoglobin may still be expressed in such a cell if the required component is added.

The protein product of the expressed globin gene may be isolated and purified using standard methods including but not limited to chromatography (e.g., ion exchange, affinity, and sizing column chromatography), centrifugation, differential solubility, or by any other standard technique for the purification of proteins. If one globin chain is expressed, the expressed globin chain may be combined with another globin chain and a source of heme to form hemoglobin. If hemoglobin is expressed in the yeast cell, no further steps are necessary.

The expressed gene and its product may be analyzed at the genomic level or the protein level using procedures known in the art. For example, hemoglobin gene expression may be analyzed by Southern or Northern hybridization. The expressed hemoglobin protein may for example be analyzed by Western Blot procedures known in the art and also described herein in Section 6.6., infra.

5.4. USES FOR EXPRESSED RECOMBINANT HEMOGLOBINS

Hemoglobin of large quantity and high purity may be obtained using the methods of the present invention. Examples of hemoglobin which may be obtained include but are not limited to HbA (alpha$_2$beta$_2$), HbA$_2$ (alpha$_2$delta$_2$), HbF (alpha$_2$gamma$_2$), HbBarts (gamma$_4$), HbH (beta$_4$), and Hb Portland I (zeta$_2$gamma$_2$), Hb Portland II (zeta$_2$beta$_2$), Hb Portland III (zeta$_2$delta$_2$) Hb Gower I (zeta$_2$epsilon$_2$), and Hb Gower II (alpha$_2$epsilon$_2$). The hemoglobin will be free of cellular material and other contaminants. Such hemoglobins and especially hemoglobin variants which autopolymerize, variants which prevent the dissociation of the tetramer, variants with lowered intrinsic oxygen affinity, variants that are stable in alkali, variants that are stable in acid, variants which do not autooxidize, and/or variants which do not bind to haptoglobin through the use of variant alpha and/or beta-globin genes described in Section 5.2, supra are of value for use in blood substitutes.

In another embodiment, alpha-like and/or beta-like globin may be chemically modified using procedures known in the art to increase tetramer stability and/or lower oxygen affinity (see Section 2.1.2., supra for examples of such procedures). A wild-type or variant alpha-like or beta-like globin may be modified. Such chemically modified hemoglobins may also be used in blood substitutes.

The hemoglobin used in the present invention is The pharmaceutical carriers may be such physiologically compatible buffers as Hank's or Ringer's solution, physiological saline, a mixture consisting of saline and glucose, and heparinized sodium-citrate-citric acid-dextrose solution. The hemoglobin produced by the methods of the present invention can be mixed with colloidal-like plasma substitutes and plasma expanders such as linear polysaccharides (e.g. dextran), hydroxyethyl starch, balanced fluid gelatin, and other plasma proteins. Additionally, the hemoglobin may be mixed with water soluble, physiologically acceptable, polymeric plasma substitutes, examples of which include polyvinyl alcohol, poly(ethylene oxide), polyvinylpyrrolidone, and ethylene oxide-polypropylene glycol condensates. Techniques and formulations for administering the compositions comprising the hemoglobin generally may be found in *Remington's Pharmaceutical Sciences*, Meade Publishing Col., Easton, Pa, latest edition.

The following examples are presented by way of illustration not by way of limitation.

6. EXAMPLE 1

EXPRESSION OF NATURAL BETA-GLOBIN IN A YEAST EXPRESSION VECTOR CONTAINING GAL10 PROMOTER AND ADH1 TERMINATOR

The beta-globin gene from plasmid pSPβC was modified and cloned into the yeast expression vector, YEp51. ADH1-transcription termination sequences were placed at the end of the beta-globin gene in this plasmid. The modified plasmid was called YEp51T/NAT (for the natural beta-globin gene). Yeast strain Sc340 was transformed with plasmids YEp51T/NAT and YEp51 (control). Total RNA was isolated from yeast strain Sc340 transformed with YEp51 (340g2C), YEp51T/NAT (340g2B). Quantitation of RNA by scanning the autoradiograph showed that mRNA for the natural beta-globin is around 3.0% of total yeast RNA. Western blot analysis indicated that natural beta-globin was expressed.

6.1. MATERIALS

The restriction enzymes, Klenow enzyme and T4-DNA ligase were obtained from New England Biolabs (Biolabs), Bethesda Research Laboratories (BRL) or Boerhinger Mannheim (BM). All enzymes were used according to the suppliers specifications. Plasmid DNA was isolated from a one liter culture of the transformed cells and purified by CsCl gradient centrifugation.

6.2. CLONING OF THE BETA-GLOBIN GENE INTO THE YEAST EXPRESSION VECTOR YEp51

Figure 2:
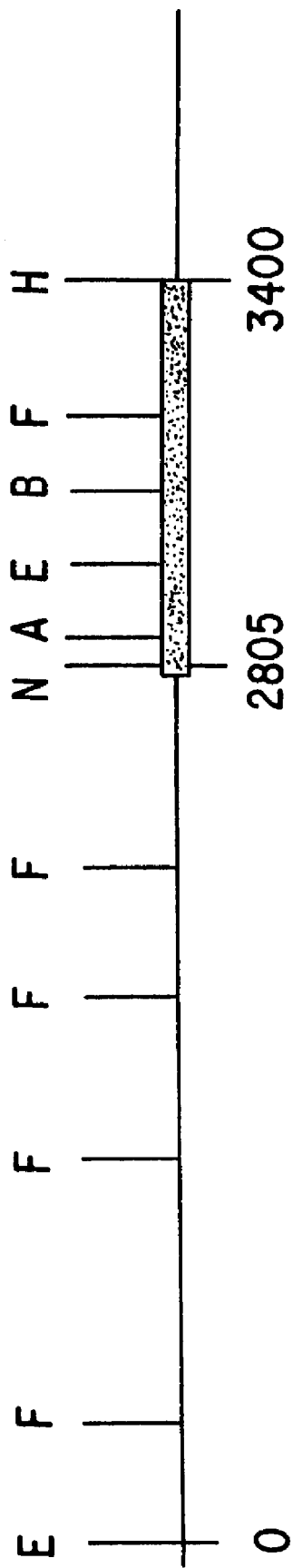

The general procedure used to clone the beta-globin gene into the yeast expression vector YEp51 is shown in FIG. 3A. The plasmid pSPβC (see FIG. 2 for restriction map of pSBβC) was digested with NcoI and HindIII. Digestion with this combination of enzymes generated two fragments, a 600 base pair DNA containing the beta-globin gene and a 2700 bp fragment from the plasmid. The 600 bp fragment was isolated from a 0.6% agarose gel. After the band was excised from the gel, the DNA was electroeluted, and ethanol precipitated. The precipitated DNA was spun in an Eppendorf Centrifuge, the supernatant was removed and the DNA pellet was dried under vacuum.

The 600 bp fragment was modified by adapter addition before cloning into the plasmid YEp51. The DNA fragment carrying the beta-globin gene isolated from pSPBC was NcoI compatible at the 5'-end while the 3'-end was HindIII compatible. These ends had to be modified so that they could be compatible with the restriction sites present in YEp51. To modify the 5'-end of the isolated fragment, a synthetic adapter was used. This adapter had a NcoI compatible end at its 3'-end and a SalI compatible end at its 5'-end (see FIG. 2). The 3'-end of the isolated fragment did not receive any adapter, as the HindIII site was compatible with the HindIII site introduced into the YEp51.

The recipient plasmid YEp51was cleaved with SalI and HindIII restriction enzymes. To insert the isolated fragment containing the beta-globin gene, a three-way ligation was set up (see FIG. 3). The ligation reaction was carried out according to the standard ligation procedures (Maniatis et al., 1989, Molecular Cloning, A Laboratory Manual, Cold Spring Harbor Laboratory, Cold Spring Harbor, N.Y.). The ligation mixture was transformed into the E. coli HB101 cells using standard transformation procedure. Cells were spread on plates containing LB-media with 100 mg/L ampicillin. Plates were incubated overnight at 37° C. Forty eight colonies from the ampicillin plates were picked and a 5 ml culture was inoculated with individual transformants. Cultures were grown overnight at 37° C. with vigorous shaking. The plasmid DNA was isolated from 1.5 ml of the overnight culture using quick plasmid isolation procedure. The plasmid from each transformant was digested with EcoRI to confirm the presence of a DNA fragment containing natural beta-globin gene. The plasmid carrying the natural beta-globin gene was called YEpWB51/NAT. The map of the plasmid YEpWB51/NAT is shown in FIG. 4.

6.3. CLONING OF THE ADH1-TERMINATOR SEQUENCES INTO YEpWB51/NAT

Figure 5:
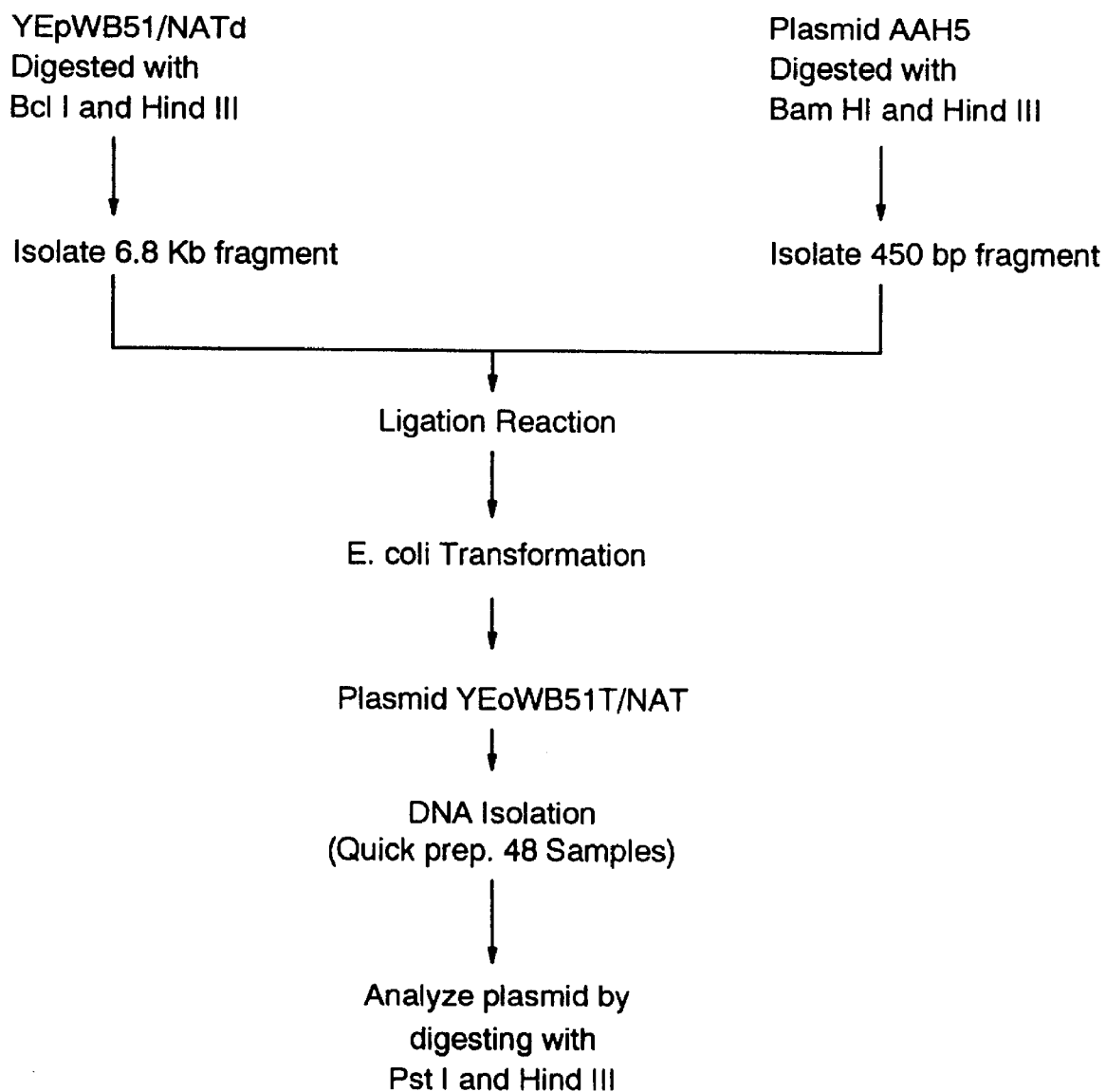
FIG. 5 shows the strategy for cloning ADH1-terminator into YEpWB51/NAT.

The strategy used to insert ADH1 terminator sequences into YEpWB51/NAT is shown in FIG. 5. The plasmids YEpWB51/NATd (d=dam and dcm, i.e. methylation minus) was digested with restriction enzymes BclI and HindIII. After the digestion, a 6.8 kb DNA fragment containing the beta-globin gene and vector was isolated from a 0.6% agarose gel (in 1× TBE, 0.1M Tris, pH 8.0, 0.09M boric acid, 1 mM EDTA). DNA was electroeluted from the gel slice and precipitated with ethanol at −20° C. The precipitated DNA was spun in an Eppendorf Centrifuge for 15 min and the pellet was dried under vacuum. The DNA was suspended in 20 μl $H_2O$.

The ADH1-transcription termination sequences were isolated from plasmid AAH5 (Ammerer, G., 1983, Methods in Enzymology, 101, pp. 192–201). AAH5 was obtained from Dr. Ben Hall at the University of Washington, Seattle. The plasmid AAH5 was digested with BamHI and HindIII (see FIG. 6 for a map of plasmid AAH5). Digestion with this combination of enzymes generated three fragments. A 450 base pair (bp) DNA fragment containing the ADH1-transcription termination sequence was isolated from the 0.6% agarose gel. DNA was electroeluted from the gel slice and precipitated with ethanol at −20° C. The precipitated DNA was spun in an Eppendorf Centrifuge for 15 min and the pellet was dried under vacuum. The DNA was suspended in 20 μl $H_2O$.

The DNA fragment carrying the ADH1-transcription terminator isolated from AAH5 was BamHI compatible at the 3'-end while the 5'-end was HindIII compatible. These ends were compatible with the restriction sites present in YEpWB51/NAT.

Figure 7:
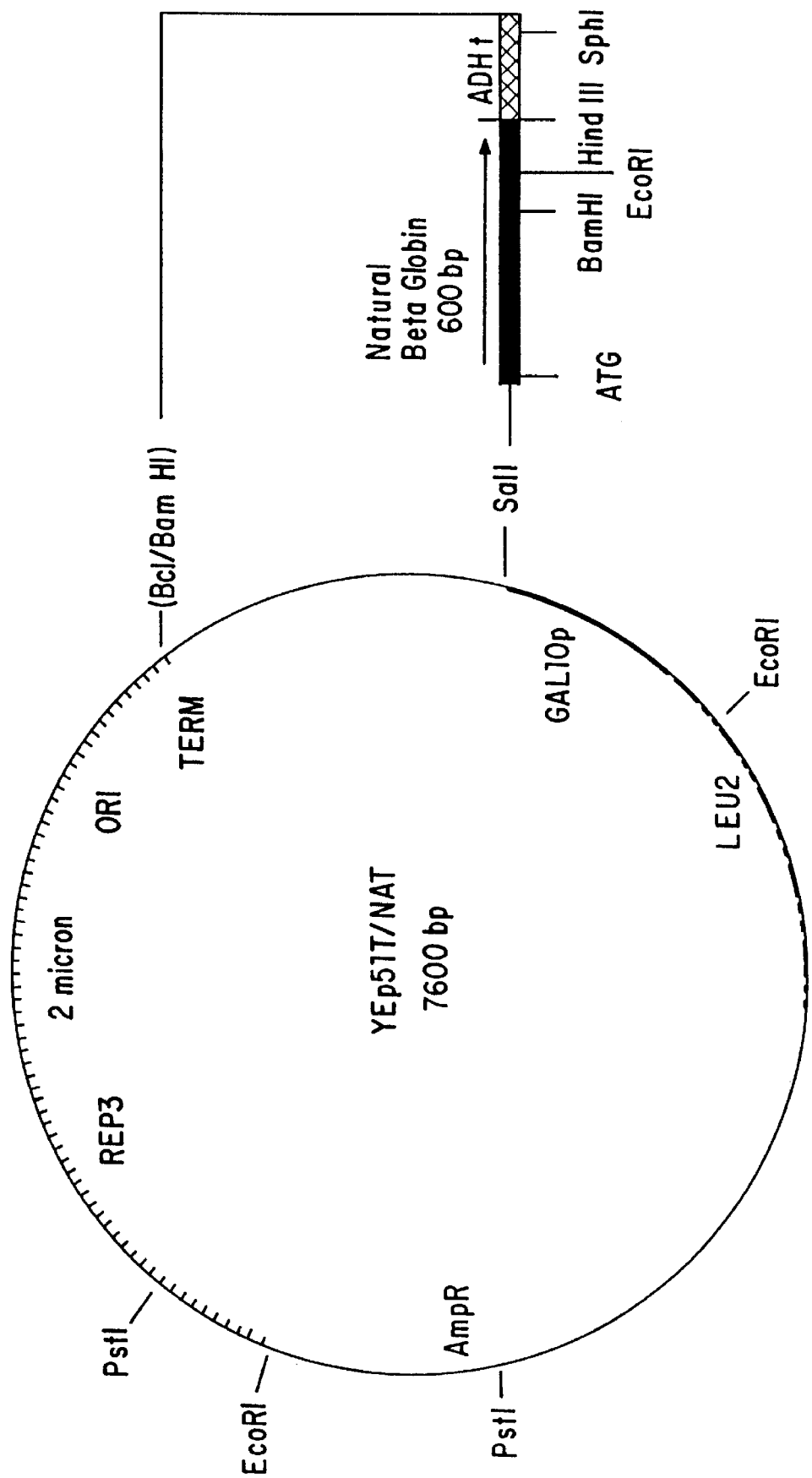
FIG. 7 shows the restriction map of the plasmid YEp51T/NAT.

The recipient plasmid YEpWB51/NATd was cleaved with BclI and HindIII restriction enzymes. As shown in FIG. 5, a two-way ligation was set up to insert the isolated fragment. The ligation mixture was transformed into E. coli HB101 cells using standard transformation procedures. Cells were spread on plates containing LB-media with 100 mg/L ampicillin. Plates were incubated overnight at 37° C. Twenty four colonies from the ampicillin plates were picked and a 5 ml culture was inoculated with individual transformants. Cultures were grown overnight at 37° C. with vigorous shaking. The plasmid DNA was isolated from 1.5 ml of the overnight culture using standard alkaline miniprep procedures (Maniatis et al., 1989, Molecular Cloning, A Laboratory Manual, Cold Spring Harbor Laboratory, Cold Spring Harbor, N.Y.). The plasmid from each transformant was digested with PstI and HindIII restriction enzyme to confirm the presence of a DNA fragment containing the ADH1-terminator. The plasmid carrying the natural beta-globin gene with the ADH1-terminator was called YEp51T/NAT and is shown in FIG. 7.

6.4. TRANSFORMATION OF YEAST STRAIN Sc340 WITH YEp51T/NAT

The yeast strain Sc340 was obtained from Dr. J. E. Hopper of Hershey Medical Center. The genotype of this strain is:

MATa ura3-52, leu2, ade1, his3:: $GAL10^{uas}$-GAL4-$URA3^+$, $MEL^+$.

Sc340 was transformed with the plasmids YEp51T/NAT and YEp51 (control). The spheroplast method of transformation was performed according to the published procedure (Hinnen et al., 1978, Proc. Natl. Acad. Sci. U.S.A. 75: 1929–1933). The transformants were selected by plating out on minimal media containing 0.67% Bacto yeast nitrogen base without amino acids, 2% glucose, 20 mg/L adenine sulfate, 20 mg/L histidine, and 20 mg/L uracil. The plates were incubated at 28° C. for three days and were examined for colony formation.

Colonies were picked from these plates following incubation and were precultured in yeast minimal media (0.67% yeast nitrogen base without amino acids) containing 0.5% glucose plus 20 mg/L each of adenine, uracil, and histidine. The overnight culture was then used to inoculate 1000 ml of the yeast minimal media containing 2% lactic acid, 3% glycerol and appropriate amino acids. The cultures were inoculated to $OD_{600}$ of 0.02. Cultures were grown at 30° C. until they reached $OD_{600}$ of 0.20 (usually after 48 hours). Induction was initiated by the addition of galactose to a final concentration of 2% in the media. After four hours, cultures were harvested by centrifugation and the pellet was washed with 150 mM NaCl. The pellet was divided into two parts. One part was used for RNA isolation and the other was kept at −70° C. for Western blot analysis.

6.5. QUANTITATION OF RNA FROM SC340 CELLS TRANSFORMED WITH PLASMIDS YEp51 YEp51T/NAT

RNA was isolated using published procedures (Meyhack et al., 1982, The EMBO Journal 1:675–680 or Carlson and Botstein, 1982, Cell 28:145). Yeast cells were washed with 150 mM NaCl and the pellet was resuspended in RNA buffer (0.5M NaCl, 0.2M Tris-HCl, pH 7.6, 0.1M EDTA and 1% SDS). Approximately 0.5 g of glass beads (0.45–0.5 mm) were added to the tubes. An equal volume of phenol mixture (phenol: chloroform: isoamyl alcohol, 25:24: 1, equilibrated with RNA buffer without SDS) was added. Yeast cells were broken by vortexing at maximum speed for 2.5 minutes and the sample was placed on ice for 3 minutes. The above step was repeated twice more. Equal volumes of RNA buffer and phenol mixture were added to the cells and tubes were centrifuged. Aqueous phase was transferred to a clean Corex tube and 2.5 volumes of ethanol were added to each tube. RNA was allowed to precipitate at −20° C. for 4 to 6 hours. RNA was pelleted by centrifugation and dried under vacuum. RNA pellet was suspended in sterile water.

Total RNA was denatured using the glyoxal method (Thomas, P., 1983, in "Methods in Enzymology", Colowhich, S. P. and Kaplan, N. O. eds. Vol. 100: pp. 255–266, Academic Press, New York). RNA was electrophoresed on 1.1% agarose gel in 10 mM $NaPO_4$ for approximately 4 hours at 75 volts (constant). After the electrophoresis was complete, RNA was transferred to Amersham Hybond-N paper (Thomas, P., 1983, in "Methods in Enzymology" Colowhick, S. P. and Kaplan, N. O. eds. Vol. 100: pp. 255–266, Academic Press, New York).

Total yeast RNA bound to the filter paper was hybridized to the radioactive labelled beta-globin DNA. Hybridizations were carried out at 42° C. overnight in 50% (v/v) formamide with 5× SSC (SSC: 3.0M NaCl, 0.3M Na citrate, pH 7.5); 50 mM $NaPO_4$, pH 6.5; 250 μg/ml salmon sperm DNA; and 1× Denhardt's solution; (Denhardt's solution: 0.02% Ficoll, 0.02% polyvinylcarbonate, and 0.02% BSA, fraction V). The CYH2 mRNA which codes for yeast ribosomal protein L19 was used as control. The probe was plasmid mp10CYH22 which carries the yeast CYH2 gene. After the hybridizations, filters were washed three times at room temperature in 2× SSC and 0.1% SDS and four times at 50° C. in 0.1× SSC and 0.1% SDS. Filters were exposed to X-ray films for 1 hour to overnight depending on the radioactivity. X-ray films were developed in a Konica automated film developer. The results from these RNA blot hybridizations are shown in FIG. 8. The results indicate that the mRNA samples from all sources were intact and no degradation was detected. It was also observed that no beta-globin mRNA could be detected in lane 1, which contains the parent plasmid only. These results indicate that nonspecific hybridization of the beta-globin probe is minimal.

Autoradiographs containing bands corresponding to both beta-globin and CYH2 mRNA were scanned using the LKB gel scanner. Results obtained from the scanner are shown in FIG. 9A. It can be clearly seen that the abundance of CYH2 mRNA in all three lanes is approximately the same while the abundance of the beta-globin mRNA was higher.

6.6. WESTERN BLOT ANALYSIS OF EXPRESSED BETA-GLOBIN

Four major steps were involved in the analysis of the expressed Porto Alegre beta-globin:

(1) Sample preparation via yeast cell disruption using glass beads followed by protein solubilization using SDS-containing buffer.

(2) Extracted protein separation via polyacrylamide gel electrophoresis.

(3) Protein transfer to nitrocellulose paper by application of a transverse electrical field.

(4) Globin protein detection via a three-stage antibody procedure. The primary antibody is specific for hemoglobin. The secondary antibody is a conjugate of biotin and antibody against IgG of the animal in which the first antibody was raised. Additionally, strepavidin conjugated to horseradish peroxidase was utilized.

The nitrocellulose membranes wee immersed in Enhanced Chemiluminescent developer ([ECL], Amersham) according to manufacturer's instructions and generated light detected by exposure to X-ray film for 15–60 seconds.

Phosphate-buffered saline (PBS; 0.9% NaCl (w/v), 0.01M phosphate, pH 7.6) solution (2 ml) was added to thawed yeast samples (0.02 g wet weight). The samples were centrifuged at 4° C. for 10 min. and decanted. Cold disruption buffer (50 mM Tris, 5 mM EDTA, 0.5 mM PMSF, pH 8.0) prepared immediately before use (0.2 ml) was added, followed by enough glass beads to just reach the top surface of the liquid. After vortexing for 30 seconds at maximum speed the samples were placed on ice for 5 min.; this step was repeated twice more. Ice-cold disruption buffer (1 ml) was added to each sample and the homogenate was transferred to an Eppendorf tube. In another Eppendorf tube, 200 μl of homogenate was combined with 200 μl of freshly prepared standard discontinuous 2× sample buffer (Laemli, 1970, Nature 227:680–685) and the sample was boiled for 10 min.

After centrifugation for 10 min., the samples were loaded onto a discontinuous denaturing gel in which the stacking gel was 3.75% acrylamide and the separating gel was 12%–15%. The stacking gel was run at a constant current of 25 $mA/cm^2$ and the separating gel was run at a current of 33 $mA/cm^2$.

After the electrophoresis was complete and the dye band had reached the bottom of the separating gel, the gels were removed from the electrophoresis unit and the plates were pried apart under running deionized water. The stacking gel was discarded and the lower gel was separated from the plate. The transfer unit was filled with transfer buffer (2 L methanol, 30.3 g Tris base, 144 g glycine, pH 8.30, in 10 L distilled water), 2 L of the transfer buffer was put into a shallow pan. The transfer sandwich consisting in sequence of large pore gauze, 3M blotting paper, the gel, a piece of nitrocellulose paper precut to just cover the gel, 3M blotting paper, and another piece of large pore gauze was assembled under the buffer in the shallow pan.

Protein was then transferred from the gel to the nitrocellulose paper by applying a voltage of 40 V for 1.5 hrs. After transfer was complete, the nitrocellulose sheet was removed and placed into a small, covered shallow pan with 50 ml blocking solution (200 g dried milk per liter PBS) and gently agitated for 1 hr. The blocking solution was discarded and the nitrocellulose was washed three times with PBS containing 0.1% Tween 20. The duration of the washes were 15, 5, and 5 minutes respectively. After discard of the third wash, 25 μl of primary antibody in 25 ml of PBS was added to the pan and the sheet agitated for 2 hrs. The washing of the above was repeated and the nitrocellulose incubated, with agitation, for 1 hour in 5 μl of secondary antibody in 25 ml PBS. The washing procedure of above was carried out and then 2 μl of streptavidin-horseradish peroxidase conjugate in 25 ml of PBS containing 0.1% Tween 20 was added. Following a 20 minute incubation with agitation, the nitrocellulose was washed as above and the presence of human globin chains detected using enhanced chemiluminescence (ECL).

The nitrocellulose was immersed in ECL developer reagents and incubated according to the manufacturer's (Amersham) instructions. After incubation, the sheet was wrapped in clear polyethylene wrap and exposed to x-ray film for the appropriate length of time (10 to 60 seconds). The film was developed and then scanned with a laser densitometer. The quantity of globin in each sample was estimated using the hemoglobin regression line. The standard was apo-human beta-globin purified from red blood cell lysate on reverse phase HPLC. The detection limit was less than 1 ng.

Total soluble protein was determined with the Bio-Rad Protein Assay Kit according to the manufacturer's instructions. Hemoglobin isolated from red blood cell lysate was used as a standard. Insoluble proteins were removed by centrifugation prior to analysis.

7. EXAMPLE 2

CLONING OF ALPHA-GLOBIN INTO A YEAST EXPRESSION VECTOR

The alpha-globin gene was isolated using Polymerase Chain Reaction (PCR). The DNA sequence of this alpha-globin gene was confirmed by sequencing. Results showed that the alpha-globin gene was complete without any deletions or mutations. The resulting plasmid was called pUT/2A.

7.1. MATERIALS

Restriction and DNA modifying enzymes were obtained from Boehringer-Mannheim, Bethesda Research Laboratories, Perkin-Elmer or New England Biolabs. All enzymes were used according to the supplier's specifications.

The *E. coli* strain used for all bacterial transformations was DH5α. The genotype of this strain is as follows:

F$^-_0$80dlacZΔM15$_A$(lacZYA-argF)U169 recA1 endA1 hsdR17 ($r_k^-$, $m_k^{30}$) supE44λ$^-$thi-1 gyrA relA1.

Oligonucleotides were synthesized on an Applied Biosystems., DNA synthesizer 380B using cyanoethyl chemistry. The Polymerase Chain Reaction (PCR or PC reaction) was carried out in a Thermal Cycler obtained from Cetus, Inc.

7.2. ISOLATION OF THE ALPHA-GLOBIN GENE

The alpha-globin gene was isolated by PCR from plasmid pJW101 (Wilson et al., 1978, Nucleic Acids Research 5: 563–580). The primers used for the PCR, 519-A-1 and 519-A-3, are shown in FIG. 10 and are described in the Sequence Description as SEQ ID NO:7 and SEQ ID NO:8 respectively. The PCR product was purified by electrophoresis on 0.6% agarose gel in 1× TBE, electroelution and ethanol precipitation. Purified PCR product was digested with restriction enzymes SalI and BamHI. Digested DNA was cleaned by phenol extraction and ethanol precipitation.

7.3. PREPARATION OF THE YEAST EXPRESSION VECTOR

The yeast expression vector used to clone the alpha-globin gene was prepared by digesting plasmid YEp51UT/NAT with SalI and BamHI. YEp51UT/NAT was prepared in the following manner. Specifically, YEp51T/NAT was digested with the restriction enzyme KpnI. The linearized plasmid was treated with T4-DNA polymerase to make it a blunt-ended molecule. The URA3 gene was isolated as a 1300 bp SmaI-ClaI fragment from plasmid YEp24. This fragment was also treated with the T4-DNA polymerase to make it blunt-ended. This 1300 bp fragment containing the URA3 gene was ligated to the YEp51T/NAT which was cleaved with KpnI and made blunt-ended. The ligation reaction was carried out according to published procedures (see Section 7.4., infra). The ligation mixture was transformed into the *E. coli* DH5α cells using standard transformation procedures (see Section 7.4., infra). The cells were spread on plates containing LB-media with 100 mg/l ampicillin. Plates were incubated overnight at 37° C. Twelve colonies from the Ampicillin plates were picked and a 5 ml culture was inoculated with individual transformant. Cultures were grown overnight at 37° C. with vigorous shaking. The plasmid DNA was isolated from a 1.5 ml culture and the DNA was digested with EcoRI to confirm the presence of 1300 bp fragment. Twelve plasmids were analyzed for the insert and all of them had the 1300 bp fragment inserted in the plasmid.

A 7200 bp fragment containing the GAL10 promoter and ADH terminator was gel purified (0.6% agarose gel in 1× TBE).

7.4. LIGATION AND TRANSFORMATION

YEpUT/NAT digested with SalI and BamHI was ligated to purified PCR product described in Section 7.2.1., supra to obtain pUT/2A. The structure of pUT/2A is shown in FIG. 11. DNA ligation was carried out using standard ligation procedures (Ligation Reactions in "Laboratory Cloning: A Laboratory Manual", Sambrook, J., Fritsch, E. F. and Maniatis, T. eds., Cold Spring Harbor Laboratory Press, 1989, Second Edition pp: 1.63–1.71) and *E. coli* transformation was also carried out using standard transformation procedures (Preparation and Transformation of Competent *E. coli* in "Laboratory Cloning: A Laboratory Manual", Sambrook, J., Fritsch, E. F. and Maniatis, T. eds., Cold Spring Harbor Laboratory Press, 1989, Second Edition pp. 1.74–1.84). Transformed cells were plated on LB-media with 100 mg/l ampicillin. Plates were incubated at 37° C. overnight. Colonies appearing on these plates were used to inoculate 5.0 ml LB media with 100 mg/l ampicillin and cultures were grown at 37° C. overnight. DNA isolated from these cultures was analyzed using restriction enzyme HindII.

7.5. DNA SEQUENCING

The reagent kit for DNA sequencing was purchased from United States Biochemical Corporation (USBC) and it is based on the dideoxy method as developed by Sanger et al. (1977, Proc. Natl. Acad. Sci. U.S.A. 74: 5463–5467). The radioisotope used comes with "Sequetide kit" (NEN Research Products). Sequetide is a S-labeled nucleotide premix used during the labeling step of the sequencing reaction. The forward primer (GAL10KG) was synthesized on a 380B DNA synthesizer from Applied Biosystem. The primer sequence was 5' CTT CTT TGC GTC CAT CCA 3'and is described in the Sequence Listing as SEQ ID NO:9. The 5' and the 3' ends of the primer were checked for optimal hybridization to ensure minimal non-specific annealing to the template using the HIBIO DNASIS program (Hitachi America, LTD). The sequencing gels were 6.0% and were prepared with Gel-Mix 6 (GIBCO BRL). The sequencing protocol was provided with the Sequetide S-labeled Premix (NEN Research Products).

The only deviations from this protocol were during the termination reaction. A supplement of 1 μl of a 1:14 dilution of the Sequenase 2.0 enzyme was used, and incubation was for ten minutes instead of five.

The sequencing gels were fixed in 2 liters fixing solution containing 10% acetic acid and 5% methanol, and were dried for 1 hour at 80° C. in a slab dryer by Bio-Rad.

Sequences of the alpha-globin gene as read from the gels and was entered into the computer using the DNASIS program. The sequences of the new alpha-globin gene was compared to the sequence of natural alpha-globin gene (Wilson et al., 1978, Nucleic Acids Research 5: 563–580). Sequencing of the alpha-globin gene in plasmid pUT/2A showed two silent mutations. These silent mutations were both in the wobble position of the mRNA codon and they did not affect the translation of the globin protein. The first mutation was carried over from plasmid pJW101 which was used to create pUT/2A. The second mutation occurred within the plasmid and was two amino acids away from the first one. These mutations might have occurred either during the PCR or was present in the original gene.

8. EXAMPLE 3

EXPRESSION OF NATURAL GAMMA-GLOBIN IN A YEAST EXPRESSION VECTOR CONTAINING GAL10 PROMOTER AND ADH1 TERMINATOR

The gamma-globin gene was obtained from plasmid pJW151 using PCR. The gamma-globin gene was modified by PCR to have a SalI site at the 5'-end and a HindIII site at the 3'-end. The modified gamma-globin gene was cloned into the yeast expression vector YEp51T/NAT, which contains the ADH1 transcription termination sequence, the GAL10 promoter, and the DNA sequence encoding the beta-globin gene. YEp51T/NAT had been cut with SalI and HindIII to remove the beta-globin gene. The plasmid containing the gamma-globin gene was called YEp51T/G. Yeast strain Sc340 was transformed with YEp51T/G and the transformant was called 340g2G. Following growth of 340g2G and induction by galactose, expressed proteins were analyzed by Western blot analysis. The results from Western blot analysis indicated that gamma-globin was expressed.

8.1. MATERIALS

Restriction and DNA modifying enzymes were obtained from Boehringer-Mannheim, Bethesda Research Laboratories, Perkin-Elmer or New England Biolabs. All enzymes were used according to the suppliers' specifications.

The *E. coli* strain used for all bacterial transformations was DH5α.

Oligonucleotides were synthesized on the Applied Biosystem Inc.'s DNA synthesizer 380B using Cyanoethyl chemistry. Polymerase Chain Reaction (PCR or PC reaction) was carried out in a DNA thermal cycler obtained from Cetus, Inc.

8.2. CLONING OF THE GAMMA-GLOBIN GENE INTO THE YEAST EXPRESSION VECTOR YEp51T/NAT

The general procedure used to clone the gamma-globin gene into the yeast expression vector YEp51T/NAT (see Section 6, supra) resulting in the construction of YEp51T/G is shown in FIG. 12.

The gamma-globin gene was synthesized by PCR using appropriate primers and plasmid pJW151 DNA (Wilson, J. T., et al., Nucleic Acids Research 5:563–581, 1978) as template. The sequence of gamma-globin DNA is shown in FIG. 13, and is described as SEQ ID NO:10. The 5' and 3' primers used for synthesizing the gene, GAM-5-S and GAM-3-H respectively, are shown in FIG. 14 and are described as SEQ ID NO:11 and SEQ ID NO:12. The PCR product was analyzed by electrophoresis in a 1.5% agarose gel (in 1× TBE). The 530 bp PCR product was removed from the gel by electroelution and the DNA was precipitated with ethanol. The purified PCR product was then digested with restriction enzymes SalI (5'-end) and HindIII (3'-end). The digested PCR product was phenol extracted and ethanol precipitated.

Plasmid YEp51T/NAT which contains the human beta-globin gene was digested with SalI and HindIII to remove the beta-globin gene. The digested plasmid was electrophoresed in 0.6% agarose gel (in 1× TBE). A 7000 bp fragment was electroeluted and ethanol precipitated.

A ligation reaction mixture was set up between the gamma-globin obtained by digestion of the PCR product described above and YEp51T/NAT cut with SalI and HindIII (7000 bp). The ligation mixture was used to transform *E. coli* DH5α cells using standard transformation procedure and plated on LB plates containing Ampicillin (100 mg/L). Plasmid DNA was isolated from 20 clones and digested with restriction enzyme PstI. The resulting plasmid was called YEp51T/G (see FIG. 15 for a restriction map).

8.3. TRANSFORMATION AND GROWTH OF YEAST STRAIN Sc340 CELLS WITH PLASMID YEp51T/G

Yeast strain Sc340 cells were transformed with plasmid YEp51T/G (Rose, et al., 1989, Methods in Yeast Genetics, Cold Spring Harbor Laboratory, Cold Spring Harbor, N.Y., pp. 112–115). The starter culture was grown in minimal media supplemented with adenine and histidine, and 3% glycerol and 2% lactate as carbon source. The preculture was used to inoculate 2 L of the above media in a Braun Biostat E fermentor. The pH was maintained at 5.5 using a 5% ammonium hydroxide solution. The $pO_2$ was maintained at 80% until the culture was induced with galactose at which point it was lowered to 10%. The stirrer speed was set at 500 rpm and then reduced to 100 rpm at galactose induction. The culture was incubated at 30° C. and grown to an O.D. 600 of 30.4 at which time it was induced with galactose added at the rate of 5 g/L/hour. Samples were collected from 0 to 74 hours after induction for globin analysis.

8.4. WESTERN BLOT ANALYSIS OF EXPRESSED GAMMA-GLOBIN

The expressed gamma-globin was quantitated by Western Blot analysis using procedures described in Section 6.6., supra. The results indicated that up to 0.05% of the total yeast protein in yeast cell line 340g2G was gamma-globin.

9. EXAMPLE 4

CLONING OF EPSILON-GLOBIN cDNA IN A YEAST EXPRESSION VECTOR AND EXPRESSION OF EPSILON-GLOBIN IN YEAST

9.1. MATERIALS

Restriction and DNA modifying enzymes were obtained from Boehringer-Mannheim, Bethesda Research Laboratories, New England Biolabs or Perkin-Elmer. All enzymes were used according to the supplier's specifications.

Oligonucleotides were synthesized on the Applied Biosystem Inc.'s DNA synthesizer 380B using cyanoethyl chemistry. PCR was carried out using DNA thermal cycler obtained from Cetus and according to the methods described by Cetus.

The genomic clone for human epsilon gene pNEV11 was obtained from the Beatson Institute for Cancer Research. The recombinant bacteriophage clones containing beta-type globin genes and flanking sequences (Fritsch et al., 1980, Cell 19: 959–972) were used by scientists at the Beatson Cancer Research Institute. The EcoRI fragment containing epsilon genomic sequences from one of these clones was recloned in pBR322 based plasmid (Montague, 1986, Ph.D. Thesis entitled "The Behaviour of Human Globin Gene Recombinants in Mammalian Cells"). This plasmid was labeled pNEV11. The DNA from plasmid pNEV11 was isolated and used as a template for PCR.

The *E. coli* strains DH5α and NM522 (Invitrogen, Inc.) were used for bacterial transformations.

9.2. SYNTHESIS OF EPSILON-GLOBIN cDNA

FIG. 16 shows the structure of the epsilon globin genome, as well as the epsilon globin cDNA synthesized. The epsilon gene contains three exons and two introns. The first 92 base exon (exon A) is separated from the second exon (exon B) by 121 bases intron. The second exon is 221 bases and the third exon (exon C) is 120 bases. The second and third exons are separated by 855 bases of intron.

The six primers used for the synthesis of epsilon globin cDNA, 5EPSL-13, INPE-1-14, INPE-2-15, INPE-3-16, INPE-4-17, and 3EPH-18, are described in the Sequence Description as SEQ ID NO:13, SEQ ID NO:14, SEQ ID NO:15, SEQ ID NO:16, SEQ ID NO:17, and SEQ ID NO:18, respectively, and are also shown in FIG. 17 with pertinent restriction sites. As shown in FIG. 17, primer 5EPSL-13 contains the 5' sequences of epsilon cDNA, primer INPE-1-14 contains a 23 base sequences at the 3' end of the exon A joined to a 15 base sequences at 5' end of the exon B, primer INPE-2-15 contains the complementary sequences present in primer INPE-1-14, primer INPE-3 contains 3' sequences at exon B joined together with 5' sequences of exon C, primer INPE-4-17 contains complementary sequences of primer INPE-3-16, and primer 3EPH-18 contains 3' end sequences complementary to the coding strand of exon C with HindIII site at the 3' end.

The genomic clone was PCRed using two outside primers EPSL-13 and 3EPH-18. The entire genomic DNA fragment containing 2 kb fragment was obtained with these two primers. This confirmed that the plasmid pNEV11 contains epsilon-globin genomic sequences.

In one reaction, all six primers were used with the template DNA. This reaction was carried out at 45° C., using 35 cycles. Equal concentrations of all primers were used in this reaction. The entire epsilon-cDNA (440 bp) was isolated using this method. The cDNA also contained appropriate cloning sites.

9.3. CLONING OF EPSILON-GLOBIN cDNA WITH YEAST EXPRESSION VECTOR YEp51NT1

The epsilon-globin cDNA was cut with SalI/HindIII. Ligation was set between SalI/HindIII cut YEp51NT1 (see Section 11.4., infra for a description of the construction of YEpNT1). The ligation mixture was transformed in competent *E. coli* NM522 cells and the DNA was isolated from 24 transformants by alkaline digestion. The DNA samples from the clones were analyzed by SalI/HindIII enzymes and the resulting plasmid was labeled pYEP51T/ε3. The map of this plasmid is shown in FIG. 18.

9.4. TRANSFORMATION OF YEAST STRAIN Sc1041 WITH YEp51T/ε3

Yeast strain Sc1041 was transformed with plasmid YEp51T/ε3 (Section 9.3., supra) using electroporation. Bio-Rad (Richmond, Calif.) Gene Pulser with Pulse Controller was used for electroporation. The 0.2 cm cuvettes were obtained from BioRad. 40 μl of yeast cells were transferred to a sterile Eppendorf tube. DNA (1–100 ng) in 5 μl TE was added to the cells. The mixture was incubated on ice for 5 min., transferred to a 0.2 cm cuvette, and pulsed at 1.5 kV, 25 uF, 200 ohms for 5 msec. 250 μl cold 1M sorbitol was immediately added to the cuvette, the contents were gently mixed and the cells were plated on appropriate plates.

For the starter culture, cells were grown in minimal media containing 0.67% yeast nitrogen base, 1% raffinose, and supplemented with 20 mg/L each of adenine, histidine, uracil, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, uracil, and tryptophan. Incubation was at 30° C. with shaking. The culture was induced by adding galactose to a final concentration of 2%. At induction, the pH was adjusted to 6.91 with $KH(2)PO(4)$ and hemin was added to a final concentration of 40 μg/ml. Samples were collected between two and 24 hours after induction.

9.5. WESTERN BLOT ANALYSIS OF EXPRESSED GLOBIN

The expressed globins were quantitated by Western Blot analysis using procedures described in Section 6.6., supra. Samples taken after induction had detectable levels of globin (0.004%).

10. EXAMPLE 5

CLONING OF ZETA-GLOBIN cDNA INTO A YEAST EXPRESSION VECTOR AND EXPRESSION OF ZETA-GLOBIN IN YEAST

10.1. MATERIALS

Restriction and DNA modifying enzymes were obtained from Boehringer-Mannheim, Bethesda Research Laboratories, New England Biolabs or Perkin-Elmer. All enzymes were used according to the supplier's specifications.

Oligonucleotides were synthesized on the Applied Biosystem Inc.'s DNA synthesizer 380B using Cyanoethyl chemistry. PCR was carried out using DNA thermal cycler obtained from Cetus and according to the methods described by Cetus.

The plasmid 4-P-7-7 containing zeta-globin cDNA was obtained from Dr. Forget's laboratory (Cohen-Solal et al., 1982, DNA 1:255). The yeast expression vector pYES2 was obtained from Invitrogen Corp. (San Diego, Calif.). The vector contains the GAL1 portion of the divergent GAL1/GAL10 promoter region, polylinker for cloning genes, the CYC1 transcription terminator and the URA3 gene for selection in yeast.

*E. coli* strain NM522 was obtained from Invitrogen. Competent cells were prepared according to the protocol provided by Invitrogen.

10.2. CLONING OF ZETA-GLOBIN cDNA IN YEAST EXPRESSION VECTOR pYES2

The zeta-globin cDNA was PCRed using appropriate primers. These primers, 5ZETASAC and ZETA3HSLS, are described in the Sequence Description as SEQ ID NO:19 and SEQ ID NO:20, and are shown in FIG. 19 with restriction sites. The PCRed DNA was cut with SacI/SphI and cloned into SacI/SphI cut DNA from plasmid pYES2. The DNA was isolated from 24 transformants by alkaline digestion. The DNA samples from the clones were analyzed by restriction digestion with SacI/SphI. The plasmid containing zeta-globin cDNA was labeled pYES2-ζ2 and is shown in FIG. 20.

10.3. TRANSFORMATION OF YEAST STRAIN Sc1041 WITH pYES2-ζ2

Yeast strain Sc104 was transformed with plasmid pYEp51/ζ2 (Section 10.2, supra) using electroporation (see Section 9.4., supra).

For the starter culture, cells were grown in minimal media containing 0.67% yeast nitrogen base, 1% raffinose, and supplemented with 20 mg/L each of adenine, histidine, uracil, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, uracil, and tryptophan. Incubation was at 30° C. with shaking. The culture was induced by adding galactose to a final concentration of 2%. At induction, the pH was adjusted to 7.00 with KH(2)PO(4) and hemin was added to a final concentration of 40 μg/ml. Samples were collected between two and 48 hours after induction.

10.4. WESTERN BLOT ANALYSIS OF EXPRESSED-GLOBIN

The expressed globins were quantitated by Western Blot analysis using procedures described in Section 6.6., supra. Samples taken after induction had detectable levels of globin (0.13%).

11. EXAMPLE 6

EXPRESSION OF VARIANT GLOBINS

The mutant globin genes were cloned into yeast expression vector YEp51NT1. This vector contains GAL10 promoter and ADH terminator sequences. The following mutant genes were cloned into this yeast expression vector:

| i. | β-Motown | (127 Gln→Glu) |
|---|---|---|
| ii. | α-Titusville | (94 Asp→Asn) |
| iii. | γ-Porto Alegre | (9 Ala→Cys) |
| iv. | β-Mississippi | (44 Ser→Cys) |
| v. | ζ-104 Ser | (104 Cys→Ser) |
| vi. | α-Titusville/104S | (94 Asp→Asn) (104 Cys→Ser) |
| vii. | γ-Motown | (127 Gln→Glu) |
| viii. | β-Bov2 | (Met Leu Thr Ala Glu Glu . . . ) |
| ix. | β-Deer Lodge | (2 His→Arg) |
| x. | β-Abruzzo | (143 His→Arg) |
| xi. | β-McKees Rock | (145 Term) |
| xii. | γ-Chico | (66 Lys→Thr) |
| xiii. | ζ-Titusville | (94 Asp→Asn) |
| xiv. | β-Chico | (66 Lys→Thr) |
| xv. | α-104 Ser | (104 Cys→Ser) |
| xvi. | β-Rainier | (145 Tyr→Cys) |
| xvii. | β-TaLi | (83 Gly→Cys) |

11.1. MATERIALS AND METHODS

Restriction and DNA modifying enzymes were obtained from Boehringer-Mannheim, Bethesda Research Laboratories, Perkin-Elmer or New England Biolabs. All enzymes were used according to the supplier's specifications.

Oligonucleotides used in the Polymerase Chain Reaction (PCR) were obtained by chemical synthesis on Applied Biosystems 380B DNA synthesizer.

The E. coli strain used for all bacterial transformations was DH5α.

11.1.1. DNA FRAGMENT ISOLATION

All DNA fragments were separated on a 0.5% agarose gel (1× TBE) and isolated by electroelution using Pharmacia Electroeluter.

11.1.2. DNA LIGATION AND E. COLI TRANSFORMATION

All DNA ligations were carried out using standard ligation procedures ("Laboratory Cloning: A Laboratory Manual", Sambrook, J., Fritsch, E. F. and Maniatis, T. eds., Cold Spring Harbor Laboratory Press, 1989, Second Edition, pp: 1.63–1.71) and E. coli transformation was carried out using standard transformation procedures ("Laboratory Cloning: A Laboratory Manual", Sambrook, J., Fritsch, E. F. and Maniatis, T. eds., Cold Spring Harbor Laboratory Press 1989, Second Edition, pp: 1.74–1.84). Transformed cells were plated on LB-media with 100 mg/L ampicillin. Plates were incubated at 37° C. overnight. Colonies appearing on these plates were used to inoculate 5.0 ml LB media with 100 mg/L ampicillin and cultures were grown at 37° C. overnight.

11.1.3. PLASMID DNA ANALYSIS

DNA was isolated from 1.5 ml of the overnight culture using alkaline lysis procedure. Plasmid DNA was analyzed by appropriate restriction enzyme digestion.

11.1.4. YEAST TRANSFORMATION

Yeast transformation was done using published procedures (Hinnen, A., Hicks, J. B. and Fink, G. R., 1978, Transformation in Yeast, Proc. Natl. Acad. Sci. U.S.A. 75, 1929–1933).

11.2. SYNTHESIS OF OLIGONUCLEOTIDES

Various oligonucleotides were synthesized as a preliminary step in the construction of several globin gene variants. The oligonucleotides to be used in the in vitro mutagenesis procedure with M13 were synthesized and purified. Polyacrylamide gel electrophoresis following kinasing demonstrated that the synthesis was efficient and that the oligonucleotides were ready for use in the M13 system.

The following oligonucleotides, Mu-145Cy, Mu-66Th, and Mu-9Cy were synthesized on the Applied Biosystems DNA synthesizer and are described respectively in the Sequence Description as SEQ ID NO:21, SEQ ID NO:22, and SEQ ID NO:23. The bold print within the sequence indicates a change from the wild type beta-globin gene sequence. (See FIG. 21). Following synthesis and incubation at 65° C., the oligonucleotides were purified using oligonucleotide purification columns (Applied Biosystems). The purified oligonucleotides were lyophilized and suspended in 100 μl water and the concentration was determined by OD260.

Approximately 100 ng of the synthetic DNA was used in a kinasing reaction to determine the efficiency of the synthesis. The [γ-$^{32}$P]ATP kinased oligonucleotides were analyzed on a 6% acrylamide sequencing gel containing 7M urea. The dye used in this electrophoresis was a mixture of bromphenol blue and xyno-cynol which separate during the procedure, with each dye migrating at different rates. Autoradiography was performed following drying of the gel.

Following autoradiography of the sequencing gel, the results indicated that the synthesis was efficient, as the majority of the radioactivity was incorporated into the larger bands that moved between the two dye fronts. Under the electrophoresis conditions described above, fragments that are approximately 25 bases should migrate with the bromphenol blue dye front, while those of about 90 bases should migrate with the xyno-cynol dye front. The synthetic oligonucleotides ranged in size from 30 to 45 bases which should run between the two dye fronts as was observed.

11.3. IN VITRO MUTAGENESIS

The in vitro mutagenesis kit from Bio Rad provides the necessary components for mutagenesis with the M13 system. Included in this kit are two strains of *E. coli* to be used in the process. *E. coli* strain CJ236 contains mutations which result in the incorporation of uracil instead of thymine in DNA. *E. coli strain MV*1190 is a wild type strain that is used to produce the single stranded DNA following mutagenesis.

11.3.1. STRAINS

The *E. coli* strains that were received in the mutagenesis kit were subcultured on appropriate media according to the genetic markers for selection. The constituents of each type of media as well as a suggested protocol for mutagenesis may be found in the brochure that was received with the kit (New England BioLabs, 1990, "M13 Cloning and Sequencing System—A Laboratory Manual").

11.3.2. TRANSFECTION OF CJ236

CJ236 competent cells for use in transfection were prepared by inoculating 100 ml LB broth containing chloramphenicol with 5 ml of an overnight culture of CJ236. The culture was incubated at 37° C. in an air shaker until the OD$_{600}$ reached 0.8. The cells were centrifuged at 3K rpm for 5 minutes, resuspended in 20 ml 50 mM cold CaCl$_2$, and held on ice for 30 minutes. The cells were centrifuged again and resuspended in 4 ml 50 mM CaCl$_2$.

The CJ236 competent cells were transfected with M13mp19BHS by adding 1 μl or 5 μl of DNA to 0.3 ml competent cells. The tubes were held on ice for 40 minutes, heat shocked at 42° C. for 3 minutes and the contents were added to 4 ml of top agar (50° C.) containing chloramphenicol and 300 μl of the overnight culture of CJ236. This top agar was poured onto H-medium plates containing chloramphenicol and incubated overnight at 37° C. The phage was isolated (from those cells which were infected) by touching a toothpick to plaques and suspending in 0.5 ml TE.

11.3.3. ISOLATION OF URACIL CONTAINING DNA

Uracil containing DNA was isolated from CJ236 by inoculating 50 ml LB medium containing chloramphenicol with 1.0 ml of an overnight culture of CJ236. The culture was incubated at 37° C. with shaking until it reached an OD$_{600}$ of 0.3. At this point, the culture was infected with 50 μl of a −70° C. stock culture that was previously infected with phage in order to amplify the production of single stranded DNA. The infected culture was allowed to grow overnight at these conditions. The following day, 30 ml of the culture was centrifuged at 16K rpm for 15 minutes. The supernatant containing the phage particles was transferred to a new tube and centrifuged a second time. The supernatant from this second centrifugation was treated with 150 μg RNase A at room temperature for 30 minutes. Single stranded DNA was precipitated by adding 7.5 ml of PEG solution (3.5M ammonium acetate, 20% PEG 8000) and held on ice for 30 minutes. The tube was centrifuged and the supernatant was discarded. The pellet was suspended in 200 μl of high salt buffer (300 mM NaCl, 100 mM Tris, pH 8.0, 1 mM EDTA), held on ice for 30 minutes, and centrifuged in a microcentrifuge for 2 minutes. The supernatant was transferred to a new tube.

The phage was titered on CJ236 and MV1190 to determine whether infection was productive. Following confirmation of productive infection, the DNA was extracted with an equal volume of phenol, an equal volume of phenol-chloroform, and an equal volume of ether. The extracted DNA was precipitated with 1/10 volume 7.8M ammonium acetate and 2.5 volumes ethanol at −20° C. overnight. The tube was centrifuged for 15 minutes and the pellet was resuspended in 20 μl TE. This DNA is the single stranded uracil-containing DNA which was used as a template for the synthesis of the mutagenic strand.

11.3.4. KINASING OF OLIGONUCLEOTIDES

The purified oligonucleotides were kinased by treating 5 μg of each of the six oligonucleotides with T4 polynucleotide kinase and ATP to ensure efficient ligation of the two ends of the newly synthesized DNA strand.

11.3.5. SYNTHESIS OF THE MUTAGENIC STRAND

The synthesis of the mutagenic strand was carried out by adding 0.25 μg (0.1 pM) of the uracil-containing single stranded DNA template and 0.03 μg (3 pM) of each of the synthetic oligonucleotide primers. The primer was annealed to the single stranded template (final reaction volume 10 ml) in 1× annealing buffer (2 mM Tris-HCl, pH 7.4, 0.2 mM MgCl$_2$, 5 mM NaCl) in a water bath with an initial temperature of 70° C. which was allowed to cool to 30° C. The reactions were then placed in an ice water bath and the following components were added to each: 1 μl 10× synthesis buffer (Final concentration=0.4 mM each dNTP, 0.75 mM ATP, 17.5 mM Tris-HCl, pH 7.4, 3.75 mM MgCl$_2$, 21.5 mM DTT), 1 μl T4 DNA Ligase (2–5 units), and 1 μl T4 DNA Polymerase (1 unit). The reactions were incubated on ice for 5 minutes in order to stabilize the primer by initiation of DNA synthesis under conditions that favor the binding of the primer to the template. The reactions were then incubated at 25° C. for 5 minutes and finally at 37° C. for 90 minutes. Following the final incubation, 90 μl of stop buffer (10 mM Tris, pH 8.0, 10 mM EDTA) was added to each reaction and were placed at −20° C. until use in the transfection of MV1190.

11.3.6. TRANSFECTION OF MV1190 CELLS

MV1190 cells were transfected with the products of the synthesis reactions by adding 3 μl and 9 μl of each reaction to 0.3 ml of competent cells. The tubes were incubated on ice for 90 minutes, heat shocked at 42° C. for 3 minutes, and then placed on ice. 50 and 100 μl of the transfected cells were added to tubes containing 0.3 ml of an overnight culture of MV1190, 50 μl 2% X-gal, 20 μl 100 mM IPTG, and 2.5 ml top agar (55° C.). The mixture was vortexed and poured onto H-agar plates. The plates were incubated overnight at 37° C. and observed for the formation of plaques the following morning. Those plaques that appeared blue did not contain the insert, while those that appeared clear were the plaques of interest.

11.3.7. ANALYSIS OF TRANSFORMANTS BY SEQUENCING

The clear plaques were picked by inserting a sterile Pasteur pipet into the agar and suspending the plug in 3 μl LB broth (24 plaques were chosen from each of the plates containing plaques).100 μl of an overnight culture of MV1190 was added and the tubes were incubated with shaking overnight at 37° C. Following the incubation period, single-stranded DNA was isolated from the cultures and this DNA was used in sequencing reactions.

Dideoxy sequencing was performed to confirm the presence of mutations. The sequencing kit used in this case was obtained from New England Biolabs. Each sequencing reaction was set up using 8 μl of the single stranded DNA to be sequenced, 1 μl of the appropriate primer, and 1 μl 10× sequencing buffer. The primer was annealed to the single stranded template by placing the tubes at 90° C. and allowing them to cool to 30° C. 2 μl of the DNA-primer mixture was used in each individual sequencing reaction along with 2 μl of the termination mix (50 μl of the appropriate dNTP's and ddNTP plus 5 μl [α-$^{32}$P] dATP and 2 μl of Klenow enzyme diluted to 0.1 units/μl. The reaction was incubated at room temperature for 15 minutes and 2 μl of a chase mixture was added that consisted of a dNTP mixture containing cold dATP and Klenow enzyme. This reaction was incubated again at room temperature for 15 minutes and 4 μl of dye mix was added to stop the reaction. The samples were denatured by boiling for 2.5 minutes and, placed in an ice water bath, and loaded onto a 6% polyacrylamide sequencing gel containing 7M urea. The gel was run at 55 watts for approximately 4 hours before it was dried under vacuum and placed in an X-ray film cassette for autoradiography.

Other sequencing kits were used to achieve the best results in conjunction with [α-$^{35}$S] dATP. A sequencing kit specifically for use with single-stranded DNA was obtained from IBI and a Pharmacia kit was used with T7 DNA polymerase rather than Klenow Enzyme in order to sequence mutants further from the point of primer annealing.

Transfection of MV1190 with the synthesis reaction products resulted in clear plaques on the plates containing Mu-66Th, Mu-145Cy, and Mu9-Cy DNA. The control which was included consisted of a transfection with template DNA without a primer for synthesis of the second strand. This control revealed some plaques, but fewer than those in which a primer for mutagenesis was used.

11.4. CONSTRUCTION OF PLASMID YEp51NT1

Yeast shuttle vector YEp51was modified to have ADH terminator sequences. The ADH terminator was inserted between the GAL10 promoter and the 2μ replication system present on this vector. Specifically, plasmid YEp51was digested with restriction enzyme Bcl1. The linearized DNA molecule was treated with Klenow enzyme and dNTPs to make it blunt ended. A double-stranded oligonucleotide was ligated to the blunt ended plasmid. This oligonucleotide was obtained from BRL and contained sequences for restriction enzyme NotI. Ligation was carried out overnight at room temperature. DNA from the ligation reaction was precipitated using polyethylene glycol (PEG). This procedure removes all unligated oligonucleotides because only large DNA molecules are precipitated with PEG. After the PEG precipitation, DNA was cleaned by phenol extraction and ethanol precipitation. Plasmid DNA was digested with NotI and HindIII.

Figure 6:
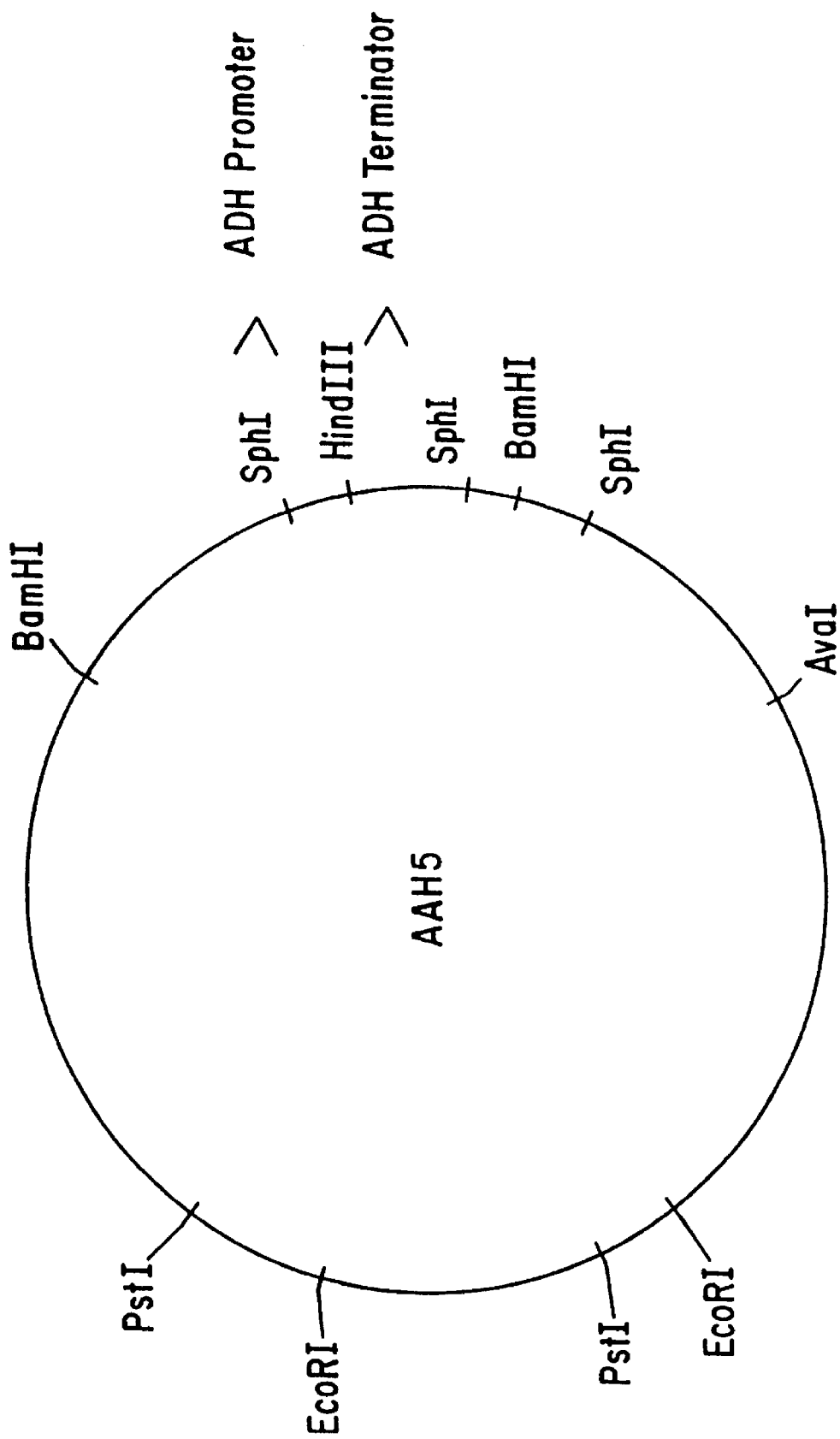
FIG. 6 shows a map of AAH5.

The ADH terminator was obtained from plasmid AAH5 (see FIG. 6). Plasmid AAH5 was digested with restriction enzyme BamHI. DNA was blunt-ended with Klenow and dNTPs. Blunt-ended DNA was subjected to phenol extraction and ethanol precipitation. The above-mentioned double-stranded oligonucleotide was ligated to the blunt-ended plasmid. Ligation was carried out overnight at room termperature. DNA from the ligation was precipitated using polyethylene glycol (PEG). After the PEG precipitation, DNA was cleaned by phenol extraction and ethanol precipitation. DNA was then digested with restriction enzyme NotI and HindIII. A 400 bp NotI-HindIII fragment was isolated from a 1.0% agarose gel (1× TBE). DNA was electroeluted from the agarose slice and precipitated with ethanol. This purified DNA fragment was ligated to the above-mentioned plasmid. The ligation mixture was used to transform DH5α-cells. Transformed cells were spread on plates containing LB-media with 100 mg/L ampicillin. Plates were incubated overnight at 37° C. Colonies appearing on these plates were used to inoculate 5.0 ml LB-media containing 100 mg/L ampicillin. Cultures were grown at 37° C. overnight. DNA was isolated from 1.5 ml of the overnight culture using the alkaline lysis procedure. Plasmid DNA was digested with restriction enzyme NotI and HindIII. The resulting plasmid was called YEp51NT1 and is shown in FIG. 22.

11.5. CLONING OF VARIANT GLOBINS

The vector for cloning the mutated β-globin gene(s) was prepared by digesting plasmids YEP51T/G (supra, Section 8.4.) or YEp51NT1/γ-PORT (infra, 11.5.1.) with SalI and HindIII. The vector for cloning the γ-globin gene was YEp51NT1. This digestion results in two fragments (7300 and 500 bp); the 7300 bp fragment was isolated.

11.5.1. CLONING OF PORTO ALEGRE (9 Ala→Cys) γ-GLOBIN GENE

The Porto Alegre γ-globin was created by substituting two bases in the natural γ-globin sequence using PCR. The γ-globin gene was obtained as a 450 bp fragment. The 5' and 3' primers used for synthesizing the sequence, respectively, G-5-9CY and GAM-3-H are shown in FIG. 23 and are described in the Sequence Description as SEQ ID NO:24 and SEQ ID NO:12 respectively.

The mutated γ-globin gene obtained by PCR was digested with SalI and HindIII. This digested DNA fragment (450 bp) was purified by phenol extraction and ethanol precipitation. This purified 450 bp fragment obtained by PCR was ligated to the vector YEp51NT1 cut with SalI and HindIII. DNA ligation, *E. coli* transformation and DNA isolation was performed as described (see Section 11.1., supra). DNA isolated from the transformed cells was digested with restriction enzyme PstI. The results obtained from this analysis showed clones that had expected fragments (three fragments when digested with PstI; two fragments from vector without insert). This plasmid was called YEp51NT1/γ-PORT.

11.5.2. CLONING OF THE MOTOWN (127 Gln→Glu) β-GLOBIN GENE

The Motown β-globin was created by a base substitution using PCR. The globin gene was isolated as two fragments.

The 3'-end of the gene (EcoRI-HindIII) was obtained by PCR. The 5' and 3' primers used for synthesizing the sequence, B-G127-5 and Beta-3-H are shown in FIG. 24 and are shown in the Sequence Description as SEQ ID NO:25 and SEQ ID NO:26.

The mutated fragment of the β-globin gene obtained by PCR was digested with EcoRI and HindIII. This digested DNA fragment (80 bp) was purified by phenol extraction and ethanol precipitation. The 5'-end of the β-globin gene was isolated from plasmid YEp51T/NAT (see Section 6.4., supra). Plasmid YEp51T/NAT was digested with restriction enzymes BamHI and HindIII. A 360 bp fragment was isolated. This purified 360 bp fragment along with the fragment obtained by PCR were ligated to the vector YEp51NT1/γ-PORT cut with SalI and HindIII. DNA ligation, *E. coli* transformation and DNA isolation was performed as described (see Section 11.1, supra). DNA isolated from the transformed cells was digested with restriction enzyme PstI. The results obtained from this analysis showed that most of the clones analyzed had expected fragments (two fragments when digested with PstI; three fragments from vector without insert). This plasmid was called pNT1/β-Mot.

11.5.3. CLONING OF THE TITUSVILLE (94 Asp→Asn) α-GLOBIN GENE

The Titusville a-globin was created by substituting one base in the natural α-globin gene using PCR. The α-globin gene was isolated as two fragments. The 3'-end of the gene (HindIII-HindIII) was obtained by PCR using plasmid p19A1GT as template. The 5' primer and 3' primers used for PCR, A-Tit-5 and G10T3H, are shown in FIG. 25 and are described in the Sequence Description as SEQ ID NO:27 and SEQ ID NO:28.

The 5'-end of the gene (SalI-HindIII) was obtained as a 450 bp fragment. Primers used for PCR were 51-A3-SL (5'-end primer) and A-Hin3-3 (3'-end primer) and are described in the Sequence Description as SEQ ID NO:29 and SEQ ID NO:30 respectively and are shown in FIG. 26. The template for the PCR was plasmid pJW101. The PCR product was digested with restriction enzymes SalI and HindIII. A 300 bp fragment was isolated. This purified 300 bp fragment along with the fragment obtained by PCR were ligated to the vector YEp51NT1/γ-PORT (See Section 11.5.1., supra) cut with SalI and HindIII. DNA ligation, *E. coli* transformation and DNA isolation was performed as described (see Section 11.1, supra). DNA isolated from the transformed cells was digested with restriction enzyme HindII. The results obtained from this analysis shows that one clone had the expected fragments (five fragments when digested with HindII). This plasmid was called pNT1/2ATit.

11.5.4. CLONING OF THE β-MISSISSIPPI (44 Ser→Cys) β-GLOBIN GENE

The Mississippi β-globin was created by substituting two bases in the natural β-globin gene using PCR. The globin gene was isolated as two fragments. The 3'-end of the gene (AccI-HindIII) was obtained by PCR. Primers used for PCR were B44C-5 (5'-end primer) and Beta-3-H (3'-end primer) and are shown in FIG. 27 with restriction sites and are described respectively in the Sequence Description as SEQ ID NO:31 and SEQ ID NO:26.

The mutated fragment of the =62 -globin gene was digested with AccI and HindIII. This digested DNA fragment was purified by phenol extraction and ethanol precipitation. The 5'-end of the β-globin gene was isolated from plasmid YEp51T/NAT (see Section 6.4., supra). Plasmid YEp51T/NAT was digested with restriction enzymes AccI and SalI. A 117 bp fragment was isolated. This purified 117 bp fragment along with the fragment obtained by PCR were ligated to the vector YEp51NT1/γ-PORT. DNA ligation, *E. coli* transformation and DNA isolation was performed as described (see Section 11.1., supra). DNA isolated from the transformed cells was digested with restriction enzyme PstI. The results obtained from this analysis showed that most of the clones analyzed had expected fragments (two fragments when digested with PstI; three fragments from vector without insert). This plasmid was called pNT1/β-Miss.

11.5.5. CLONING OF 104-Ser (104 Cys→Ser) ALPHA-GLOBIN GENE

The 104-Ser alpha-globin was created by substituting one base in the natural alpha-globin gene using PCR. The alpha-globin gene was isolated as two fragments. The 3'-end of the gene (HindIII-HindIII) was obtained by PCR using plasmid pA1GT (Wilson et al., 1978, Nucl. Acids Res. 5:563–580) as template. The primers used for PCR, A-104Ser (5'-end primer) and G10T3H (3'-end primer), are described in the Sequence Description as SEQ ID NO:32 and SEQ ID NO:28, respectively, and are shown in FIG. 28 with restriction sites. The mutated fragment of the alpha-globin gene was digested HindIII. This digested DNA fragment was purified by phenol extraction and ethanol precipitation.

The 5'-end of the gene (SalI-HindIII) was obtained by PCR using plasmid pJW101 as template. Primers used for PCR were 51-A3-SL (5'-end primer) and A-Hin3-3 (3'-end primer), are described in the Sequence Description as SEQ ID NO:29 and SEQ ID NO:30, respectively, and are shown in FIG. 26 with restriction sites. PCR product was digested with SalI and HindIII. This digested DNA fragment was purified by phenol extraction and ethanol precipitation. This purified 300 bp fragment along with the fragment obtained by PCR for the 5'-end were ligated to the vector pNT1/γ-PORT cut with SalI and HindIII. DNA ligation, *E. coli* transformation and DNA isolation was performed as described in Section 11.1., supra. DNA isolated from the transformed cells was digested with restriction enzyme HindII. The results obtained from this analysis showed that one clone had expected fragments (five fragments when digested with HindII). This plasmid was called pNT1/2A104S.

The 104 Ser alpha-globin gene was also cloned in yeast expression vector YEp51UT/NAT. Plasmid p51UT/NAT was digested with SalI and BamHI. A 7000 bp fragment was gel purified. The 5'-end of the gene (SalI-HindIII) was obtained by PCR using plasmid pJW101 as template. Primers used for PCR 51-A3-SL (5'-end primer) and A-Hin3-3 (3'-end primer), are described in the Sequence Description as SEQ ID NO:29 and SEQ ID NO:30, respectively, and are shown in FIG. 26 with restriction sites. The PCR product was digested with SalI and HindIII. This digested DNA fragment was purified by phenol extraction and ethanol precipitation. The 3'-end of the gene (HindIII-HindII) was obtained by PCR using plasmid pA1GT as template. Primers used for PCR were A-104Ser (5'-end primer) and 519-A-3 (3'-end primer), are described in the Sequence Description as SEQ ID NO:32 and SEQ ID NO:8, respectively. The mutated fragment of the alpha-globin gene was digested HindIII. This digested DNA fragment was purified by phenol extraction and ethanol precipitation.

Purified fragments obtained by PCR for the 5' and 3'-ends were ligated to the vector YEp51UT/NAT cut with SalI and BamHI. DNA ligation, E. coli transformation and DNA isolation was performed as described in Section 11.1., supra. DNA isolated from the transformed cells was digested with restriction enzyme HindII. The results obtained from this analysis showed that one clone had expected fragments (five fragments when digested with HindII). This plasmid was called pUT/2A104S.

11.5.6. CLONING OF 104-Ser (104 Cys→Ser) ZETA-GLOBIN GENE

The 104-Ser ζ-globin was created by substituting one base in the natural ζ-globin gene using PCR. The ζ-globin gene was isolated as two fragments. Both fragments were obtained by PCR. The 5'-end of the gene (SalI-BstEII) was obtained by PCR using plasmid 4P-7-7 as template. Primers used for PCR, Z-5-SAL (5'-end primer) and Z-104S-B (3'-end primer) are shown in FIG. 29 and are described in the Sequence Description as SEQ ID NO:33 and SEQ ID NO:34 respectively.

The 3'-end of the gene (BstEII-HindIII) was obtained by PCR using plasmid p4-7-7 as template. Primers used for PCR are Z-BST-5 (5'-end primer) and Z2-3-H (3'-end primer) are shown in FIG. 30 and are described in the Sequence Description as SEQ ID NO:35 and SEQ ID NO:36 respectively.

The mutated fragment of the ζ-globin gene was digested with SalI and BstEII. This digested DNA fragment (330 bp) was purified by phenol extraction and ethanol precipitation. The 3'-end of the ζ-globin gene obtained by PCR was digested with restriction enzymes BstEII and HindIII. A 100 bp fragment was isolated. Purified fragments (330 and 100 bp) were ligated to the vector YEp51NT1 cut with SalI and HindIII. DNA ligation, E. coli transformation and DNA isolation was performed as described (see Section 11.1., supra). DNA isolated from the transformed cells was digested with restriction enzyme HindII. The results obtained from this analysis showed that one clone had expected fragments (five fragments when digested with HindII). This plasmid was called pNT1/ζ104S.

11.5.7. CLONING OF TITUSVILLE (94 Asp→Asn)ζ-GLOBIN GENE

The 94-Asn ζ-globin was created by substituting one base in the natural ζ-globin gene using PCR. The ζ-globin gene was isolated as two fragments. Both fragments were obtained by PCR. The 5'-end of the gene (SalI-BstEII) was obtained by PCR using plasmid 4p7-7 as template. The 5' primer used for synthesizing the sequence, Z-5-SAL, is described in the Sequence Description as SEQ ID NO:33 and the 3' primer used for synthesizing the sequence, Z-A95-3, is described in the Sequence Description as SEQ ID NO:37. Restriction sites on these two primers are shown in FIG. 31.

The 5'-end of the gene (BstEII-HindIII) was obtained by PCR using plasmid 4p7-7 as template. The 5' primer used for synthesizing the sequence, Z-BST-5, is described in the Sequence Description as SEQ ID NO:35 and the 3' primer used for synthesizing the sequence, Z2-3-H, is described in the Sequence Description as SEQ ID NO:36. Restriction sites on these two primers are shown in FIG. 30.

A mutated fragment of the ζ-globin gene obtained by PCR was digested SalI and BstEII. This digested DNA fragment (330 bp) was purified by phenol extraction and ethanol precipitation. The 3'-end of the ζ-globin gene obtained by PCR was digested with restriction enzymes BstEII and HindIII. A 100 bp fragment was isolated. Purified fragments (330 and 100 bp) were ligated to the vector YEp51NT1 cut with Sal I and HindIII. DNA ligation, E. coli transformation and DNA isolation were performed as described (see Section 11.1., supra). DNA isolated from the transformed cells was digested with restriction enzyme HindII. The results obtained from this analysis showed that one clone had expected fragments (five fragments when digested with HindII). This plasmid was called pNT1/Z95An.

11.5.8. CLONING OF ALPHA-GLOBIN GENE CONTAINING ALPHA TITUSVILLE AND ALPHA-104 Ser MUTATIONS: 94 Asp→Asn; 104 Cys→Ser)

The double mutant (Titusville+104 Ser) alpha-globin was created by substituting one base in the 104 Ser alpha-globin gene using PCR. The alpha-globin gene was isolated as two fragments. The 3'-end of the gene (HindIII - HindIII) was obtained by PCR using plasmid pNT1/α104S as template. Primers used for PCR were A-Tit-5 (5'-end primer) and G10T3H (3'-end primer), are described in the Sequence Description as SEQ ID NO:27 and SEQ ID NO:28, respectively.

The alpha-globin gene fragment containing double mutation was digested HindIII. This digested DNA fragment was purified by phenol extraction and ethanol precipitation. The 5'-end of the alpha-globin gene was obtained from plasmid PJW101 using PCR. The 5'-end of the gene (SalI-HindIII) was obtained by PCR using plasmid pJW101 as template. Primers used for PCR were 51-A3-SL (5'-end primer) and A-Hin3-3 (3'-end primer), are described in the Sequence Description as SEQ ID NO:29 and SEQ ID NO:30, respectively, and are shown in FIG. 26 with restriction sites. The PCR product was digested with SalI and HindIII. This digested DNA fragment was purified by phenol extraction and ethanol precipitation. This purified 300 bp fragment along with the fragment obtained by PCR for the 5'-end were ligated to the vector (pNT1/γ-PORT cut with SalI and HindIII). DNA ligation, E. coli transformation and DNA isolation was performed as described in Section 11.1., supra. DNA isolated from the transformed cells was digested with restriction enzyme HindII. The results obtained from this analysis showed that one clone had expected fragments (five fragments when digested with HindII). This plasmid was called pNT1/2ATiS.

11.5.9. CLONING OF THE MOTOWN GAMMA-GLOBIN GENE: (127 Gln→Glu)

The Motown gamma-globin was created by base substitution the natural gamma-globin sequence using PCR. The gamma-globin gene was obtained as two fragments. The 5'-end of the gene was isolated as SalI-EcoRI fragment (320 bp) from plasmid YEp51T/G. The 3'-end of the gene (containing mutation) was obtained by PCR. Template used for the PCR was pJW151. Primers used for PCR, G2-Mot-5 (5'-end primer) and GAM-3-H (3'-end primer), are described in the Sequence Description as SEQ ID NO:38 and SEQ ID NO:12, respectively, and are shown in FIG. 32 with restriction sites. PCR product was digested with restriction enzymes EcoRI and HindIII. Digested fragment was purified by phenol extraction and ethanol precipitation.

The purified fragments obtained by PCR and isolated from plasmid was YEp51T/G were ligated to the vector (YEp51NT1 cut with SalI and HindIII). DNA ligation, E. coli transformation and DNA isolation was performed as described in Section 11.1., supra. DNA isolated from the transformed cells was digested with restriction enzyme PstI.

The results obtained from this analysis showed that the clones had expected fragments (three fragments when digested with PstI; two fragments from vector without insert). This plasmid was called YEp51NT1/γ-Mo2.

11.5.10. CLONING OF THE BOVI2 β-GLOBIN GENE (Met Leu Thr Ala Glu Glu )

The Bov2 (human globin gene with 5'-end with four amino acids of the bovine globin gene) β-globin was created by replacing six amino acids of the human β-globin at the 5'-end with four amino acids from the bovine β-globin gene's 5'-end. The mutated β-globin gene was obtained as a 450 bp fragment. The 5' primer used for synthesizing the sequence is described in the Sequence Description as SEQ ID NO:39 and the 3' primer used for synthesizing the sequence is described in the Sequence Description as SEQ ID NO:26. Restriction sites on these two primers are shown in FIG. 33.

The mutated β-globin gene obtained by PCR was digested with SalI and HindIII. This digested DNA fragment (450 bp) was purified by phenol extraction and ethanol precipitation. This purified 450 bp fragment obtained by PCR was ligated to the vector YEp51NT1/γ-PORT cut with SalI and HindIII. DNA ligation, *E. coli* transformation and DNA isolation was performed as described (see Section 11.1., supra). DNA isolated from the transformed cells was digested with restriction enzyme PstI. The results obtained from this analysis showed that most of the clones analyzed had expected fragments (two fragments when digested with PstI; three fragments from vector without insert). This plasmid was called pNT1/β-Bov2.

11.5.11. CLONING OF β-2 Arg GLOBIN GENE: (2 His→Arg)

The β-2 Arg beta-globin was created by replacing amino acid His (amino acid #2) of the human beta-globin with amino acid Arg. The mutated beta-globin gene was obtained as a 450 bp fragment. Primers used for PCR, B-2ARG-5 (5'-end primer) and Beta-3-H (3'-end primer) are described in the Sequence Description as SEQ ID NO:40 and SEQ ID NO:26, respectively, and are shown in FIG. 34 with restriction sites.

The mutated beta globin gene obtained by PCR was digested with SalI and HindIII. This digested DNA fragment (450 bp) was purified by phenol extraction and ethanol precipitation. This purified 450 bp fragment obtained by PCR was ligated to the vector (YEp51NT1/γ-PORT cut with SalI cut with HindIII). DNA ligation, *E. coli* transformation and DNA isolation was performed as described in Materials and Methods section. DNA isolated from the transformed cells was digested with restriction enzyme PstI. The results obtained from this analysis showed that most of the clones analyzed had expected fragments (two fragments when digested with PstI; three fragments from vector without insert). This plasmid was called pNT1/β2Arg.

11.5.12. CLONING OF THE 143 Arg BETA-GLOBIN GENE: (143 His-→Arg)

The 143 Arg beta-globin was created by replacing amino acid His (amino acid #143) of the human beta-globin with amino acid Arg. The mutated beta-globin gene was obtained as a 450 bp fragment. Primers used for PCR, BN-5-SAL (5'-end primer) and B-143A-3 (3'-end primer), are described in the Sequence Description as SEQ ID NO:33 and SEQ ID NO:41, respectively, and are shown in FIG. 35 with restriction sites.

The mutated gamma-globin gene obtained by PCR was digested with SalI and HindIII. This digested DNA fragment (450 bp) was purified by phenol extraction and ethanol precipitation. This purified 450 bp fragment obtained by PCR was ligated to the vector (YEp51NT1/γ-PORT cut with SalI and HindIII). DNA ligation, *E. coli* transformation and DNA isolation was performed as described in Section 11.1., supra. DNA isolated from the transformed cells was digested with restriction enzyme PstI. The results obtained from this analysis showed that most of the clones analyzed had expected fragments (two fragments when digested with PstI; three fragments from vector without insert). This plasmid was called pNT1/β143Arg.

11.5.13. CLONING OF THE 145 Term BETA-GLOBIN GENE: (145 Tyr→TAA)

The 145 Term beta-globin was created by replacing amino acid Tyr (amino acid #145) of the human beta-globin with protein termination codon (TAA). The mutated beta-globin gene was obtained as a 450 bp fragment. Primers used for PCR, BN-5-SAL (5'-end primer) and B-145T-3 (3'-end primer), are described in the Sequence Description as SEQ ID NO:33 and SEQ ID NO:42, respectively, and are shown in FIG. 36 with restriction sites.

The mutated beta-globin gene obtained by PCR was digested with SalI and HindIII. This digested DNA fragment (450 bp) was purified by phenol extraction and ethanol precipitation. This purified 450 bp fragment obtained by PCR was ligated to the vector (YEp51NT1/γ-PORT cut with SalI and HindIII). DNA ligation, *E. coli* transformation and DNA isolation was performed as described in Section 11.1., supra. DNA isolated from the transformed cells was digested with restriction enzyme PstI. The results obtained from this analysis showed that most of the clones analyzed had expected fragments (two fragments when digested with PstI; three fragments from vector without insert). This plasmid was called pNT1/β145Term.

11.5.14. CLONING OF THE CHICO (66 Lys→Thr) γ-GLOBIN GENE

The Chico γ-globin was created by substituting one base in the natural γ-globin gene using PCR. The γ-globin gene was isolated as two fragments. The 5'-end of the gene (SalI-XcmI) was obtained by PCR using plasmid pJW151 as template. The 5' primer used for synthesizing the sequence, GAM-5-S is described in the Sequence Description as SEQ ID NO:11 and the 3' primer used for synthesizing the sequence, G66T-3' is described in the Sequence Description as SEQ ID NO:43. Restriction sites on these two primers are shown in FIG. 37.

The mutated fragment of the γ-globin gene was digested with SalI and XcmI. This digested DNA fragment (230 bp) was purified by phenol extraction and ethanol precipitation. The 3'-end of the γ-globin gene was isolated from plasmid YEp51NT1/γ-PORT. Plasmid YEp51NT1/γ PORT was digested with restriction enzymes XcmI and HindIII. A 220 bp fragment was isolated. This purified 220 bp fragment along with the fragment obtained by PCR were ligated to the vector YEp51NT1 cut with SalI and HindIII. DNA ligation, *E. coli* transformation and DNA isolation were performed as described (supra, 11.1). DNA isolated from the transformed cells was digested with restriction enzyme PstI. The results obtained from this analysis showed that one clone had expected fragments (three fragments when digested with PstI; two fragments from vector without insert). This plasmid was called pNT1/γ-Chi.

11.5.15. CLONING OF THE CHICO (66 Lys→Thr) γ-GLOBIN GENE

The Chico γ-globin was created by a site-directed mutagenesis (supra, 11.2 and 11.3). The mutated β-globin gene was digested with restriction enzymes SalI and HindIII. A 600 bp fragment was isolated. This purified 600 bp fragment was ligated to the vector YEp51NT1/γ-PORT. DNA ligation, *E. coli* transformation and DNA isolation was performed as described (supra, 11.1). DNA isolated from the transformed cells was digested with restriction enzyme PstI or EcoRI. The results obtained from this analysis showed that most of the clones analyzed had the expected fragments (two fragments when digested with PstI and three fragments when digested with EcoRI). This plasmid was called pNT1/β-Chico.

11.5.16. CLONING OF THE RAINIER (145 Tyr→Cys) β-GLOBIN GENE

The Rainier β-globin was created by a site-directed mutagenesis (supra, 11.2 and 11.3). The mutated β-globin gene was digested with restriction enzymes SalI and HindIII. A 600 bp fragment was isolated. This purified 600 bp fragment was ligated to the vector YEp51NT1/γ-Port. DNA ligation, *E. coli* transformation and DNA isolation was performed as described (supra, 11.1). DNA isolated from the transformed cells was digested with restriction enzyme PstI or EcoRI. The results obtained from this analysis showed that most of the clones analyzed had expected fragments (two fragments when digested with PstI and three fragments when digested with EcoRI). This plasmid was called pNT1/β-Ran.

11.5.17. CLONING OF THE TaLi (83 GLY→CYS) β-GLOBIN GENE

The TaLi β-globin was created by a base substitution using PCR. The globin gene was isolated as two fragments. The 5'-end of the gene (SalI-BamHI) was obtained by PCR. The 5' primer used for synthesizing the sequence is described in the Sequence Description as SEQ ID NO:44 and the 3' primer used for synthesizing the sequence is described in the Sequence Description as SEQ ID NO:45. Restriction sites on these two primers are shown in FIG. 38.

11.6. EXPRESSION OF VARIANT GLOBINS

11.6.1. EXPRESSION OF GAMMA-GLOBIN MOTOWN IN A YEAST

11.6.1.1. TRANSFORMATION OF YEAST STRAIN Sc1114 WITH pNT1/γ-Mot2

Yeast strain Sc1114 was transformed with plasmid pNT1/γ-Mot2 (see Section 11.5.9., supra) using electroporation (see Section 9.4., supra).

For the starter culture, cells were grown in minimal media containing 0.67% yeast nitrogen base, 1% raffinose, and supplemented with 20 mg/L each of adenine, histidine, uracil, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, uracil, and tryptophan. Incubation was at 30° C. with shaking. The culture was induced by adding galactose to a final concentration of 2%. At induction, the pH was adjusted to 7.27 with KH(2)PO(4) and hemin was added to a final concentration of 40 µg/ml. Samples were collected between two and 30 hours after induction.

11.6.1.2. WESTERN BLOT ANALYSIS OF EXPRESSED GLOBIN

The expressed globins was quantitated by Western Blot analysis using procedures described in Section 6.6. Samples taken after induction had detectable levels of globin (0.01%).

11.6.2. EXPRESSION OF BETA-GLOBIN Bov2 IN YEAST

11.6.2.1. TRANSFORMATION OF YEAST STRAIN Sc1115 WITH pNT1/β-Bov2

Yeast strain Sc1115 was transformed with plasmid pNT1/β-Bov2 (see Section 11.5.10., supra) using electroporation (see Section 9.4., supra).

For the starter culture, cells were grown in minimal media containing 0.67% yeast nitrogen base, 1% raffinose, and supplemented with 20 mg/L each of adenine, histidine, uracil, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, uracil, and tryptophan. Incubation was at 30° C. with shaking. The culture was induced by adding galactose to a final concentration of 2%. At induction, the pH was adjusted to 6.94 with KH(2)PO(4) and hemin was added to a final concentration of 40 µg/ml. Samples were collected between two and 24 hours after induction.

11.6.2.1. WESTERN BLOT ANALYSIS OF EXPRESSED GLOBIN

The expressed globins was quantitated by Western Blot analysis using procedures described in section 6.6. Samples taken 5 hours after induction had detectable levels of globin (0.5%).

11.6.3. EXPRESSION OF ZETA-GLOBIN 104 SER IN YEAST

11.6.3.1. TRANSFORMATION OF YEAST STRAIN

Sc340 WITH pNT1/Z104S

Yeast strain Sc340 was transformed with plasmid pNT1/Z104S (see Section 11.5.6., supra) using electroporation (see Section 9.4., supra).

For the starter culture, cells were grown in minimal media containing 0.67% yeast nitrogen base, 1% raffinose, and supplemented with 20 mg/L each of adenine, histidine, uracil, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, uracil, and tryptophan. Incubation was at 30° C. with shaking. The culture was induced by adding galactose to a final concentration of 2%. At induction, the pH was adjusted to 7.01 with KH(2)PO(4) and hemin was added to a final concentration of 40 µg/ml. Samples were collected between two and 48 hours after induction.

11.6.3.2. WESTERN BLOT ANALYSIS OF EXPRESSED GLOBIN

The expressed globins was quantitated by Western Blot analysis using procedures described in Section 6.6., supra. Samples taken after induction had detectable levels of globin (0.09%).

11.6.4. EXPRESSION OF BETA-GLOBIN TaLi IN YEAST

Yeast strain Sc340 was transformed with plasmid pNT1/β-TaLiS using electroporation. For the starter culture, cells were grown in minimal media containing 0.67% yeast nitrogen base, 1% raffinose, and supplemented with 20 mg/L each of adenine, histidine, uracil and tryptophan at 30° C. in a shake flask to log phase. The starter culture was used to inoculate 500 ml of media containing 0.67% yeast nitrogen base, 3% glycerol, 2% lactic acid, 1% raffinose, 0.4% Tween 80, and supplemented with 20 mg/L each of adenine, histidine, uracil, and tryptophan. Incubation was at 30° C. with shaking. The culture was induced by adding galactose to a final concentration of 2%. At induction, the pH was adjusted to 7.03 with $KH_2PO_4$ and hemin was added to a final concentration of 40 μg/ml. Samples were collected between two and 50 hours after induction.

The expressed globins were quantitated by Western Blot analysis using procedures described in Section 6.6., supra. Globin was detected at 0.4% of soluble protein.

11.6.5. EXPRESSION OF GAMMA-GLOBIN PORTO ALEGRE IN YEAST

Yeast strain Sc1114 was transformed with plasmid YEp51NT1/γ-PORT (see Section 11.5.1, supra) using electroporation (see Section 9.4., supra). For the starter culture, cells were grown in minimal media containing 0.67% yeast nitrogen base, 1% raffinose, and supplemented with 20 mg/L each of adenine, histidine, uracil and tryptophan at 30° C. in a shake flask to log phase. The starter culture was used to inoculate 500 ml of media containing 0.67% yeast nitrogen base, 3% glycerol, 2% lactic acid, 1% raffinose, 0.4% Tween 80, and supplemented with 20 mg/L each of adenine, histidine, uracil, and tryptophan. Incubation was at 30° C. with shaking. The culture was induced by adding galactose to a final concentration of 2%. At induction, the pH was adjusted to 7.03 with $KH_2PO_4$ and hemin was added to a final concentration of 40 μg/ml. Samples were collected between two and 27 hours after induction.

The expressed globins were quantitated by Western Blot analysis using procedures described in Section 6.6., supra. All samples contained detectable levels of globin (0.1–1.3% protein).

11.6.6. EXPRESSION OF GAMMA-GLOBIN CHICO IN YEAST

Yeast strain Sc340 was transformed with plasmid pNT1/γ-Chi (see Section 11.5.14., supra) using electroporation (see Section 9.4., supra). For the starter culture,cells were grown in minimal media containing 0.67% yeast nitrogen base, 1% raffinose, and supplemented with 20 mg/L each of adenine, histidine, uracil and tryptophan at 30° C. in a shake flask to log phase. The starter culture was used to inoculate 500 ml of media containing 0.67% yeast nitrogen base, 3% glycerol, 2% lactic acid, 1% raffinose, 0.4% Tween 80, and supplemented with 20 mg/L each of adenine, histidine, uracil, and tryptophan. Incubation was at 30° C. with shaking. The culture was induced by adding galactose to a final concentration of 2%. At induction, the pH was adjusted to 7.06 with $KH_2PO_4$ and hemin was added to a final concentration of 40 μg/ml. Samples were collected between two and eight hours after induction.

The expressed globins were quantitated by Western Blot analysis using procedures described in Section 6.6., supra. Globin was detected.

The whole yeast cell visible carbon monoxide difference spectrum is generated using a procedure adapted from the methods of Springer and Slager (1987, Proc. Natl. Acad. Sci. U.S.A. 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite, vortexed, and allowed to sit for one minute. One ml is then removed and placed in a full length small volume cuvette. This suspension is used as the baseline for a scan in a single beam Beckman DU-70 Recording spectrophotomer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned.

Lastly, the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

11.6.7. EXPRESSION OF BETA-GLOBIN MISSISSIPPI IN YEAST

Yeast strain Sc340 was transformed with plasmid pNT1/β-Miss (see Section 11.5.4., supra) using electroporation (see Section 9.4., supra). For the starter culture, cells were grown in minimal media containing 0.67% yeast nitrogen base, 1% raffinose, and supplemented with 20 mg/L each of adenine, histidine, uracil and tryptophan at 30° C. in a shake flask to log phase. The starter culture was used to inoculate 500 ml of media containing 0.67% yeast nitrogen base, 3% glycerol, 2% lactic acid, 1% raffinose, 0.4% Tween 80, and supplemented with 20 mg/L each of adenine, histidine, uracil, and tryptophan. Incubation was at 30° C. with shaking. The culture was induced by adding galactose to a final concentration of 2%. At induction, the pH was adjusted to 7.06 with $KH_2PO_4$ and hemin was added to a final concentration of 40 μg/ml. Samples were collected between two and 50 hours after induction.

The expressed globins were quantitated by Western Blot analysis using procedures described in Section 6.6. Globin was detected at 0.4% of soluble protein.

11.6.8. EXPRESSION OF BETA-GLOBIN RAINIER IN YEAST

Yeast strain Sc1090 was transformed with plasmid pNT1/β-Ran (see Section 11.5.16., supra) using electroporation (see Section 9.4., supra). For the starter culture, cells were grown in minimal media containing 0.67% yeast nitrogen base, 1% raffinose, and supplemented with 20 mg/L each of adenine, histidine, uracil and tryptophan at 30° C. in a shake flask to log phase. The starter culture was used to inoculate 500 ml of media containing 0.67% yeast nitrogen base, 3% glycerol, 2% lactic acid, 1% raffinose, 0.4% Tween 80, and supplemented with 20 mg/L each of adenine, histidine, uracil, and tryptophan. Incubation was at 30° C. with shaking. The culture was induced by adding galactose to a final concentration of 2%. At induction, the pH was adjusted to 7.06 with $KH_2PO_4$ and hemin was added to a final concentration of 40 μg/ml. Samples were collected between two and 50 hours after induction.

The expressed globins were quantitated by Western Blot analysis using procedures described in Section 6.6., supra. Globin was detected at 0.4% of soluble protein.

11.6.9. EXPRESSION OF BETA-GLOBIN MOTOWN IN YEAST

Yeast strain Sc340 was transformed with plasmid pNT1/β-Mot (see Section 11.5.2., supra) using electroporation (see Section 9.4., supra). For the starter culture, cells were grown in minimal media containing 0.67% yeast nitrogen base, 1% raffinose, and supplemented with 20 mg/L each of adenine, histidine, uracil and tryptophan at 30° C. in a shake flask to log phase. The starter culture was used to inoculate 500 ml of media containing 0.67% yeast nitrogen base, 3% glycerol, 2% lactic acid, 1% raffinose, 0.4% Tween 80, and supplemented with 20 mg/L each of adenine, histidine, uracil, and tryptophan. Incubation was at 30° C. with shaking. The culture was induced by adding galactose to a final concentration of 2%. At induction, the pH was adjusted to 7.06 with $KH_2PO_4$ and hemin was added to a final concentration of 40 μg/ml. Samples were collected between two and 8 hours after induction.

The expressed globins were quantitated by Western Blot analysis using procedures described in Section 6.6., supra. Globin was detected at 0.1% of soluble protein.

12. EXAMPLE 7

COEXPRESSION OF ALPHA-GLOBIN AND BETA-GLOBIN BOV2 IN YEAST

12.1. TRANSFORMATION OF YEAST STRAINS Sc389 WITH pUT/2A AND pNT1/β-Bov2

Yeast strain Sc389 was transformed with plasmids pUT/2A (see Section 7, supra) and pNT1/β-Bov2 (see Section 11.5.10., supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 7.12 with KH(2)PO(4) and hemin was added to a final concentration of 40 μg/ml. Samples were collected between two and 30 hours after induction.

12.2. WESTERN BLOT ANALYSIS OF EXPRESSED GLOBIN

The expressed globins were quantitated by Western Blot analysis using procedures described in section 6.6., supra. Globin was detected at a level of 0.6% of soluble protein.

12.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. USA, 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

13. EXAMPLE 8

COEXPRESSION OF ALPHA-GLOBIN AND BETA-GLOBIN 143 ARG IN YEAST

13.1. TRANSFORMATION OF YEAST STRAIN Sc340 WITH pUT/2A AND pNT1/β143Arg

Yeast strain Sc340 was transformed with plasmids pUT/2A (see Section 7, supra) and pNT1/β143Arg (see Section 11.5.12., supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 7.18 with KH(2)PO(4) and hemin was added to a final concentration of 40 μg/ml. Samples were collected between four and 74 hours after induction.

13.2. WESTERN BLOT ANALYSIS OF EXPRESSED GLOBIN

The expressed globins were quantitated by Western Blot analysis using procedures described in Section 6.6., supra. Globin was detected at a level of 0.16% of soluble protein.

13.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. U.S.A. 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly, the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

14. EXAMPLE 9
COEXPRESSION OF ALPHA-GLOBIN AND BETA-GLOBIN 145 TERM IN YEAST

14.1. TRANSFORMATION OF YEAST STRAIN Sc1090 WITH pUT/2A AND pNT1/β145T

Yeast strain Sc1090 was transformed with plasmids pUT/2A (see Section 7, supra) and pNT1/β45T (see Section 11.5.13., supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 7.04 with KH(2)PO(4) and hemin was added to a final concentration of 40 μg/ml. Samples were collected between two and six hours after induction.

14.2. WESTERN BLOT ANALYSIS OF EXPRESSED GLOBIN

The expressed globins were quantitated by Western Blot analysis using procedures described in Section 6.6., supra. Globin was detected at a level of 0.11% of soluble protein.

14.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. U.S.A. 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly, the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

14.4. WESTERN BLOT ANALYSIS OF EXPRESSED ALPHA AND BETA GLOBINS

The expressed alpha and beta globins were separated using an 18% SDS polyacrylamide gel.

Phosphate-buffered saline (PBS; 0.9M NaCl, 0.01M phosphate, pH 7.6) solution (2 ml) was added to thawed yeast samples (0.2 g wet weight). The samples were centrifuged at 4° C. for 10 minutes at 2700 rpm in a Sorvall RT6000B and the supernatant decanted. Cold disruption buffer (50 mM Tris, 5 mM EDTA, 0.5 mM PMSF, pH 8.0) prepared immediately before use (0.2 ml) was added to the pellet, followed by enough ice-cold glass beads to just reach the top surface of the liquid. After vortexing for 30 seconds at maximum speed the samples were placed on ice for 5 minutes. This step was repeated twice. Ice-cold disruption buffer (1 ml) was added to each sample and the homogenate was transferred to an Eppendorf tube. In another Eppendorf tube, 200 microl of homogenate was combined with 200 microl of freshly prepared standard discontinuous 2× sample buffer (Laemli, 1970, Nature 227:680–685) and the sample was boiled for 10 min.

After centrifuging the samples for 10 min., the samples were loaded onto a 20×18 cm discontinuous denaturing gel in which the stacking gel was 3% acrylamide and the separating gel was 18% (Laemli, 1970, Nature 227:680–685). Gels were run at a constant current of 15 mA per gel.

After the electrophoresis was complete and the dye band had reached the bottom of the separating gel, the gels were removed from the electrophoresis unit and the plates were pried apart under running deionized water. The stacking gel was discarded and the lower gel was separated from the plate. The transfer unit was filled with transfer buffer (2 L methanol, 30.3 g Tris base, 144 g glycine in a final volume of 10 L, pH 8.3) and 2 L of the transfer buffer was put into a shallow pan. The transfer sandwich consisting of large pore gauze, 3M blotting paper, the gel, a piece of nitrocellulose paper precut to just cover the gel, 3M blotting paper, and another piece of large pore gauze was assembled under the buffer in the shallow pan.

Protein was transferred from the gel to the nitrocellulose paper by applying a voltage of 40 V for 1.5 hrs. After transfer was complete, the nitrocellulose was removed and placed in a shallow pan with 50 ml of blocking solution [5%(w/v) BSA in PBS]. The nitrocellulose membrane was incubated for 1 hour with agitation, after which the blocking solution was replaced with washing solution [0.1% Tween 20 (v/v) in PBS]. Three washings of 15, 5 and 5 minutes were carried out. The final wash solution was discarded and 25 μl of primary antibody in 25 ml of PBS was added to the pan. After incubation for 2 hours, with agitation, the nitrocellulose was washed three times (1×15 and 2×5 minutes). The final wash was discarded and 2.5 μl of secondary antibody in 25 ml of PBS added for a 1 hour incubation with agitation. After three washes (1×15 and 2×5 minutes), 5 μl of streptavidin-HRP (horseradish peroxidase) was added in 25 ml of PBS containing 0.1% Tween 20 (v/v). After a 20 minute incubation with agitation, the membrane was washed three times (1×15 and 2×5 minutes). The nitrocellulose was then placed in ECL (enhanced chemiluminescent) developing solution that had been prepared immediately prior to use by mixing equal volumes of detection reagent 1 and detection reagent 2 (Amersham). The membrane was incubated for 1 minute with agitation, removed from the developing solution, the excess reagent drained off and the membrane then wrapped in SaranWrap. The wrapped nitrocellulose was then exposed to X-ray film for an appropriate length of time. After development, the X-ray film was scanned using a laser densitometer and the quantity of globin in each sample estimated by comparison with globin standards run on the same gel.

Alpha and beta globins are separated on this gel by molecular weight. Alpha and beta globin were detected in the protein extracts of the cotransformed yeast.

15. EXAMPLE 10

COEXPRESSION OF ALPHA-GLOBIN AND GAMMA-GLOBIN MOTOWN IN YEAST

15.1. TRANSFORMATION OF YEAST STRAIN Sc1114 WITH pUT/2A AND pNT1/γ-Mot2

Yeast strain Sc1114 was transformed with plasmids pUT/2A (see Section 7, supra) and pNT1/γ-Mot2 (see Section 11.5.9., supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 7.09 with $KH(2)PO(4)$ and hemin was added to a final concentration of 40 μg/ml. Samples were collected between four and 51 hours after induction.

15.2. WESTERN BLOT ANALYSIS OF EXPRESSED GLOBIN

The expressed globins were quantitated by Western Blot analysis using procedures described in Section 6.6., supra. Globin was detected at a level of 0.3% of soluble protein.

15.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. USA 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

16. EXAMPLE 11

COEXPRESSION OF ZETA-GLOBIN 104 SERINE AND BETA-GLOBIN IN YEAST

16.1. TRANSFORMATION OF YEAST STRAIN Sc1114 WITH pNT1/Z104S AND YEp51T/NAT

Yeast strain Sc1114 was transformed with plasmids pNT1/Z104S (see Section 11.5.6., supra) and YEp51T/NAT (see Section 6, supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 6.96 with $KH(2)PO(4)$ and hemin was added to a final concentration of 40 μg/ml. Samples were collected between two and 30 hours after induction.

16.2. WESTERN BLOT ANALYSIS OF EXPRESSED GLOBIN

The expressed globins were quantitated by Western Blot analysis using procedures described in Section 6.6., supra. Globin was detected at a level of 0.09% of soluble protein.

16.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. USA 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

17. EXAMPLE 12

COEXPRESSION OF ALPHA-GLOBIN AND BETA-GLOBIN 2 ARG IN YEAST

17.1. TRANSFORMATION OF YEAST STRAIN Sc1090 WITH pUT/2A AND pNT1/β2Arg

Yeast strain Sc1090 was transformed with plasmids pUT/2A (see Section 7, supra) and pNT1/β2Arg (see Section 11.5.11., supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C.

with shaking. The culture was induced by adding galactose to a final concentration of 2%. At induction, the pH was adjusted to 6.93 with KH(2)PO(4) and hemin was added to a final concentration of 40 μg/ml. Samples were collected between four and eight hours after induction.

17.2. WESTERN BLOT ANALYSIS OF EXPRESSED GLOBIN

The expressed globins were quantitated by Western Blot analysis using procedures described in Section 6.6., supra. Globin was detected at a level of 0.17% of soluble protein.

17.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. USA 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

18. EXAMPLE 13

EXPRESSION OF HEMOGLOBIN PORTLAND I IN YEAST

18.1. TRANSFORMATION OF YEAST STRAIN Sc1012 WITH pYES2-ζ2 AND YEp51T/G

Yeast strain Sc1012 was cotransformed with plasmids pYES2-ζ2 (see Section 10, supra) and YEp51T/G (see Section 8, supra).

For the starter culture, cells were grown in minimal media containing 0.67% yeast nitrogen base, 1% raffinose, 4 ppm aminolevulinic acid (ALV), and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 4 ppm ALV, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 6.93 with KH(2)PO(4) and hemin was added to a final concentration of 40 μg/ml. Samples were collected between two and 30 hours after induction.

18.2. WESTERN BLOT ANALYSIS OF EXPRESSED GLOBIN

The expressed globins were quantitated by Western Blot analysis using procedures described in Section 6.6., supra. Globin was detected at a level of 0.06% of soluble protein.

18.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. USA 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

19. EXAMPLE 14

EXPRESSION OF BETA-GLOBIN IN A YEAST EXPRESSION VECTOR CONTAINING A HYBRID PROMOTER AND ADH1 TRANSCRIPTION TERMINATION SEQUENCE

A hybrid promoter was constructed by the fusion of the upstream activating sequence of GAL1-10 promoter with the downstream promoter elements of the TDH3 promoter (referred to hereafter as the 3' end of the TDH3 promoter or TDH3-3'). The cassette containing the hybrid promoter+ beta-globin gene+ADH1 terminator were excised and cloned into the yeast shuttle vector, YEp13. Yeast strain Sc340 was transformed with the resulting plasmid, pNML-V-G-1 and the proteins expressed were analyzed by Western Blot Analysis.

19.1. MATERIALS

The restriction enzymes, Klenow enzyme and T4-DNA ligase were obtained from New England Biolabs (Biolabs), Bethesda Research Laboratories (BRL) or Boehringer Mannheim (BM). All enzymes were used according to the suppliers specifications. Plasmid DNA was isolated from a one liter culture of the transformed cells and purified by CsCl gradient centrifugation.

19.2. CONSTRUCTION OF PLASMID L19βt CONTAINING BETA-GLOBIN GENE AND THE ADH1 TERMINATOR

The beta-globin gene was obtained by digestion of plasmid mp18βHS with SalI and HindIII (see FIG. 39 for map of mp18βHS). The 600 bp fragment was isolated by electroelution.

Plasmid AAH5 was digested with HindIII and BamH1 (Ammerer, G., Methods in Enzymology, 101, pp. 192–201, 1983). The resulting 450 bp fragment was isolated by gel electrophoresis. Subsequently, the band containing the 450 bp fragment was precipitated with ethanol and digested with SpHI. The 320 bp fragment (HindIII-SphI) containing ADH1 transcription termination sequences was isolated by electroelution.

Plasmid pUC19 was cut with SalI and SphI. A three way ligation reaction mixture was set up between the pUC19 fragment, the SalI-HindIII beta-globin fragment, and the HindIII-SphI ADH1 terminator fragment. The ligation was used for transforming competent *E. coli* cells (DH5α). The transformants were selected on ampicillin plates (100 mg/L). Plasmid DNA was isolated from twenty transformants (clones) and analyzed by restriction digestion with SalI-HindIII. The resulting plasmid containing the above two inserts in pUC19 was called L19βAt, and is shown in FIG. 40. The DNA was digested with SphI and ApaLI and a 920 bp fragment containing the beta-globin gene and the ADH1 terminator was isolated by electroelution and used for the construction of the plasmid containing the TDH3 promoter, the beta-globin gene and the ADH1 terminator.

19.3. CONSTRUCTION OF PLASMID pUC19-HβAt

The TDH3-3' promoter fragment was synthesized by PCR using appropriate primers and template DNA from plasmid gp491. The primers, TDH3-5' (5'-primer) and TDH3-3'(3'-primer) are shown in FIG. 41 and are described in the Sequence Description as SEQ ID NO:46 and SEQ ID NO:47. The 180 bp promoter fragment (TDH3-3') synthesized by PCR was digested with ApaLI and SmaI. The plasmid pUC19 was cut with SmaI and SphI. The DNA from plasmid L19βAt was cut with ApaLI and SphI and 920 bp fragment was isolated. Three way ligation was set between these three fragments. The transformation of *E. coli* DH5α cells was carried out as described earlier. The DNA isolated from the transformants were screened by restriction enzyme analysis with PvuII, ApaLI, and PvuII-HindII to check for the correct insert. The map of the resulting plasmid, pUC19-HβAt, is shown in FIG. 42.

19.4. CLONING OF GAL1-10 UAS INTO pUC19-HβAt

GAL1-10 upstream activator sequence (UAS), which is shown in FIG. 43 and described in the Sequence Description as SEQ ID NO:48, was synthesized by polymerase chain reaction using GAL1-10-5' and GAL1-10-3' primers and DNA from YEp51as a template. The sequences of these primers, GAL1-10-5' and GAL1-10-3' are shown in FIG. 44 and are described in the Sequence Description as SEQ ID NO:49 and SEQ ID NO:50. The restriction sites SacI and SmaI were added to facilitate cloning.

The GAL1-10 UAS PCR product was digested with SacI, blunt ended and cut with SmaI. It was cloned by blunt end ligation into SmaI digested pUC19-HβAt which contains the 3' end of the TDH3 promoter with the beta-globin gene and ADH1 terminator. The structure of the resulting plasmid, pUC19-GHβAt is shown in FIG. 45. Transformation was carried out using *E. coli* DH5α cells. The DNA isolated from the transformants were screened by restriction enzyme analysis with PvuII, EcoRI, and HindIII to check for the correct insert.

19.5. CLONING OF THE HYBRID PROMOTER-BETA-GLOBIN GENE CASSETTE IN SHUTTLE VECTOR, YEp13 pUC19-GHβAt was digested with SacI-SphI to excise the GAL10-UAS+TDH3-3'+beta-globin gene+ADH1-terminator cassette from pUC19 which was subsequently blunt-ended. The resulting 1.43 kb fragment was isolated by electroelution.

Plasmid YEp13 (obtained from Fred Winston, Harvard Medical School) which contains LEU2 (yeast) and Amp$^R$ (*E. coli*) markers, was digested with BamHI and blunt-ended; the resulting linear DNA was isolated by electroelution.

Ligation was set between the insert and the vector and the ligation mixture was used for transforming competent *E. coli* cells (DH5α). The transformants were selected on ampicillin plates (100 mg/L). The plasmid DNA was isolated from 24 transformants and analyzed by restriction digestion with HindIII, EcoRI, EcoRI/SalI. A map of the resulting plasmid, pNML-V-G-1 is shown in FIG. 46.

19.6. TRANSFORMATION OF YEAST STRAIN Sc340 CELLS WITH pNML-V-G-1

Strain Sc340 has the following genotype: MATa, ura3-52, leu2, ade1, MEL+, [his3:: GAL10 (UAS+P)+GAL4+URA3]. Yeast strain Sc340 was transformed with plasmid pNML-V-G-1 using the spheroplast procedure (Rose, M. et al., 1989, Methods in Yeast Genetics, Cold Spring Harbor Laboratory, Cold Spring Harbor, N.Y., pp 112–115). To minimize background in the control plates and increase efficiency of transformation, the regeneration media contained 1M sorbitol, 10 mM $CaCl_2$, 0.1% yeast nitrogen base, and 2% glucose. The medium was filter sterilized. The plating media was prepared by mixing 182 g sorbitol, 20 g agar, 6.7 g Difco YNB without amino acids, glucose, required amino acids except leucine in 1 L distilled water. The top agar was made by mixing 18.2 g sorbitol, 2 g agar, 0.67 g Difco YNB without amino acids, 2 g glucose and required amino acids in 100 ml distilled water.

For the starter culture, cells were grown overnight in minimal media containing 0.67% yeast nitrogen base, 0.5% glucose, and supplemented with uracil, adenine, and histidine. 500 ml of SD media supplemented with 200 μM ferric citrate and 20 mg/L each of adenine, uracil, and histidine was inoculated with the starter culture to an $OD_{600}$ of 0.02. The culture was incubated with shaking (300 rpm) at 30° C., and was induced with 2% galactose for a period of 4 hours before sampling for analysis.

19.7. WESTERN BLOT ANALYSIS OF EXPRESSED BETA-GLOBIN

The expressed beta-globin was quantitated by Western Blot analysis using procedures described in Section 6.6., supra. The results indicated that up to 5.4% of the total yeast protein expressed in transformed Sc340 cells was beta-globin.

20. EXAMPLE 15

EXPRESSION OF HEMOGLOBIN PORTLAND II IN YEAST

20.1. TRANSFORMATION OF YEAST STRAIN Sc1041 WITH pYES2-ζ2 AND pNML-V-G-1

Yeast strain Sc1041 was cotransformed with plasmids pYES2-ζ2 (see Section 10, supra) and pNML-V-G-1 (see Section 19, supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 7.16 with KH(2)PO(4) and hemin was added to a final concentration of 40 μg/ml. Samples were collected between two and 30 hours after induction.

20.2. WESTERN BLOT ANALYSIS OF EXPRESSED GLOBIN

The expressed globins were quantitated by Western Blot analysis using procedures described in Section 6.6., supra. Globin was detected at a level of 1.8% of soluble protein.

20.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. USA 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

21. EXAMPLE 16

COEXPRESSION OF ALPHA-GLOBIN AND BETA-GLOBIN MISSISSIPPI IN YEAST

21.1. TRANSFORMATION OF YEAST STRAIN Sc389 WITH PUT/2A AND pNT1/βMiss

Yeast strain Sc389 was transformed with plasmids pUT/2A (see Section 7, supra) and pNT1/βMiss (see Section 11.5.4., supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 7.10 with KH(2)PO(4) and hemin was added to a final concentration of 40 μg/ml. Samples were collected between two and 30 hours after induction.

21.2. WESTERN BLOT ANALYSIS OF EXPRESSED GLOBIN

The expressed globins were quantitated by Western Blot analysis using procedures described in Section 6.6., supra. Globin was detected at a level of 0.16% of soluble protein.

21.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. USA 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

22. EXAMPLE 16

COEXPRESSION OF ALPHA-GLOBIN TITUSVILLE AND BETA-GLOBIN IN YEAST

22.1. TRANSFORMATION OF YEAST STRAIN Sc1114 WITH pNT1/2ATit and YEp51T/NAT

Yeast strain Sc1114 was transformed with plasmids pNT1/2ATit (see Section 11.5.3., supra) and YEp51T/NAT (see Section 6, supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 6.98 with KH(2)PO(4) and hemin was added to a final concentration of 40 μg/ml. Samples were collected between four and 51 hours after induction.

22.2. WESTERN BLOT ANALYSIS OF EXPRESSED GLOBIN

The expressed globins were quantitated by Western Blot analysis using procedures described in Section 6.6., supra. Globin was detected at a level of 0.01% of soluble protein.

22.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. USA 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

23. EXAMPLE 18

COEXPRESSION OF ALPHA-GLOBIN TITUSVILLE/104 SERINE AND BETA-GLOBIN IN YEAST

23.1. TRANSFORMATION OF YEAST STRAIN Sc1114 WITH pNT1/2ATiS and YEp51T/NAT

Yeast strain Sc1114 was transformed with plasmids pNT1/2ATiS (see Section 11.5.8., supra) and YEp51T/NAT (see Section 6, supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 7.10 with KH(2)PO(4) and hemin was added to a final concentration of 40 µg/ml. Samples were collected between four and 51 hours after induction.

23.2. WESTERN BLOT ANALYSIS OF EXPRESSED GLOBIN

The expressed globins were quantitated by Western Blot analysis using procedures described in Section 6.6., supra. Globin was detected at a level of 0.2% of soluble protein.

23.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. USA 84:8961). Approximately 1.2 ml of suspension of yeast with a final O.D. at 600 nm of about 2.0 is prepared using 0–1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

24. EXAMPLE 19

COEXPRESSION OF ALPHA-GLOBIN AND BETA-GLOBIN MOTOWN IN YEAST

24.1. TRANSFORMATION OF YEAST STRAIN Sc389 WITH pUT/2A AND pNT1/β-Mot

Yeast strain Sc389 was transformed with plasmids pUT/2A (see Section 7, supra) and pNT1/β-Mot (see Section 11.5.2., supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 7.17 with KH(2)PO(4) and hemin was added to a final concentration of 40 µg/ml. Samples were collected between four and 51 hours after induction.

24.2. WESTERN BLOT ANALYSIS OF EXPRESSED GLOBIN

The expressed globins were quantitated by Western Blot analysis using procedures described in Section 6.6., supra. Globin was detected at a level of 0.4% of soluble protein.

24.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. U.S.A. 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

24.4. WESTERN BLOT ANALYSIS OF EXPRESSED ALPHA AND BETA-GLOBINS

The expressed alpha and beta globins were separated using an 18% SDS polyacrylamide gel.

Phosphate-buffered saline (PBS; 0.9M NaCl, 0.01M phosphate, pH 7.6) solution (2 ml) was added to thawed yeast samples (0.2 g wet weight). The samples were centrifuged at 4° C. for 10 minutes at 2700 rpm in a Sorvall RT6000B and the supernatant decanted. Cold disruption buffer (50 mM Tris, 5 mM EDTA, 0.5 mM PMSF, pH 8.0) prepared immediately before use (0.2 ml) was added to the pellet, followed by enough ice-cold glass beads to just reach the top surface of the liquid. After vortexing for 30 seconds at maximum speed the samples were placed on ice for 5 minutes. This step was repeated twice. Ice-cold disruption buffer (1 ml) was added to each sample and the homogenate was transferred to an Eppendorf tube. In another Eppendorf tube, 200 μl of homogenate was combined with 200 μl of freshly prepared standard discontinuous 2× sample buffer (Laemli, 1970, Nature 227:680–685) and the sample was boiled for 10 min.

After centrifuging the samples for 10 min., the samples were loaded onto a 20×18 cm discontinuous denaturing gel in which the stacking gel was 3% acrylamide and the separating gel was 18% (Laemeli, 1970, Nature 227: 680–685). Gels were run at a constant current of 15 mA per gel.

After the electrophoresis was complete and the dye band had reached the bottom of the separating gel, the gels were removed from the electrophoresis unit and the plates were pried apart under running deionized water. The stacking gel was discarded and the lower gel was separated from the plate. The transfer unit was filled with transfer buffer (2L methanol, 30.3 g Tris base, 144 g glycine in a final volume of 10L, pH 8.3) and 2L of the transfer buffer was put into a shallow pan. The transfer sandwich consisting of large pore gauze, 3M blotting paper, the gel, a piece of nitrocellulose paper precut to just cover the gel, 3M blotting paper, and another piece of large pore gauze was assembled under the buffer in the shallow pan.

Protein was transferred from the gel to the nitrocellulose paper by applying a voltage of 40 V for 1.5 hrs. After transfer was complete, the nitrocellulose was removed and placed in a shallow pan with 50 ml of blocking solution [5%(w/v) BSA in PBS]. The nitrocellulose membrane was incubated for 1 hour with agitation, after which the blocking solution was replaced with washing solution [0.1% Tween 20 (v/v) in PBS]. Three washings of 15, 5 and 5 minutes were carried out. The final wash solution was discarded and 25 μl of primary antibody in 25 ml of PBS was added to the pan. After incubation for 2 hours, with agitation, the nitrocellulose was washed three times (1×15 and 2×5 minutes). The final wash was discarded and 2.5 μl of secondary antibody in 25 ml of PBS added for a 1 hour incubation with agitation. After three washes (1×15 and 2×5 minutes), 5 μl of streptavidin-HRP (horseradish peroxidase) was added in 25 ml of PBS containing 0.1% Tween 20 (v/v). After a 20 minute incubation with agitation, the membrane was washed three times (1×15 and 2×5 minutes). The nitrocellulose was then placed in ECL (enhanced chemiluminescent) developing solution that had been prepared immediately prior to use by mixing equal volumes of detection reagent 1 and detection reagent 2 (Amersham). The membrane was incubated for 1 minute with agitation, removed from the developing solution, the excess reagent drained off and the membrane then wrapped in SaranWrap. The wrapped nitrocellulose was then exposed to X-ray film for an appropriate length of time. After development, the X-ray film was scanned using a laser densitometer and the quantity of globin in each sample estimated by comparison with globin standards run on the same gel.

Alpha and beta-globins are separated on this gel by molecular weight. Alpha and beta-globin were detected in the protein extracts of the cotransformed yeast.

25. EXAMPLE 20

EXPRESSION OF THE PORTO ALEGRE BETA-GLOBIN IN A YEAST EXPRESSION VECTOR CONTAINING THE GAL10 PROMOTER

As detailed herein, the natural beta-globin was modified to obtain a Porto Alegre beta-globin gene by replacing a 104 bp AccI-NcoI fragment from the natural beta-globin gene with a synthetic oligonucleotide containing a cysteine as amino acid 9 (instead of a serine). The Porto Alegre beta-globin gene was subsequently cloned into the yeast expression vector YEp51 to obtain plasmid YEpWB51/PORT. YEpWB51/PORT was transformed into yeast strain Sc340, a hem1 strain. Quantitation of RNA by scanning the autoradiograph showed that mRNA for the Porto Alegre beta-globin was around 6.0% of total yeast RNA. Western blot analysis indicated that Porto Alegre beta-globin was expressed.

25.1. MATERIALS

The restriction enzymes, Klenow enzyme and T4-DNA ligase were obtained from New England Biolabs (Biolabs), Bethesda Research Laboratories (BRL) or Boehringer Mannheim (BM). All enzymes were used according to the suppliers specifications. Plasmid DNA was isolated from a one liter culture of the transformed E. coli cells and purified by CsCl gradient centrifugation.

25.2. CLONING OF THE PORTO ALEGRE BETA-GLOBIN GENE INTO THE YEAST EXPRESSION VECTOR YEp51

Figure 3B:
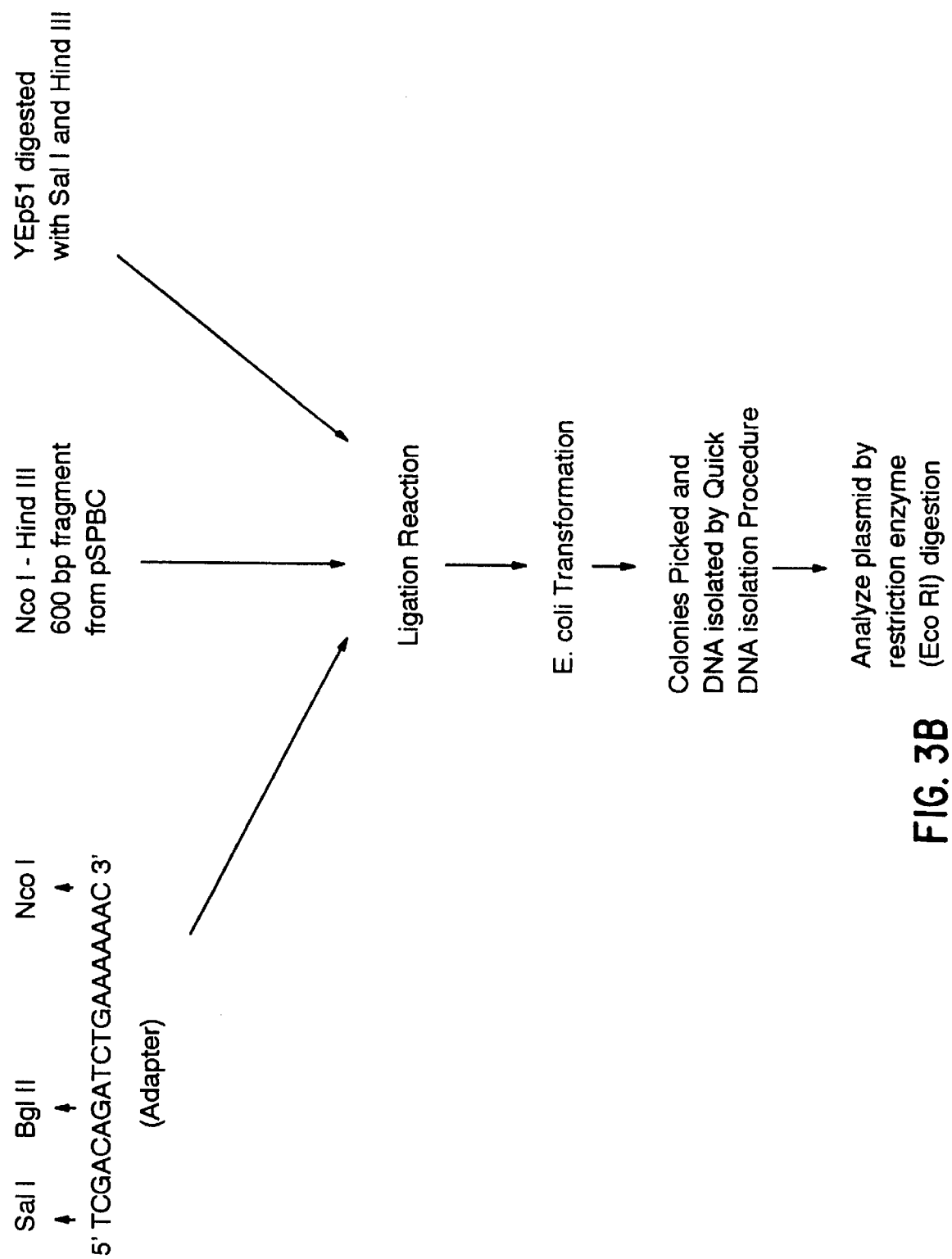
FIG. 3B shows the strategy used to clone the Porto Alegre beta-globin gene.
Figure 4:
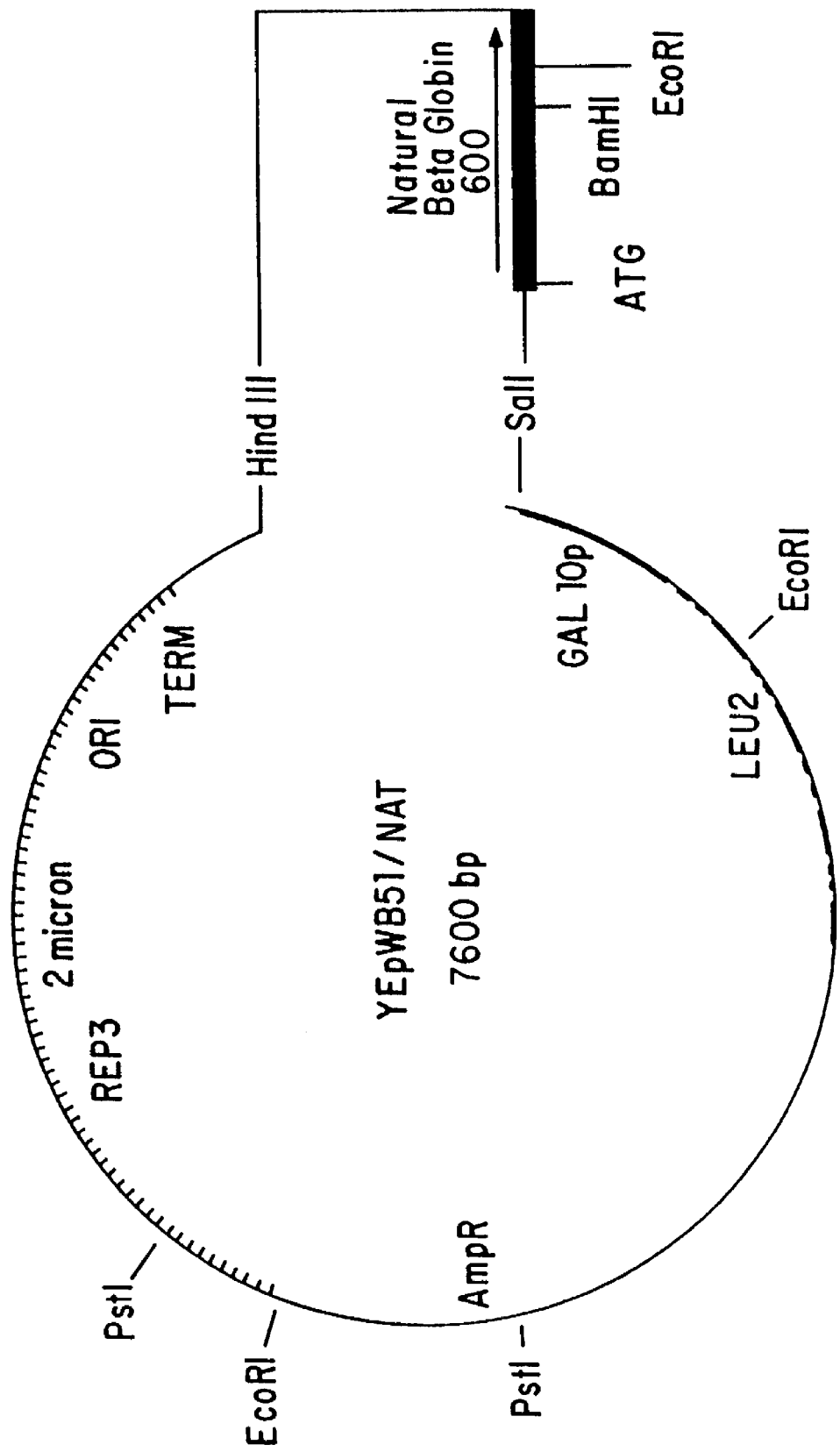
FIG. 4 shows the restriction map of the plasmid YEpWB51/NAT.

The general procedure used to clone the Porto Alegre beta-globin gene into the yeast expression vector YEp51 is shown in FIG. 3B. The plasmid pSPβC (see FIG. 2 for the partial restriction map of pSBβC) was digested with AccI and HindIII. Digestion with this combination of enzymes generated two fragments. A 500 base pair (bp) DNA containing the beta-globin gene and a 2800 bp fragment from the plasmid. The 500 bp fragment was isolated from a 0.6% agarose gel. After the band was excised from the gel, the DNA was electroeluted, and ethanol precipitated. The precipitated DNA was spun in an Eppendorf Centrifuge, the supernatant was removed and the DNA pellet was dried under vacuum.

The 500 bp DNA fragment carrying the natural beta-globin gene fragment isolated from pSPβC was AccI compatible at the 5'-end while the 3'-end was HindIII compatible. To modify the 5'-end of the isolated fragment, a synthetic oligonucleotide was used. This double stranded oligonucleotide (104 bp) contained a codon for cysteine as amino acid 9 instead of a codon for serine and had a AccI compatible end at its 3'-end and a SalI compatible end at it 5'-end (see FIG. 3B). The 3'-end of the isolated fragment did not receive any adapter as the HindIII site was compatible with the HindIII site introduced into the YEp51.

The recipient plasmid YEp51 was cleaved with SalI and HindIII restriction enzymes. To insert the isolated fragment containing the beta-globin gene, a three-way ligation was set up (see FIG. 3B). The ligation reaction was carried out using the standard ligation procedures (Maniatis et al., 1982, Molecular Cloning, A Laboratory Manual, Cold Spring Harbor Laboratory, Cold Spring Harbor, N.Y.). The ligation mixture was transformed into the *E. coli* HB101 cells using standard transformation procedure. Cells were spread on plates containing LB-media with 100 mg/L ampicillin. Plates were incubated overnight at 37° C. Forty eight colonies from the ampicillin plates were picked and a 5 ml culture was inoculated with individual transformant. Cultures were grown overnight at 37° C. with vigorous shaking. The plasmid DNA was isolated from 1.5 ml of the overnight culture using the quick alkaline plasmid isolation procedure (Maniatis et al., 1982, Molecular Cloning, A Laboratory Manual, Cold Spring Harbor Laboratory, Cold Spring Harbor, N.Y.). The plasmid from each transformant was digested with EcoRI to confirm the presence of a DNA fragment containing the Porto Alegre beta-globin gene. The plasmid carrying the Porto Alegre beta-globin gene was called YEpWB51/PORT. The map of plasmid YEpWB51/PORT is shown in FIG. 47.

25.3. TRANSFORMATION OF Sc340 CELLS WITH YEpWB51/PORT

The yeast strain Sc340 was obtained from Dr. J. E. Hopper of Hershey Medical Center. The genotype of this strain is:

MATa ura3-52, leu2, ade1, his3::GAL10$^{uas}$-GAL4-URA3$^+$,MEL$^+$.

Sc340 cells were transformed with the plasmids YEpWB51/PORT and YEp51 (control). The spheroplast method of transformation was performed according to the published procedure (Hinnen et al., 1978, Proc. Natl. Acad. Sci. U.S.A. 75: 1929–1933). The transformants were selected by plating out on minimal media containing 0.67% Bacto yeast nitrogen base without amino acids, 2% glucose, 20 mg/L adenine sulfate, 20 mg/L histidine, and 20 mg/L uracil. The plates were incubated at 28° C. for three days and were examined for colony formation.

Colonies were picked from these plates following incubation and were precultured in yeast minimal media (0.67% yeast nitrogen base without amino acids) containing 0.5% glucose plus 20 mg/L each of adenine, uracil, and histidine. The overnight culture was then used to inoculate 1000 ml of the yeast minimal media containing 2% lactic acid, 3% glycerol and appropriate amino acids. The cultures were inoculated to OD$_{600}$ of 0.02. Cultures were grown at 30° C. until they reached OD$_{600}$ of 0.20 (usually after 48 hours). Induction was initiated by the addition of galactose to a final concentration of 2% in the media. After four hours, cultures were harvested by centrifugation and the pellet was washed with 150 mM NaCl. The pellet was divided into two parts. One part was used for RNA isolation and the other was kept at −70° C. for Western blot analysis.

25.4. QUANTITATION OF RNA FROM SC340 CELLS TRANSFORMED WITH PLASMIDS YEp51 AND YEp51WB/PORT

RNA was isolated using published procedures (Meyhack et al., 1982, The EMBO Journal 1:675–680 or Carlson and Botstein, 1982, Cell 28:145). Yeast cells were washed with 150 mM NaCl and the pellet was resuspended in RNA buffer (0.5M NaCl, 0.2M Tris-HCl, pH 7.6, 0.1M EDTA and 1% SDS). Approximately 0.5 g of glass beads (0.45–0.5 mm) were added to the tubes. An equal volume of phenol mixture (phenol:chloroform:isoamyl alcohol 25:24:1, equilibrated with RNA buffer without SDS) was added. Yeast cells were broken by vortexing at maximum speed for 2.5 minutes and the sample was placed on ice for 3 minutes. The above step was repeated twice more. Equal volumes of RNA buffer and phenol mixture were added to the cells and tubes were centrifuged. Aqueous phase was transferred to a clean Corex tube and 2.5 volumes of ethanol were added to each tube. RNA was allowed to precipitate at −20° C. for 4 to 6 hours. RNA was pelleted by centrifugation and dried under vacuum. RNA pellet was suspended in sterile water.

Total RNA was denatured using the glyoxal method (Thomas, P., 1983, in "Methods in Enzymology", Colowhich, S. P. and Kaplan, N. O. eds. Vol. 100: pp. 255–266, Academic Press, New York). RNA was electrophoresed on 1.1% agarose gel in 10 mM NaPO$_4$ for approximately 4 hours at 75 volts (constant). After the electrophoresis was complete, RNA was transferred to Amersham Hybond-N paper (Thomas, P., 1983, in "Methods in Enzymology" Colowhich, S. P. and Kaplan, N. O. eds. Vol. 100: pp 255–266, Academic Press, New York).

Total yeast RNA bound to the filter paper was hybridized to the radioactive labelled beta-globin DNA. Hybridizations were carried out at 42° C. overnight in 50% (v/v) formamide with 5× SSC (SSC: 3.0M NaCl, 0.3M Na citrate, pH 7.5); 50 mM NaPO$_4$, pH 6.5; 250 μg/ml Salmon sperm DNA; and 1× Denhardt's solution; (Denhardt's solution: 0.02% Ficoll, 0.02% polyvinylcarbonate, and 0.02% BSA, fraction V). The CYH2 mRNA which codes for yeast ribosomal protein L19 was used as control. The probe was plasmid mp10CYH22 which carries the yeast CYH2 gene. After the hybridizations, filters were washed three times at room temperature in 2× SSC and 0.1% SDS and four times at 50° C. in 0.1× SSC and 0.1% SDS. Filters were exposed to X-ray films for 1 hour to overnight depending on the radioactivity. X-ray films were developed in a Konica automated film developer.

The results from these RNA blot hybridizations are shown in FIG. 8, which show results from RNA isolated from yeast transformed with a control plasmid containing no globin sequences (lane 1), a plasmid containing sequences encoding beta-globin (lane 2), and a plasmid containing sequences encoding Porto Alegre beta-globin (lane 3). The results indicate that the mRNA samples from all sources were intact and no degradation was detected. It was also observed that no beta-globin mRNA could be detected in lane 1, which contains the parent plasmid only. These results indicate that nonspecific hybridization of the beta-globin probe is minimal.

Autoradiographs containing bands corresponding to both beta-globin and CYH2 mRNA were scanned using the LKB gel scanner. Results obtained from the scanner are shown in FIG. 9. It can be clearly seen that the abundance of CYH2 mRNA in all three lanes is approximately the same while the abundance of the Porto Alegre beta-globin mRNA in 340g2P was high.

25.5. WESTERN BLOT ANALYSIS OF EXPRESSED PORTO ALEGRE BETA-GLOBIN

The expressed Porto Alegre beta-globin was analyzed by Western Blot analysis (see Section 6.6., supra). Globin was detected at a level of 0.09% of soluble protein.

26. EXAMPLE 21

COEXPRESSION OF ZETA-GLOBIN TITUSVILLE AND GAMMA-GLOBIN IN YEAST

26.1. TRANSFORMATION OF YEAST STRAIN Sc1115 WITH pNT1/z95An AND YEp51T/G

Yeast strain Sc1115 was transformed with plasmids pNT1/z95An (see Section 11.5.7., supra) and YEp51T/G (see Section 8, supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 7.17 with $KH_{(2)}PO_{(4)}$ and hemin was added to a final concentration of 40 µg/ml. Samples were collected between four and 51 hours after induction.

26.2. WESTERN BLOT ANALYSIS OF EXPRESSED GLOBIN

The expressed globins were quantitated by Western Blot analysis using procedures described in Section 6.6., supra. Globin was detected at a level of 0.3% of soluble protein.

26.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. U.S.A. 84: 8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present the difference spectrum will produce a peak around 420 nm and a valley around 435 nm. A single peak at 420 nm does not indicate the presence of hemoglobin.

Functional hemoglobin was detected in this strain by this method.

27. EXAMPLE 22

COEXPRESSION OF ALPHA-GLOBIN AND GAMMA-GLOBIN CHICO IN YEAST

27.1. TRANSFORMATION OF YEAST STRAIN Sc340 WITH pUT/2A AND pNT1/γ-Chi

Yeast strain Sc340 was transformed with plasmids pUT/2A (see Section 7, supra) and pNT1/γ-Chi (see Section 11.5.14., supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 7.17 with $KH_{(2)}PO_{(4)}$ and hemin was added to a final concentration of 40 µg/ml. Samples were collected between four and 51 hours after induction.

27.2. WESTERN BLOT ANALYSIS OF EXPRESSED GLOBIN

The expressed globins were quantitated by Western Blot analysis using procedures described in Section 6.6., supra. Globin was detected at a level of 0.1% of soluble protein.

27.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. U.S.A. 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

28. EXAMPLE 23

COEXPRESSION OF ALPHA-GLOBIN AND GAMMA-GLOBIN PORTO ALEGRE IN YEAST

28.1. TRANSFORMATION OF YEAST STRAIN Sc1115 WITH pUT/2A AND pNT1/γ-PORT

Yeast strain Sc1115 was transformed with plasmids pUT/2A (see Section 7, supra) and pNT1/γ-PORT (see Section 11.5.1., supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C.

with shaking. The culture was induced by adding galactose to a final concentration of 2%. At induction, the pH was adjusted to 7.17 with KH(2)PO(4) and hemin was added to a final concentration of 40 μg/ml. Samples were collected between four and 51 hours after induction.

28.2. WESTERN BLOT ANALYSIS OF EXPRESSED GLOBIN

The expressed globins were quantitated by Western Blot analysis using procedures described in Section 6.6., supra. Globin was detected at a level of 0.01% of soluble protein.

28.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. U.S.A. 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present, the difference spectrum will produce a peak around 420 nm and a valley around 435 nm. A single peak at 420 nm does not indicate the presence of hemoglobin.

Functional hemoglobin was detected in this strain by this method.

29. EXAMPLE 24

COEXPRESSION OF ALPHA-GLOBIN AND BETA-GLOBIN PORTO ALEGRE IN YEAST

29.1. TRANSFORMATION OF YEAST STRAIN Sc1090 WITH pUT/2A AND YEpWB51T/PORT

Yeast strain Sc1090 was transformed with plasmids pUT/2A (see Section 7, supra) and YEpWB51T/PORT (see Section 25, supra) using electroporation (see Section 9.4., supra).

For the starter culture, cells were grown in minimal media containing 0.67% yeast nitrogen base, 1% raffinose, and supplemented with 20 mg/L each of adenine, histidine, and tryptophan at 30° C. in a shake flask to log phase. The starter culture was used to inoculate 500 ml of media containing 0.67% yeast nitrogen base, 3% glycerol, 2% lactic acid, 0.4% Tween 80, and supplemented with 20 mg/L each of adenine, histidine, and tryptophan. Incubation was at 30° C. with shaking. The culture was induced by adding galactose to a final concentration of 2%. At induction, the pH was adjusted to 7.17 with KH(2)PO(4) and hemin was added to a final concentration of 40 μg/ml. Samples were collected between four and 51 hours after induction.

29.2. WESTERN BLOT ANALYSIS OF EXPRESSED GLOBIN

The expressed globins were quantitated by Western Blot analysis using procedures described in Section 6.6., supra. Globin was detected at a level of 0.02% of soluble protein.

29.3. DETECTION OF HEMOGLOBIN IN YEAST BY CARBON MONOXIDE DIFFERENCE SPECTRUM

The whole yeast cell visible carbon monoxide difference spectrum is generated using a procedure adapted from the methods of Springer and Slager (1987, Proc. Natl. Acad. Sci. U.S.A. 84:8961). Approximately 1.2 ml of suspension of yeast with a final O.D. at 600 nm of about 2.0 is prepared using 0.1 mM $PO_4$, pH 7.0, as a buffer. The suspension is then reduced with a small amount of sodium dithionite vortexed, and allowed to sit for one minute. One ml is then removed and placed in a full length small volume cuvette. This suspension is used as the baseline for a scan in a single beam Beckman DU-70 Recording spectrophotometer from 400 to 500 nm. The cuvette is then removed and the suspension is bubbled steadily but not vigorously with oxygen-scrubbed carbon monoxide (CO) for two minutes. The suspension is mixed by gentle rocking for one minute and the spectrum from 400 to 500 nm is scanned. Lastly the O.D. at 600 nm is measured on the same instrument.

If hemoglobin is present the difference spectrum will produce a peak around 420 nm and a valley around 435 nm. A single peak at 420 nm does not indicate the presence of hemoglobin.

Functional hemoglobin was detected in this strain by this method.

EXAMPLE 25

EXPRESSION OF ALPHA-GLOBIN IN A YEAST EXPRESSION VECTOR CONTAINING A HYBRID PROMOTER AND ADH1 TRANSCRIPTION TERMINATION SEQUENCE

A hybrid promoter was constructed by the fusion of the upstream activating sequence of ADH2 promoter with the downstream promoter elements of the TDH3 promoter (referred to hereafter as the 3' end of the TDH3 promoter or TDH3-3'). Specifically, the ADH2-UAS-TDH3-3' hybrid promoter, alpha-globin gene, and GAL10 terminator were cloned into plasmid pUC19. The resulting plasmid was labeled pUC19-AHαGt. The cassette containing the hybrid promoter+alpha-globin gene+GAL10 terminator was excised and cloned into the yeast shuttle vector, pPM40. Yeast strain Sc1012 was transformed with the resulting plasmid, pNM-R-A-α1 and the proteins expressed were analyzed by Western Blot Analysis.

30.1. MATERIALS

The restriction enzymes, Klenow enzyme and T4-DNA ligase were obtained from New England Biolabs (Biolabs), Bethesda Research Laboratories (BRL) or Boehringer Mannheim (BM). All enzymes were used according to the suppliers' specifications. Plasmid DNA was isolated from a one liter culture of the transformed E. coli cells and purified by CsCl gradient centrifugation.

30.2. CONSTRUCTION OF pUC19-GHαGt

30.2.1. CONSTRUCTION OF PLASMID p19A1

To construct plasmid p19A1, the alpha-globin gene was obtained by Polymerase Chain Reaction (PCR). Template used for the PCR was plasmid pJW101 (Wilson et al., 1978, Nucl, Acids Res. 5: 563–580) and primers used in the reaction were 51-A-1 and 519-A-3. The sequence of the primers used in the PCR are also described in the Sequence Description as SEQ ID NO:7 and SEQ ID NO:51 respectively, as well as in FIG. 48.

The PCR product was digested with SalI and BamHI restriction enzymes, and the 460 bp fragment was isolated from a 0.6% agarose gel (1× TBE). DNA was electroeluted from the gel slice and was precipitated with ethanol at −20° C. The precipitated DNA was spun in an Eppendorf centrifuge for 15 minutes. The pellet was dried under vacuum. The DNA was suspended in 20° C. water. Purified PCR product was ligated to plasmid pUC19 digested with restriction enzymes SalI and BamHI. The ligation reaction was carried out at 15° C. according to standard ligation procedures (Maniatis et al., 1982, Molecular Cloning, A Laboratory Manual, Cold Spring Harbor Laboratory, Cold Spring Harbor, N.Y.). Ligation mixture was used to transform *E. coli* DH5α cells using standard transformation procedures. The cells were spread on plates containing LB-media with 100 mg/1 ampicillin. Plates were incubated overnight at 37° C. Twenty-four colonies from ampicillin plates were picked and a 5 ml culture was inoculated with individual transformants. Cultures were grown overnight at 37° C. with vigorous shaking. The plasmid DNA was isolated from 1.5 ml culture and DNA was digested with restriction enzyme HindIII. Eight clones showed the expected length of fragments (2900 bp and 200 bp). The resulting plasmid was called p19A1.

30.2.2. CONSTRUCTION OF PLASMID p19A1GT

To construct plasmid p19A1GT, the GAL10 terminator was obtained by Polymerase Chain Reaction (PCR). Template used for the PCR was plasmid pCLUI and the primers used in the reaction, G10T-5B, described in the Sequence Description as SEQ ID NO:52 and G10T3ESS and described in the Sequence Description as SEQ ID NO:53. The sequence of the primers, G10T-5B and G10T3ESS are shown in FIG. 49.

The PCR product was digested with BamHI and EcoRI restriction enzymes and 450 bp fragment was isolated from a 0.6% agarose gel (1× TBE). DNA was electroeluted from the gel slice and was precipitated with ethanol at −20° C. The precipitated DNA was spun in an Eppendorf Centrifuge for 15 minutes. The pellet was dried under vacuum. The DNA was suspended in 20° C water. Purified PCR product was ligated to plasmid p19A1 digested with restriction enzymes BamHI and EcoRI. The ligation reaction was carried out at 15° C. according to standard ligation procedures (Maniatis et al., 1982, Molecular cloning, A Laboratory Manual, Cold Spring Harbor Laboratory, Cold Spring Harbor, N.Y.). The ligation mixture was used to transform *E. coli* DH5α cells using standard transformation procedures. The cells were spread on plates containing LB-media with 100 mg/l ampicillin. Plates were incubated overnight at 37° C. Twenty-four colonies from ampicillin plates were picked and a 5 ml culture was inoculated with individual transformants. Cultures were grown overnight at 37° C. with vigorous shaking. The plasmid DNA was isolated from 1.5 ml culture and DNA was digested with restriction enzyme SalI. Eight clones showed the expected length of fragments (2700 bp and 900 bp). The resulting plasmid was called p19A1GT.

30.2.3. CONSTRUCTION OF PLASMID pUC19-GHαGt

PCR was used to synthesize a hybrid promoter fragment, GHαGt, which contains the hybrid promoter, GAL1-10 UAS/TDH3-3' and the first 36 bases of the alpha-globin gene up to and including the StuI site in the gene. The resulting 570 bp PCR fragment was cloned into SmaI cut pUC19 plasmid by blunt end ligation. The transformation was carried out using *E. coli* strain 510α.

The first restriction site in the alpha-globin coding sequence is StuI which begins 31 bases downstream from the ATG initiation codon. The 3' primer was synthesized to contain sequences complementary to the 3' end of the TDH3-3' promoter and the first 36 bases of the alpha-globin gene up to the StuI site. The 5' and 3' primers are described in the Sequence Description as SEQ ID NO:54 and SEQ ID NO:55, respectively and in FIG. 50. The template used for the PCR was DNA from plasmid pUC19-GHβAt, which contains GAL1-10 UAS/TDH3-3' hybrid promoter.

The 570 bp fragment containing the hybrid promoter and the first 36 bases of alpha-globin, synthesized using the above primers, was cloned into the vector, pUC19 by blunt end ligation. This plasmid was labeled pUC19-GHα'.

The 3' alpha globin gene fragment containing appropriate cloning sites was made by PCR. Plasmid pUC19-A1 was used as template. The 5' and 3' primers used to synthesize the gene are described in the Sequence Description as SEQ ID NO:56 and SEQ ID NO:57, respectively. The sequences of and the restriction sites present on the primers are shown in FIG. 51.

The resulting 460 bp fragment was cut with BamHI and SalI and cloned into pUC19 cut with BamHI-SalI. The *E. coli* 510α strain was used for transformation because this strain produces unmethylated DNA. StuI enzyme is inefficient in cutting methylated DNA. The transformants were analyzed by digestion with PvuII and the resulting plasmid containing the appropriate fragment was labeled pUC19-A2.

The DNA from plasmids pUC19-A2 and pUC19-GHα' were each cut with StuI-SalI and the resulting linear fragment A and the 580 bp fragment B respectively were isolated by electroelution. Ligation was set between fragments A and B and the ligation mixture was used for transforming *E. coli* 510α cells. The resulting plasmid containing both the fragments in correct orientation was labeled pUC19-GHA (see FIG. 52).

The DNA from vector plasmid pUC19 was cut with SphI. The linear DNA was isolated and dephosphorylated (fragment C). The DNA from plasmid pUC19-GHA was cut with SphI and HindIII and the resulting fragment was isolated by electroelution (fragment D). The DNA from plasmid p19A1GT was cut with SphI and HindIII and the resulting fragment containing part of alpha-globin gene and GAL10 terminator (580 bp) was isolated (fragment E). A three way ligation was set between fragments C, D and E. The ligation mixture was used for transforming *E. coli* DH5α cells. The plasmid containing both of the inserts in the correct orientation was named pUC19-GHαGt (FIG. 53).

30.3. CLONING OF ADH-2-UAS AND TDH3-3'/α-GLOBIN GENE/GAL10 INTO pUC19

The plasmid pUC19-ADH2-UAS DNA was cut with XbaI/SphI. The linear DNA fragment was isolated (Fragment #1). The DNA fragment containing TDH3-3'/α-globin gene/GAL10 terminator (HαGt) was made by PCR using plasmid pUC19-GHαGt as template. The sequence of the primers used to synthesize the DNA fragment by PCR are described in the Sequence Description as SEQ ID NO:58 and SEQ ID NO:53. The sequence of the DNA fragments along with their restriction sites are shown in FIG. 54.

The resulting 1.04 kb fragment, containing TDH3-3'/alpha-globin gene/GAL10 terminator (HαGt) was cut with XbaI/SphI (fragment #2). Ligation was set up between fragment #1 and #2. E. coli DH5α cells were transformed and restriction digests of the DNA from the transformants were analyzed. The plasmid containing the fragments in correct orientation was labeled pUC19-AHαGt. The map of this plasmid is shown in FIG. 55.

30.4. CLONING OF AHαGt CASSETTE INTO pPM40

The expression cassette, AHαGt, was excised by cutting the pUC19-AHαGt plasmid DNA with SacI/SphI. The resulting 1.3 kb fragment was cloned into BamHI cut, blunt ended pPM40. The map of pPM40 is shown in FIG. 56. The resulting plasmid is called pNM-R-A-α1. The map of this plasmid is shown in FIG. 57.

30.5. TRANSFORMATION OF YEAST STRAIN Sc1012 WITH pNM-R-A-α1

The yeast strain Sc1012 is a hem1 mutant which is blocked in 5-aminolevulinic acid synthetase, the first enzyme in the heme biosynthetic pathway. Sc1012 has the following genotype: ade1, ade2, hem1-1, his3, leu2-3, 112, ura3-1. Yeast strain Sc1012 was transformed with plasmid pNM-R-A-α1 using the spheroplast procedure (Rose, M. et al., 1989, Methods in Yeast Genetics, Cold Spring Harbor Laboratory, Cold Spring Harbor, N.Y., pp 112–115). Two changes were made in the above protocol. The amount of YEP added during the regeneration step was reduced from 1% to 0.1%. No YEP broth was added to the regeneration agar.

For the starter culture, cells were grown in 500 ml of minimal media containing 0.67% yeast nitrogen base, 2% glucose, and supplemented with 20 mg/L each of leucine, adenine, and histidine, and 4 mg/L aminolevulinic acid at 30° C. in a shake flask to log phase. The cells were then harvested, washed with uracil drop-out media containing 0.67% yeast nitrogen base, 2% glucose, and supplemented with 40 mg/L each of leucine, adenine, and histidine, and 4 mg/L of aminolevulinic acid and used to inoculate 2 L of the uracil drop-out medium in a Braun Biostat E fermentor. The pH was maintained at pH 5.5 with a 5% ammonium hydroxide solution. The $pO_2$ was maintained at 80% of saturation during the growth phase and then adjusted to 10% at glucose depletion. The stirrer speed was set at 500 rpm, and then reduced to 100 rpm at induction. Samples were taken every 2 hours after glucose depletion over a period of fifty hours.

30.6. WESTERN BLOT ANALYSIS OF EXPRESSED ALPHA-GLOBIN

The expressed alpha-globin was quantitated by Western Blot analysis using procedures described in section 6.6. supra. The results indicated that up to 0.74% of the total yeast protein expressed in transformed Sc1012 cells was alpha-globin.

31. EXAMPLE 26

SORET SPECTRA OF HEMOGLOBIN IN YEAST

The porphyrin ring found in functional hemoglobin is responsible for the molecule's ability to reversibly bind oxygen. In addition, the many double bonds of the ring result in hemoglobin being able to absorb light in the 200 to 600 nm (ultraviolet to visible) range. The exact wavelengths of maximum absorbance (i.e. peaks) are a function of several factors including the exact structure of the ring, the protein with which the ring is associated (e.g. hemoglobin, myoglobin, cytochromes, etc.), differences in the environment near the ring within a given protein (e.g. $HbA_0$ versus $HbAO_2$, etc.) and small inorganic molecules bound to the ring (e.g. oxygen, carbon monoxide, nitric oxide, etc.). The hemoglobin absorbance peaks in the 415 to 430 nm range are particularly intense and can be used to monitor the presence of hemoglobin. This region is termed the Soret region and the hemoglobin absorbances here are referred to as Soret bands. The presence of HbA can be confirmed by the shift in the Soret band observed when CO displaces $O_2$. In this case, the Soret band shifts from 415 to 419 nm.

The yeast cells were suspended in Tris buffer, pH 7.5 at 25° C. The Soret spectrum was scanned initially, followed by exposure to carbon monoxide (3–4 minutes) and reduction with dithionite solution (20 mM in nitrogen saturated buffer). The Soret spectrum indicated absorbance in the region of 416–418 nm which is characteristic of hemoglobin and is not present in control yeast that do not express functional hemoglobins.

32. EXAMPLE 27

COEXPRESSION OF ALPHA AND BETA GLOBIN USING A TWIN CASSETTE PLASMID

Two coexpression plasmids were constructed by twin cassette strategy. Two separate expression cassettes one containing human a globin the other β globin genes were cloned at two unique sites in a single yeast vector. The resulting plasmids pBM-V-X1-G-αβ (like orientation) and pBM-V-X2-G-αβ (opposite orientation) carry both α-globin and β-globin genes under the control of two separate (identical) promoters. Yeast Sc1115 cells were transformed with plasmid pBM-V-X2-G-αβ, grown and induced with galactose. The yeast transformed with this twin cassette produced functional HbA.

32.1. MATERIALS

The restriction enzymes, Klenow enzyme and T4-DNA ligase were obtained from New England Biolabs (Biolabs), Bethesda Research Laboratories (BRL) or Boehringer Mannheim (BM). All enzymes were used according to the suppliers specifications. Plasmid DNA was isolated from a one liter culture of the transformed cells and purified by CsCl gradient centrifugation.

32.2. CLONING OF pBM-V-X1-G-αβ and pBM-V-X2-G-αβ

Construction of the plasmid pNML-V-G-1 was described in Section 19.5., supra. The plasmid pNML-V-G-1 contains the expression cassette, GAL1-10 UAS-TDH3-3' hybrid promoter, β-globin gene and ADH1 terminator (GHβAT) which was cloned in at the BamH1 site of the yeast expression vector, YEp13. The plasmid pUC19-GHαGt (Section 30.2.3. supra) contains the same hybrid promoter, the α-globin gene and the GAL10 terminator. This expression cassette was labeled GHαGt.

The DNA from plasmid pNML-B-G-1 was digested with PvuII and the linear DNA was isolated by electroelution and dephosphorylated (fragment 1). The DNA from plasmid pUC19-GHαGt was cut with SacI/SphI and the resulting 1.3 kb fragment containing GHαGt cassette was isolated and blunt ended (fragment 2). Ligation was set between fragments 1 and 2. *E. coli* Sure cells were used for transformation and the transformants were isolated on ampicillin selection plates.

The DNA from 48 transformants was isolated by alkaline lysis and analyzed by digestion with ApaLI enzyme.

The positive clones containing all the fragments were further analyzed by restriction enzyme digestions. The plasmids containing both the expression cassettes in the yeast vector YEp13 were labeled, pBM-V-X1-G-αβ and pBM-V-X2-G-αβ. The X1 refers to the orientation in which both cassettes are transcribed in the same direction and X2 refers to the opposite orientation.

FIG. 58 describes the strategy used for cloning GHαGt cassette into a yeast vector carrying GHβAt expression cassette.

32.3. TRANSFORMATION OF YEAST STRAIN Sc1115 WITH pBM-V-X1-G-αβ AND pBM-V-X2-G-αβ

Sc1115 has the following genotype: MATa, leu2-3,112; his3-115, Can$^R$. Yeast strain Sc1115 was transformed with plasmid pBM-V-X1-G-αβ (1115X1VGalb1) or pBM-V-X2-G-αβ (1115X2VGalb1) using the electroporation procedure.

For the starter culture, cells were grown in 500 ml of minimal media containing 0.67% yeast nitrogen base, 2% lactic acid, 3% glycerol, 1% raffinose, and supplemented with 20 mg/L of histidine at 30° C. in a shake flask to log phase. The cells were then harvested, washed with leucine drop-out media containing 0.67% yeast nitrogen base, 2% lactic acid and 3% glycerol, and supplemented with 40 mg/L histidine and used to inoculate 1700 ml of the leucine drop-out medium in a Braun Biostat E fermenter. The pH was maintained at 5.0; the pO2 was maintained at 30%; the stirrer speed was maintained at 300 rpm. The culture was induced with galactose at the rate of 0.05% per hour. Samples were collected at intervals for sampling.

32.4. WESTERN BLOT ANALYSIS OF EXPRESSED GLOBIN

The expressed globins were quantitated by Western Blot analysis using procedures described in Section 6.6. Detectable levels of globin were observed (1% of total soluble protein).

32.5. WESTERN BLOT ANALYSIS OF EXPRESSED ALPHA AND BETA GLOBINS

The expressed alpha and beta globins were separated and quantitated using an 18% SDS polyacrylamide gel (supra, 14.4.). Detectable levels of both alpha and beta globins were observed.

32.6. SORET SPECTRA OF HEMOGLOBIN IN YEAST

The Soret spectrum (supra, 31.) indicated absorbance in the region of 418 nm which is characteristic of hemoglobin and is not present in control yeast that do not express globins. A concentration of 5 μM heme was detected.

33. EXAMPLE 28

COEXPRESSION OF ALPHA AND GAMMA$_{VAL}$ GLOBIN USING A TWIN CASSETTE PLASMID

Two coexpression plasmids were constructed by twin cassette strategy. Two separate expression cassettes, one containing human α globin and the other γ(val) globin genes were cloned at two unique sites in a single yeast vector. The resulting plasmids pBM-R-X7-A-αγ$_{val}$ (like orientation) and pBM-R-X8-A-αγ$_{val}$ (opposite orientation) carry both α-globin and γ(val) globin genes under the control of two separate promoters.

33.1. MATERIALS

The restriction enzymes, Klenow enzyme and T4-DNA ligase were obtained from New England Biolabs (Biolabs), Bethesda Research Laboratories (BRL) or Boehringer Mannheim (BM). All enzymes were used according to the suppliers specifications. Plasmid DNA was isolated from a one liter culture of the transformed cells and purified by CsCl gradient centrifugation.

33.2. CLONING OF PLASMIDS pBM-R-X7-A-αγ$_{VAL}$ AND pBM-R-X8-A-αγ$_{VAL}$

The plasmid pNM-R-A-α1 (Section 30.4., supra) contains the expression cassette, ADH2-UAS-TDH3-3' hybrid promoter, α-globin gene and GAL10 terminator (AHαGt) which was cloned in at the BamHI site of the yeast expression vector, pPM40. FIG. 59 describes the strategy used for cloning AHγ$_{val}$At cassette into yeast expression plasmid pNM-R-A-α1. The resulting twin cassettes were named pBM-R-X7-A-αγ$_{val}$ (like orientation) and pBM-R-X8-A-αγ$_{val}$ (opposite orientation).

33.2.1. CLONING OF PLASMID pUC19-AHγ$_{val}$At

The plasmid pUC19-AHγ$_{val}$t contains the ADH2-UAS-TDH3-3' hybrid promoter, the γ$_{val}$-globin gene and the ADH terminator. This expression cassette was labeled AHγ$_{val}$At.

33.2.1.1. CONSTRUCTION OF pUC19 -AHβAt

The ADH2-UAS DNA fragment was generated by PCR. Genomic DNA was isolated from yeast strain S173-6B. The 5' primer used for synthesizing the ADH2-UAS DNA fragment is described in the Sequence Description as SEQ ID NO:59 and the 3' primer used for synthesizing the ADH2-UAS DNA fragment is described in the Sequence Description as SEQ ID NO:60. Restriction sites on these two primers are shown in FIG. 60.

The resulting ADH2-UAS fragment (200 bp) was isolated by electroelution and cut with SacI (5'-end) and XbaI (3'-end) and cloned into pUC19 cut with SacI and XbaI. The ligation mixture was transformed in competent *E. coli* cells and the DNA was isolated from 24 transformants by alkaline digestion. The DNA samples from the clones were analyzed by appropriate enzymes and the resulting plasmid was labeled pUC19-ADH2-UAS. The map of this plasmid is shown in FIG. 61. The DNA from plasmid pUC19-ADH2-UAS was cut with XbaI/SphI. The linear DNA fragment was isolated (Fragment #1).

PCR was carried out using DNA from the plasmid, pUC19-GHβAt as a template. The 5' primer used for synthesizing the sequence is described in the Sequence Description as SEQ ID NO:61 and the 3' primer used for synthesizing the sequence is described in the Sequence Description as SEQ ID NO:62. Restriction sites on these two primers are shown in FIG. 62. The resulting 1.1 kb fragment was labeled HβAt (fragment #2). The resulting 1.1 kb fragment, containing TDH3-3'-β-globin gene-ADH1 terminator (HβAt) was cut with XbaI/SphI (fragment #2).

Ligation was set between fragment #1 and #2. The *E. coli* DH5α cells were transformed and the DNA from the transformants was analyzed by appropriate enzymes. The plasmid containing the fragments in correct orientation was labeled pUC19-AHβAt.

33.2.1.2. CLONING OF γ(val)-GLOBIN INTO pUC19-AHβAt

Using appropriate primers and DNA from plasmid YEp51TG, γ(val)-globin containing the ADH terminator was synthesized by PCR. The 5' primer used for synthesizing the sequence is described in the Sequence Description as SEQ ID NO:63 and the 3' primer used for synthesizing the sequence is described in the Sequence Description as SEQ ID NO:64. Restrictions sites on these two primers are shown in FIG. 63. The PCR fragment was cut with ApaLI and SphI (fragment #1). The DNA from pUC19 plasmid was cut with SacI/SphI and linear DNA fragment was isolated (fragment #2). The DNA from pUC19-AHβAt (supra, 33.2.1.1.) was cut with ApaLI and SacI, and the 360 bp fragment containing the ADH2-UAS-TDH3-3' hybrid promoter was isolated by electroelution (fragment #3).

A three way ligation was set between the above three fragments. *E. coli* DH5α cells were used for transformation. The DNA from 24 transformants was isolated by alkaline digestions and analyzed by restriction digestions. The resulting plasmid containing all fragments in correct orientation was labeled pUC19-AHγ$_{val}$At; the map of this plasmid is shown in FIG. 64.

33.2.2. CLONING OF AHγ$_{val}$At CASSETTE INTO YEAST EXPRESSION PLASMID pNM-R-A-α1

FIG. 59 describes the strategy used for cloning the AHγ$_{val}$At cassette into yeast expression plasmid pNM-R-A-α1.

The DNA from plasmid pNM-R-A-α1 (see Section 30., supra) was digested with PvuII and the linear DNA was isolated by electroelution and dephosphorylated (fragment 1). The DNA from plasmid pUC19-AHγ$_{val}$At was cut with SacI/SphI and the resulting 1.3 kb fragment containing AHγ$_{val}$At cassette was isolated and blunt ended (fragment 2). Ligation was set between fragments 1 and 2. *E. coli* Sure cells were used for transformation and the transformants was isolated on ampicillin selection plates. The DNA from 48 transformants was isolated by alkaline lysis and analyzed by digestion with ApaLI enzyme.

The positive clones containing all the fragments were further analyzed by restriction enzyme digestions. The plasmids containing both the expression cassettes in the yeast vector pPM40 (see FIG. 56) were labeled pBM-R-X7-A-αγ$_{val}$ (like orientation) and pBM-R-X8-A-αγ$_{val}$ (opposite orientation).

33.3. TRANSFORMATION OF YEAST STRAIN Sc1113 WITH pBM-R-X8-A-αγ$_{val}$

Yeast strain Sc1113 was transformed with plasmid pBM-R-X8-A-αγ$_{val}$ (1113X8VGa1gVAL1) using the spheroblast procedure.

For the starter culture, cells were grown in 500 ml of minimal media containing 0.67% yeast nitrogen base, 2% lactic acid, 3% glycerol, 1% raffinose, and supplemented with 20 mg/L of histidine at 30° C. in a shake flask to log phase. The cells were then harvested, washed with leucine drop-out media containing 0.67% yeast nitrogen base, 2% lactic acid and 3% glycerol, and supplemented with 40 mg/L histidine and used to inoculate 1700 ml of the leucine drop-out medium in a Braun Biostat E fermenter. The pH was adjusted to 6.93. The culture was grown to glucose exhaustion and samples were taken between one and 30 hours after exhaustion for testing.

The expressed globins were quantitated by Western Blot analysis using procedures described in Section 6.6. Globin was detected at a level of 0.03% of soluble protein.

24. DEPOSIT OF MICROORGANISMS

The following yeast strains of the species *Saccharomyces cerevisiae* carrying the listed plasmids were deposited with the Agricultural Research Culture Collection (NRRL), Peoria, Ill.

| Yeast strain | Plasmid | Accession Number | Date of Deposit |
|---|---|---|---|
| 340g2P | YEp51WB/PORT | Y-18640 | April 4, 1990 |
| 340VGTB | pNML-V-G-1 | Y-18641 | April 4, 1990 |
| 340g2G | YEp51T/G | Y-18695 | August 7, 1990 |
| 340g2B | YEp51T/NAT | Y-18639 | April 4, 1990 |
| 1090g2BRa | pNT1/β-Ran | Y-18802 | March 29, 1991 |
| 1114g2GP | pNT1/γ-PORT | Y-18798 | March 27, 1991 |
| 340g2BTaS | pNT1/β-TaLiS | Y-18804 | March 29, 1991 |
| 340g2BMo | pNT1/β-Mot | Y-18799 | March 29, 1991 |
| 340g2BMS | pNT1/β-Miss | Y-18803 | March 29, 1991 |
| 389g2Bv22A | pUT/2A pNT1/β-Bov2 | Y-18900 | October 24, 1991 |
| 340g22AB143Ar | pUT/2A pNT1/β143Arg | Y-18901 | October 24, 1991 |
| 1090g2B145T2A | pUT/2A pNT1/β145T | Y-18902 | October 24, 1991 |
| 1114g2GM22A | pUT/2A pNT1/γ-Mot2 | Y-18908 | October 24, 1991 |
| 1114g2BZ104S | pNT1/Z104S YEp51T/NAT | Y-18903 | October 24, 1991 |
| 1041-2-GZ2 | YES2-ζ2 | Y-18899 | October 24, 1991 |
| 1090g2B2Arg2A | pUT/2A pNT1/B2Arg | Y-18904 | October 24, 1991 |
| 1012-G-Z2G-Cot19 | YES2-ζ2 YEp51T/G | Y-18914 | October 25, 1991 |
| 1041-G-Z2B1-Cot18 | YES2-ζ2 pNML-V-G-1 | Y-18898 | October 24, 1991 |
| 389g2BMs2A | pUT/2A pNT1/β-Miss | Y-18905 | October 24, 1991 |
| 1114g2B2ATiS | pNT1/2ATiS YEp51T/NAT | Y-18907 | October 24, 1991 |
| 1114g2B2ATit | pNT1/2ATit YEp51T/NAT | Y-18906 | October 24, 1991 |
| 389g2BMot2A | pUT/2A pNT1/β-Mot | Y-18909 | October 24, 1991 |
| 1115g2GZTi | pNT1/Z95An YEp51T/G | Y-18910 | October 24, 1991 |
| 340g22AGC | pUT/2A pNT1/γ-Chi | Y-18911 | October 24, 1991 |
| 1115g22AGP | pUT/2A pNT1/γ-PORT | Y-18912 | October 24, 1991 |
| 1090g2BP2A | pUT/2A YEpWB51T/PORT | Y-18913 | October 24, 1991 |

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A recombinant DNA vector which expresses a globin chain in a yeast cell comprising:
   (a) a first DNA sequence encoding a globin chain;
   (b) a yeast transcriptional promoter which promotes the transcription of the first DNA sequence;
   (c) a second DNA sequence encoding a yeast selectable marker or functionally active portion thereof; and
   (d) a yeast replication origin.

2. The recombinant DNA vector of claim 1 in which the globin chain is an alpha-like globin chain, in which the alpha-like globin chain is an embryonic zeta-globin chain or an adult alpha-globin chain, or substantially homologous variant thereof, in which said substantially homologous variant is a variant in which a DNA sequence encoding said variant has the ability to hybridize to a DNA sequence encoding said alpha-like globin chain under stringent conditions comprising 0.1× SSC and a temperature of about 65° C.

3. The recombinant DNA vector of claim 2 in which the alpha-like globin chain is a human embryonic zeta-globin chain.

4. The recombinant DNA vector of claim 2 in which the alpha-like globin chain is a human adult alpha-globin chain.

5. The recombinant DNA vector of claim 1 in which the globin chain is a beta-like globin chain, in which the beta-like globin chain is an embryonic epsilon-globin chain, a fetal gamma-globin chain, an adult delta-globin chain or an adult beta-globin chain, or substantially homologous variant thereof, in which said substantially homologous variant is a variant in which a DNA sequence encoding said variant has the ability to hybridize to a DNA sequence encoding said beta-like globin chain under stringent conditions comprising 0.1× SSC and a temperature of about 65° C.

6. The recombinant DNA vector of claim 5 in which the beta-like globin chain is a human adult beta-globin chain.

7. The recombinant DNA vector of claim 5 in which the beta-like globin chain is a human fetal gamma-globin chain.

8. The recombinant DNA vector of claim 5 in which the beta-like globin chain is a human embryonic epsilon-globin chain.

9. The recombinant DNA vector of claim 1 in which the yeast transcriptional promoter is a yeast inducible transcriptional promoter.

10. The recombinant DNA vector of claim 9 in which the yeast inducible transcriptional promoter is a unidirectional promoter.

11. The recombinant DNA vector of claim 10 in which the unidirectional promoter is regulated by galactose.

12. The recombinant DNA vector of claim 11 in which the unidirectional promoter is a GAL10 promoter.

13. The recombinant DNA vector of claim 10 in which the unidirectional promoter is regulated by glucose.

14. The recombinant DNA vector of claim 10 in which the unidirectional promoter is an ADH2 promoter.

15. The recombinant DNA vector of claim 9 in which the inducible promoter is a bidirectional promoter.

16. The recombinant DNA vector of claim 15 in which the bidirectional promoter is regulated by galactose.

17. The recombinant DNA vector of claim 16 in which the bidirectional promoter is a GAL1-10 promoter.

18. The recombinant DNA vector of claim 1 in which the yeast transcriptional promoter is a yeast constitutive transcriptional promoter.

19. The recombinant DNA vector of claim 18 in which the yeast constitutive transcriptional promoter is a TDH3 promoter.

20. The recombinant DNA vector of claim 1 in which the yeast transcriptional promoter comprises: (i) a first sequence containing a transcriptional regulatory region of an inducible promoter; and (ii) a second sequence containing a transcription initiation region of a constitutive promoter located downstream from the first sequence.

21. The recombinant DNA vector of claim 20 in which the first sequence of the promoter is an upstream activating sequence of a yeast inducible promoter.

22. The recombinant DNA vector of claim 21 in which the upstream activating sequence of the yeast inducible promoter is unidirectional.

23. The recombinant DNA vector of claim 21 in which the upstream activating sequence of the yeast inducible promoter is bidirectional.

24. The recombinant DNA vector of claim 1 in which the second DNA sequence is the LEU2 gene.

25. The recombinant DNA vector of claim 1 in which the second DNA sequence is the leu2d gene.

26. The recombinant DNA vector of claim 1 in which the second DNA sequence is the URA3 gene.

27. The recombinant DNA vector of claim 1 in which the yeast replication origin is a yeast $2\mu$ plasmid replication system or functionally active portion thereof.

28. The recombinant DNA vector of claim 1 in which the yeast replication origin is an autonomous replicating sequence.

29. The recombinant DNA vector of claim 1 in which the recombinant DNA vector further comprises a transcription termination sequence located downstream from the first DNA sequence.

30. The recombinant DNA vector of claim 29 in which the transcription termination sequence is selected from the group consisting of the ADH1 transcription termination sequence and the GAL10 transcription termination sequence.

31. A recombinant DNA vector which expresses a globin chain in a yeast cell comprising:
   (a) a DNA sequence encoding a globin chain;
   (b) a yeast hybrid promoter which promotes the transcription of the DNA sequence encoding the globin chain, comprising: (i) a first sequence containing a transcriptional regulatory region of an inducible promoter; and (ii) a second sequence containing a transcription region of a constitutive promoter located downstream from the first sequence;
   (c) a DNA sequence encoding a yeast selectable marker or functionally active portion thereof;
   (d) a yeast replication origin; and
   (e) a transcription termination sequence located downstream from the DNA sequence encoding the globin chain.

32. A recombinant DNA vector which expresses a human adult beta-globin chain in a yeast cell comprising:
   (a) a hybrid promoter comprising a first sequence containing a transcriptional regulatory region of an inducible promoter regulated by galactose and a second sequence containing a transcription initiation region of a TDH3 constitutive promoter located downstream from the first sequence;
   (b) a DNA sequence located downstream from the hybrid promoter, encoding a human adult beta-globin chain;
   (c) a LEU2 selectable marker or functionally active portion thereof;
   (d) a $2\mu$ plasmid replication system or functionally active portion thereof; and
   (e) a transcription termination sequence located downstream from the DNA sequence encoding the human adult beta-globin chain, which comprises the transcription termination region of the alcohol dehydrogenase I gene.

33. The recombinant DNA vector of claim 31 which is plasmid pNML-V-G-1.

34. A yeast cell containing the recombinant DNA vector of claim 32.

35. The yeast cell of claim 34 which is a *Saccharomyces cerevisiae* as deposited with the NRRL and assigned accession number Y-18641.

36. A recombinant DNA vector which expresses a human Porto Alegre beta-globin chain in a yeast cell comprising:
   (a) yeast inducible transcriptional promoter regulated by galactose;
   (b) a DNA sequence located downstream from the yeast inducible transcriptional promoter, encoding a human Porto Alegre beta-globin chain;
   (c) a LEU2 selectable marker or functionally active portion thereof; and
   (d) a $2\mu$ plasmid replication system or functionally active portion thereof.

37. The recombinant DNA vector of claim 36 which is plasmid YEpWB51/PORT.

38. A yeast cell containing the recombinant DNA vector of claim 37.

39. The yeast cell of claim 38 which is a *Saccharomyces cerevisiae* as deposited with the NRRL and assigned accession number Y-18640.

40. A recombinant DNA vector which expresses a human embryonic epsilon-globin chain in a yeast cell comprising:
   (a) a yeast inducible transcriptional promoter regulated by galactose;
   (b) a DNA sequence located downstream from the transcriptional promoter, encoding a human embryonic epsilon-globin chain;
   (c) a LEU2 selectable marker or functionally active portion thereof;
   (d) a $2\mu$ plasmid replication system or functionally active portion thereof; and
   (e) a transcription termination sequence located downstream from the DNA sequence encoding the human embryonic epsilon-globin chain, which comprises the transcription termination region of the alcoholdehydrogenase I gene.

41. The recombinant DNA vector of claim 40 which is plasmid YEp51T/ε3.

42. A yeast cell containing the recombinant DNA vector of claim 41.

43. The yeast cell of claim 42 which is a *Saccharomyces cerevisiae* as deposited with the NRRL and assigned accession number Y-18897.

44. A recombinant DNA vector which expresses a human embryonic zeta-globin chain in a yeast cell comprising:
   (a) a yeast inducible transcriptional promoter regulated by galactose;
   (b) a DNA sequence located downstream from the transcriptional promoter, encoding a human embryonic zeta-globin chain;
   (c) a URA3 selectable marker or functionally active portion thereof;
   (d) a $2\mu$ plasmid replication system or functionally active portion thereof; and
   (e) a transcription termination sequence located downstream from the DNA sequence encoding the embryonic zeta-globin chain, which comprises the transcription termination region of the CYC1 gene.

45. The recombinant DNA vector of claim 44 which is plasmid YES2/ζ2.

46. A yeast cell containing the recombinant DNA vector of claim 45.

47. The yeast cell of claim 46 which is a *Saccharomyces cerevisiae* as deposited with the NRRL and assigned accession number Y-18899.

48. A yeast cell containing
   (a) a recombinant DNA vector which expresses a human embryonic zeta-globin chain in a yeast cell comprising:
      (i) a yeast inducible transcriptional promoter regulated by galactose;
      (ii) a DNA sequence located downstream from the transcriptional promoter, encoding a human embryonic zeta-globin chain;
      (iii) a URA3 selectable marker or functionally active portion thereof;

(iv) a 2μ plasmid replication system or functionally active portion thereof; and
(v) transcription termination sequence located downstream from the DNA sequence encoding the human embryonic zeta-globin chain, which comprises the transcription termination region of the CYC1 gene; and (b) a recombinant DNA vector which expresses a human fetal gamma-globin chain in a yeast cell comprising:
(i) a yeast inducible transcriptional promoter regulated by galactose;
(ii) a DNA sequence located downstream from the transcriptional promoter, encoding a human fetal gamma-globin chain;
(iii) a LEU2 selectable marker or functionally active portion thereof;
(iv) a 2μ plasmid replication system or functionally active portion thereof; and
(v) a transcription termination sequence located downstream from the DNA sequence encoding the fetal gamma-globin chain, which comprises the transcription termination region of the alcohol dehydrogenase I gene.

49. The yeast cell of claim 48 which is a *Saccharomyces cerevisiae* as deposited with the NRRL and assigned accession number Y-18914.

50. A yeast cell containing
(a) a recombinant DNA vector which expresses a human embryonic zeta-globin chain in a yeast cell comprising:
(i) a yeast inducible transcriptional promoter regulated by galactose;
(ii) a DNA sequence located downstream from the hybrid promoter, encoding a human embryonic zeta-globin chain;
(iii) a URA3 selectable marker or functionally active portion thereof;
(iv) a 2μ plasmid replication system or functionally active portion thereof; and
(v) a transcription termination sequence located downstream from the DNA sequence encoding the human embryonic zeta-globin chain, which comprises the transcription termination region of the CYC1 gene; and (b) a recombinant DNA vector which expresses a human adult beta-globin chain in a yeast cell comprising:
(i) a hybrid promoter comprising a first sequence containing a transcriptional regulatory region of an inducible promoter regulated by galactose and a second sequence containing a transcription initiation region of a TDH3 constitutive promoter located downstream from the first sequence;
(ii) a DNA sequence located downstream from the hybrid promoter, encoding a human adult beta-globin chain;
(iii) a LEU2 selectable marker or functionally active portion thereof;
(iv) a 2μ plasmid replication system or functionally active portion thereof; and
(v) a transcription termination sequence located downstream from the DNA sequence encoding the adult beta-globin chain, which comprises the transcription termination region of the alcohol dehydrogenase I gene.

51. The yeast cell of claim 50 which is a *Saccharomyces cerevisiae* as deposited with the NRRL and assigned accession number Y-18898.

52. A yeast cell containing
(a) a recombinant DNA vector which expresses a human adult alpha-globin chain in a yeast cell comprising:
(i) a first DNA sequence encoding a human adult alpha-globin chain;
(ii) a yeast inducible transcriptional promoter regulated by galactose which promotes the transcription of the first DNA sequence;
(iii) a second DNA sequence encoding a URA3 selectable marker or functionally active portion thereof;
(iv) a 2μ plasmid replication system or functionally active portion thereof; and
(v) a transcription termination sequence located downstream from the DNA sequence encoding the human adult alpha-globin chain, which comprises the transcription termination region of the alcohol dehydrogenase I gene; and (b) a recombinant DNA vector which expresses in a yeast cell a variant globin chain substantially homologous to a human adult beta-globin chain and comprising an arginine at the beta-143 position, comprising:
(i) a first DNA sequence encoding a variant globin chain substantially homologous to a human adult beta-globin chain and comprising an arginine at the beta-143 position which corresponds to beta-globin amino acid position His 143 of SEQ ID NO:70, in which said substantially homologous variant is a variant in which a DNA sequence encoding said variant has the ability to hybridize to a DNA sequence encoding said human adult beta-globin chain under stringent conditions comprising 0.1× SSC and a temperature of about 65° C.;
(ii) a yeast inducible transcriptional promoter regulated by galactose which promotes the transcription of the first DNA sequence;
(iii) a second DNA sequence encoding a LEU2 selectable marker or functionally active portion thereof;
(iv) a 2μ plasmid replication system or functionally active portion thereof; and
(v) a transcription termination sequence located downstream from the DNA sequence encoding the human variant adult beta-globin chain, which comprises the transcription termination region of the alcohol dehydrogenase I gene.

53. The yeast cell of claim 52 which is a *Saccharomyces cerevisiae* as deposited with the NRRL and assigned accession number Y-18901.

54. A yeast cell containing
(a) a recombinant DNA vector which expresses a human adult alpha-globin chain in a yeast cell comprising:
(i) a first DNA sequence encoding a human adult alpha-globin chain;
(ii) a yeast inducible transcriptional promoter regulated by galactose which promotes the transcription of the first DNA sequence;
(iii) a second DNA sequence encoding a URA3 selectable marker or functionally active portion thereof;
(iv) a 2μ plasmid replication system or functionally active portion thereof; and
(v) a transcription termination sequence located downstream from the DNA sequence encoding the human adult alpha-globin chain, which comprises the transcription termination region of the alcohol dehydrogenase I gene; and (b) a recombinant DNA vector which expresses in a yeast cell a variant globin chain substantially homologous to a human adult beta-globin chain which terminates at the beta-145 position, comprising:

(i) a first DNA sequence encoding a variant globin chain substantially homologous to a human adult beta-globin chain and which terminates at the beta-145 position which corresponds to beta-globin amino acid position Tyr 145 of SEQ ID NO:70, in which said substantially homologous variant is a variant in which a DNA sequence encoding said variant has the ability to hybridize to a DNA sequence encoding said human adult beta-globin chain under stringent conditions comprising 0.1× SSC and a temperature of about 65° C.;

(ii) a yeast inducible transcriptional promoter regulated by galactose which promotes the transcription of the first DNA sequence;

(iii) a second DNA sequence encoding a LEU2 selectable marker or functionally active portion thereof;

(iv) a 2μ plasmid replication system or functionally active portion thereof; and (v) a transcription termination sequence located downstream from the DNA sequence encoding the human variant adult beta-globin chain, which comprises the transcription termination region of the alcohol dehydrogenase I gene.

55. The yeast cell of claim 54 which is a *Saccharomyces cerevisiae* as deposited with the NRRL and assigned accession number Y-18902.

56. A yeast cell containing (a) a recombinant DNA vector which expresses a human adult alpha-globin chain in a yeast cell comprising:

(i) a first DNA sequence encoding a human adult alpha-globin chain;

(ii) a yeast inducible transcriptional promoter regulated by galactose which promotes the transcription of the first DNA sequence;

(iii) a second DNA sequence encoding a URA3 selectable marker or functionally active portion thereof;

(iv) a 2μ plasmid replication system or functionally active portion thereof; and (v) a transcription termination sequence located downstream from the DNA sequence encoding the human adult alpha-globin chain, which comprises the transcription termination region of the alcohol dehydrogenase I gene; and (b) a recombinant DNA vector which expresses in a yeast cell a variant globin chain substantially homologous to a human adult beta-globin chain and which comprises an arginine at the beta-2 position, comprising:

(i) a first DNA sequence encoding a variant globin chain substantially homologous to a human adult beta-globin chain and which comprises an arginine at the beta-2 position which corresponds to beta-globin amino acid position His 2 of SEQ ID NO:70, in which said substantially homologous variant is a variant in which a DNA sequence encoding said variant has the ability to hybridize to a DNA sequence encoding said human adult beta-globin chain under stringent conditions comprising 0.1× SSC and a temperature of about 65° C.;

(ii) a yeast inducible transcriptional promoter regulated by galactose which promotes the transcription of the first DNA sequence;

(iii) a second DNA sequence encoding a LEU2 selectable marker or functionally active portion thereof;

(iv) a 2μ plasmid replication system or functionally active portion thereof; and (v) a transcription termination sequence located downstream from the DNA sequence encoding the human variant adult beta-globin chain, which comprises the transcription termination region of the alcohol dehydrogenase I gene.

57. The yeast cell of claim 56 which is a *Saccharomyces cerevisiae* as deposited with the NRRL and assigned accession number Y-18904.

58. A yeast cell containing (a) a recombinant DNA vector which expresses a human adult alpha-globin chain in a yeast cell comprising:

(i) a first DNA sequence encoding a human adult alpha-globin chain;

(ii) a yeast inducible transcriptional promoter regulated by galactose which promotes the transcription of the first DNA sequence;

(iii) a second DNA sequence encoding a URA3 selectable marker or functionally active portion thereof;

(iv) a 2μ plasmid replication system or functionally active portion thereof; and (v) a transcription termination sequence located downstream from the DNA sequence encoding the human adult alpha-globin chain, which comprises the transcription termination region of the alcohol dehydrogenase I gene; and (b) a recombinant DNA vector which expresses in a yeast cell a variant globin chain substantially homologous to a human adult beta-globin chain and which comprises an N-terminal sequence of Met Leu Thr Ala (SEQ ID NO:71), comprising:

(i) a first DNA sequence encoding a variant globin chain substantially homologous to a human adult beta-globin chain and which comprises an N-terminal sequence of Met Leu Thr Ala at a position corresponding to beta-globin amino acid position Leu 3 to Glu 6 of SEQ ID NO:70, in which said substantially homologous variant is a variant in which a DNA sequence encoding said variant has the ability to hybridize to a DNA sequence encoding said adult beta-globin chain under stringent conditions comprising 0.1× SSC and a temperature of about 65° C.;

(ii) a yeast inducible transcriptional promoter regulated by galactose which promotes the transcription of the first DNA sequence;

(iii) a second DNA sequence encoding a LEU2 selectable marker or functionally active portion thereof;

(iv) a 2μ plasmid replication system or functionally active portion thereof; and (v) a transcription termination sequence located downstream from the DNA sequence encoding the human variant adult beta-globin chain, which comprises the transcription termination region of the alcohol dehydrogenase I gene.

59. The yeast cell of claim 58 which is a *Saccharomyces cerevisiae* as deposited with the NRRL and assigned accession number Y-18900.

60. A yeast cell containing (a) a recombinant DNA vector which expresses a variant globin chain which is substantially homologous to a human embryonic zeta-globin chain and comprises a serine at the zeta-104 position in a yeast cell comprising:

(i) a first DNA sequence encoding a variant globin chain which is substantially homologous to a human embryonic zeta-globin chain and comprises a serine at the zeta-104 position which corresponds to zeta-globin amino acid position Cys 104 of SEQ ID NO:65, in which said substantially homologous variant is a variant in which a DNA sequence encoding said variant has the ability to hybridize to a DNA sequence encoding said human embryonic zeta-globin chain under stringent conditions comprising 0.1× SSC and a temperature of about 65° C.;

(ii) a yeast inducible transcriptional promoter regulated by galactose which promotes the transcription of the first DNA sequence;

(iii) a second DNA sequence encoding a URA3 selectable marker or functionally active portion thereof;

(iv) a 2μ plasmid replication system or functionally active portion thereof; and (v) a transcription termination sequence located downstream from the DNA sequence encoding the variant globin chain, which comprises the transcription termination region of the alcohol dehydrogenase I gene; and (b) a recombinant DNA vector which expresses in a yeast cell a human adult beta-globin chain, comprising:

(i) a first DNA sequence encoding a human adult beta-globin chain;

(ii) a yeast inducible transcriptional promoter regulated by galactose which promotes the transcription of the first DNA sequence;

(iii) a second DNA sequence encoding a LEU2 selectable marker or functionally active portion thereof;

(iv) a 2μ plasmid replication system or functionally active portion thereof; and (v) a transcription termination sequence located downstream from the DNA sequence encoding the human globin chain, which comprises the transcription termination region of the alcohol dehydrogenase I gene.

61. The yeast cell of claim 60 which is a *Saccharomyces cerevisiae* as deposited with the NRRL and assigned accession number Y-18903.

62. A yeast cell containing (a) a recombinant DNA vector which expresses a variant globin chain which is substantially homologous to a human adult alpha-globin chain and comprises a serine at the alpha-104 position and an asparagine at the alpha-94 position in a yeast cell comprising:

(i) a first DNA sequence encoding a variant globin chain which is substantially homologous to a human adult alpha-globin chain and comprises a serine at the alpha-104 position which corresponds to alpha-globin amino acid position Cys 104 of SEQ ID NO:69 and an asparagine at the alpha-94 position which corresponds to alpha-globin amino acid position Asp 94 of SEQ ID NO:69, in which said substantially homologous variant is a variant in which a DNA sequence encoding said variant has the ability to hybridize to a DNA sequence encoding said human adult alpha-globin chain under stringent conditions comprising 0.1× SSC and a temperature of about 65° C.;

(ii) a yeast inducible transcriptional promoter regulated by galactose which promotes the transcription of the first DNA sequence;

(iii) a second DNA sequence encoding a URA3 selectable marker or functionally active portion thereof;

(iv) a 2μ plasmid replication system or functionally active portion thereof; and (v) a transcription termination sequence located downstream from the DNA sequence encoding the variant globin chain, which comprises the transcription termination region of the alcohol dehydrogenase I gene; and (b) a recombinant DNA vector which expresses in a yeast cell an adult beta-globin chain, comprising:

(i) a first DNA sequence encoding a human adult beta-globin chain;

(ii) a yeast inducible transcriptional promoter regulated by galactose which promotes the transcription of the first DNA sequence;

(iii) a second DNA sequence encoding a LEU2 selectable marker or functionally active portion thereof;

(iv) a 2μ plasmid replication system or functionally active portion thereof; and (v) a transcription termination sequence located downstream from the DNA sequence encoding the human adult beta-globin chain, which comprises the transcription termination region of the alcohol dehydrogenase I gene.

63. The yeast cell of claim 62 which is a *Saccharomyces cerevisiae* as deposited with the NRRL and assigned accession number Y-18907.

64. A yeast cell containing (a) a recombinant DNA vector which expresses a human adult alpha-globin chain in a yeast cell comprising:

(i) a yeast inducible transcriptional promoter regulated by galactose;

(ii) a DNA sequence located downstream from the transcriptional promoter, encoding a human adult alpha-globin chain;

(iii) a DNA sequence encoding a LEU2 selectable marker or functionally active portion thereof;

(iv) a 2μ plasmid replication system or functionally active portion thereof; and (v) a transcription termination sequence located downstream from the DNA sequence encoding the variant human adult alpha-globin chain, which comprises the transcription termination region of the alcohol dehydrogenase I gene; and (b) a recombinant DNA vector which expresses in a yeast cell a variant human globin chain which is substantially homologous to a human adult beta-globin chain, and comprises a cysteine at the beta-44 position, comprising:

(i) a yeast inducible transcriptional promoter regulated by galactose;

(ii) a DNA sequence encoding a human variant globin chain which is substantially homologous to a human adult beta-globin chain, and comprises a cysteine at the beta-44 position which corresponds to beta-globin amino acid position Ser 44 of SEQ ID NO:70, in which said substantially homologous variant is a variant in which a DNA sequence encoding said variant has the ability to hybridize to a DNA sequence encoding said human adult beta-globin chain under stringent conditions comprising 0.1× SSC and a temperature of about 65° C.;

(iii) a DNA sequence encoding an LEU2 selectable marker or functionally active portion thereof;

(iv) a 2μ plasmid replication system or functionally active portion thereof; and (v) a transcription termination sequence located downstream from the DNA sequence encoding the human variant globin chain, which comprises the transcription termination region of the alcohol dehydrogenase I gene.

65. The yeast cell of claim 64 which is a *Saccharomyces cerevisiae* as deposited with the NRRL and assigned accession number Y-18905.

66. A yeast cell containing
(a) a recombinant DNA vector which expresses a human adult alpha-globin chain in a yeast cell comprising:
  (i) a yeast inducible transcriptional promoter induced by galactose;
  (ii) a DNA sequence located downstream from the transcriptional promoter, encoding a human adult alpha-globin chain;
  (iii) a DNA sequence encoding an LEU2 selectable marker or functionally active portion thereof;
  (iv) a 2μ plasmid replication system or functionally active portion thereof; and
  (v) a transcription termination sequence located downstream from the DNA sequence encoding the human adult alpha-globin chain, which comprises the transcription termination region of the alcohol dehydrogenase I gene; and
(b) a recombinant DNA vector which expresses in a yeast cell a human variant globin chain which is substantially homologous to a human adult beta-globin chain, and comprises a glutamic acid at the beta-127 position, comprising:
  (i) a yeast inducible transcriptional promoter induced by galactose;
  (ii) a DNA sequence encoding a human variant globin chain which is substantially homologous to a human adult beta-globin chain, and comprises a glutamic acid at the beta-127 position which corresponds to beta-globin amino acid position Gln 127 of SEQ ID NO:70, in which said substantially homologous variant is a variant in which a DNA sequence encoding said variant has the ability to hybridize to a DNA sequence encoding said human adult beta-globin chain under stringent conditions comprising 0.1× SSC and a temperature of about 65° C.;
  (iii) a DNA sequence encoding an LEU2 selectable marker or functionally active portion thereof;
  (iv) a 2μ plasmid replication system or functionally active portion thereof; and
  (v) a transcription termination sequence located downstream from the DNA sequence encoding the human variant globin chain, which comprises the transcription termination region of the alcohol dehydrogenase I gene.

67. The yeast cell of claim 66, which is a *Saccharomyces cervisiae* as deposited with the NRRL and assigned accession number Y-18909.

68. A yeast cell containing
(a) a recombinant DNA vector which expresses a variant globin chain substantially homologous to a human adult alpha-globin chain and comprising an asparagine at the alpha-94 position in a yeast cell comprising:
  (i) a yeast inducible transcriptional promoter induced by galactose;
  (ii) a DNA sequence located downstream from the transcriptional promoter, encoding a variant globin chain substantially homologous to a human adult alpha-globin chain and comprising an asparagine at the alpha-94 position which corresponds to alpha-globin amino acid position Asp 94 of SEQ ID NO:69, in which said substantially homologous variant is a variant in which a DNA sequence encoding said variant has the ability to hybridize to a DNA sequence encoding said human adult alpha-globin chain under stringent conditions comprising 0.1× SSC and a temperature of about 65° C.;
  (iii) a DNA sequence encoding an LEU2 selectable marker or functionally active portion thereof;
  (iv) a 2μ plasmid replication system or functionally active portion thereof; and
  (v) a transcription termination sequence located downstream from the DNA sequence encoding the human variant globin chain, which comprises the transcription termination region of the alcohol dehydrogenase I gene; and
(b) a recombinant DNA vector which expresses in a yeast cell a human adult beta-globin chain, comprising:
  (i) a yeast inducible transcriptional promoter induced by galactose;
  (ii) a DNA sequence encoding a human adult beta-globin chain;
  (iii) a DNA sequence encoding an LEU2 selectable marker or functionally active portion thereof;
  (iv) a 2μ plasmid replication system or functionally active portion thereof; and
  (v) a transcription termination sequence located downstream from the DNA sequence encoding the human adult beta-globin chain, which comprises the transcription termination region of the alcohol dehydrogenase I gene.

69. The yeast cell of claim 68 which is a *Saccharomyces cerevisiae* as deposited with the NRRL and assigned accession number Y-18906.

70. A yeast cell containing
(a) a recombinant DNA vector which expresses a variant globin chain substantially homologous to a human embryonic zeta-globin chain and comprising an asparagine at the zeta-94 position in a yeast cell comprising:
  (i) a yeast inducible transcriptional promoter regulated by galactose;
  (ii) a DNA sequence located downstream from the transcriptional promoter, encoding a variant globin chain substantially homologous to a human embryonic zeta-globin chain and comprising an asparagine at the zeta-94 position which corresponds to zeta-globin amino acid position Asp 94 of SEQ ID NO:65, in which said substantially homologous variant is a variant in which a DNA sequence encoding said variant has the ability to hybridize to a DNA sequence encoding said human embryonic zeta-globin chain under stringent conditions comprising 0.1× SSC and a temperature of about 65° C.;
  (iii) a DNA sequence encoding an LEU2 selectable marker or functionally active portion thereof;
  (iv) a 2μ plasmid replication system or functionally active portion thereof; and
  (v) a transcription termination sequence located downstream from the DNA sequence encoding the variant globin chain, which comprises the transcription termination region of the alcohol dehydrogenase gene; and
(b) a recombinant DNA vector which expresses in a yeast cell a human fetal gamma-globin chain, comprising:
  (i) a yeast inducible transcriptional promoter regulated by galactose;
  (ii) a DNA sequence located downstream from the transcriptional promoter, encoding a human fetal gamma-globin chain;
  (iii) a DNA sequence encoding an LEU2 selectable marker or functionally active portion thereof;
  (iv) a 2μ plasmid replication system or functionally active portion thereof; and
  (v) a transcription termination sequence located downstream from the DNA sequence encoding the human fetal gamma-globin chain, which comprises the transcription termination region of the alcohol dehydrogenase I gene.

71. The yeast cell of claim 70 which is a *Saccharomyces cerevisiae* as deposited with the NRRL and assigned accession number Y-18910.

72. A yeast cell containing
   (a) a recombinant DNA vector which expresses a human adult alpha-globin chain in a yeast cell comprising:
      (i) a yeast inducible transcriptional promoter induced by galactose;
      (ii) a DNA sequence located downstream from the transcriptional promoter, encoding a human adult alpha-globin chain;
      (iii) a DNA sequence encoding an LEU2 selectable marker or functionally active portion thereof;
      (iv) a 2μ plasmid replication system or functionally active portion thereof; and
      (v) a transcription termination sequence located downstream from the DNA sequence encoding the human adult alpha-globin chain, which comprises the transcription termination region of the alcohol dehydrogenase I gene; and
   (b) a recombinant DNA vector which expresses in a yeast cell a human variant globin chain which is substantially homologous to a human fetal gamma-globin chain, and comprises a glutamic acid at the gamma-127 position, comprising:
      (i) a yeast inducible transcriptional promoter regulated by galactose;
      (ii) a DNA sequence encoding a human variant globin chain which is substantially homologous to a human fetal gamma-globin chain, and comprises a glutamic acid at the gamma-127 position which corresponds to gamma-globin amino acid position Gln 127 of SEQ ID NO:67, in which said substantially homologous variant is a variant in which a DNA sequence encoding said variant has the ability to hybridize to a DNA sequence encoding said human fetal gamma-globin chain under stringent conditions comprising 0.1× SSC and a temperature of about 65° C.;
      (iii) a DNA sequence encoding an LEU2 selectable marker or functionally active portion thereof;
      (iv) a 2μ plasmid replication system or functionally active portion thereof; and
      (v) a transcription termination sequence located downstream from the DNA sequence encoding the human variant globin chain, which comprises the transcription termination region of the alcohol dehydrogenase I gene.

73. The yeast cell of claim 72 which is a *Saccharomyces cerevisiae* as deposited with the NRRL and assigned accession number Y-18908.

74. A yeast cell containing
   (a) a recombinant DNA vector which expresses a human adult alpha-globin chain in a yeast cell comprising:
      (i) a first DNA sequence encoding a human adult alpha-globin chain;
      (ii) a yeast inducible transcriptional promoter regulated by galactose which promotes the transcription of the first DNA sequence;
      (iii) a second DNA sequence encoding a URA3 selectable marker or functionally active portion thereof;
      (iv) a 2μ yeast replication system or functionally active portion thereof; and
      (v) a transcription termination sequence located downstream from the DNA sequence encoding the human adult alpha-globin chain, which comprises the transcription termination region of the alcohol dehydrogenase I gene; and
   (b) a recombinant DNA vector which expresses in a yeast cell a human variant globin chain which is substantially homologous to a human beta-globin chain, and comprises a threonine at the gamma-66 position, comprising:
      (i) a first DNA sequence encoding a human variant globin chain which is substantially homologous to a human beta-globin chain, and comprises a threonine at the gamma-66 position which corresponds to gamma-globin amino acid position Lys 66 of SEQ ID NO:67, in which said substantially homologous variant is a variant in which a DNA sequence encoding said variant has the ability to hybridize to a DNA sequence encoding said human beta-globin chain under stringent conditions comprising 0.1× SSC and a temperature of about 65° C.;
      (ii) a yeast inducible transcriptional promoter regulated by galactose which promotes the transcription of the first DNA sequence;
      (iii) a second DNA sequence encoding an LEU2 selectable marker or functionally active portion thereof;
      (iv) a 2μ plasmid replication system or functionally active portion thereof; and
      (v) a transcription termination sequence located downstream from the DNA sequence encoding the human variant globin chain, which comprises the transcription termination region of the alcohol dehydrogenase I gene.

75. The yeast cell of claim 74 which is a *Saccharomyces cerevisiae* as deposited with the NRRL and assigned accession number Y-18911.

76. A yeast cell containing
   (a) a recombinant DNA vector which expresses a human adult alpha-globin chain in a yeast cell comprising:
      (i) a first DNA sequence encoding a human adult alpha-globin chain;
      (ii) a yeast inducible transcriptional promoter regulated by galactose which promotes the transcription of the first DNA sequence;
      (iii) a second DNA sequence encoding a URA3 selectable marker or functionally active portion thereof;
      (iv) a 2μ yeast replication system or functionally active portion thereof; and
      (v) a transcription termination sequence located downstream from the DNA sequence encoding the human adult alpha-globin chain, which comprises the transcription termination region of the alcohol dehydrogenase I gene; and
   (b) a recombinant DNA vector which expresses in a yeast cell a human variant globin chain which is substantially homologous to a human fetal gamma-globin chain, and comprises a cysteine at the gamma-9 position, comprising:
      (i) a first DNA sequence encoding a human variant globin chain which is substantially homologous to a human fetal gamma-globin chain, and comprises a cysteine at the gamma-9 position which corresponds to gamma-globin amino acid position Ala 9 of SEQ ID NO:67, in which said substantially homologous variant is a variant in which a DNA sequence encoding said variant has the ability to hybridize to a DNA sequence encoding said human fetal gamma-globin chain under stringent conditions comprising 0.1× SSC and a temperature of about 65° C.;
      (ii) a yeast inducible transcriptional promoter regulated by galactose which promotes the transcription of the first DNA sequence;

(iii) a second DNA sequence encoding an LEU2 selectable marker or functionally active portion thereof;
(iv) a 2μ plasmid replication system or functionally active portion thereof; and
(v) a transcription termination sequence located downstream from the DNA sequence encoding the human variant globin chain, which comprises the transcription termination region of the alcohol dehydrogenase I gene.

77. The yeast cell of claim 76 which is a *Saccharomyces cerevisiae* as deposited with the NRRL and assigned accession number Y-18912.

78. A yeast cell containing
(a) a recombinant DNA vector which expresses a human adult alpha-globin chain in a yeast cell comprising:
  (i) a first DNA sequence encoding a human adult alpha-globin chain;
  (ii) a yeast inducible transcriptional promoter regulated by galactose which promotes the transcription of the first DNA sequence;
  (iii) a second DNA sequence encoding a URA3 selectable marker or functionally active portion thereof;
  (iv) a 2μ yeast replication system or functionally active portion thereof; and
  (v) a transcription termination sequence located downstream from the DNA sequence encoding the human adult alpha-globin chain; and
(b) a recombinant DNA vector which expresses in a yeast cell a human variant globin chain which is substantially homologous to a human adult beta-globin chain, and comprises a cysteine at the beta-9 position, comprising:
  (i) a first DNA sequence encoding a human variant globin chain which is substantially homologous to a human adult beta-globin chain, and comprises a cysteine at the beta-9 position which corresponds to beta-globin amino acid position Ser 9 of SEQ ID NO:70, in which said substantially homologous variant is a variant in which a DNA sequence encoding said variant has the ability to hybridize to a DNA sequence encoding said human adult beta-globin chain under stringent conditions comprising 0.1× SSC and a temperature of about 65° C.;
  (ii) a yeast inducible transcriptional promoter regulated by galactose which promotes the transcription of the first DNA sequence;
  (iii) a second DNA sequence encoding an LEU2 selectable marker or functionally active portion thereof; and
  (iv) a 2μ plasmid replication system or functionally active portion thereof.

79. The yeast cell of claim 78 which is a *Saccharomyces cerevisiae* as deposited with the NRRL and assigned accession number Y-18913.

80. A recombinant DNA vector which expresses a human fetal gamma-globin chain in a yeast cell comprising:
(a) yeast inducible transcription promoter regulated by galactose;
(b) a DNA sequence located downstream from the yeast inducible transcriptional promoter, encoding a human fetal gamma-globin chain;
(c) a LEU2 selectable marker or functionally active portion thereof;
(d) a 2μ plasmid replication system or functionally active portion thereof; and
(e) a transcription termination sequence located downstream from the DNA sequence encoding the fetal gamma-globin chain, which comprises the transcription termination region of the alcohol dehydrogenase I gene.

81. The recombinant DNA vector of claim 80 which is plasmid YEp51T/G.

82. A yeast cell containing the recombinant DNA vector of claim 81.

83. The yeast cell of claim 82 which is a *Saccharomyces cerevisiae* as deposited with the NRRL and assigned accession number Y-18695.

84. A recombinant DNA vector which expresses in a yeast cell a variant globin chain substantially homologous to a fetal gamma-globin chain and comprising a cysteine at the gamma-9 position, comprising:
(a) yeast inducible transcriptional promoter regulated by galactose;
(b) a DNA sequence located downstream from the yeast inducible transcriptional promoter, encoding a variant globin chain substantially homologous to a human fetal gamma-globin chain and comprising a cysteine at the gamma-9 position which corresponds to gamma-globin amino acid position Ala 9 of SEQ ID NO:67, in which said substantially homologous variant is a variant in which a DNA sequence encoding said variant has the ability to hybridize to a DNA sequence encoding said human fetal gamma-globin chain under stringent conditions comprising 0.1× SSC and a temperature of about 65° C.;
(c) a LEU2 selectable marker or functionally active portion thereof;
(d) a 2μ plasmid replication system or functionally active portion thereof; and
(e) a transcription termination sequence located downstream from the DNA sequence encoding the variant globin chain, which comprises the transcription termination region of the alcohol dehydrogenase I gene.

85. The recombinant DNA vector of claim 84 which is plasmid YEpNT1/γ-PORT.

86. A yeast cell containing the recombinant DNA vector of claim 85.

87. The yeast cell of claim 86 which is a *Saccharomyces cerevisiae* as deposited with the NRRL and assigned accession number Y-18798.

88. A recombinant DNA vector which expresses in a yeast cell a variant globin chain substantially homologous to a human fetal gamma-globin chain and comprising a threonine at the gamma-66 position, comprising:
(a) yeast inducible transcriptional promoter regulated by galactose;
(b) a DNA sequence located downstream from the yeast inducible transcriptional promoter, encoding a variant globin chain substantially homologous to a fetal gamma-globin chain and comprising a threonine at the gamma-66 position which corresponds to gamma-globin amino acid position Lys 66 of SEQ ID NO:67, in which said substantially homologous variant is a variant in which a DNA sequence encoding said variant has the ability to hybridize to a DNA sequence encoding said fetal gamma-globin chain under stringent conditions comprising 0.1× SSC and a temperature of about 65° C.;
(c) a LEU2 selectable marker or functionally active portion thereof;
(d) a 2μ plasmid replication system or functionally active portion thereof; and
(e) a transcription termination sequence located downstream from the DNA sequence encoding the variant globin chain, which comprises the transcription termination region of the alcohol dehydrogenase I gene.

89. The recombinant DNA vector of claim 88 which is plasmid pNT1/γ-Chi.

90. A yeast cell containing the recombinant DNA vector of claim 89.

91. The yeast cell of claim 90 which is a *Saccharomyces cerevisiae* as deposited with the NRRL and assigned accession number Y-18801.

92. A recombinant DNA vector which expresses in a yeast cell, a variant globin chain substantially homologous to a human adult beta-globin chain and comprising a glutamic acid at the beta-127 position, comprising:

(a) yeast inducible transcriptional promoter regulated by galactose;

(b) a DNA sequence located downstream from the yeast inducible transcriptional promoter, encoding a variant globin chain substantially homologous to an adult beta-globin chain and comprising a glutamic acid at the beta-127 position which corresponds to beta-globin amino acid position Gln 127 of SEQ ID NO:70, in which said substantially homologous variant is a variant in which a DNA sequence encoding said variant has the ability to hybridize to a DNA sequence encoding said adult beta-globin chain under stringent conditions comprising 0.1× SSC and a temperature of about 65° C.;

(c) a LEU2 selectable marker or functionally active portion thereof;

(d) a 2μ plasmid replication system or functionally active portion thereof; and (e) a transcription termination sequence located downstream from the DNA sequence encoding the variant globin chain, which comprises the transcription termination region of the alcohol dehydrogenase I gene.

93. The recombinant DNA vector of claim 92 which is plasmid pNT1/β-Mot.

94. A yeast cell containing the recombinant DNA vector of claim 93.

95. The yeast cell of claim 94 which is a *Saccharomyces cerevisiae* as deposited with the NRRL and assigned accession number Y-18799.

96. A recombinant DNA vector which expresses in a yeast cell a variant globin chain substantially homologous to an adult beta-globin chain and comprising a cysteine at the beta-83 position comprising:

(a) yeast inducible transcriptional promoter regulated by galactose;

(b) a DNA sequence located downstream from the yeast inducible transcriptional promoter, encoding a variant globin chain substantially homologous to an adult beta-globin chain and comprising a cysteine at the beta-83 position which corresponds to beta-globin amino acid position Gly 83 of SEQ ID NO:70, in which said substantially homologous variant is a variant in which a DNA sequence encoding said variant has the ability to hybridize to a DNA sequence encoding said adult beta-globin chain under stringent conditions comprising 0.1× SSC and a temperature of about 65° C.;

(c) a LEU2 selectable marker or functionally active portion thereof;

(d) a 2μ plasmid replication system or functionally active portion thereof; and (e) a transcription termination sequence located downstream from the DNA sequence encoding the variant globin chain, which comprises the transcription termination region of the alcohol dehydrogenase I gene.

97. The recombinant DNA vector of claim 96 which is plasmid pNT1/β-TaliS.

98. A yeast cell containing the recombinant DNA vector of claim 97.

99. The yeast cell of claim 98 which is a *Saccharomyces cerevisiae* as deposited with the NRRL and assigned accession number Y-18804.

100. A recombinant DNA vector which expresses in a yeast cell a variant globin chain substantially homologous to an adult beta-globin chain and comprising a cysteine at the beta-44 position comprising:

(a) yeast inducible transcriptional promoter regulated by galactose;

(b) a DNA sequence located downstream from the yeast inducible transcriptional promoter, encoding a variant globin chain substantially homologous to an adult beta-globin chain and comprising a cysteine at the beta-44 position which corresponds to beta-globin amino acid position Ser 44 of SEQ ID NO:70, in which said substantially homologous variant is a variant in which a DNA sequence encoding said variant has the ability to hybridize to a DNA sequence encoding said adult beta-globin chain under stringent conditions comprising 0.1× SSC and a temperature of about 65° C.;

(c) a LEU2 selectable marker or functionally active portion thereof;

(d) a 2μ plasmid replication system or functionally active portion thereof; and (e) a transcription termination sequence located downstream from the DNA sequence encoding the variant globin chain, which comprises the transcription termination region of the alcohol dehydrogenase I gene.

101. The recombinant DNA vector of claim 100 which is plasmid pNT1/β-Miss.

102. A yeast cell containing the recombinant DNA vector of claim 101.

103. The yeast cell of claim 102 which is a *Saccharomyces cerevisiae* as deposited with the NRRL and assigned accession number Y-18803.

104. A recombinant DNA vector which expresses in a yeast cell a variant globin chain substantially homologous to an adult beta-globin chain and comprising a cysteine at the beta-145 position, comprising:

(a) a GAL10 promoter;

(b) a DNA sequence located downstream from the GAL10 promoter, encoding a variant substantially homologous to an adult beta-globin chain and comprising a cysteine at the beta-145 position which corresponds to beta-globin amino acid position Tyr 145 of SEQ ID NO:70, in which said substantially homologous variant is a variant in which a DNA sequence encoding said variant has the ability to hybridize to a DNA sequence encoding said adult beta-globin chain under stringent conditions comprising 0.1× SSC and a temperature of about 65° C.;

(c) a LEU2 selectable marker or functionally active portion thereof;

(d) a 2μ plasmid replication system or functionally active portion thereof; and (e) a transcription termination sequence located downstream from the DNA sequence encoding the variant globin chain, which comprises the transcription termination region of the alcohol dehydrogenase I gene.

105. The recombinant DNA vector of claim 104 which is plasmid pNT1/β-Ran.

106. A yeast cell containing the recombinant DNA vector of claim 105.

107. The yeast cell of claim 106 which is a *Saccharomyces cerevisiae* as deposited with the NRRL and assigned accession number Y-18802.

108. A recombinant DNA vector which expresses a human adult beta-globin chain in a yeast cell comprising:
 (a) a GAL10 promoter;
 (b) a DNA sequence encoding the human adult beta-globin chain located downstream from the GAL10 promoter;
 (c) a LEU2 selectable marker or functionally active portion thereof;
 (d) a 2μ plasmid replication system or functionally active portion thereof; and
 (e) a transcription termination sequence located downstream from the DNA sequence encoding the human adult beta-globin chain which comprises the transcription termination region of the alcohol dehydrogenase I gene.

109. The recombinant DNA vector of claim 108 which is plasmid YEp51T/NAT.

110. A yeast cell containing the recombinant DNA vector of claim 109.

111. The yeast cell of claim 110 which is a *Saccharomyces cerevisiae* as deposited with the NRRL and assigned accession number Y-18639.

112. A method for producing a globin chain or in a yeast cell comprising:
 (a) introducing into a yeast cell a recombinant DNA vector comprising: (i) a DNA sequence encoding a globin chain; (ii) a yeast transcriptional promoter which promotes the transcription of the DNA sequence encoding the globin chain; (iii) a DNA sequence encoding a yeast selectable marker or functionally active portion thereof; and (iv) a yeast replication origin; and
 (b) growing the yeast cell in an appropriate medium such that the globin chain is expressed.

113. The method of claim 112 in which the yeast transcriptional promoter is an inducible transcriptional promoter.

114. The method of claim 113 in which the inducible transcriptional promoter is a unidirectional transcriptional promoter.

115. The method of claim 113 in which the inducible transcriptional promoter is a bidirectional transcriptional promoter.

116. The method of claim 112 in which the yeast transcriptional promoter is a constitutive transcriptional promoter.

117. The method of claim 112 in which the yeast transcriptional promoter is a hybrid transcriptional promoter comprising a first sequence containing a transcriptional regulatory region of an inducible promoter and a second sequence containing a transcription initiation region of a constitutive promoter located downstream from the first sequence.

118. The method of claim 112 in which the recombinant vector further comprises a transcription termination sequence located downstream from the DNA sequence encoding a globin chain.

119. A method for producing hemoglobin comprising an alpha-like globin chain or substantially homologous variant thereof, and a beta-like globin chain or substantially homologous variant thereof, comprising the steps of:
 (a) introducing into a first yeast cell a recombinant DNA vector comprising: (i) a DNA sequence encoding an alpha-like globin chain, in which the alpha-like chain is an embryonic zeta-globin chain or an adult alpha-globin chain, or substantially homologous variant thereof, in which said substantially homologous variant is a variant in which a DNA sequence encoding said variant has the ability to hybridize to a DNA sequence encoding said alpha-like globin chain under stringent conditions comprising 0.1× SSC and a temperature of about 65°; (ii) a yeast transcriptional promoter which promotes the transcription of the DNA sequence encoding the alpha-like globin chain or substantially homologous variant thereof; and (iii) a DNA sequence encoding at least one yeast selectable marker or functionally active portion thereof; and (iv) a yeast replication origin or functionally active portion thereof;
 (b) introducing into a second yeast cell a recombinant DNA vector that comprises (i) a DNA sequence encoding a beta-like globin chain, in which the beta-like chain is an embryonic epsilon-globin chain, a fetal gamma-globin chain, an adult delta-globin chain or an adult beta-globin chain, or substantially homologous variant thereof, in which said substantially homologous variant is a variant in which a DNA sequence encoding said variant has the ability to hybridize to a DNA sequence encoding said beta-like globin chain under stringent conditions comprising 0.1× SSC and a temperature of about 65°; (ii) a yeast transcriptional promoter which promotes the transcription of the DNA sequence encoding the beta-like globin chain or substantially homologous variant thereof; and (iii) a DNA sequence encoding at least one yeast selectable marker or functionally active portion thereof; and (iv) a yeast replication origin or functionally active portion thereof;
 (c) growing the first yeast cell such that the alpha-like globin chain or substantially homologous variant thereof is expressed;
 (d) growing the second yeast cell such that the beta-like globin chain or substantially homologous variant thereof is expressed;
 (e) isolating the alpha-like globin chain or substantially homologous variant thereof from the first yeast cell;
 (f) isolating the beta-like globin chain or substantially homologous variant thereof from the second yeast cell; and
 (g) combining the isolated alpha-like globin chain or substantially homologous variant thereof, and the isolated beta-like globin chain or substantially homologous variant thereof, with a source of heme.

120. A method for producing hemoglobin comprising an alpha-like globin chain or substantially homologous variant thereof, and a beta-like globin chain or substantially homologous variant thereof, comprising the steps of:
 (a) introducing into a yeast cell two recombinant DNA vectors in which the first recombinant DNA vector comprises: (i) a DNA sequence encoding an alpha-like globin chain, in which the alpha-like chain is an embryonic zeta-globin chain or an adult alpha-globin chain, or substantially homologous variant thereof, in which said substantially homologous variant is a variant in which a DNA sequence encoding said variant has the ability to hybridize to a DNA sequence encoding said alpha-like globin chain under stringent conditions comprising 0.1× SSC and a temperature of about 65°; (ii) a yeast transcriptional promoter which promotes the transcription of the DNA sequence encoding the alpha-like globin chain or substantially homologous variant thereof; and (iii) a DNA sequence encoding at least one yeast selectable marker or functionally active portion thereof; and (iv) a yeast replication origin or functionally active portion thereof, and in which the second recombinant DNA vector comprises (i) a DNA sequence encoding a beta-like globin chain, in which the beta-like chain is an embryonic epsilon-globin chain, a fetal gamma-globin chain, an adult delta-globin chain or an adult beta-globin chain, or substantially homologous variant thereof, in which said substantially homologous variant is a variant in which a DNA sequence encoding said variant has the ability to hybridize to a DNA sequence encoding said beta-like globin chain under stringent conditions comprising 0.1× SSC and a temperature of about 65°; (iii) a DNA sequence encoding at least one yeast selectable marker or functionally active portion thereof; and (iv) a yeast replication origin or functionally active portion thereof; and (b) growing the yeast cell such that the alpha-like globin chain or substantially homologous variant thereof, and a beta-like globin chain or substantially homologous variant thereof are expressed;

(c) isolating the alpha-like globin chain or substantially homologous variant thereof, and beta-like globin chain or substantially homologous variant thereof from the yeast cell; and (d) combining the alpha-like globin chain or substantially homologous variant thereof, and a beta-like globin chain or substantially homologous variant thereof with a source of heme.

121. A method for producing hemoglobin comprising an alpha-like globin chain or substantially homologous variant thereof and a beta-like globin chain or substantially homologous variant thereof comprising the steps of:

(a) introducing into a yeast cell two recombinant DNA vectors in which the first recombinant DNA vector comprises: (i) a DNA sequence encoding an alpha-like globin chain, in which the alpha-like chain is an embryonic zeta-globin chain or an adult alpha-globin chain, or substantially homologous variant thereof, in which said substantially homologous variant is a variant in which a DNA sequence encoding said variant has the ability to hybridize to a DNA sequence encoding said alpha-like globin chain under stringent conditions comprising 0.1× SSC and a temperature of about 65°; (ii) a yeast transcriptional promoter which promotes the transcription of the DNA sequence encoding the alpha-like globin chain or substantially homologous variant thereof; and (iii) a DNA sequence encoding at least one yeast selectable marker or functionally active portion thereof; and (iv) a yeast replication origin or functionally active portion thereof, and in which the second recombinant DNA vector comprises (i) a DNA sequence encoding a beta-like globin chain, in which the beta-like chain is an embryonic epsilon-globin chain, a fetal gamma-globin chain, an adult delta-globin chain or an adult beta-globin chain, or substantially homologous variant thereof, in which said substantially homologous variant is a variant in which a DNA sequence encoding said variant has the ability to hybridize to a DNA sequence encoding said beta-like globin chain under stringent conditions comprising 0.1× SSC and a temperature of about 65°; (ii) a yeast transcriptional promoter which promotes the transcription of the DNA sequence encoding the beta-like globin chain or substantially homologous variant thereof; and (iii) a DNA sequence encoding at least one yeast selectable marker or functionally active portion thereof; and (iv) a yeast replication origin; and (b) growing the yeast cell in an appropriate medium such that the alpha-like globin chain or substantially homologous variant thereof, and a beta-like globin chain or substantially homologous variant thereof are expressed and assembled together with heme in the yeast cell to form hemoglobin.

122. A recombinant DNA vector which expresses an alpha-like globin chain and a beta-like globin chain in a yeast cell comprising:

(a) a DNA sequence I encoding the alpha-like globin chain;

(b) a first yeast transcriptional promoter which promotes the transcription of the DNA sequence I;

(c) a DNA sequence II encoding the beta-like globin chain;

(d) a second yeast transcriptional promoter which promotes the transcription of the DNA sequence II;

(e) a DNA sequence encoding a yeast selectable marker or functionally active portion thereof; and (f) a yeast replication origin; wherein the alpha-like globin chain is an embryonic zeta-globin chain, adult alpha-globin chain or substantially homologous alpha-like globin chain variant, the beta-like globin chain is an embryonic epsilon-globin chain, fetal gamma-globin chain, adult delta-globin chain, adult beta-globin chain or substantially homologous beta-like globin chain variant, which substantially homologous alpha-like globin chain variant is a variant in which a DNA sequence encoding the alpha-like globin chain variant has the ability to hybridize to a DNA sequence encoding the embryonic zeta-globin chain or adult alpha-globin chain under stringent conditions comprising 0.1× SSC and a temperature of about 65° C., and which substantially homologous beta-like globin chain variant is a variant in which a DNA sequence encoding the beta-like globin chain variant has the ability to hybridize to a DNA sequence encoding the embryonic epsilon-globin chain, fetal gamma-globin chain, adult delta-globin chain or adult beta-globin chain under stringent conditions comprising 0.1× SSC and a temperature of about 65° C.

123. The recombinant DNA vector of claim 122 in which the alpha-like globin chain is an embryonic zeta-globin chain or an adult alpha-globin chain, the beta-like globin chain is an embryonic epsilon-globin chain, a fetal gamma-globin chain, an adult delta-globin chain or an adult beta-globin chain.

124. The recombinant DNA vector of claim 122 in which the alpha-like globin chain is a human embryonic zeta-globin chain.

125. The recombinant DNA vector of claim 122 in which the alpha-like globin chain is a human adult alpha-globin chain.

126. The recombinant DNA vector of claim 122, in which the beta-like chain is a human adult beta-globin chain.

127. The recombinant DNA vector of claim 122 in which the beta-like globin chain is a human fetal gamma-globin chain.

128. The recombinant DNA vector of claim 122 in which the beta-like globin chain is a human embryonic epsilon-globin chain.

129. The recombinant DNA vector of claim 122 in which the beta-like globin chain is a human delta-globin chain.

130. The recombinant DNA vector of claim 122 in which the first yeast transcriptional promoter or the second yeast transcriptional promoter is a yeast inducible transcriptional promoter.

131. The recombinant DNA vector of claim 130 in which the yeast inducible promoter is regulated by galactose.

132. The recombinant DNA vector of claim 131 in which the yeast inducible promoter is a GAL10 promoter.

133. The recombinant DNA vector of claim 131 in which the yeast inducible promoter is a GAL1-10 promoter.

134. The recombinant DNA vector of claim 130 in which the yeast inducible promoter is regulated by glucose.

135. The recombinant DNA vector of claim 130 in which the yeast inducible promoter is an ADH2 promoter.

136. The recombinant DNA vector of claim 122 in which the first yeast transcriptional promoter and the second yeast transcriptional promoter each is a yeast inducible transcriptional promoter.

137. The recombinant DNA vector of claim 136 in which the yeast inducible promoter is regulated by galactose.

138. The recombinant DNA vector of claim 137 in which the yeast inducible promoter is a GAL10 promoter.

139. The recombinant DNA vector of claim 137 in which the yeast inducible promoter is a GAL1-10 promoter.

140. The recombinant DNA vector of claim 136 in which the yeast inducible promoter is regulated by glucose.

141. The recombinant DNA vector of claim 136 in which the yeast inducible promoter is an ADH2 promoter.

142. The recombinant DNA vector of claim 122 in which the first yeast transcriptional promoter or the second transcriptional promoter is a yeast constitutive transcriptional promoter.

143. The recombinant DNA vector of claim 142 in which the yeast constitutive transcriptional promoter is a TDH3 promoter.

144. The recombinant DNA vector of claim 122 in which the first yeast transcriptional promoter and the second transcriptional promoter each is a yeast constitutive transcriptional promoter.

145. The recombinant DNA vector of claim 144 in which the yeast constitutive transcriptional promoter is a TDH3 promoter.

146. The recombinant DNA vector of claim 122 in which the first yeast transcriptional promoter or the second yeast transcriptional promoter is a hybrid promoter which comprises: (i) a first sequence containing a transcriptional regulatory region of an inducible promoter; and (ii) a second sequence containing a transcription initiation region of a constitutive promoter located downstream from the first sequence.

147. The recombinant DNA vector of claim 146 in which the first sequence is an upstream activating sequence of a yeast inducible promoter.

148. The recombinant DNA vector of claim 147 in which the yeast inducible promoter is regulated by galactose.

149. The recombinant DNA vector of claim 148 in which the yeast inducible promoter is a GAL10 promoter.

150. The recombinant DNA vector of claim 148 in which the yeast inducible promoter is a GAL1-10 promoter.

151. The recombinant DNA vector of claim 147 in which the yeast inducible promoter is regulated by glucose.

152. The recombinant DNA vector of claim 147 in which the yeast inducible promoter is an ADH2 promoter.

153. The recombinant DNA vector of claim 146 in which the constitutive promoter is a yeast TDH3 promoter.

154. The recombinant DNA vector of claim 122 in which the first yeast transcriptional promoter and the second yeast transcriptional promoter each is a hybrid promoter, which comprises: (i) a first sequence containing a transcriptional regulatory region of an inducible promoter; and (ii) a second sequence containing a transcription initiation region of a constitutive promoter located downstream from the first sequence.

155. The recombinant DNA vector of claim 154 in which the first sequence is an upstream activating sequence of a yeast inducible promoter.

156. The recombinant DNA vector of claim 155 in which the yeast inducible promoter is regulated by galactose.

157. The recombinant DNA vector of claim 156 in which the yeast inducible promoter is a GAL10 promoter.

158. The recombinant DNA vector of claim 156 in which the yeast inducible promoter is a GAL1-10 promoter.

159. The recombinant DNA vector of claim 155 in which the yeast inducible promoter is regulated by glucose.

160. The recombinant DNA vector of claim 155 in which the yeast inducible promoter is an ADH2 promoter.

161. The recombinant DNA vector of claim 154 in which the constitutive promoter is a yeast TDH3 promoter.

162. The recombinant DNA vector of claim 122 in which the yeast selectable marker is the LEU2 gene.

163. The recombinant DNA vector of claim 122 in which the yeast selectable marker is the leu2d gene.

164. The recombinant DNA vector of claim 122 in which the yeast selectable marker is the URA3 gene.

165. The recombinant DNA vector of claim 122 in which the yeast replication origin is a yeast $2\mu$ plasmid replication system or functionally active portion thereof.

166. The recombinant DNA vector of claim 122 in which the yeast replication origin is an autonomous replicating sequence.

167. The recombinant DNA vector of claim 122 in which the recombinant DNA vector further comprises a transcription termination sequence located downstream from the DNA sequence I or the DNA sequence II.

168. The recombinant DNA vector of claim 167 in which the transcription termination sequence is selected from the group consisting of the ADH1 transcription termination sequence and the GAL10 transcription termination sequence.

169. The recombinant DNA vector of claim 122 in which the recombinant DNA vector further comprises a first transcription termination sequence located downstream from the DNA sequence I, and a second transcription termination sequence located downstream from the DNA sequence II.

170. The recombinant DNA vector of claim 169 in which the first or second transcription termination sequence is selected from the group consisting of the ADH1 transcription termination sequence and the GAL10 transcription termination sequence.

171. A recombinant DNA vector which expresses an human alpha-globin chain and an human beta-globin chain in a yeast cell comprising:
   (a) a DNA sequence I encoding the human alpha-globin chain;
   (b) a first yeast hybrid promoter which promotes the transcription of the DNA sequence I;
   (c) an ADH1 transcription termination sequence located downstream from the DNA sequence I;
   (d) a DNA sequence II encoding the human beta-globin chain;
   (e) a second yeast hybrid promoter which promotes the transcription of the DNA sequence II;

(f) a GAL10 transcription termination sequence located downstream from the DNA sequence II;

(g) a DNA sequence encoding a yeast LEU2 selectable marker or functionally active portion thereof; and (h) a yeast 2μ plasmid replication origin; wherein the first and second yeast hybrid promoters each comprises: (i) a first sequence containing a transcriptional regulatory region of a yeast GAL1-10 inducible promoter; and (ii) a second sequence containing a transcription initiation region of a yeast TDH3 constitutive promoter located downstream from the first sequence.

172. The recombinant DNA vector of claim 171 in which the DNA sequence I encoding the human alpha-globin chain is in the like orientation as the DNA sequence II encoding the human beta-globin chain.

173. The recombinant DNA vector of claim 172 which is plasmid pBM-V-X1-G-αβ.

174. The recombinant DNA vector of claim 171 in which the DNA sequence I encoding the human alpha-globin chain is in the opposite orientation as the DNA sequence II encoding the human beta-globin chain.

175. The recombinant DNA vector of claim 174 which is plasmid pBM-V-X2-G-αβ.

176. A recombinant DNA vector which expresses an human alpha-globin chain and an human gamma-globin chain in a yeast cell comprising:

(a) a DNA sequence I encoding the human alpha-globin chain;

(b) a first yeast hybrid promoter which promotes the transcription of the DNA sequence I;

(c) a GAL10 transcription termination sequence located downstream from the DNA sequence I;

(d) a DNA sequence II encoding the human gamma-globin chain;

(e) a second yeast hybrid promoter which promotes the transcription of the DNA sequence II;

(f) an ADH1 transcription termination sequence located downstream from the DNA sequence II;

(g) a DNA sequence encoding a yeast leu2d selectable marker or functionally active portion thereof; and (h) a yeast autonomous replicating sequence; wherein the first and second yeast hybrid promoters each comprises: (i) a first sequence containing a transcriptional regulatory region of a yeast ADH2 inducible promoter; and (ii) a second sequence containing a transcription initiation region of a yeast TDH3 constitutive promoter located downstream from the first sequence.

177. The recombinant DNA vector of claim 176 in which the DNA sequence I encoding the human alpha-globin chain is in the like orientation as the DNA sequence II encoding the human gamma-globin chain.

178. The recombinant DNA vector of claim 177 which is plasmid pBM-R-X7-A-αγ$_{val}$.

179. The recombinant DNA vector of claim 178 in which the DNA sequence I encoding the human alpha-globin chain is in the opposite orientation as the DNA sequence II encoding the human gamma-globin chain.

180. The recombinant DNA vector of claim 179 which is plasmid pBM-R-X8-A-αγ$_{val}$.

181. A yeast cell containing the recombinant DNA vector of any of claims 122 to 180.

182. A method for producing an alpha-like globin chain or a beta-like globin chain, which method comprises growing a yeast cell containing the recombinant DNA vector of any of claims 122, 123 and 145 in an appropriate medium such that the alpha-like globin chain or the beta-like globin chain is expressed.

183. A method for producing an alpha-like globin chain and a beta-like globin chain, which method comprises growing a yeast cell containing the recombinant DNA vector of any of claims 122, 123 and 145 in an appropriate medium such that the alpha-like globin chain and the beta-like globin chain are expressed.

184. A method for producing a hemoglobin comprising an alpha-like globin chain and a beta-like globin chain, which method comprises:

(a) growing a yeast cell containing the recombinant DNA vector of any of claims 145, 146 and 168 in an appropriate medium such that the alpha-like globin chain and the beta-like globin chain are expressed;

(b) isolating the alpha-like globin chain and the beta-like globin chain from the yeast cell; and (c) combining the alpha-like globin chain and the beta-like globin chain with a source of heme to form the hemoglobin.

185. A method for producing a hemoglobin comprising an alpha-like globin chain and a beta-like globin chain in a yeast cell, which method comprises growing a yeast cell containing the recombinant DNA vector of any of claims 122, 123 and 145 in an appropriate medium such that the alpha-like globin chain and the beta-like globin chain are expressed and assembled together with heme in the yeast cell to form hemoglobin.

* * * * *

SEQUENCE LISTING ( 1 ) GENERAL INFORMATION:

( i i i ) NUMBER OF SEQUENCES: 71

( 2 ) INFORMATION FOR SEQ ID NO:1:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..423

( x i ) SEQUENCE DESCRIPTION: SEQ ID NO:1:

```
TCT  CTG  ACC  AAG  ACT  GAG  AGG  ACC  ATC  ATT  GTG  TCC  ATG  TGG  GCC  AAG      48
Ser  Leu  Thr  Lys  Thr  Glu  Arg  Thr  Ile  Ile  Val  Ser  Met  Trp  Ala  Lys
 1              5                        10                       15

ATC  TCC  ACG  CAG  GCC  GAC  ACC  ATC  GGC  ACC  GAG  ACT  CTG  GAG  AGG  CTC      96
Ile  Ser  Thr  Gln  Ala  Asp  Thr  Ile  Gly  Thr  Glu  Thr  Leu  Glu  Arg  Leu
             20                       25                       30

TTC  CTC  AGC  CAC  CCG  CAG  ACC  AAG  ACC  TAC  TTC  CCG  CAC  TTC  GAC  CTG     144
Phe  Leu  Ser  His  Pro  Gln  Thr  Lys  Thr  Tyr  Phe  Pro  His  Phe  Asp  Leu
             35                       40                       45

CAC  CCG  GGG  TCC  GCG  CAG  TTG  CGC  GCG  CAC  GGC  TCC  AAG  GTG  GTG  GCC     192
His  Pro  Gly  Ser  Ala  Gln  Leu  Arg  Ala  His  Gly  Ser  Lys  Val  Val  Ala
             50                       55                       60

GCC  GTG  GGC  GAC  GCG  GTG  AAG  AGC  ATC  GAC  GAC  ATC  GGC  GGC  GCC  CTG     240
Ala  Val  Gly  Asp  Ala  Val  Lys  Ser  Ile  Asp  Asp  Ile  Gly  Gly  Ala  Leu
 65                       70                       75                       80

TCC  AAG  CTG  AGC  GAG  CTG  CAC  GCC  TAC  ATC  CTG  CGC  GTG  GAC  CCG  GTC     288
Ser  Lys  Leu  Ser  Glu  Leu  His  Ala  Tyr  Ile  Leu  Arg  Val  Asp  Pro  Val
                     85                       90                       95

AAC  TTC  AAG  CTC  CTG  TCC  CAC  TGC  CTG  CTG  GTC  ACC  CTG  GCC  GCG  CGC     336
Asn  Phe  Lys  Leu  Leu  Ser  His  Cys  Leu  Leu  Val  Thr  Leu  Ala  Ala  Arg
                    100                      105                      110

TTC  CCC  GCC  GAC  TTC  ACG  GCC  GAG  GCC  CAC  GCC  GCC  TGG  GAC  AAG  TTC     384
Phe  Pro  Ala  Asp  Phe  Thr  Ala  Glu  Ala  His  Ala  Ala  Trp  Asp  Lys  Phe
            115                      120                      125

CTA  TCG  GTC  GTA  TCC  TCT  GTC  CTG  ACC  GAG  AAG  TAC  CGC                    423
Leu  Ser  Val  Val  Ser  Ser  Val  Leu  Thr  Glu  Lys  Tyr  Arg
            130                      135                      140
```

( 2 ) INFORMATION FOR SEQ ID NO:2:

( i ) SEQUENCE CHARACTERISTICS:
        ( A ) LENGTH: 438 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..438

( x i ) SEQUENCE DESCRIPTION: SEQ ID NO:2:

```
GTG  CAT  TTT  ACT  GCT  GAG  GAG  AAG  GCT  GCC  GTC  ACT  AGC  CTG  TGG  AGC      48
Val  His  Phe  Thr  Ala  Glu  Glu  Lys  Ala  Ala  Val  Thr  Ser  Leu  Trp  Ser
 1              5                        10                       15
```

| | | | | | | | | | | | | | | | | |
|---|---|---|---|---|---|---|---|---|---|---|---|---|---|---|---|---|
| AAG | ATG | AAT | GTG | GAA | GAG | GCT | GGA | GGT | GAA | GCC | TTG | GGC | AGG | CTC | CTC | 96 |
| Lys | Met | Asn | Val | Glu | Glu | Ala | Gly | Gly | Glu | Ala | Leu | Gly | Arg | Leu | Leu | |
| | | | 20 | | | | | 25 | | | | | 30 | | | |
| GTT | GTT | TAC | CCC | TGG | ACC | CAG | AGA | TTT | TTT | GAC | AGC | TTT | GGA | AAC | CTG | 144 |
| Val | Val | Tyr | Pro | Trp | Thr | Gln | Arg | Phe | Phe | Asp | Ser | Phe | Gly | Asn | Leu | |
| | | 35 | | | | | 40 | | | | | 45 | | | | |
| TCG | TCT | CCC | TCT | GCC | ATC | CTG | GGC | AAC | CCC | AAG | GTC | AAG | GCC | CAT | GGC | 192 |
| Ser | Ser | Pro | Ser | Ala | Ile | Leu | Gly | Asn | Pro | Lys | Val | Lys | Ala | His | Gly | |
| | 50 | | | | | 55 | | | | | 60 | | | | | |
| AAG | AAG | GTG | CTG | ACT | TCC | TTT | GGA | GAT | GCT | ATT | AAA | AAC | ATG | GAC | AAC | 240 |
| Lys | Lys | Val | Leu | Thr | Ser | Phe | Gly | Asp | Ala | Ile | Lys | Asn | Met | Asp | Asn | |
| 65 | | | | | 70 | | | | | 75 | | | | | 80 | |
| CTC | AAG | CCC | GCC | TTT | GCT | AAG | CTG | AGT | GAG | CTG | CAC | TGT | GAC | AAG | CTG | 288 |
| Leu | Lys | Pro | Ala | Phe | Ala | Lys | Leu | Ser | Glu | Leu | His | Cys | Asp | Lys | Leu | |
| | | | | 85 | | | | | 90 | | | | | 95 | | |
| CAT | GTG | GAT | CCT | GAG | AAC | TTC | AAG | CTC | CTG | GGT | AAC | GTG | ATG | GTG | ATT | 336 |
| His | Val | Asp | Pro | Glu | Asn | Phe | Lys | Leu | Leu | Gly | Asn | Val | Met | Val | Ile | |
| | | | 100 | | | | | 105 | | | | | 110 | | | |
| ATT | CTG | GCT | ACT | CAC | TTT | GGC | AAG | GAG | TTC | ACC | CCT | GAA | GTG | CAG | GCT | 384 |
| Ile | Leu | Ala | Thr | His | Phe | Gly | Lys | Glu | Phe | Thr | Pro | Glu | Val | Gln | Ala | |
| | | 115 | | | | | 120 | | | | | 125 | | | | |
| GCC | TGG | CAG | AAG | CTG | GTG | TCT | GCT | GTC | GCC | ATT | GCC | CTG | GGC | CAT | AAG | 432 |
| Ala | Trp | Gln | Lys | Leu | Val | Ser | Ala | Val | Ala | Ile | Ala | Leu | Gly | His | Lys | |
| | 130 | | | | | 135 | | | | | 140 | | | | | |
| TAC | CAC | | | | | | | | | | | | | | | 438 |
| Tyr | His | | | | | | | | | | | | | | | |
| 145 | | | | | | | | | | | | | | | | |

( 2 ) INFORMATION FOR SEQ ID NO:3:

( i ) SEQUENCE CHARACTERISTICS:
        ( A ) LENGTH: 438 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..438

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| GGT | CAT | TTC | ACA | GAG | GAG | GAC | AAG | GCT | ACT | ATC | ACA | AGC | CTG | TGG | GGC | 48 |
| Gly | His | Phe | Thr | Glu | Glu | Asp | Lys | Ala | Thr | Ile | Thr | Ser | Leu | Trp | Gly | |
| 1 | | | | 5 | | | | | 10 | | | | | 15 | | |
| AAG | GTG | AAT | GTG | GAA | GAT | GCT | GGA | GGA | GAA | ACC | CTG | GGA | AGG | CTC | CTG | 96 |
| Lys | Val | Asn | Val | Glu | Asp | Ala | Gly | Gly | Glu | Thr | Leu | Gly | Arg | Leu | Leu | |
| | | | 20 | | | | | 25 | | | | | 30 | | | |
| GTT | GTC | TAC | CCA | TGG | ACC | CAG | AGG | TTC | TTT | GAC | AGC | TTT | GGC | AAC | CTG | 144 |
| Val | Val | Tyr | Pro | Trp | Thr | Gln | Arg | Phe | Phe | Asp | Ser | Phe | Gly | Asn | Leu | |
| | | 35 | | | | | 40 | | | | | 45 | | | | |
| TCC | TCT | GCC | TCT | GCC | ATC | ATG | GGC | AAC | CCC | AAA | GTC | AAG | GCA | CAT | GGC | 192 |
| Ser | Ser | Ala | Ser | Ala | Ile | Met | Gly | Asn | Pro | Lys | Val | Lys | Ala | His | Gly | |
| | 50 | | | | | 55 | | | | | 60 | | | | | |
| AAG | AAG | GTG | CTG | ACT | TCC | TTG | GGA | GAT | GCC | ATA | AAG | CAC | CTG | GAT | GAT | 240 |
| Lys | Lys | Val | Leu | Thr | Ser | Leu | Gly | Asp | Ala | Ile | Lys | His | Leu | Asp | Asp | |
| 65 | | | | | 70 | | | | | 75 | | | | | 80 | |
| CTC | AAG | GGC | ACC | TTT | GCC | CAG | CTG | AGT | GAA | CTG | CAC | TGT | GAC | AAG | CTG | 288 |
| Leu | Lys | Gly | Thr | Phe | Ala | Gln | Leu | Ser | Glu | Leu | His | Cys | Asp | Lys | Leu | |
| | | | | 85 | | | | | 90 | | | | | 95 | | |

| CAT | GTG | GAT | CCT | GAG | AAC | TTC | AAG | CTC | CTG | GGA | AAT | GTG | CTG | GTG | ACC | 336 |
| His | Val | Asp | Pro | Glu | Asn | Phe | Lys | Leu | Leu | Gly | Asn | Val | Leu | Val | Thr | |
| | | | 100 | | | | 105 | | | | | 110 | | | | |
| GTT | TTG | GCA | ATC | CAT | TTC | GGC | AAA | GAA | TTC | ACC | CCT | GAG | GTG | CAG | GCT | 384 |
| Val | Leu | Ala | Ile | His | Phe | Gly | Lys | Glu | Phe | Thr | Pro | Glu | Val | Gln | Ala | |
| | | 115 | | | | | 120 | | | | | 125 | | | | |
| TCC | TGG | CAG | AAG | ATG | GTG | ACT | GCA | GTG | GCC | AGT | GCC | CTG | TCC | TCC | AGA | 432 |
| Ser | Trp | Gln | Lys | Met | Val | Thr | Ala | Val | Ala | Ser | Ala | Leu | Ser | Ser | Arg | |
| | 130 | | | | | 135 | | | | | 140 | | | | | |
| TAC | CAC | | | | | | | | | | | | | | | 438 |
| Tyr | His | | | | | | | | | | | | | | | |
| 145 | | | | | | | | | | | | | | | | |

( 2 ) INFORMATION FOR SEQ ID NO:4:

( i ) SEQUENCE CHARACTERISTICS:
  ( A ) LENGTH: 438 base pairs
  ( B ) TYPE: nucleic acid
  ( C ) STRANDEDNESS: double
  ( D ) TOPOLOGY: unknown ( i i ) MOLECULE TYPE: cDNA ( i x ) FEATURE:
  ( A ) NAME/KEY: CDS
  ( B ) LOCATION: 1..438

( x i ) SEQUENCE DESCRIPTION: SEQ ID NO:4:

| GTG | CAT | CTG | ACT | CCT | GAG | GAG | AAG | ACT | GCT | GTC | AAT | GCC | CTG | TGG | GGC | 48 |
| Val | His | Leu | Thr | Pro | Glu | Glu | Lys | Thr | Ala | Val | Asn | Ala | Leu | Trp | Gly | |
| 1 | | | | 5 | | | | | 10 | | | | | 15 | | |
| AAA | GTG | AAC | GTG | GAT | GCA | GTG | GGT | GGT | GAG | GCC | CTG | GGC | AGG | TTA | CTG | 96 |
| Lys | Val | Asn | Val | Asp | Ala | Val | Gly | Gly | Glu | Ala | Leu | Gly | Arg | Leu | Leu | |
| | | | 20 | | | | | 25 | | | | | 30 | | | |
| GTG | GTC | TAC | CCT | TGG | ACC | CAG | AGG | TTC | TTT | GAG | TCC | TTT | GGG | GAT | CTG | 144 |
| Val | Val | Tyr | Pro | Trp | Thr | Gln | Arg | Phe | Phe | Glu | Ser | Phe | Gly | Asp | Leu | |
| | | 35 | | | | | 40 | | | | | 45 | | | | |
| TCC | TCT | CCT | GAT | GCT | GTT | ATG | GGC | AAC | CCT | AAG | GTG | AAG | GCT | CAT | GGC | 192 |
| Ser | Ser | Pro | Asp | Ala | Val | Met | Gly | Asn | Pro | Lys | Val | Lys | Ala | His | Gly | |
| | 50 | | | | | 55 | | | | | 60 | | | | | |
| AAG | AAG | GTG | CTA | GGT | GCC | TTT | AGT | GAT | GGC | CTG | GCT | CAC | CTG | GAC | AAC | 240 |
| Lys | Lys | Val | Leu | Gly | Ala | Phe | Ser | Asp | Gly | Leu | Ala | His | Leu | Asp | Asn | |
| 65 | | | | | 70 | | | | | 75 | | | | | 80 | |
| CTC | AAG | GGC | ACT | TTT | TCT | CAG | CTG | AGT | GAG | CTG | CAC | TGT | GAC | AAG | CTG | 288 |
| Leu | Lys | Gly | Thr | Phe | Ser | Gln | Leu | Ser | Glu | Leu | His | Cys | Asp | Lys | Leu | |
| | | | | 85 | | | | | 90 | | | | | 95 | | |
| CAC | GTG | GAT | CCT | GAG | AAC | TTC | AGG | CTC | TTG | GGC | AAT | GTG | CTG | GTG | TGT | 336 |
| His | Val | Asp | Pro | Glu | Asn | Phe | Arg | Leu | Leu | Gly | Asn | Val | Leu | Val | Cys | |
| | | | 100 | | | | 105 | | | | | 110 | | | | |
| GTG | CTG | GCC | CGC | AAC | TTT | GGC | AAG | GAA | TTC | ACC | CCA | CAA | ATG | CAG | GCT | 384 |
| Val | Leu | Ala | Arg | Asn | Phe | Gly | Lys | Glu | Phe | Thr | Pro | Gln | Met | Gln | Ala | |
| | | 115 | | | | | 120 | | | | | 125 | | | | |
| GCC | TAT | CAG | AAG | GTG | GTG | GCT | GGT | GTC | GCT | AAT | GCC | TTG | GCT | CAC | AAG | 432 |
| Ala | Tyr | Gln | Lys | Val | Val | Ala | Gly | Val | Ala | Asn | Ala | Leu | Ala | His | Lys | |
| | 130 | | | | | 135 | | | | | 140 | | | | | |
| TAC | CAT | | | | | | | | | | | | | | | 438 |
| Tyr | His | | | | | | | | | | | | | | | |
| 145 | | | | | | | | | | | | | | | | |

( 2 ) INFORMATION FOR SEQ ID NO:5:

( i ) SEQUENCE CHARACTERISTICS:
  ( A ) LENGTH: 423 base pairs
  ( B ) TYPE: nucleic acid
  ( C ) STRANDEDNESS: double (D) TOPOLOGY: unknown (ii) MOLECULE TYPE: cDNA (ix) FEATURE:
  (A) NAME/KEY: CDS
  (B) LOCATION: 1..423

(xi) SEQUENCE DESCRIPTION: SEQ ID NO:5:

| GTG | CTG | TCT | CCT | GCC | GAC | AAG | ACC | AAC | GTC | AAG | GCC | GCC | TGG | GGC | AAG | 48 |
| Val | Leu | Ser | Pro | Ala | Asp | Lys | Thr | Asn | Val | Lys | Ala | Ala | Trp | Gly | Lys | |
| 1 | | | | 5 | | | | | 10 | | | | | 15 | | |

| GTT | GGC | GCG | CAC | GCT | GGC | GAG | TAT | GGT | GCG | GAG | GCC | CTG | GAG | AGG | ATG | 96 |
| Val | Gly | Ala | His | Ala | Gly | Glu | Tyr | Gly | Ala | Glu | Ala | Leu | Glu | Arg | Met | |
| | | | 20 | | | | | 25 | | | | | 30 | | | |

| TTC | CTG | TCC | TTC | CCC | ACC | ACC | AAG | ACC | TAC | TTC | CCG | CAC | TTC | GAC | CTG | 144 |
| Phe | Leu | Ser | Phe | Pro | Thr | Thr | Lys | Thr | Tyr | Phe | Pro | His | Phe | Asp | Leu | |
| | | 35 | | | | | 40 | | | | | 45 | | | | |

| AGC | CAC | GGC | TCT | GCC | CAG | GTT | AAG | GGC | CAC | GGC | AAG | AAG | GTG | GCC | GAC | 192 |
| Ser | His | Gly | Ser | Ala | Gln | Val | Lys | Gly | His | Gly | Lys | Lys | Val | Ala | Asp | |
| | 50 | | | | | 55 | | | | | 60 | | | | | |

| GCG | CTG | ACC | AAC | GCC | GTG | GCG | CAC | GTG | GAC | GAC | ATG | CCC | AAC | GCG | CTG | 240 |
| Ala | Leu | Thr | Asn | Ala | Val | Ala | His | Val | Asp | Asp | Met | Pro | Asn | Ala | Leu | |
| 65 | | | | | 70 | | | | | 75 | | | | | 80 | |

| TCC | GCC | CTG | AGC | GAC | CTG | CAC | GCG | CAC | AAG | CTT | CGG | GTG | GAC | CCG | GTC | 288 |
| Ser | Ala | Leu | Ser | Asp | Leu | His | Ala | His | Lys | Leu | Arg | Val | Asp | Pro | Val | |
| | | | | 85 | | | | | 90 | | | | | 95 | | |

| AAC | TTC | AAG | CTC | CTA | AGC | CAC | TGC | CTG | CTG | GTG | ACC | CTG | GCC | GCC | CAC | 336 |
| Asn | Phe | Lys | Leu | Leu | Ser | His | Cys | Leu | Leu | Val | Thr | Leu | Ala | Ala | His | |
| | | | 100 | | | | | 105 | | | | | 110 | | | |

| CTC | CCC | GCC | GAG | TTC | ACC | CCT | GCG | GTG | CAC | GCC | TCC | CTG | GAC | AAG | TTC | 384 |
| Leu | Pro | Ala | Glu | Phe | Thr | Pro | Ala | Val | His | Ala | Ser | Leu | Asp | Lys | Phe | |
| | | 115 | | | | | 120 | | | | | 125 | | | | |

| CTG | GCT | TCT | GTG | AGC | ACC | GTG | CTG | ACC | TCC | AAA | TAC | CGT | | | | 423 |
| Leu | Ala | Ser | Val | Ser | Thr | Val | Leu | Thr | Ser | Lys | Tyr | Arg | | | | |
| | 130 | | | | | 135 | | | | | 140 | | | | | |

(2) INFORMATION FOR SEQ ID NO:6:

(i) SEQUENCE CHARACTERISTICS:
  (A) LENGTH: 438 base pairs
  (B) TYPE: nucleic acid
  (C) STRANDEDNESS: double
  (D) TOPOLOGY: unknown (ii) MOLECULE TYPE: cDNA (ix) FEATURE:
  (A) NAME/KEY: CDS
  (B) LOCATION: 1..438

(xi) SEQUENCE DESCRIPTION: SEQ ID NO:6:

| GTG | CAC | CTG | ACT | CCT | GAG | GAG | AAG | TCT | GCC | GTT | ACT | GCC | CTG | TGG | GGC | 48 |
| Val | His | Leu | Thr | Pro | Glu | Glu | Lys | Ser | Ala | Val | Thr | Ala | Leu | Trp | Gly | |
| 1 | | | | 5 | | | | | 10 | | | | | 15 | | |

| AAG | GTG | AAC | GTG | GAT | GAA | GTT | GGT | GGT | GAG | GCC | CTG | GGC | AGG | CTG | CTG | 96 |
| Lys | Val | Asn | Val | Asp | Glu | Val | Gly | Gly | Glu | Ala | Leu | Gly | Arg | Leu | Leu | |
| | | | 20 | | | | | 25 | | | | | 30 | | | |

| GTG | GTC | TAC | CCT | TGG | ACC | CAG | AGG | TTC | TTT | GAG | TCC | TTT | GGG | GAT | CTG | 144 |
| Val | Val | Tyr | Pro | Trp | Thr | Gln | Arg | Phe | Phe | Glu | Ser | Phe | Gly | Asp | Leu | |
| | | 35 | | | | | 40 | | | | | 45 | | | | |

| TCC | ACT | CCT | GAT | GCT | GTT | ATG | GGC | AAC | CCT | AAG | GTG | AAG | GCT | CAT | GGC | 192 |
| Ser | Thr | Pro | Asp | Ala | Val | Met | Gly | Asn | Pro | Lys | Val | Lys | Ala | His | Gly | |
| | 50 | | | | | 55 | | | | | 60 | | | | | |

| AAG | AAA | GTG | CTC | GGT | GCC | TTT | AGT | GAT | GGC | CTG | GCT | CAC | CTG | GAC | AAC | 240 |

| Lys | Lys | Val | Leu | Gly | Ala | Phe | Ser | Asp | Gly | Leu | Ala | His | Leu | Asp | Asn | |
|---|---|---|---|---|---|---|---|---|---|---|---|---|---|---|---|---|
| 65 | | | | 70 | | | | | 75 | | | | | | 80 | |

| CTC | AAG | GGC | ACC | TTT | GCC | ACA | CTG | AGT | GAG | CTG | CAC | TGT | GAC | AAG | CTG | 288 |
|---|---|---|---|---|---|---|---|---|---|---|---|---|---|---|---|---|
| Leu | Lys | Gly | Thr | Phe | Ala | Thr | Leu | Ser | Glu | Leu | His | Cys | Asp | Lys | Leu | |
| | | | | 85 | | | | | 90 | | | | | 95 | | |

| CAC | GTG | GAT | CCT | GAG | AAC | TTC | AGG | CTC | CTG | GGC | AAC | GTG | CTG | GTC | TGT | 336 |
|---|---|---|---|---|---|---|---|---|---|---|---|---|---|---|---|---|
| His | Val | Asp | Pro | Glu | Asn | Phe | Arg | Leu | Leu | Gly | Asn | Val | Leu | Val | Cys | |
| | | | 100 | | | | | 105 | | | | 110 | | | | |

| GTG | CTG | GCC | CAT | CAC | TTT | GGC | AAA | GAA | TTC | ACC | CCA | CCA | GTG | CAG | GCT | 384 |
|---|---|---|---|---|---|---|---|---|---|---|---|---|---|---|---|---|
| Val | Leu | Ala | His | His | Phe | Gly | Lys | Glu | Phe | Thr | Pro | Pro | Val | Gln | Ala | |
| | | | 115 | | | | 120 | | | | | 125 | | | | |

| GCC | TAT | CAG | AAA | GTG | GTG | GCT | GGT | GTG | GCT | AAT | GCC | CTG | GCC | CAC | AAG | 432 |
|---|---|---|---|---|---|---|---|---|---|---|---|---|---|---|---|---|
| Ala | Tyr | Gln | Lys | Val | Val | Ala | Gly | Val | Ala | Asn | Ala | Leu | Ala | His | Lys | |
| | 130 | | | | | 135 | | | | | 140 | | | | | |

| TAT | CAC | | | | | | | | | | | | | | | 438 |
|---|---|---|---|---|---|---|---|---|---|---|---|---|---|---|---|---|
| Tyr | His | | | | | | | | | | | | | | | |
| 145 | | | | | | | | | | | | | | | | |

( 2 ) INFORMATION FOR SEQ ID NO:7:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:7:

AAGGGTCGAC AATATAAAAT GGTGCTGTCT CCTGCCGACA AGACCAACGT CAAGGC 56

( 2 ) INFORMATION FOR SEQ ID NO:8:

( i ) SEQUENCE CHARACTERISTICS:
        ( A ) LENGTH: 92 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:8:

GGGAATTCCC GGGGATCCTT AACGGTATTT GGAGGTCAGC ACGGTGCTCA CAGAAGCCAG 60

GAACTTGTCC AGGGAGGCGT GCACCGCAGG GG 92

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:9:

CTT CTT TGC GTC CAT CCA 18

( 2 ) INFORMATION FOR SEQ ID NO:10:

( i ) SEQUENCE CHARACTERISTICS:
        ( A ) LENGTH: 534 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
    ( A ) NAME/KEY: CDS
    ( B ) LOCATION: 1..534

( x i ) SEQUENCE DESCRIPTION: SEQ ID NO:10:

```
CCATGGGTCA  TTTCACAGAG  GAGGACAAGG  CTACTATCAC  AAGCCTGTGG  GGCAAGGTGA      60
ATGTGGAAGA  TGCTGGAGGA  GAAACCCTGG  GAAGGCTCCT  GGTTGTCTAC  CCATGGACCC     120
AGAGGTTCTT  TGACAGCTTT  GGCAACCTGT  CCTCTGCCTC  TGCCATCATG  GGCAACCCCA     180
AAGTCAAGGC  ACATGGCAAG  AAGGTGCTGA  CTTCCTTGGG  AGATGCCATA  AAGCACCTGG     240
ATGATCTCAA  GGGCACCTTT  GCCCAGCTGA  GTGAACTGCA  CTGTGACAAG  CTGCATGTGG     300
ATCCTGAGAA  CTTCAAGCTC  CTGGGAAATG  TGCTGGTGAC  CGTTTTGGCA  ATCCATTTCG     360
GCAAAGAATT  CACCCCTGAG  GTGCAGGCTT  CCTGGCAGAA  GATGGTGACT  GCAGTGGCCA     420
GTGCCCTGTC  CTCCAGATAC  CACTGAGCCT  CTTGCCCATG  ATTCAGAGCT  TTCAAGGATA     480
GGCTTTATTC  TGCAAGCAAT  ACAAATAATA  AATCTATTCT  GCTGAGAGAG  TCAC           534
```

( 2 ) INFORMATION FOR SEQ ID NO:11:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:11:

```
CAAGTTGGGT  CGACAAAAAA  ATATGGGTCA  TTTCACAGAG  GAGGACAAGG  CTACTATCAA      60
GCCTGTGG                                                                    68
```

( 2 ) INFORMATION FOR SEQ ID NO:12:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:12:

```
GCCCGATGCT  AAGCTTGGTC  AGTGGTATCT  GGAGGACAGG  GCACTGGCCA  CTGC            54
```

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:13:

```
CTGATGTCGA  CATCATGGTG  CATTTACTG  CTGAGG                                   36
```

( 2 ) INFORMATION FOR SEQ ID NO:14:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: unknown (ii) MOLECULE TYPE: cDNA (xi) SEQUENCE DESCRIPTION: SEQ ID NO:14:

CTGGAGGTGA AGCCTTGGGC AGGCTCCTCG TTGTTTAC   38

(2) INFORMATION FOR SEQ ID NO:15:

(i) SEQUENCE CHARACTERISTICS:
        (A) LENGTH: 38 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:15:

GTAAACAACG AGGAGCCTGC CCAAGGCTTC ACCTCCAG   38

(2) INFORMATION FOR SEQ ID NO:16:

(i) SEQUENCE CHARACTERISTICS:
        (A) LENGTH: 43 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:16:

GCATGTGGAT CCTGAGAACT TCAAGCTCCT GGGTAACGTG ATG   43

(2) INFORMATION FOR SEQ ID NO:17:

(i) SEQUENCE CHARACTERISTICS:
        (A) LENGTH: 43 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:17:

CATCACGTTA CCCAGGAGCT TGAAGTTCTC AGGATCCACA TGG   43

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:18:

TGATAGAAGC TTTCAGTGGT ACTTATGGCC CAGGGC   36

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:19:

CAGTCGAGCT CATGTCTCTG ACCAAGACT  29

(2) INFORMATION FOR SEQ ID NO:20:

(i) SEQUENCE CHARACTERISTICS:
        (A) LENGTH: 41 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:20:

TATTAGCATG CGTCGACAAG CTTTTAGCGG TACTTCTCGG T  41

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:21:

GCCCTGGCCC ACAAGTGTCA CTAAGCTCGC  30

(2) INFORMATION FOR SEQ ID NO:22:

(i) SEQUENCE CHARACTERISTICS:
        (A) LENGTH: 36 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:22:

GAAGGCTCAT GGCAAGACTG TGCTCGGTGC CTTTAG  36

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:23:

CTCCTGAGGA GAAGTGTGCC GTTACT  26

(2) INFORMATION FOR SEQ ID NO:24:

(i) SEQUENCE CHARACTERISTICS:
        (A) LENGTH: 55 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:24:

CAAGTTGGGT CGACAAAAAA ATATGCCTCA TTTCAGAGGA GGACAAGTGT ACTAT  55

(2) INFORMATION FOR SEQ ID NO:25:

-continued (i) SEQUENCE CHARACTERISTICS:
 (A) LENGTH: 54 base pairs
 (B) TYPE: nucleic acid
 (C) STRANDEDNESS: single
 (D) TOPOLOGY: unknown (ii) MOLECULE TYPE: cDNA (xi) SEQUENCE DESCRIPTION: SEQ ID NO:25:

CATCACTTTG GCAAAGAATT CACCCCACCA GTGGAGGCTG CCTATCAGAA AGTG    54

(2) INFORMATION FOR SEQ ID NO:26:

(i) SEQUENCE CHARACTERISTICS:
 (A) LENGTH: 32 base pairs
 (B) TYPE: nucleic acid
 (C) STRANDEDNESS: single
 (D) TOPOLOGY: unknown (ii) MOLECULE TYPE: cDNA (xi) SEQUENCE DESCRIPTION: SEQ ID NO:26:

ATCGCGAAGC TTTTAGTGAT ACTTGTGGGC CA    32

(2) INFORMATION FOR SEQ ID NO:27:

(i) SEQUENCE CHARACTERISTICS:
 (A) LENGTH: 37 base pairs
 (B) TYPE: nucleic acid
 (C) STRANDEDNESS: single
 (D) TOPOLOGY: unknown (ii) MOLECULE TYPE: cDNA (xi) SEQUENCE DESCRIPTION: SEQ ID NO:27:

GACCTGCACG CGCACAAGCT TCGGGTGAAC CCGGTCA    37

(2) INFORMATION FOR SEQ ID NO:28:

(i) SEQUENCE CHARACTERISTICS:
 (A) LENGTH: 44 base pairs
 (B) TYPE: nucleic acid
 (C) STRANDEDNESS: single
 (D) TOPOLOGY: unknown (ii) MOLECULE TYPE: cDNA (xi) SEQUENCE DESCRIPTION: SEQ ID NO:28:

AGCTAGCTAA GCTTGCTATA TTCTTGTGCT ACCGTCCATA TCTT    44

(2) INFORMATION FOR SEQ ID NO:29:

(i) SEQUENCE CHARACTERISTICS:
 (A) LENGTH: 70 base pairs
 (B) TYPE: nucleic acid
 (C) STRANDEDNESS: single
 (D) TOPOLOGY: unknown (ii) MOLECULE TYPE: cDNA (xi) SEQUENCE DESCRIPTION: SEQ ID NO:29:

AAGGGTCGAC AATATAAAAT GGTGCTGTCT CCTGCCGACA AGACCAACGT CAAGGCCGCC    60

TGGGGCAAGG    70

(2) INFORMATION FOR SEQ ID NO:30:

(i) SEQUENCE CHARACTERISTICS:
 (A) LENGTH: 30 base pairs
 (B) TYPE: nucleic acid ( C ) STRANDEDNESS: single
        ( D ) TOPOLOGY: unknown ( i i ) MOLECULE TYPE: cDNA ( x i ) SEQUENCE DESCRIPTION: SEQ ID NO:30:

CGGGTCCACC CGAAGCTTGT GCGCGTGCAG 30

( 2 ) INFORMATION FOR SEQ ID NO:31:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:31:

AGGCTGCTGG TGGTCTACCC TTGGACCCAG AGGTTCTTTG AGTGTTTTGG GGATCTGTC 59

( 2 ) INFORMATION FOR SEQ ID NO:32:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:32:

CTGCACGCGC ACAAGCTTCG GGTGGACCCG GTCAACTTCA AGCTCCTAAG CCACTCCCTG 60

CTGGTG 66

( 2 ) INFORMATION FOR SEQ ID NO:33:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:33:

CAAGTTGGGT CGACAAAAAA ATATGTCTCT GACCAAGACT GAGAGGACCA TCATTGTG 58

( 2 ) INFORMATION FOR SEQ ID NO:34:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:34:

GCGCGCGGCC AGGGTGACCA GCAGGCAGTG GGACAGGAGC TTGAAGTTGA CCGGGTTCAC 60

GCGCA 65

( 2 ) INFORMATION FOR SEQ ID NO:35:

( i ) SEQUENCE CHARACTERISTICS:
        ( A ) LENGTH: 40 base pairs
        ( B ) TYPE: nucleic acid
        ( C ) STRANDEDNESS: single ( D ) TOPOLOGY: unknown ( i i ) MOLECULE TYPE: cDNA ( x i ) SEQUENCE DESCRIPTION: SEQ ID NO:35:

CACTGCCTGC TGGTCACCCT GGCCGCGCTT CCCCGCCGAC    40

( 2 ) INFORMATION FOR SEQ ID NO:36:

( i ) SEQUENCE CHARACTERISTICS:
    ( A ) LENGTH: 57 base pairs
    ( B ) TYPE: nucleic acid
    ( C ) STRANDEDNESS: single
    ( D ) TOPOLOGY: unknown ( i i ) MOLECULE TYPE: cDNA ( x i ) SEQUENCE DESCRIPTION: SEQ ID NO:36:

TTTACCAGAC GATAACGTTA TCGCTTAGCG GTACTTCTCG GTCAGGACAG AGGATAC    57

( 2 ) INFORMATION FOR SEQ ID NO:37:

( i ) SEQUENCE CHARACTERISTICS:
    ( A ) LENGTH: 65 base pairs
    ( B ) TYPE: nucleic acid
    ( C ) STRANDEDNESS: single
    ( D ) TOPOLOGY: unknown ( i i ) MOLECULE TYPE: cDNA ( x i ) SEQUENCE DESCRIPTION: SEQ ID NO:37:

GCGCGCGGCC AGGGTGACCA GCAGGCAGTG GGACAGGAGC TTGAAGTTGA CCGGGTTCAC    60

GCGCA    65

( 2 ) INFORMATION FOR SEQ ID NO:38:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: unknown ( i i ) MOLECULE TYPE: cDNA ( x i ) SEQUENCE DESCRIPTION: SEQ ID NO:38:

CATTTCGGCA AAGAATTCAC CCCTGAGGTG GAGGCTTCC    39

( 2 ) INFORMATION FOR SEQ ID NO:39:

( i ) SEQUENCE CHARACTERISTICS:
    ( A ) LENGTH: 64 base pairs
    ( B ) TYPE: nucleic acid
    ( C ) STRANDEDNESS: single
    ( D ) TOPOLOGY: unknown ( i i ) MOLECULE TYPE: cDNA ( x i ) SEQUENCE DESCRIPTION: SEQ ID NO:39:

CAAGTTGGGT CGACAAAAAA AT ATG TTG ACT GCT GAGGAGAAGT CTGCCGTTAC    54
                         Met Leu Thr Ala

TGCCCTGTGG    64

( 2 ) INFORMATION FOR SEQ ID NO:40:

( i ) SEQUENCE CHARACTERISTICS:
    ( A ) LENGTH: 33 base pairs
    ( B ) TYPE: nucleic acid
    ( C ) STRANDEDNESS: single (D) TOPOLOGY: unknown (ii) MOLECULE TYPE: cDNA (xi) SEQUENCE DESCRIPTION: SEQ ID NO:40:

TTTAAAAAAG TCGACATGGT GCGCATGACT CCT 33

(2) INFORMATION FOR SEQ ID NO:41:

(i) SEQUENCE CHARACTERISTICS:
        (A) LENGTH: 55 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:41:

CAAGTTGGGT CGACAAAAAA ATATGGTGCA CCTGACTCCT GAGGAGAAGT CTGCC 55

(2) INFORMATION FOR SEQ ID NO:42:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:42:

ATCGCGAAGC TTTTAGTGAT ACTTGCGGGC CAG 33

(2) INFORMATION FOR SEQ ID NO:43:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:43:

AAAATCGCGA AGCTTTTACT TGTGGGCCAG 30

(2) INFORMATION FOR SEQ ID NO:44:

(i) SEQUENCE CHARACTERISTICS:
        (A) LENGTH: 59 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:44:

CCCTTGAGAT CATCCAGGTG CTTTATGGCA TCTCCCAAGG AAGTCAGCAC CGTCTTGCC 59

(2) INFORMATION FOR SEQ ID NO:45:

(i) SEQUENCE CHARACTERISTICS:
        (A) LENGTH: 69 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:45:

GAAGTTCTCA GGATCCACGT GCAGCTTGTC ACAGTGCAGC TCACTCAGTG TGGCAAAGGT 60

GCACTTGAG 69

( 2 ) INFORMATION FOR SEQ ID NO:46:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:46:

ATCCCGGGAA GGTTGAAACC AGTTCCCTG 29

( 2 ) INFORMATION FOR SEQ ID NO:47:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:47:

GTGTGTATTT ATTTGTTTTA CCACGTGCGC 30

( 2 ) INFORMATION FOR SEQ ID NO:48:

( i ) SEQUENCE CHARACTERISTICS:
        ( A ) LENGTH: 663 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:48:

GATCAAAAAT CATCGCTTCG CTGATTAATT ACCCCAGAAA TAAGGCTAAA AAACTAATCG 60

CATTATCATC CTATGGTTGT TAATTTGATT CGTTCATTTG AAGGTTTGTG GGCCAGGTT 120

ACTGCCAATT TTTCCTCTTC ATAACCATAA AAGCTAGTAT TGTAGAATCT TTATTGTTCG 180

GAGCAGTGCG GCGCGAGGCA CATCTGCGTT TCAGGAACGC GACCGGTGAA GACGAGGACG 240

CACGGAGGAG AGTCTTCCTT CGGAGGGCTG TCACCCGCTC GGCGGCTTCT AATCCGTACT 300

TCAATATAGC AATGAGCAGT TAAGCGTATT ACTGAAAGTT CCAAAGAGAA GGTTTTTTTA 360

GGCTAAGATA ATGGGGCTCT TTACATTTCC ACAACATATA AGTAAGATTA GATATGGATA 420

TGTATATGGA TATGTATATG GTGGTAATGC CATGTAATAT GATTATTAAA CTTCTTTGCG 480

TCCATCCAAA AAAAAAGTAA GAATTTTTGA AAATTCAATA TAAATGACAG CTCAGTTACA 540

AAGTGAAAGT ACTTCTAAAA TTGTTTTGGT TACAGGTGGT GCTGGATACA TTGGTTCACA 600

CACTGTGGTA GAGCTAATTG AGAATGGATA TGACTGTGTT GTTGCTGATA ACCTGTCGAA 660

TTC 663

( 2 ) INFORMATION FOR SEQ ID NO:49:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: unknown (i i) MOLECULE TYPE: cDNA (x i) SEQUENCE DESCRIPTION: SEQ ID NO:49:

TTGAGCTCCC CAGAAATAAG GC 22

(2) INFORMATION FOR SEQ ID NO:50:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (i i) MOLECULE TYPE: cDNA (x i) SEQUENCE DESCRIPTION: SEQ ID NO:50:

TCTTCCAAAA AAATCGGGCC CGT 23

(2) INFORMATION FOR SEQ ID NO:51:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:51:

GGGAATTCCC GGGGATCCTT AACGGTATTT GGAGGTCAGC ACGGTGCTCA CAGAAGCCAG 60

GAACTTGTCC AGCAGGGAGG CG 82

(2) INFORMATION FOR SEQ ID NO:52:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:52:

AGCTAGCTGG ATCCGGTAGA TACATTGATG CTATCAATCA AGAGAACTGG 50

(2) INFORMATION FOR SEQ ID NO:53:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:53:

AGCTAGCTGA ATTCGTCGAC GCATGCGTAA CGAAATAAAT CCGCGGCTCG TGC 53

(2) INFORMATION FOR SEQ ID NO:54:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA ( x i ) SEQUENCE DESCRIPTION: SEQ ID NO:54:

GCTAGTCGAC CCCAGAAATA AGGC 24

( 2 ) INFORMATION FOR SEQ ID NO:55:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:55:

GCCCCAGGCC TTGACGTTGG TCTTGTCGGC AGGAGACAGC ACCATTTTGT TTATTTATGT 60

GTGTTTATTC GAAACTAAGT TCTTGGTGTT 90

( 2 ) INFORMATION FOR SEQ ID NO:56:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:56:

ATCGCGTCGA CATGGTGCTG TCTCCTGCCG ACAAGACCAA CGTCAAGGCC TG 52

( 2 ) INFORMATION FOR SEQ ID NO:57:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:57:

TGCGAAGCTT GGATCCAATT GCCATAAACC TCCAGTCGTG CCACGAGTG 49

( 2 ) INFORMATION FOR SEQ ID NO:58:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:58:

GACGAGATCT AGAAGATCTG TCGACATGGT GCTGTCTCCT GCCGACAAGA CCAACG 56

( 2 ) INFORMATION FOR SEQ ID NO:59:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:59:

CGATCGGAGC TCATTAACGG CTTTCGCTCA TAA 33

( 2 ) INFORMATION FOR SEQ ID NO:60:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:60:

AGCGCGTCTA GAAACCCCAT TTCTATGCTC TCCTGTG     37

( 2 ) INFORMATION FOR SEQ ID NO:61:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:61:

AGCGCCTCTA GAAAGGTTGA AACCAGTTCC CTC     33

( 2 ) INFORMATION FOR SEQ ID NO:62:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:62:

AATTTGAGCT CGGATCCGCA TGCGCATGCC GGTAGAGGTG TGGTCAATAA GAGCGACCTC     60

ATGC     64

( 2 ) INFORMATION FOR SEQ ID NO:63:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:63:

TGATCGATGG TGCACTTCAC AGAGGAGGAC AAGGCTACTA TCACA     45

( 2 ) INFORMATION FOR SEQ ID NO:64:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:64:

AATTTGAGCT CGGATCCGCA TGCGCATGCC GGTAGAGGTG TGGTGAATAA GAGCGACCTC     60

ATGC     64

(2) INFORMATION FOR SEQ ID NO:65:

(i) SEQUENCE CHARACTERISTICS:
        (A) LENGTH: 141 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:65:

```
Ser Leu Thr Lys Thr Glu Arg Thr Ile Ile Val Ser Met Trp Ala Lys
 1               5                  10                  15
Ile Ser Thr Gln Ala Asp Thr Ile Gly Thr Glu Thr Leu Glu Arg Leu
            20                  25                  30
Phe Leu Ser His Pro Gln Thr Lys Thr Tyr Phe Pro His Phe Asp Leu
            35                  40                  45
His Pro Gly Ser Ala Gln Leu Arg Ala His Gly Ser Lys Val Val Ala
        50                  55                  60
Ala Val Gly Asp Ala Val Lys Ser Ile Asp Asp Ile Gly Gly Ala Leu
65                  70                  75                  80
Ser Lys Leu Ser Glu Leu His Ala Tyr Ile Leu Arg Val Asp Pro Val
                85                  90                  95
Asn Phe Lys Leu Leu Ser His Cys Leu Leu Val Thr Leu Ala Ala Arg
            100                 105                 110
Phe Pro Ala Asp Phe Thr Ala Glu Ala His Ala Ala Trp Asp Lys Phe
            115                 120                 125
Leu Ser Val Val Ser Ser Val Leu Thr Glu Lys Tyr Arg
        130                 135                 140
```

(2) INFORMATION FOR SEQ ID NO:66:

(i) SEQUENCE CHARACTERISTICS:
        (A) LENGTH: 146 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:66:

```
Val His Phe Thr Ala Glu Glu Lys Ala Ala Val Thr Ser Leu Trp Ser
 1               5                  10                  15
Lys Met Asn Val Glu Glu Ala Gly Gly Glu Ala Leu Gly Arg Leu Leu
            20                  25                  30
Val Val Tyr Pro Trp Thr Gln Arg Phe Phe Asp Ser Phe Gly Asn Leu
            35                  40                  45
Ser Ser Pro Ser Ala Ile Leu Gly Asn Pro Lys Val Lys Ala His Gly
        50                  55                  60
Lys Lys Val Leu Thr Ser Phe Gly Asp Ala Ile Lys Asn Met Asp Asn
65                  70                  75                  80
Leu Lys Pro Ala Phe Ala Lys Leu Ser Glu Leu His Cys Asp Lys Leu
                85                  90                  95
His Val Asp Pro Glu Asn Phe Lys Leu Leu Gly Asn Val Met Val Ile
            100                 105                 110
Ile Leu Ala Thr His Phe Gly Lys Glu Phe Thr Pro Glu Val Gln Ala
            115                 120                 125
Ala Trp Gln Lys Leu Val Ser Ala Val Ala Ile Ala Leu Gly His Lys
        130                 135                 140
```

Tyr His
145

(2) INFORMATION FOR SEQ ID NO:67:

(i) SEQUENCE CHARACTERISTICS:
        (A) LENGTH: 146 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:67:

```
Gly His Phe Thr Glu Glu Asp Lys Ala Thr Ile Thr Ser Leu Trp Gly
 1               5                  10                  15
Lys Val Asn Val Glu Asp Ala Gly Gly Glu Thr Leu Gly Arg Leu Leu
                20                  25                  30
Val Val Tyr Pro Trp Thr Gln Arg Phe Phe Asp Ser Phe Gly Asn Leu
            35                  40                  45
Ser Ser Ala Ser Ala Ile Met Gly Asn Pro Lys Val Lys Ala His Gly
        50                  55                  60
Lys Lys Val Leu Thr Ser Leu Gly Asp Ala Ile Lys His Leu Asp Asp
65                  70                  75                  80
Leu Lys Gly Thr Phe Ala Gln Leu Ser Glu Leu His Cys Asp Lys Leu
                85                  90                  95
His Val Asp Pro Glu Asn Phe Lys Leu Leu Gly Asn Val Leu Val Thr
               100                 105                 110
Val Leu Ala Ile His Phe Gly Lys Glu Phe Thr Pro Glu Val Gln Ala
           115                 120                 125
Ser Trp Gln Lys Met Val Thr Ala Val Ala Ser Ala Leu Ser Ser Arg
       130                 135                 140
Tyr His
145
```

(2) INFORMATION FOR SEQ ID NO:68:

(i) SEQUENCE CHARACTERISTICS:
        (A) LENGTH: 146 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:68:

```
Val His Leu Thr Pro Glu Glu Lys Thr Ala Val Asn Ala Leu Trp Gly
 1               5                  10                  15
Lys Val Asn Val Asp Ala Val Gly Gly Glu Ala Leu Gly Arg Leu Leu
                20                  25                  30
Val Val Tyr Pro Trp Thr Gln Arg Phe Phe Glu Ser Phe Gly Asp Leu
            35                  40                  45
Ser Ser Pro Asp Ala Val Met Gly Asn Pro Lys Val Lys Ala His Gly
        50                  55                  60
Lys Lys Val Leu Gly Ala Phe Ser Asp Gly Leu Ala His Leu Asp Asn
65                  70                  75                  80
Leu Lys Gly Thr Phe Ser Gln Leu Ser Glu Leu His Cys Asp Lys Leu
                85                  90                  95
His Val Asp Pro Glu Asn Phe Arg Leu Leu Gly Asn Val Leu Val Cys
               100                 105                 110
```

| Val | Leu | Ala | Arg | Asn | Phe | Gly | Lys | Glu | Phe | Thr | Pro | Gln | Met | Gln | Ala |
|     |     |     | 115 |     |     |     | 120 |     |     |     |     | 125 |     |     |     |

| Ala | Tyr | Gln | Lys | Val | Val | Ala | Gly | Val | Ala | Asn | Ala | Leu | Ala | His | Lys |
|     |     | 130 |     |     |     | 135 |     |     |     |     | 140 |     |     |     |     |

| Tyr | His |
| 145 |     |

( 2 ) INFORMATION FOR SEQ ID NO:69:

( i ) SEQUENCE CHARACTERISTICS:
        ( A ) LENGTH: 141 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:69:

| Val | Leu | Ser | Pro | Ala | Asp | Lys | Thr | Asn | Val | Lys | Ala | Ala | Trp | Gly | Lys |
| 1   |     |     |     | 5   |     |     |     |     | 10  |     |     |     |     | 15  |     |

| Val | Gly | Ala | His | Ala | Gly | Glu | Tyr | Gly | Ala | Glu | Ala | Leu | Glu | Arg | Met |
|     |     |     | 20  |     |     |     |     | 25  |     |     |     |     | 30  |     |     |

| Phe | Leu | Ser | Phe | Pro | Thr | Thr | Lys | Thr | Tyr | Phe | Pro | His | Phe | Asp | Leu |
|     |     | 35  |     |     |     |     | 40  |     |     |     |     | 45  |     |     |     |

| Ser | His | Gly | Ser | Ala | Gln | Val | Lys | Gly | His | Gly | Lys | Lys | Val | Ala | Asp |
|     | 50  |     |     |     |     | 55  |     |     |     |     | 60  |     |     |     |     |

| Ala | Leu | Thr | Asn | Ala | Val | Ala | His | Val | Asp | Asp | Met | Pro | Asn | Ala | Leu |
| 65  |     |     |     |     | 70  |     |     |     |     | 75  |     |     |     |     | 80  |

| Ser | Ala | Leu | Ser | Asp | Leu | His | Ala | His | Lys | Leu | Arg | Val | Asp | Pro | Val |
|     |     |     |     | 85  |     |     |     |     | 90  |     |     |     |     | 95  |     |

| Asn | Phe | Lys | Leu | Leu | Ser | His | Cys | Leu | Leu | Val | Thr | Leu | Ala | Ala | His |
|     |     |     |     | 100 |     |     |     |     | 105 |     |     |     |     | 110 |     |

| Leu | Pro | Ala | Glu | Phe | Thr | Pro | Ala | Val | His | Ala | Ser | Leu | Asp | Lys | Phe |
|     |     |     | 115 |     |     |     |     | 120 |     |     |     |     | 125 |     |     |

| Leu | Ala | Ser | Val | Ser | Thr | Val | Leu | Thr | Ser | Lys | Tyr | Arg |
|     |     | 130 |     |     |     |     | 135 |     |     |     |     | 140 |

( 2 ) INFORMATION FOR SEQ ID NO:70:

( i ) SEQUENCE CHARACTERISTICS:
        ( A ) LENGTH: 146 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:70:

| Val | His | Leu | Thr | Pro | Glu | Glu | Lys | Ser | Ala | Val | Thr | Ala | Leu | Trp | Gly |
| 1   |     |     |     | 5   |     |     |     |     | 10  |     |     |     |     | 15  |     |

| Lys | Val | Asn | Val | Asp | Glu | Val | Gly | Gly | Glu | Ala | Leu | Gly | Arg | Leu | Leu |
|     |     |     | 20  |     |     |     |     | 25  |     |     |     |     | 30  |     |     |

| Val | Val | Tyr | Pro | Trp | Thr | Gln | Arg | Phe | Phe | Glu | Ser | Phe | Gly | Asp | Leu |
|     |     | 35  |     |     |     |     | 40  |     |     |     |     | 45  |     |     |     |

| Ser | Thr | Pro | Asp | Ala | Val | Met | Gly | Asn | Pro | Lys | Val | Lys | Ala | His | Gly |
|     | 50  |     |     |     |     | 55  |     |     |     |     | 60  |     |     |     |     |

| Lys | Lys | Val | Leu | Gly | Ala | Phe | Ser | Asp | Gly | Leu | Ala | His | Leu | Asp | Asn |
| 65  |     |     |     |     | 70  |     |     |     |     | 75  |     |     |     |     | 80  |

| Leu | Lys | Gly | Thr | Phe | Ala | Thr | Leu | Ser | Glu | Leu | His | Cys | Asp | Lys | Leu |
|     |     |     |     | 85  |     |     |     |     | 90  |     |     |     |     | 95  |     |

-continued

| His | Val | Asp | Pro | Glu | Asn | Phe | Arg | Leu | Leu | Gly | Asn | Val | Leu | Val | Cys |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |
| Val | Leu | Ala | His | His | Phe | Gly | Lys | Glu | Phe | Thr | Pro | Pro | Val | Gln | Ala |
|     |     | 115 |     |     |     |     | 120 |     |     |     |     | 125 |     |     |     |
| Ala | Tyr | Gln | Lys | Val | Val | Ala | Gly | Val | Ala | Asn | Ala | Leu | Ala | His | Lys |
|     | 130 |     |     |     |     | 135 |     |     |     |     | 140 |     |     |     |     |
| Tyr | His |
| 145 |     |

( 2 ) INFORMATION FOR SEQ ID NO:71:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:71:

Met Leu Thr Ala